(12) United States Patent
Scheib et al.

(10) Patent No.: US 11,931,018 B2
(45) Date of Patent: Mar. 19, 2024

(54) SURGICAL INSTRUMENT HAVING DUAL ROTATABLE MEMBERS TO EFFECT DIFFERENT TYPES OF END EFFECTOR MOVEMENT

(71) Applicant: Cilag GmbH International, Zug (CH)

(72) Inventors: Charles J. Scheib, Loveland, OH (US); Adam D. Hensel, Gahanna, OH (US); Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 397 days.

(21) Appl. No.: 17/101,830

(22) Filed: Nov. 23, 2020

(65) Prior Publication Data

US 2021/0315561 A1 Oct. 14, 2021

Related U.S. Application Data

(63) Continuation of application No. 15/908,012, filed on Feb. 28, 2018, now Pat. No. 10,842,473.

(60) Provisional application No. 62/578,844, filed on Oct. 30, 2017, provisional application No. 62/578,793, filed on Oct. 30, 2017, provisional application No. 62/578,804, filed on Oct. 30, 2017, provisional
(Continued)

(51) Int. Cl.
*A61B 17/00* (2006.01)
*A61B 17/29* (2006.01)
*A61B 90/00* (2016.01)

(52) U.S. Cl.
CPC ........ *A61B 17/00234* (2013.01); *A61B 17/29* (2013.01); *A61B 2017/00367* (2013.01); *A61B 2017/00398* (2013.01); *A61B 2017/0042* (2013.01); *A61B 2017/0046* (2013.01); *A61B 2017/00477* (2013.01); *A61B 2017/00734* (2013.01); *A61B 2017/2902* (2013.01); *A61B 2017/2903* (2013.01); *A61B 2017/2905* (2013.01); *A61B 2017/2919* (2013.01); *A61B 2017/2926* (2013.01); *A61B 2017/2927* (2013.01); *A61B 2017/2929* (2013.01); *A61B 2017/2931* (2013.01); *A61B 2090/0811* (2016.02)

(58) Field of Classification Search
CPC .......... A61B 17/29; A61B 2017/00367; A61B 2017/00371; A61B 2017/00389; A61B 2017/00393; A61B 2017/00398; A61B 2017/00402; A61B 2017/00685; A61B 2017/00734; A61B 2017/2902; A61B 2017/2903; A61B 2017/2934
See application file for complete search history.

(56) References Cited

U.S. PATENT DOCUMENTS 3,082,426 A 3/1963 Miles
3,497,083 A 2/1970 Anderson
(Continued)

FOREIGN PATENT DOCUMENTS

AU 2015201140 A1 3/2015
CN 101617950 A 1/2010
(Continued)

*Primary Examiner* — Martin T Ton
(74) *Attorney, Agent, or Firm* — Barnes & Thorburg LLP

(57) ABSTRACT

A surgical instrument comprising an end effector configured to perform a plurality of end effector functions is disclosed. The surgical instrument further comprises a drive shaft which is both rotatable and translatable to drive the end effector functions.

20 Claims, 70 Drawing Sheets

Related U.S. Application Data application No. 62/578,817, filed on Oct. 30, 2017, provisional application No. 62/578,835, filed on Oct. 30, 2017, provisional application No. 62/578,855, filed on Oct. 30, 2017.

(56) References Cited

U.S. PATENT DOCUMENTS

| | | |
|---|---|---|
| 3,584,628 A | 6/1971 | Green |
| 4,412,539 A | 11/1983 | Jarvik |
| 4,448,193 A | 5/1984 | Ivanov |
| 4,523,695 A | 6/1985 | Braun et al. |
| 4,779,687 A | 10/1988 | Schreiber et al. |
| 5,084,057 A | 1/1992 | Green et al. |
| 5,151,102 A | 9/1992 | Kamiyama et al. |
| 5,383,880 A | 1/1995 | Hooven |
| 5,396,900 A | 3/1995 | Slater et al. |
| 5,403,327 A | 4/1995 | Thornton et al. |
| 5,403,342 A | 4/1995 | Tovey et al. |
| 5,417,699 A | 5/1995 | Klein et al. |
| 5,439,468 A | 8/1995 | Schulze et al. |
| 5,456,695 A | 10/1995 | Herve Dallemagne |
| 5,467,911 A | 11/1995 | Tsuruta et al. |
| 5,474,566 A | 12/1995 | Alesi et al. |
| 5,547,117 A | 8/1996 | Hamblin et al. |
| 5,643,291 A | 7/1997 | Pier et al. |
| 5,725,542 A | 3/1998 | Yoon |
| 5,893,835 A | 4/1999 | Witt et al. |
| 5,906,625 A | 5/1999 | Bito et al. |
| 6,059,799 A | 5/2000 | Aranyi et al. |
| 6,099,537 A | 8/2000 | Sugai et al. |
| 6,220,368 B1 | 4/2001 | Ark et al. |
| 6,257,351 B1 | 7/2001 | Ark et al. |
| 6,258,105 B1 | 7/2001 | Hart et al. |
| 6,273,887 B1 | 8/2001 | Yamauchi et al. |
| 6,446,693 B1 | 9/2002 | Anderson et al. |
| 6,530,933 B1 | 3/2003 | Yeung et al. |
| 6,602,262 B2 | 8/2003 | Griego et al. |
| 6,793,663 B2 | 9/2004 | Kneifel et al. |
| 6,869,435 B2 | 3/2005 | Blake, III |
| 6,921,285 B2 | 7/2005 | Glauning |
| 6,955,864 B1 | 10/2005 | Vaisnys et al. |
| 7,104,949 B2 | 9/2006 | Anderson et al. |
| 7,182,775 B2 | 2/2007 | de Guillebon et al. |
| 7,371,227 B2 | 5/2008 | Zeiner |
| 7,407,074 B2 | 8/2008 | Ortiz et al. |
| 7,575,144 B2 * | 8/2009 | Ortiz ................ A61B 17/07207 227/19 |
| 7,608,083 B2 | 10/2009 | Lee et al. |
| 7,637,410 B2 | 12/2009 | Marczyk |
| 7,845,537 B2 | 12/2010 | Shelton, IV et al. |
| 7,855,012 B2 | 12/2010 | Takeshita et al. |
| 7,862,579 B2 | 1/2011 | Ortiz et al. |
| 7,963,433 B2 | 6/2011 | Whitman et al. |
| 7,976,553 B2 | 7/2011 | Shelton, IV et al. |
| 8,062,306 B2 | 11/2011 | Nobis et al. |
| 8,123,764 B2 | 2/2012 | Meade et al. |
| 8,286,845 B2 | 10/2012 | Perry et al. |
| 8,377,044 B2 | 2/2013 | Coe et al. |
| 8,403,946 B2 | 3/2013 | Whitfield et al. |
| 8,409,245 B2 | 4/2013 | Lee |
| 8,419,760 B2 | 4/2013 | Wiebe, III |
| 8,469,973 B2 | 6/2013 | Meade et al. |
| 8,485,413 B2 | 7/2013 | Scheib et al. |
| 8,622,274 B2 | 1/2014 | Yates et al. |
| 8,628,545 B2 | 1/2014 | Cabrera et al. |
| 8,632,525 B2 | 1/2014 | Kerr et al. |
| 8,636,736 B2 | 1/2014 | Yates et al. |
| 8,657,174 B2 | 2/2014 | Yates et al. |
| 8,684,253 B2 | 4/2014 | Giordano et al. |
| 8,685,056 B2 | 4/2014 | Evans et al. |
| 8,740,840 B2 | 6/2014 | Foley et al. |
| 8,752,749 B2 | 6/2014 | Moore et al. |
| 8,763,879 B2 | 7/2014 | Shelton, IV et al. |
| 8,789,741 B2 | 7/2014 | Baxter, III et al. |
| 8,806,973 B2 | 8/2014 | Ross et al. |
| 8,820,607 B2 | 9/2014 | Marczyk |
| 8,852,174 B2 | 10/2014 | Burbank |
| 8,905,977 B2 | 12/2014 | Shelton et al. |
| 8,906,001 B2 | 12/2014 | Williams |
| 8,920,433 B2 | 12/2014 | Barrier et al. |
| 8,931,682 B2 | 1/2015 | Timm et al. |
| 8,962,062 B2 | 2/2015 | Podhajsky et al. |
| 8,968,309 B2 | 3/2015 | Roy et al. |
| 8,968,337 B2 | 3/2015 | Whitfield et al. |
| 8,968,358 B2 | 3/2015 | Reschke |
| 8,992,565 B2 | 3/2015 | Brisson et al. |
| 9,017,333 B2 | 4/2015 | Beale et al. |
| 9,028,494 B2 | 5/2015 | Shelton, IV et al. |
| 9,028,495 B2 | 5/2015 | Mueller et al. |
| 9,033,960 B2 | 5/2015 | Isbell, Jr. |
| 9,072,535 B2 | 7/2015 | Shelton, IV et al. |
| 9,078,671 B2 | 7/2015 | Beale et al. |
| 9,095,362 B2 | 8/2015 | Dachs, II et al. |
| 9,101,374 B1 | 8/2015 | Hoch et al. |
| 9,107,573 B2 | 8/2015 | Birnkrant |
| 9,119,657 B2 | 9/2015 | Shelton, IV et al. |
| 9,179,912 B2 | 11/2015 | Yates et al. |
| 9,220,398 B2 | 12/2015 | Woodley et al. |
| 9,282,974 B2 | 3/2016 | Shelton, IV |
| 9,283,054 B2 | 3/2016 | Morgan et al. |
| 9,289,212 B2 | 3/2016 | Shelton, IV et al. |
| 9,345,481 B2 | 5/2016 | Hall et al. |
| 9,351,727 B2 | 5/2016 | Leimbach et al. |
| 9,364,231 B2 | 6/2016 | Wenchell |
| 9,398,905 B2 | 7/2016 | Martin |
| 9,398,911 B2 | 7/2016 | Auld |
| 9,402,604 B2 | 8/2016 | Williams et al. |
| 9,415,510 B2 | 8/2016 | Hourtash et al. |
| 9,421,014 B2 | 8/2016 | Ingmanson et al. |
| 9,427,279 B2 | 8/2016 | Muniz-Medina et al. |
| 9,492,237 B2 | 11/2016 | Kang et al. |
| 9,504,520 B2 | 11/2016 | Worrell et al. |
| 9,539,006 B2 | 1/2017 | Collings et al. |
| 9,549,750 B2 | 1/2017 | Shelton, IV et al. |
| 9,554,803 B2 | 1/2017 | Smith et al. |
| 9,561,038 B2 | 2/2017 | Shelton, IV et al. |
| 9,561,045 B2 | 2/2017 | Hinman et al. |
| 9,566,121 B2 | 2/2017 | Staunton et al. |
| 9,629,623 B2 | 4/2017 | Lytle, IV et al. |
| 9,629,629 B2 | 4/2017 | Leimbach et al. |
| 9,655,616 B2 | 5/2017 | Aranyi |
| 9,700,309 B2 | 7/2017 | Jaworek et al. |
| 9,717,548 B2 | 8/2017 | Couture |
| 9,724,123 B2 | 8/2017 | Rydberg et al. |
| 9,724,153 B2 | 8/2017 | Jadhav |
| 9,750,522 B2 | 9/2017 | Scheib et al. |
| 9,782,164 B2 | 10/2017 | Mumaw et al. |
| 9,795,436 B2 | 10/2017 | Yates et al. |
| 9,801,626 B2 | 10/2017 | Parihar et al. |
| 9,801,679 B2 | 10/2017 | Trees et al. |
| 9,808,246 B2 | 11/2017 | Shelton, IV et al. |
| 9,814,460 B2 | 11/2017 | Kimsey et al. |
| 9,826,976 B2 | 11/2017 | Parihar et al. |
| 9,833,239 B2 | 12/2017 | Yates et al. |
| 9,839,420 B2 | 12/2017 | Shelton, IV et al. |
| 9,844,368 B2 | 12/2017 | Boudreaux et al. |
| 9,844,374 B2 | 12/2017 | Lytle, IV et al. |
| 9,844,375 B2 | 12/2017 | Overmyer et al. |
| 9,861,272 B2 | 1/2018 | Pell et al. |
| 9,861,354 B2 | 1/2018 | Saliman et al. |
| 9,867,612 B2 | 1/2018 | Parihar et al. |
| 9,868,198 B2 | 1/2018 | Nicholas et al. |
| 9,888,919 B2 | 2/2018 | Leimbach et al. |
| 9,907,550 B2 | 3/2018 | Sniffin et al. |
| 9,918,778 B2 | 3/2018 | Walberg et al. |
| 9,918,788 B2 | 3/2018 | Paul et al. |
| 9,931,118 B2 | 4/2018 | Shelton, IV et al. |
| 9,931,124 B2 | 4/2018 | Gokharu |
| 9,936,955 B2 | 4/2018 | Miller et al. |
| 9,991,069 B2 | 6/2018 | Nicholas et al. |
| 9,993,258 B2 | 6/2018 | Shelton, IV et al. |
| 10,004,491 B2 | 6/2018 | Martin et al. |
| 10,004,529 B2 | 6/2018 | Stokes et al. |

(56) References Cited

U.S. PATENT DOCUMENTS

| | | |
|---|---|---|
| 10,028,761 B2 | 7/2018 | Leimbach et al. |
| 10,039,595 B2 | 8/2018 | Sakaguchi et al. |
| 10,041,822 B2 | 8/2018 | Zemlok |
| 10,045,813 B2 | 8/2018 | Mueller |
| 10,076,326 B2 | 9/2018 | Yates et al. |
| D829,902 S | 10/2018 | Aranyi et al. |
| 10,085,748 B2 | 10/2018 | Morgan et al. |
| 10,105,142 B2 | 10/2018 | Baxter, III et al. |
| 10,117,702 B2 | 11/2018 | Danziger et al. |
| 10,159,481 B2 | 12/2018 | Whitman et al. |
| 10,188,385 B2 | 1/2019 | Kerr et al. |
| 10,189,157 B2 | 1/2019 | Schlegel et al. |
| 10,194,913 B2 | 2/2019 | Nalagatla et al. |
| 10,231,775 B2 | 3/2019 | Shelton, IV et al. |
| 10,238,385 B2 | 3/2019 | Yates et al. |
| 10,245,037 B2 | 4/2019 | Conklin et al. |
| 10,258,363 B2 | 4/2019 | Worrell et al. |
| 10,263,171 B2 | 4/2019 | Wiener et al. |
| 10,265,090 B2 | 4/2019 | Ingmanson et al. |
| 10,265,130 B2 | 4/2019 | Hess et al. |
| 10,271,840 B2 | 4/2019 | Sapre |
| 10,292,758 B2 | 5/2019 | Boudreaux et al. |
| 10,307,199 B2 | 6/2019 | Farritor et al. |
| 10,342,543 B2 | 7/2019 | Shelton, IV et al. |
| 10,368,876 B2 | 8/2019 | Bhatnagar et al. |
| 10,390,831 B2 | 8/2019 | Holsten et al. |
| 10,420,552 B2 | 9/2019 | Shelton, IV et al. |
| 10,441,281 B2 | 10/2019 | Shelton, IV et al. |
| 10,464,431 B2 | 11/2019 | Ger |
| 10,498,269 B2 | 12/2019 | Zemlok et al. |
| 10,537,351 B2 | 1/2020 | Shelton, IV et al. |
| 10,548,504 B2 | 2/2020 | Shelton, IV et al. |
| 10,548,612 B2 | 2/2020 | Martinez et al. |
| 10,559,967 B2 | 2/2020 | Hunger |
| 10,561,471 B2 | 2/2020 | Nichogi |
| 10,568,651 B2 | 2/2020 | Kostrzewski et al. |
| 10,575,868 B2 | 3/2020 | Hall et al. |
| 10,582,931 B2 | 3/2020 | Mujawar |
| 10,603,128 B2 | 3/2020 | Zergiebel et al. |
| 10,610,286 B2 | 4/2020 | Wiener et al. |
| 10,610,313 B2 | 4/2020 | Bailey et al. |
| 10,624,634 B2 | 4/2020 | Shelton, IV et al. |
| 10,624,691 B2 | 4/2020 | Wiener et al. |
| 10,639,027 B2 | 5/2020 | Shelton, IV et al. |
| 10,675,021 B2 | 6/2020 | Harris et al. |
| 10,695,060 B2 | 6/2020 | Satti, III et al. |
| 10,722,222 B2 | 7/2020 | Aranyi |
| 10,736,616 B2 | 8/2020 | Scheib et al. |
| 10,736,743 B2 | 8/2020 | Lim et al. |
| 10,779,818 B2 | 9/2020 | Zemlok et al. |
| 10,828,028 B2 | 11/2020 | Harris et al. |
| 10,835,247 B2 | 11/2020 | Shelton, IV et al. |
| 10,842,473 B2 | 11/2020 | Scheib et al. |
| 10,842,523 B2 * | 11/2020 | Shelton, IV ....... A61B 18/1206 |
| 10,881,399 B2 | 1/2021 | Shelton, IV et al. |
| 10,905,466 B2 | 2/2021 | Chacon Quiros et al. |
| 10,905,511 B2 | 2/2021 | Rodriguez-Navarro et al. |
| 10,932,784 B2 | 3/2021 | Mozdzierz et al. |
| 10,932,804 B2 | 3/2021 | Scheib et al. |
| 10,952,708 B2 | 3/2021 | Scheib et al. |
| 10,959,797 B2 | 3/2021 | Licht et al. |
| 11,064,997 B2 | 7/2021 | Shelton, IV et al. |
| 11,116,485 B2 | 9/2021 | Scheib et al. |
| 11,129,634 B2 | 9/2021 | Scheib et al. |
| 11,129,670 B2 | 9/2021 | Shelton, IV et al. |
| 11,179,150 B2 | 11/2021 | Yates et al. |
| 11,229,471 B2 | 1/2022 | Shelton, IV et al. |
| 11,241,230 B2 | 2/2022 | Shelton, IV et al. |
| 2005/0044051 A1 | 2/2005 | Selby et al. |
| 2005/0192633 A1 | 9/2005 | Montpetit |
| 2006/0020272 A1 | 1/2006 | Gildenberg |
| 2007/0225754 A1 | 9/2007 | Measamer et al. |
| 2008/0255413 A1 | 10/2008 | Zemlok et al. |
| 2008/0262654 A1 | 10/2008 | Omori et al. |
| 2008/0296346 A1 | 12/2008 | Shelton, IV et al. |
| 2009/0206131 A1 | 8/2009 | Weisenburgh, II et al. |
| 2009/0299439 A1 | 12/2009 | Mire et al. |
| 2010/0198248 A1 | 8/2010 | Vakharia |
| 2011/0174099 A1 * | 7/2011 | Ross ................... A61B 17/115 74/89.32 |
| 2012/0130217 A1 | 5/2012 | Kauphusman et al. |
| 2012/0211542 A1 | 8/2012 | Racenet |
| 2012/0253328 A1 | 10/2012 | Cunningham et al. |
| 2012/0292367 A1 | 11/2012 | Morgan et al. |
| 2014/0107697 A1 | 4/2014 | Patani et al. |
| 2014/0188091 A1 | 7/2014 | Vidal et al. |
| 2014/0207124 A1 | 7/2014 | Aldridge et al. |
| 2014/0263552 A1 | 9/2014 | Hall et al. |
| 2015/0032150 A1 | 1/2015 | Ishida et al. |
| 2015/0053746 A1 | 2/2015 | Shelton, IV et al. |
| 2015/0053748 A1 | 2/2015 | Yates et al. |
| 2015/0272557 A1 | 10/2015 | Overmyer et al. |
| 2015/0302157 A1 | 10/2015 | Collar et al. |
| 2016/0113732 A1 | 4/2016 | Steege et al. |
| 2016/0270835 A1 | 9/2016 | Reed |
| 2016/0296246 A1 | 10/2016 | Schaller |
| 2017/0296213 A1 | 10/2017 | Swensgard et al. |
| 2018/0049798 A1 * | 2/2018 | Shelton, IV ... A61B 17/320068 |
| 2018/0125594 A1 | 5/2018 | Beardsley |
| 2018/0168575 A1 | 6/2018 | Simms et al. |
| 2018/0303493 A1 | 10/2018 | Chapolini |
| 2018/0310986 A1 | 11/2018 | Batchelor et al. |
| 2019/0090963 A1 | 3/2019 | Canady et al. |
| 2019/0261984 A1 | 8/2019 | Nelson et al. |
| 2019/0290314 A1 | 9/2019 | Gemer et al. |
| 2019/0298400 A1 | 10/2019 | Horeman |

FOREIGN PATENT DOCUMENTS

| | | |
|---|---|---|
| CN | 104490448 A | 4/2015 |
| DE | 102005051367 A1 | 4/2007 |
| EA | 0000756 A1 | 2/1979 |
| EA | 3095399 A2 | 11/2016 |
| GB | 2509523 A | 7/2014 |
| JP | 2017513561 A | 6/2017 |
| WO | WO-0024322 A1 | 5/2000 |
| WO | WO-2008069816 A1 | 6/2008 |
| WO | WO-2016206015 A1 | 12/2016 |
| WO | WO-2017011382 A1 | 1/2017 |

* cited by examiner

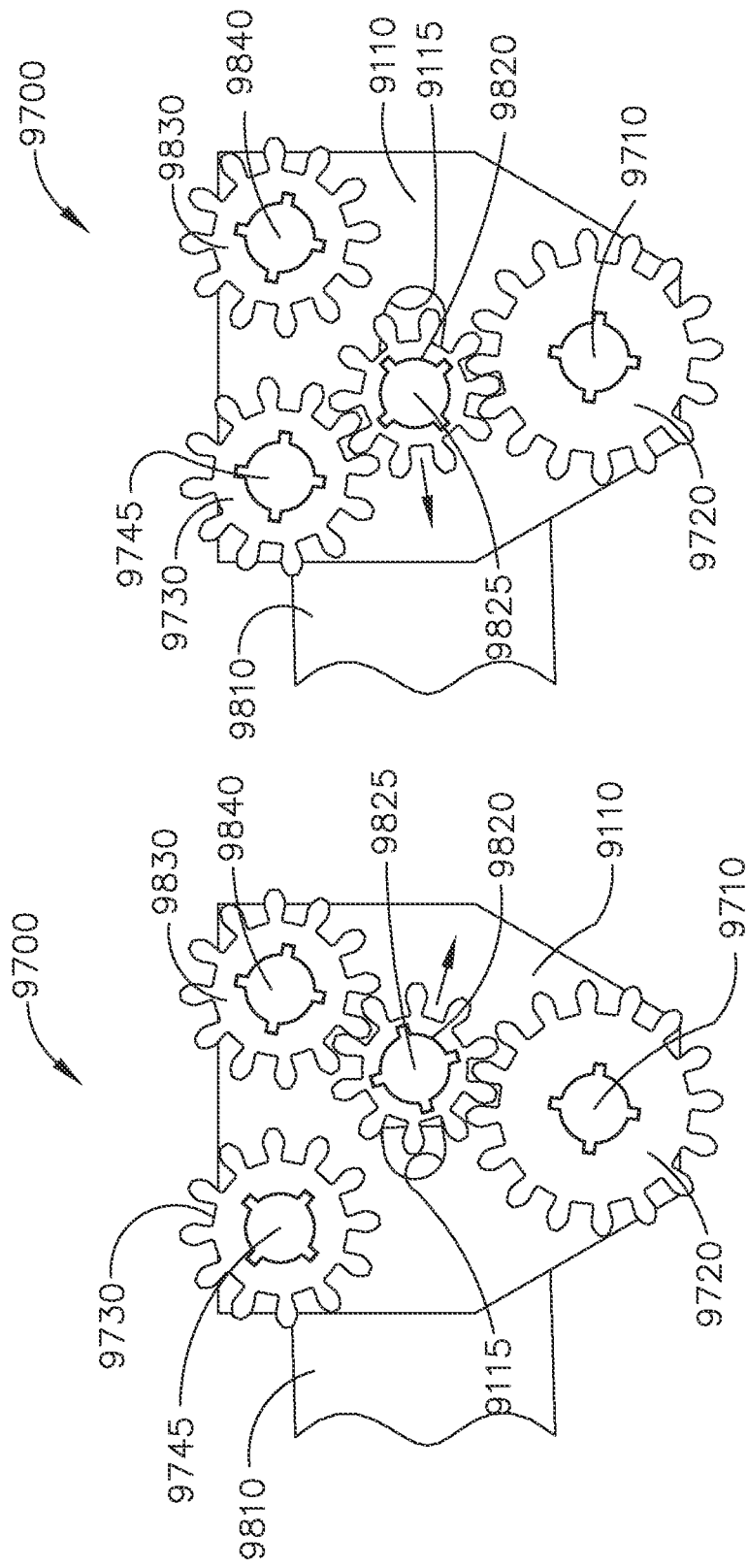

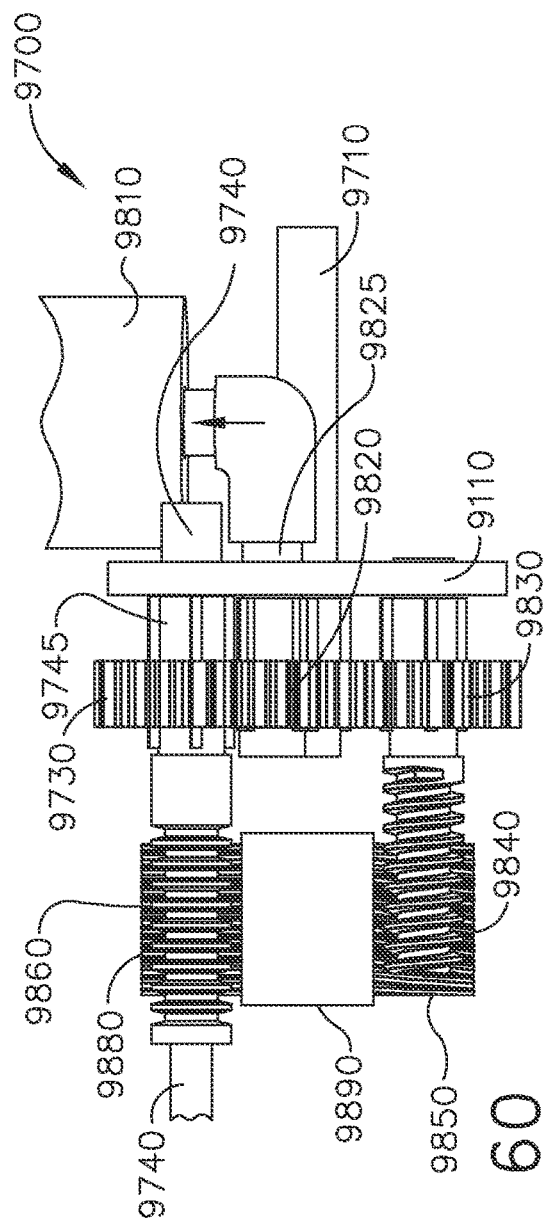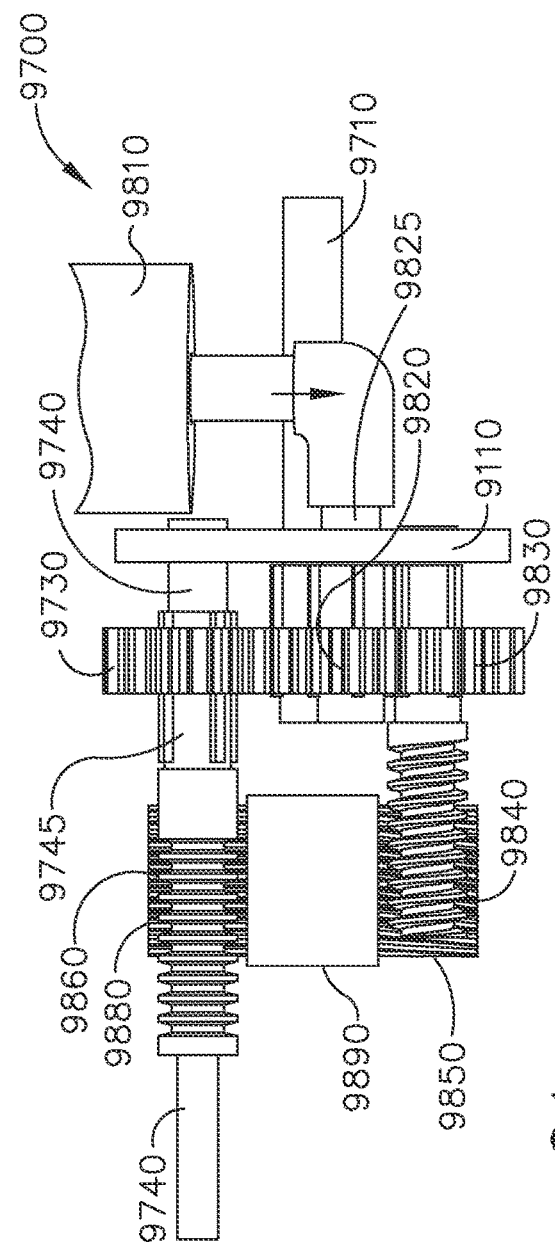

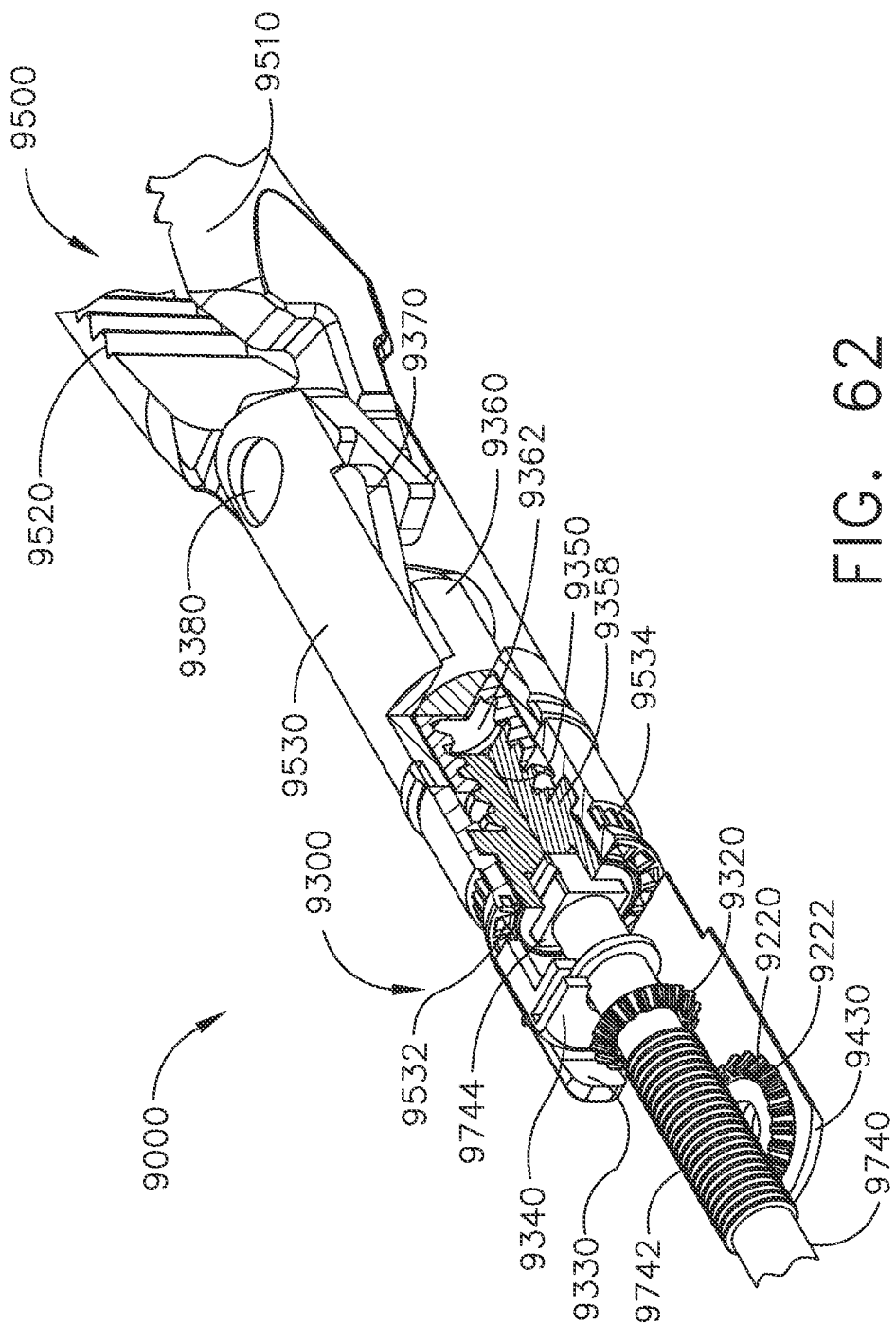

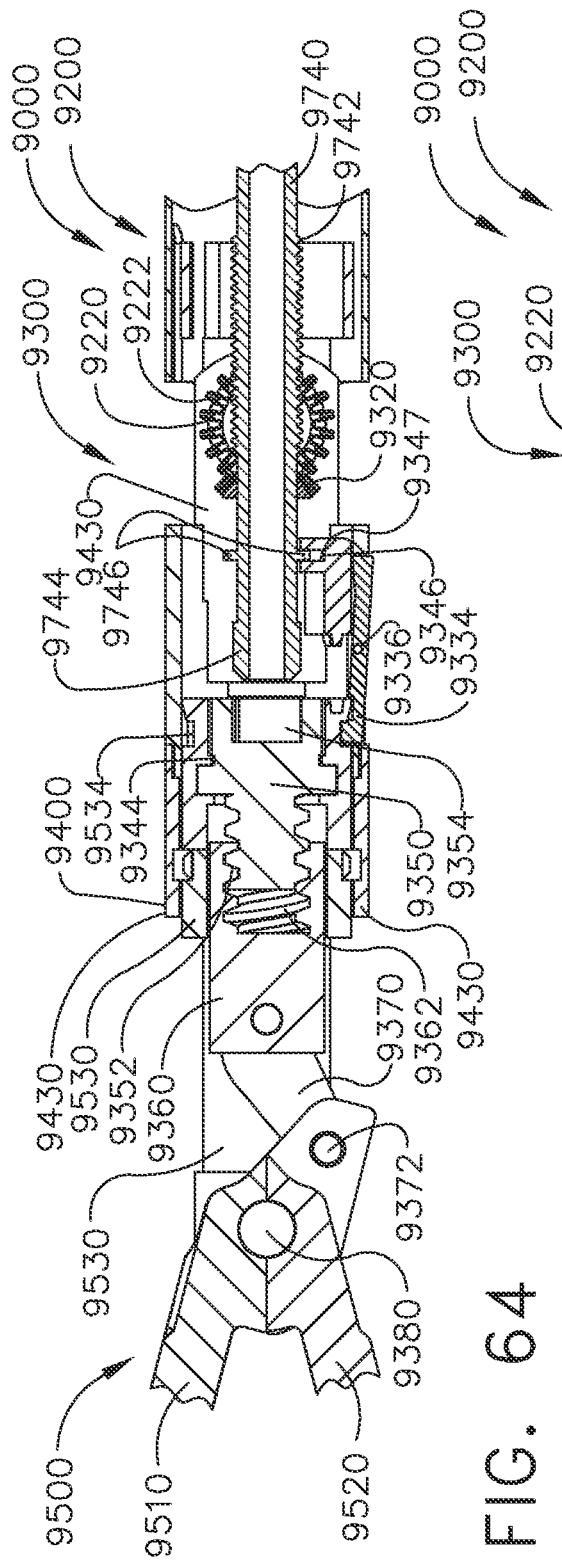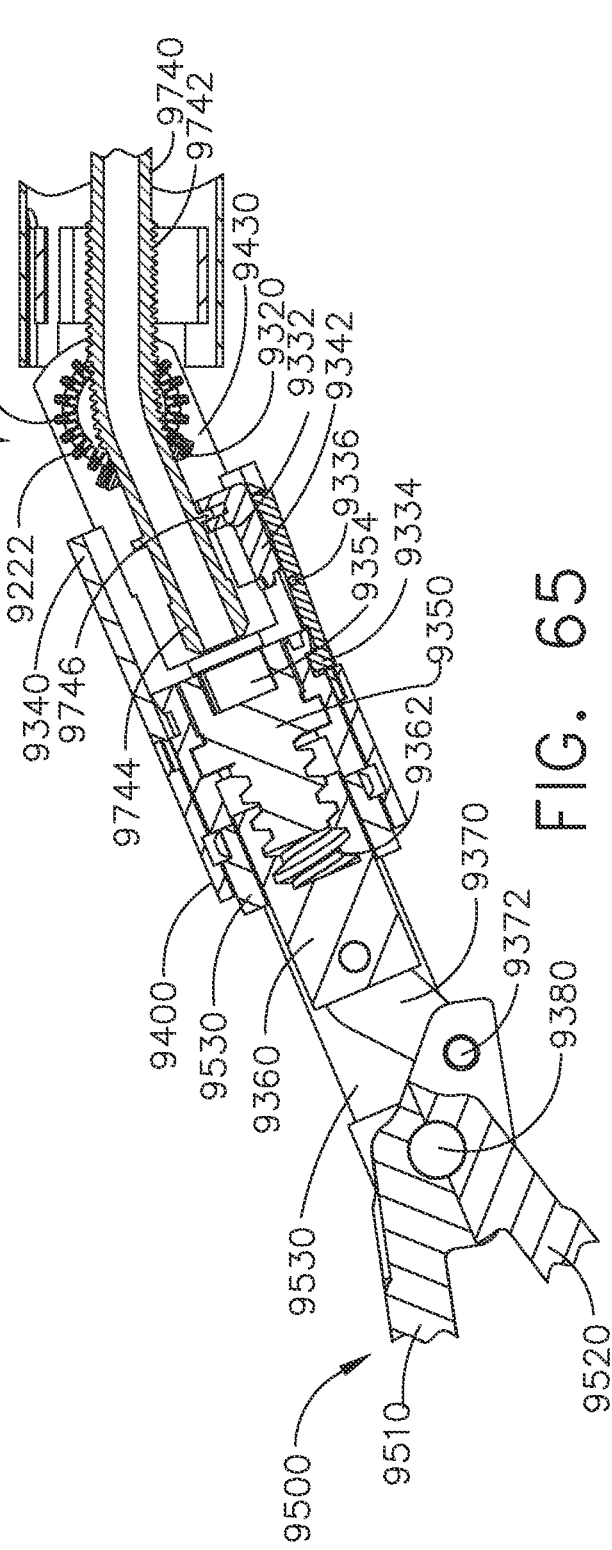

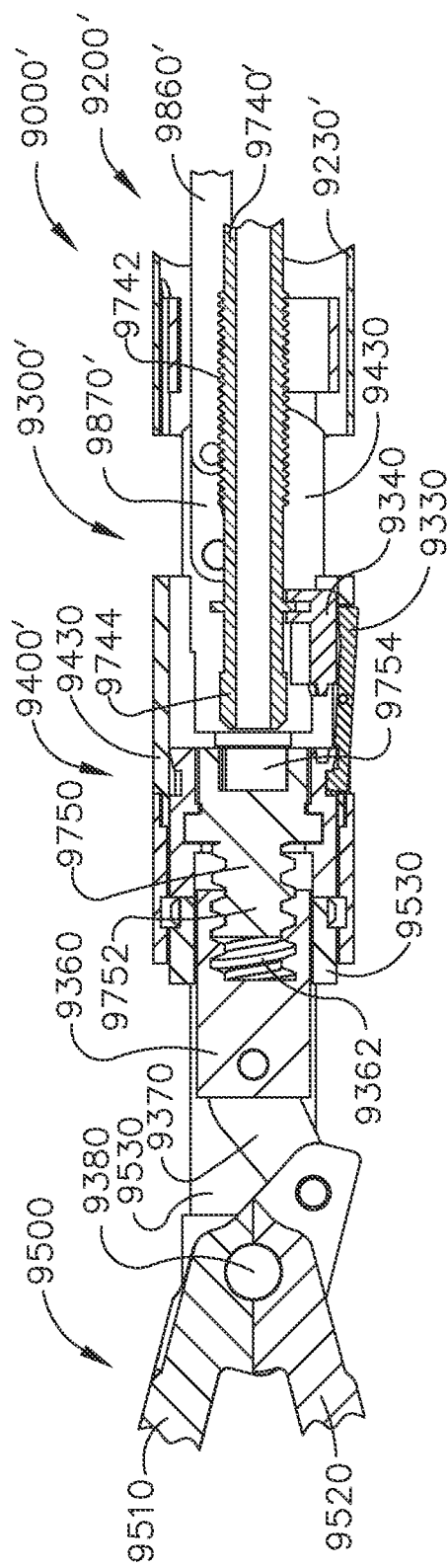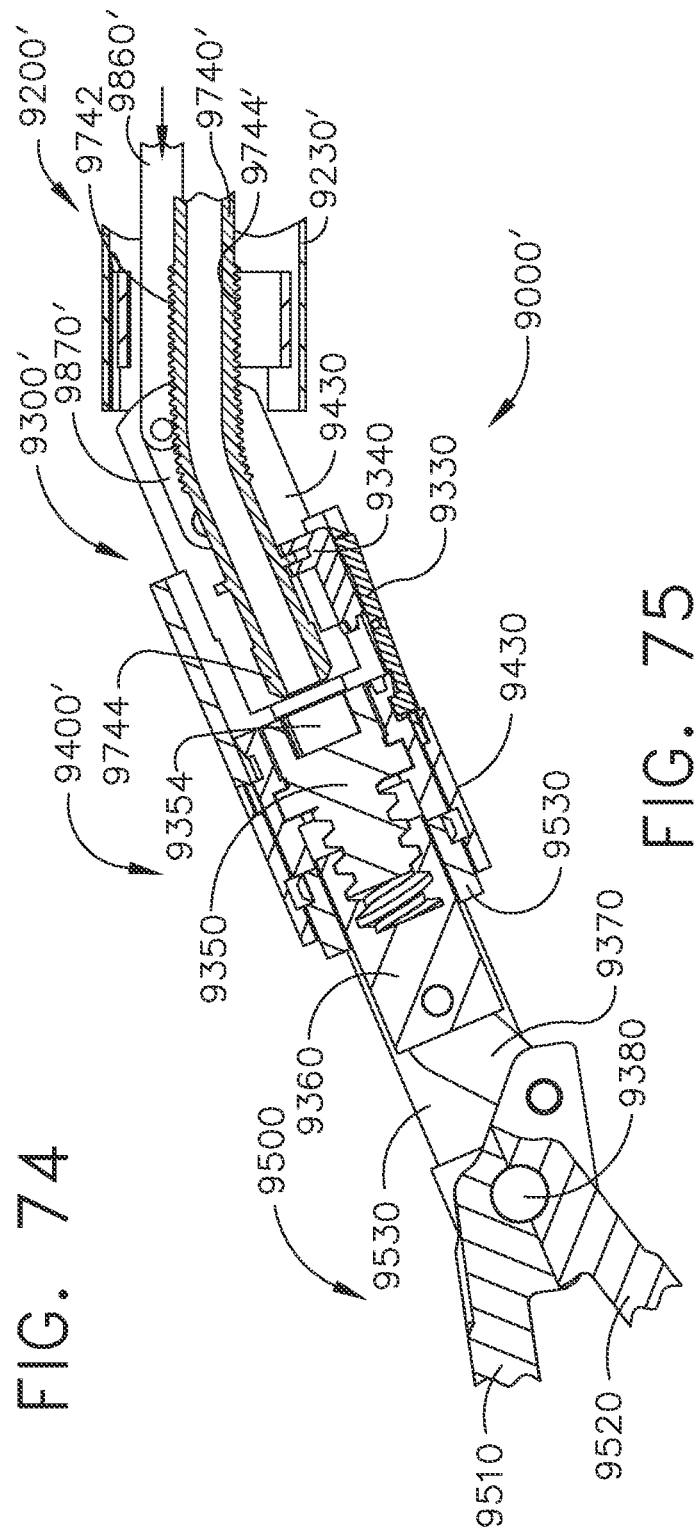
FIG. 74
FIG. 75

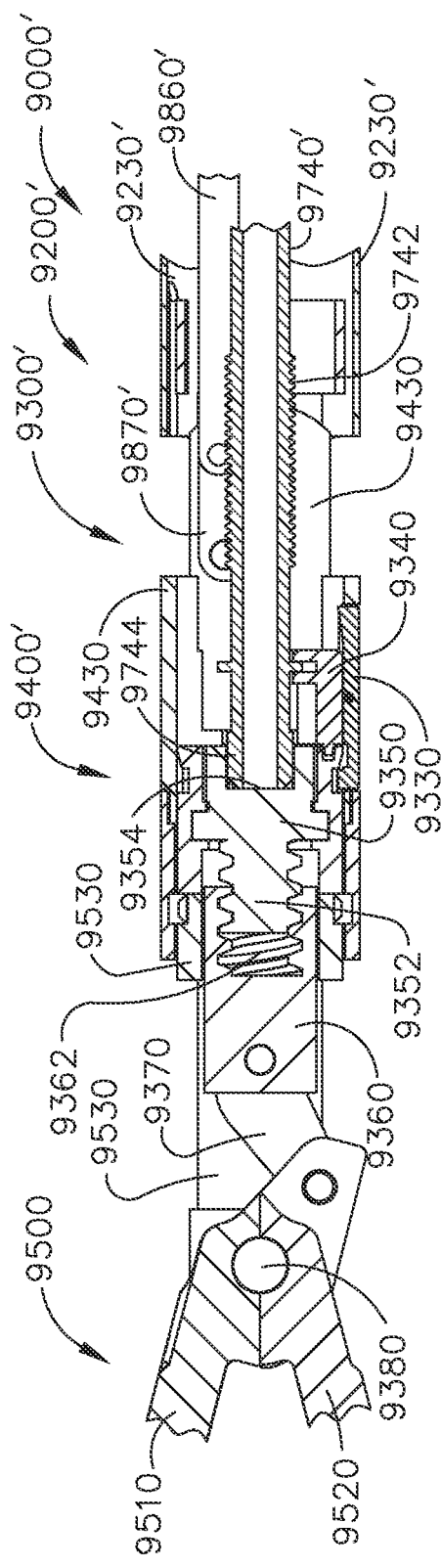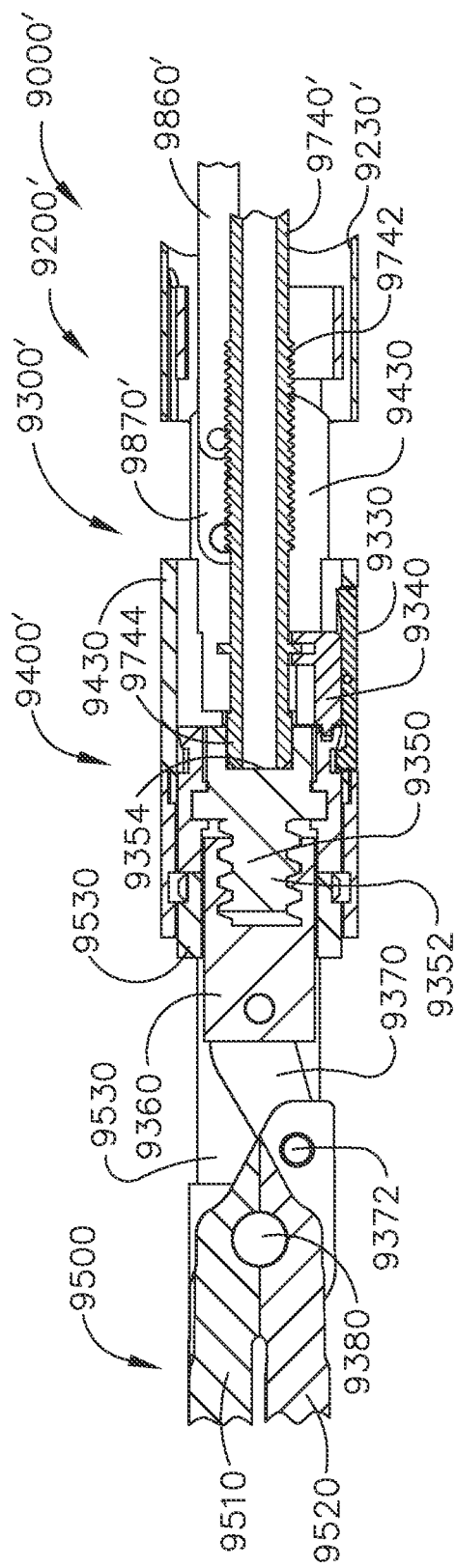

SURGICAL INSTRUMENT HAVING DUAL ROTATABLE MEMBERS TO EFFECT DIFFERENT TYPES OF END EFFECTOR MOVEMENT

CROSS-REFERENCE TO RELATED APPLICATIONS

This application is a continuation application claiming priority under 35 U.S.C. § 120 of U.S. patent application Ser. No. 15/908,012, entitled SURGICAL INSTRUMENT HAVING DUAL ROTATABLE MEMBERS TO EFFECT DIFFERENT TYPES OF END EFFECTOR MOVEMENT, filed Feb. 28, 2018, which is issuing on Nov. 24, 2020 as U.S. Pat. No. 10,842,473, which claims the benefit under 35 U.S.C. § 119(e) of U.S. Provisional Patent Application Ser. No. 62/578,793, entitled SURGICAL INSTRUMENT WITH REMOTE RELEASE, filed Oct. 30, 2017, of U.S. Provisional Patent Application Ser. No. 62/578,804, entitled SURGICAL INSTRUMENT HAVING DUAL ROTATABLE MEMBERS TO EFFECT DIFFERENT TYPES OF END EFFECTOR MOVEMENT, filed Oct. 30, 2017, of U.S. Provisional Patent Application Ser. No. 62/578,817, entitled SURGICAL INSTRUMENT WITH ROTARY DRIVE SELECTIVELY ACTUATING MULTIPLE END EFFECTOR FUNCTIONS, filed Oct. 30, 2017, of U.S. Provisional Patent Application Ser. No. 62/578,835, entitled SURGICAL INSTRUMENT WITH ROTARY DRIVE SELECTIVELY ACTUATING MULTIPLE END EFFECTOR FUNCTIONS, filed Oct. 30, 2017, of U.S. Provisional Patent Application Ser. No. 62/578,844, entitled SURGICAL INSTRUMENT WITH MODULAR POWER SOURCES, filed Oct. 30, 2017, and of U.S. Provisional Patent Application Ser. No. 62/578,855, entitled SURGICAL INSTRUMENT WITH SENSOR AND/OR CONTROL SYSTEMS, filed Oct. 30, 2017, the disclosures of which are incorporated by reference herein in their entirety.

BACKGROUND

The present invention relates to surgical systems and, in various arrangements, to grasping instruments that are designed to grasp the tissue of a patient, dissecting instruments configured to manipulate the tissue of a patient, clip appliers configured to clip the tissue of a patient, and suturing instruments configured to suture the tissue of a patient, among others.

BRIEF DESCRIPTION OF THE DRAWINGS

Various features of the embodiments described herein, together with advantages thereof, may be understood in accordance with the following description taken in conjunction with the accompanying drawings as follows:

FIG. 58 is an elevational view of the drive assembly of FIG. 54 illustrated in a shifting configuration with some components removed;

FIG. 59 is an elevational view of the drive assembly of FIG. 54 illustrated in a drive configuration with some components removed;

FIG. 60 is a top view of the drive assembly of FIG. 54 in the drive configuration;

FIG. 61 is a top view of the drive assembly of FIG. 54 in the shifting configuration;

FIG. 62 is a partial perspective cross-sectional view of the end effector of FIG. 53;

FIG. 64 is a partial top cross-sectional view of the end effector of FIG. 53 in an articulation drive mode;

FIG. 65 is a partial top cross-sectional view of the end effector of FIG. 53 in an articulated configuration;

FIG. 74 is a partial top cross-sectional view of the end effector of FIG. 71 in an articulation drive mode;

FIG. 75 is a partial top cross-sectional view of the end effector of FIG. 71 in an articulated configuration;

FIG. 78 is a partial top cross-sectional view of the end effector of FIG. 71 in a jaw open/closure drive mode;

FIG. 79 is a partial top cross-sectional view of the end effector of FIG. 71 in a closed configuration;

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
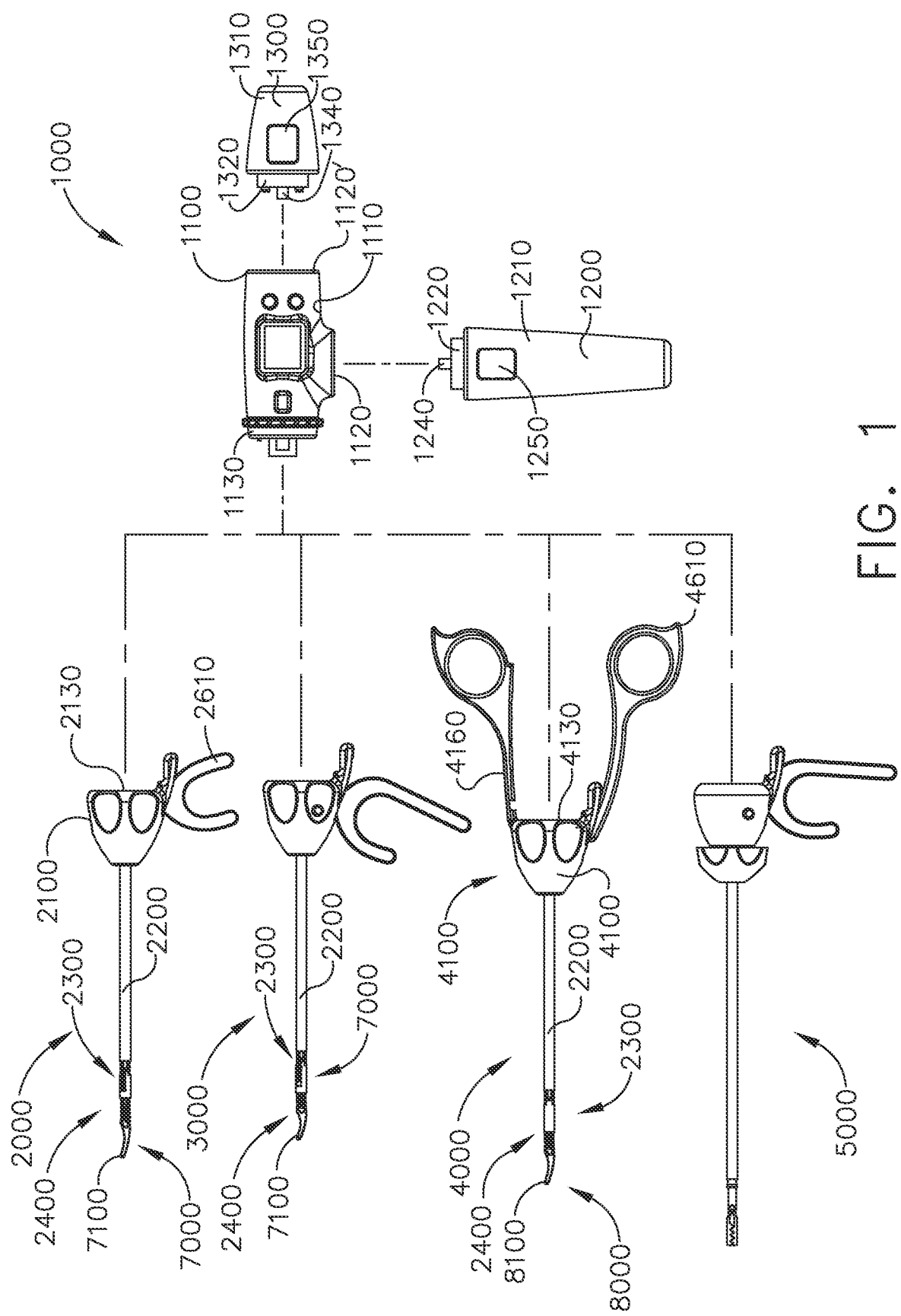
FIG. 1 illustrates a surgical system comprising a handle and several shaft assemblies—each of which are selectively attachable to the handle in accordance with at least one embodiment.

Applicant of the present application owns the following U.S. Patent Applications that were filed on Feb. 28, 2018 and which are each herein incorporated by reference in their respective entireties:

U.S. patent application Ser. No. 15/908,021, entitled SURGICAL INSTRUMENT WITH REMOTE RELEASE, now U.S. Pat. No. 10,736,616;

U.S. patent application Ser. No. 15/908,040, entitled SURGICAL INSTRUMENT WITH ROTARY DRIVE SELECTIVELY ACTUATING MULTIPLE END EFFECTOR FUNCTIONS, now U.S. Patent Application Publication No. 2019/0125383;

U.S. patent application Ser. No. 15/908,057, entitled SURGICAL INSTRUMENT WITH ROTARY DRIVE SELECTIVELY ACTUATING MULTIPLE END EFFECTOR FUNCTIONS, now U.S. Patent Application Publication No. 2019/0125384;

U.S. patent application Ser. No. 15/908,058, entitled SURGICAL INSTRUMENT WITH MODULAR POWER SOURCES, now U.S. Patent Application Publication No. 2019/0125324; and U.S. patent application Ser. No. 15/908,143, entitled SURGICAL INSTRUMENT WITH SENSOR AND/OR CONTROL SYSTEMS, now U.S. Patent Application Publication No. 2019/0125385.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, a surgical system, device, or apparatus that "comprises," "has," "includes", or "contains" one or more elements possesses those one or more elements, but is not limited to possessing only those one or more elements. Likewise, an element of a system, device, or apparatus that "comprises," "has," "includes", or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical instrument, such as a grasper, for example, can comprise a handle, a shaft extending from the handle, and an end effector extending from the shaft. In various instances, the end effector comprises a first jaw and a second jaw, wherein one or both of the jaws are movable relative to the other to grasp the tissue of a patient. That said, an end effector of a surgical instrument can comprise any suitable arrangement and can perform any suitable function. For instance, an end effector can comprise first and second jaws configured to dissect or separate the tissue of a patient. Also, for instance, an end effector can be configured to suture and/or clip the tissue of a patient. In various instances, the end effector and/or shaft of the surgical instrument are configured to be inserted into a patient through a trocar, or cannula, and can have any suitable diameter, such as approximately 5 mm, 8 mm, and/or 12 mm, for example. U.S. patent application Ser. No. 11/013,924, entitled TROCAR SEAL ASSEMBLY, now U.S. Pat. No. 7,371,227, is incorporated by reference in its entirety. The shaft can define a longitudinal axis and at least a portion of the end effector can be rotatable about the longitudinal axis. Moreover, the surgical instrument can further comprise an articulation joint which can permit at least a portion of the end effector to be articulated relative to the shaft. In use, a clinician can rotate and/or articulate the end effector in order to maneuver the end effector within the patient.

Figure 2:
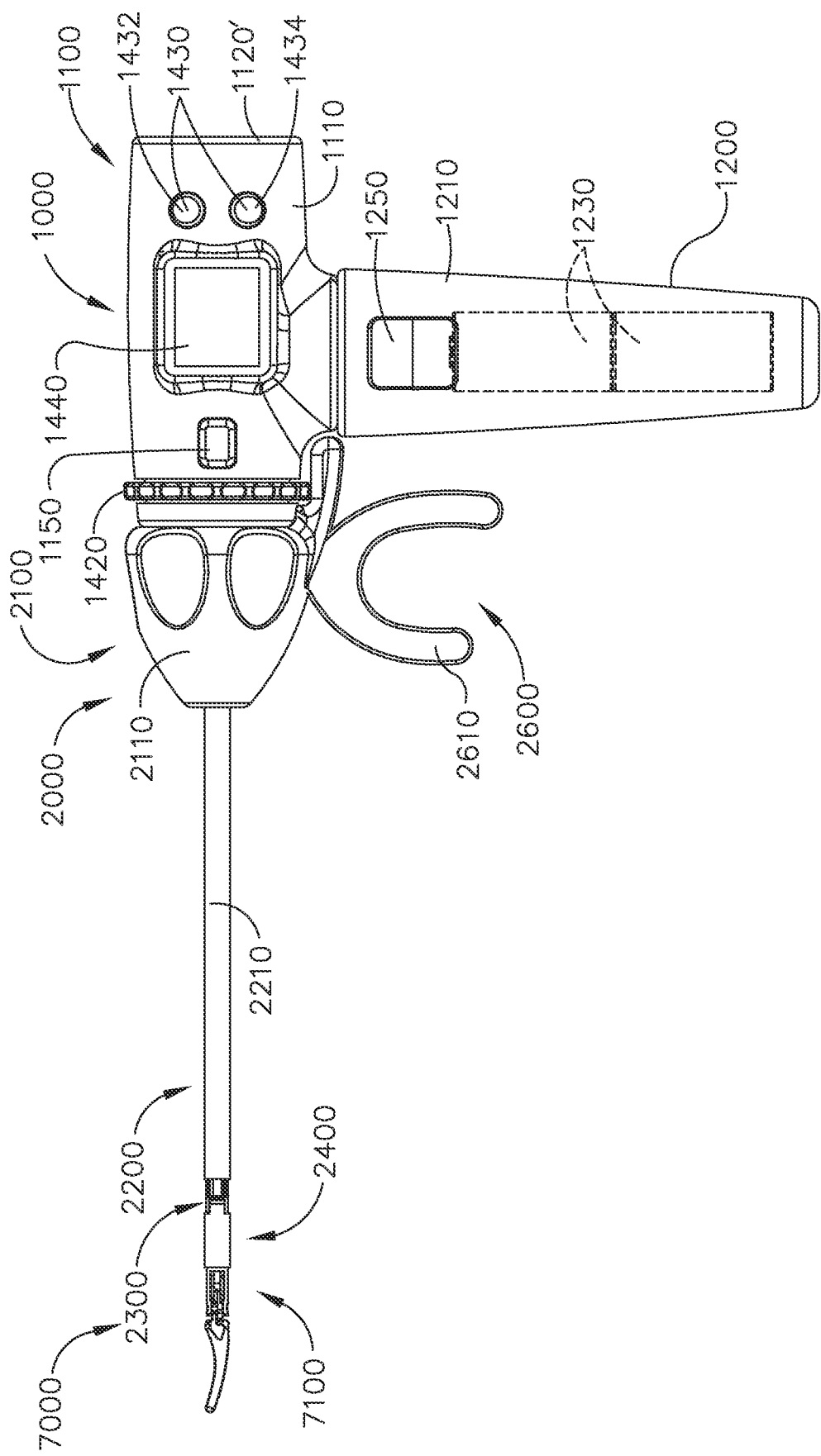
FIG. 2 is an elevational view of the handle and one of the shaft assemblies of the surgical system of FIG. 1.
Figure 3:
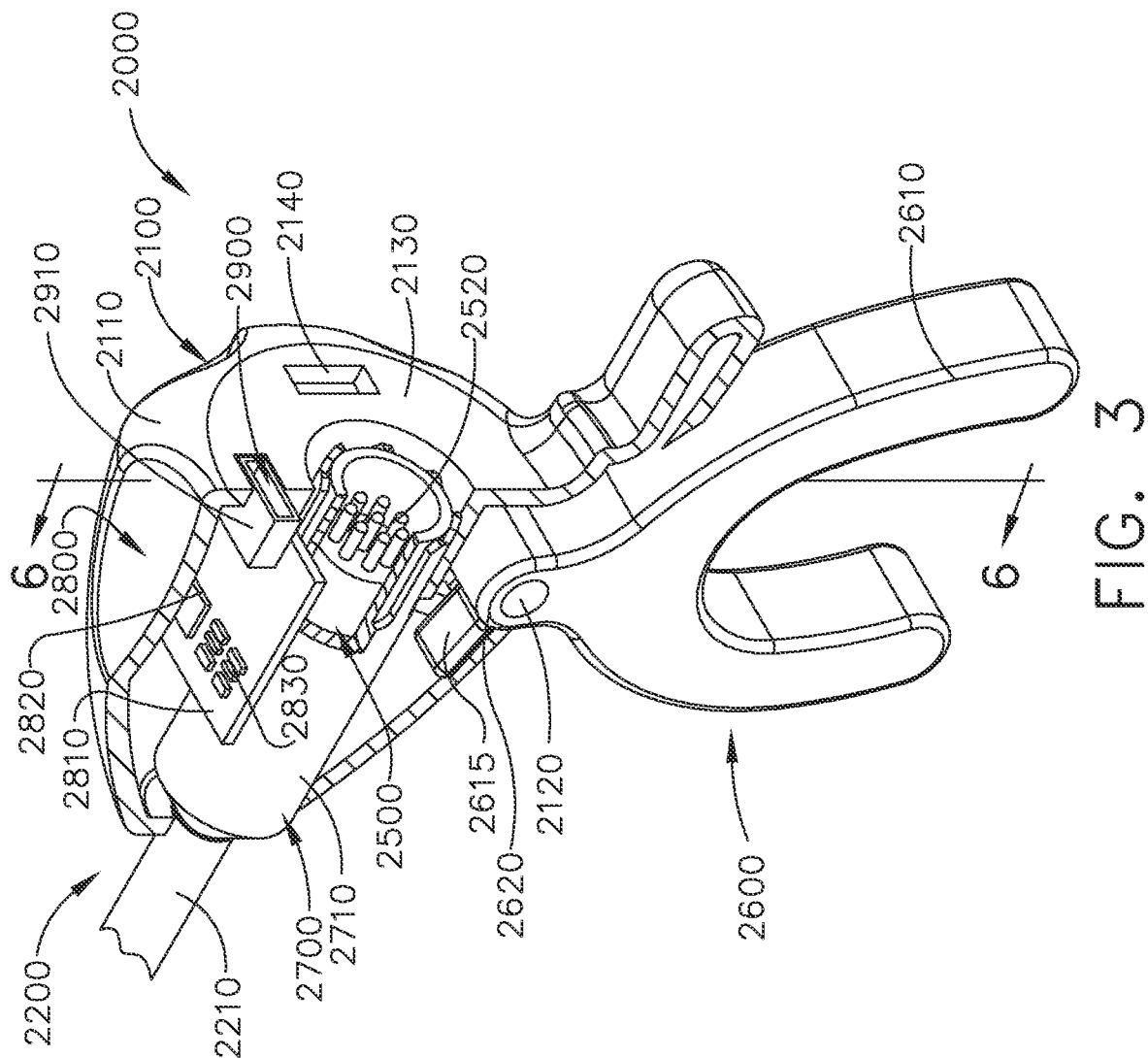
FIG. 3 is a partial cross-sectional perspective view of the shaft assembly of FIG. 2.
Figure 4:
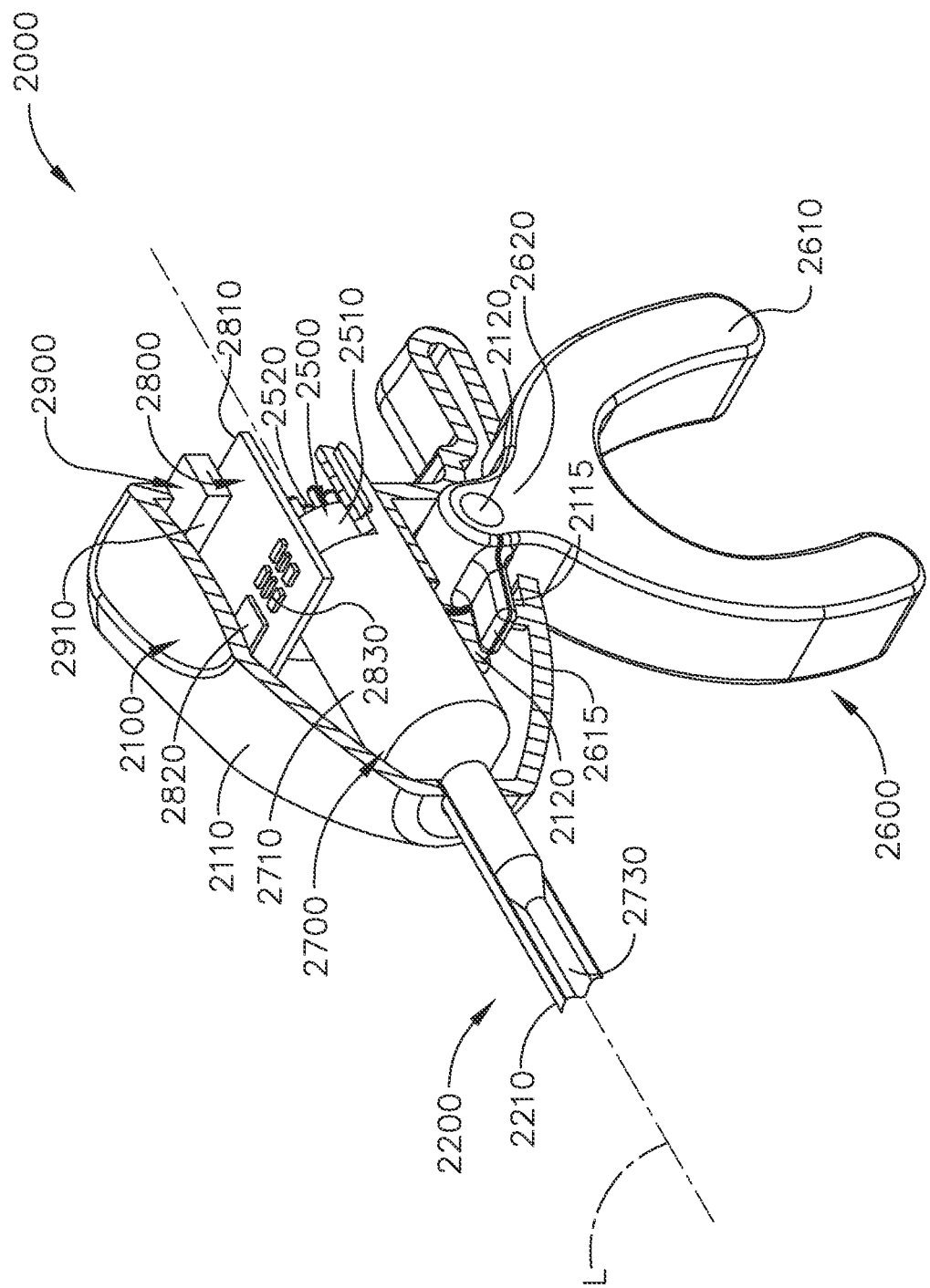
FIG. 4 is another partial cross-sectional perspective view of the shaft assembly of FIG. 2.
Figure 45:
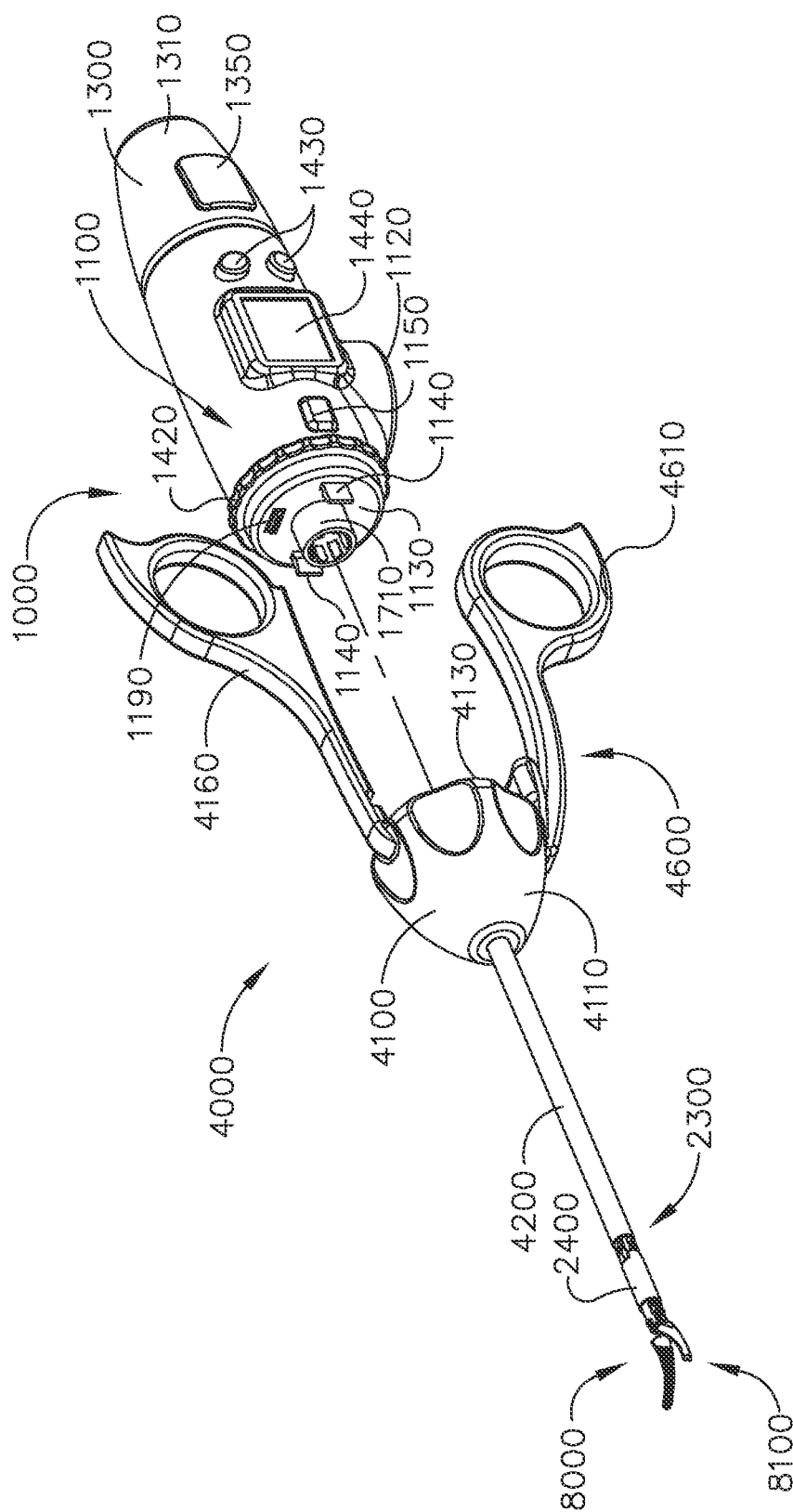
FIG. 45 is a perspective view of the handle drive module of FIG. 7 and one of the shaft assemblies of the surgical system of FIG. 1.
Figure 46:
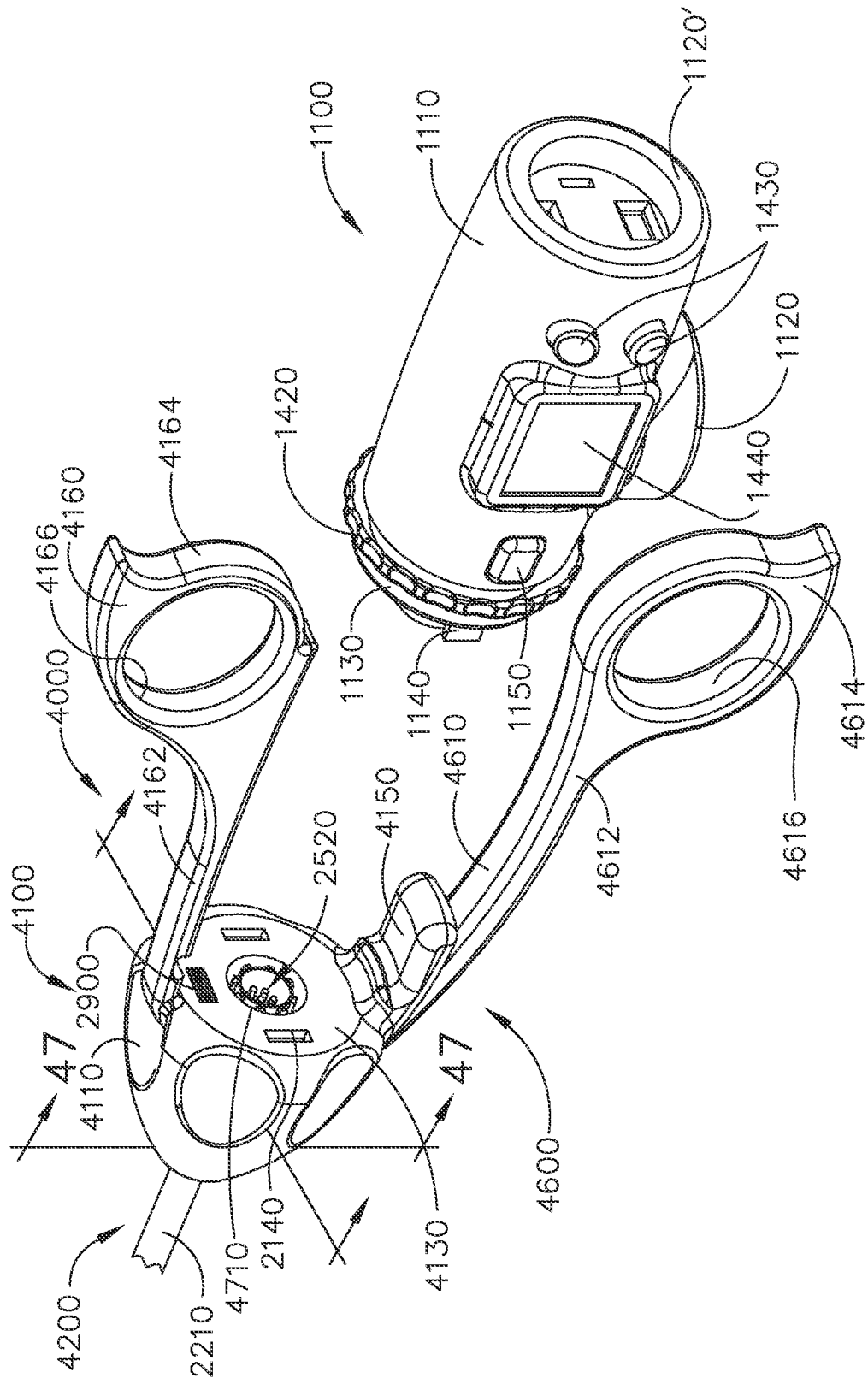
FIG. 46 is another perspective view of the handle drive module of FIG. 7 and the shaft assembly of FIG. 45.

A surgical instrument system is depicted in FIG. 1. The surgical instrument system comprises a handle assembly 1000 which is selectively usable with a shaft assembly 2000, a shaft assembly 3000, a shaft assembly 4000, a shaft assembly 5000, and/or any other suitable shaft assembly. The shaft assembly 2000 is attached to the handle assembly 1000 in FIG. 2 and the shaft assembly 4000 is attached to the handle assembly 1000 in FIG. 45. The shaft assembly 2000 comprises a proximal portion 2100, an elongate shaft 2200 extending from the proximal portion 2100, a distal attachment portion 2400, and an articulation joint 2300 rotatably connecting the distal attachment portion 2400 to the elongate shaft 2200. The shaft assembly 2000 further comprises a replaceable end effector assembly 7000 attached to the distal attachment portion 2400. The replaceable end effector assembly 7000 comprises a jaw assembly 7100 configured to be opened and closed to clamp and/or manipulate the tissue of a patient. In use, the end effector assembly 7000 can be articulated about the articulation joint 2300 and/or rotated relative to the distal attachment portion 2400 about a longitudinal axis to better position the jaw assembly 7100 within the patient, as described in greater detail further below.

Referring again to FIG. 1, the handle assembly 1000 comprises, among other things, a drive module 1100. As described in greater detail below, the drive module 1100 comprises a distal mounting interface which permits a clinician to selectively attach one of the shaft assemblies 2000, 3000, 4000, and 5000, for example, to the drive module 1100. Thus, each of the shaft assemblies 2000, 3000, 4000, and 5000 comprises an identical, or an at least similar, proximal mounting interface which is configured to engage the distal mounting interface of the drive module 1100. As also described in greater detail below, the mounting interface of the drive module 1100 mechanically secures and electrically couples the selected shaft assembly to the drive module 1100. The drive module 1100 further comprises at least one electric motor, one or more controls and/or displays, and a controller configured to operate the electric motor—the rotational output of which is transmitted to a drive system of the shaft assembly attached to the drive module 1100. Moreover, the drive module 1100 is usable with one or more power modules, such as power modules 1200 and 1300, for example, which are operably attachable to the drive module 1100 to supply power thereto.

Further to the above, referring again to FIGS. 1 and 2, the handle drive module 1100 comprises a housing 1110, a first module connector 1120, and a second module connector 1120'. The power module 1200 comprises a housing 1210, a connector 1220, one or more release latches 1250, and one or more batteries 1230. The connector 1220 is configured to be engaged with the first module connector 1120 of the drive module 1100 in order to attach the power module 1200 to the drive module 1100. The connector 1220 comprises one or more latches 1240 which mechanically couple and fixedly secure the housing 1210 of the power module 1200 to the housing 1110 of the drive module 1100. The latches 1240 are movable into disengaged positions when the release latches 1250 are depressed so that the power module 1200 can be detached from the drive module 1100. The connector 1220 also comprises one or more electrical contacts which place the batteries 1230, and/or an electrical circuit including the batteries 1230, in electrical communication with an electrical circuit in the drive module 1100.

Figure 47:
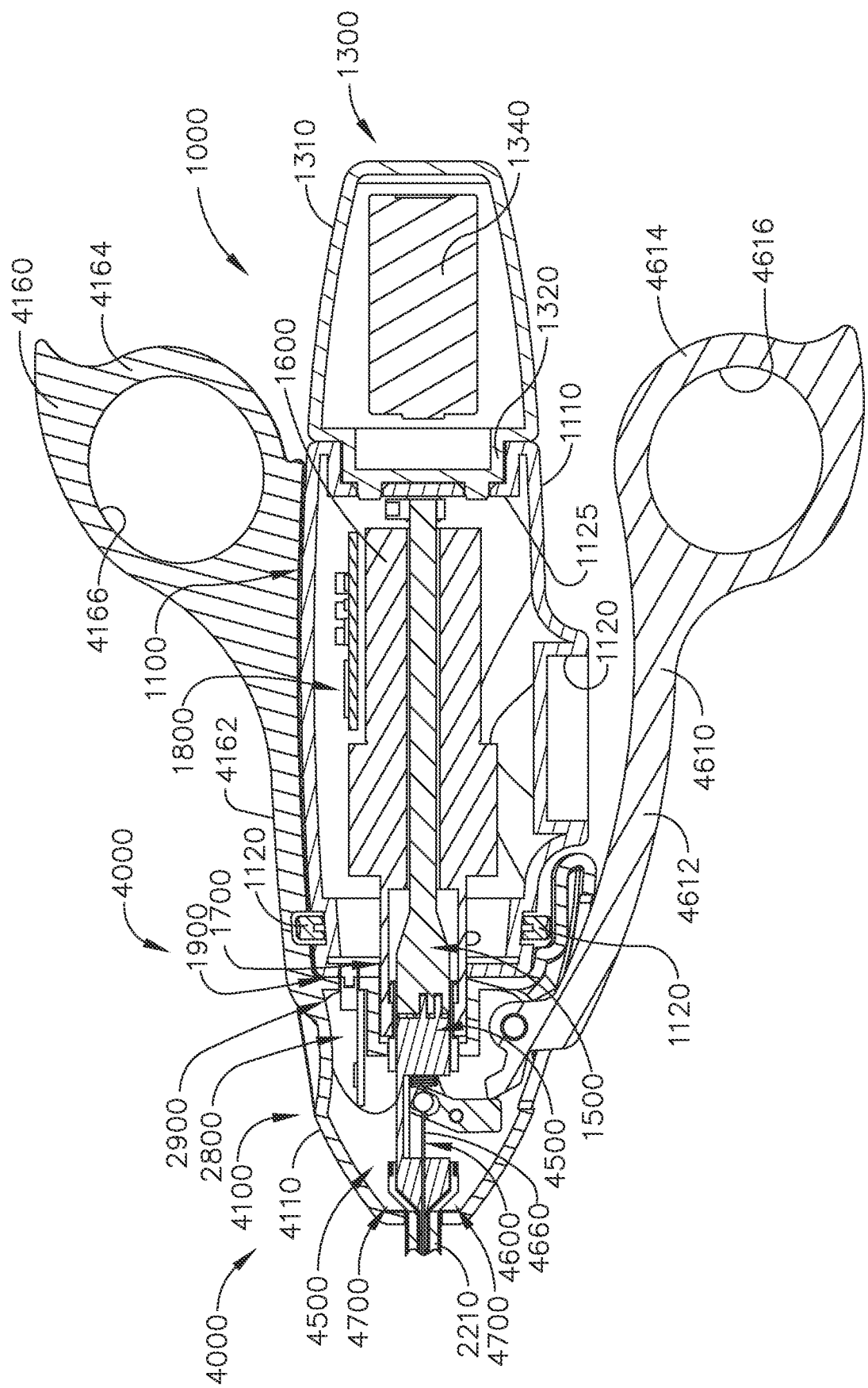
FIG. 47 is a partial cross-sectional view of the shaft assembly of FIG. 45 attached to the handle of FIG. 1.

Further to the above, referring again to FIGS. 1 and 2, the power module 1300 comprises a housing 1310, a connector 1320, one or more release latches 1350, and one or more batteries 1330 (FIG. 47). The connector 1320 is configured to be engaged with the second module connector 1120' of the drive module 1100 to attach the power module 1300 to the drive module 1100. The connector 1320 comprises one or more latches 1340 which mechanically couple and fixedly secure the housing 1310 of the power module 1300 to the housing 1110 of the drive module 1100. The latches 1340 are movable into disengaged positions when the release latches 1350 are depressed so that the power module 1300 can be detached from the drive module 1100. The connector 1320 also comprises one or more electrical contacts which place the batteries 1330 of the power module 1300, and/or an electrical power circuit including the batteries 1330, in electrical communication with an electrical power circuit in the drive module 1100.

Further to the above, the power module 1200, when attached to the drive module 1100, comprises a pistol grip which can allow a clinician to hold the handle 1000 in a manner which places the drive module 1100 on top of the clinician's hand. The power module 1300, when attached to the drive module 1100, comprises an end grip which allows a clinician to hold the handle 1000 like a wand. The power module 1200 is longer than the power module 1300, although the power modules 1200 and 1300 can comprise any suitable length. The power module 1200 has more battery cells than the power module 1300 and can suitably accommodate these additional battery cells owing to its length. In various instances, the power module 1200 can provide more power to the drive module 1100 than the power module 1300 while, in some instances, the power module 1200 can provide power for a longer period of time. In some instances, the housing 1110 of the drive module 1100 comprises keys, and/or any other suitable features, which prevent the power module 1200 from being connected to the second module connector 1120' and, similarly, prevent the power module 1300 from being connected to the first module connector 1120. Such an arrangement can assure that the longer power module 1200 is used in the pistol grip arrangement and that the shorter power module 1300 is used in the wand grip arrangement. In alternative embodiments, the power module 1200 and the power module 1300 can be selectively coupled to the drive module 1100 at either the first module connector 1120 or the second module connector 1120'. Such embodiments provide a clinician with more options to customize the handle 1000 in a manner suitable to them.

In various instances, further to the above, only one of the power modules 1200 and 1300 is coupled to the drive module 1100 at a time. In certain instances, the power module 1200 can be in the way when the shaft assembly 4000, for example, is attached to the drive module 1100. Alternatively, both of the power modules 1200 and 1300 can be operably coupled to the drive module 1100 at the same time. In such instances, the drive module 1100 can have access to power provided by both of the power modules 1200 and 1300. Moreover, a clinician can switch between a pistol grip and a wand grip when both of the power modules 1200 and 1300 are attached to the drive module 1100. Moreover, such an arrangement allows the power module 1300 to act as a counterbalance to a shaft assembly, such as shaft assemblies 2000, 3000, 4000, or 5000, for example, attached to the drive module 1100.

Figure 7:
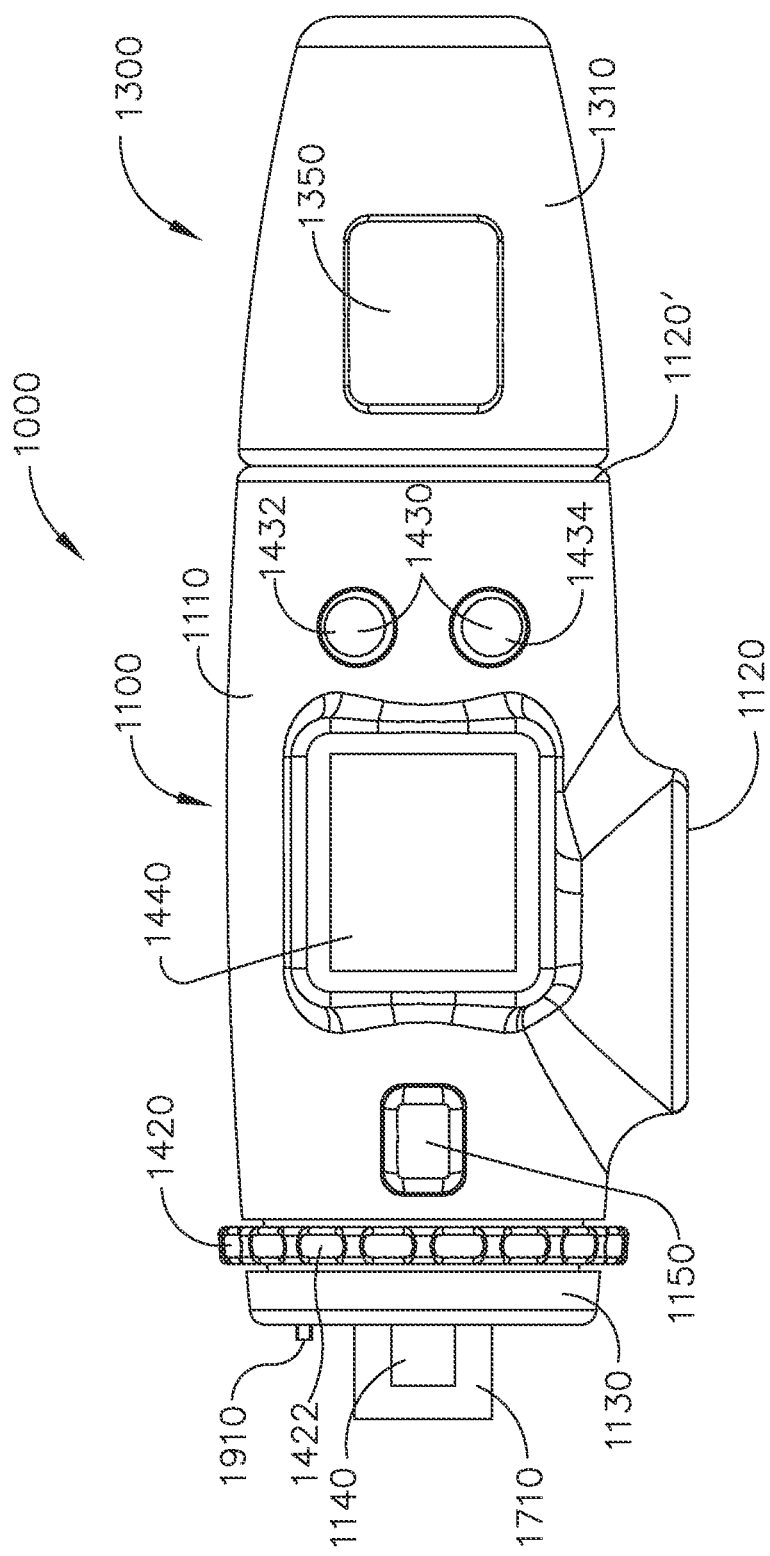
FIG. 7 is an elevational view of a drive module of the handle of FIG. 1.
Figure 8:
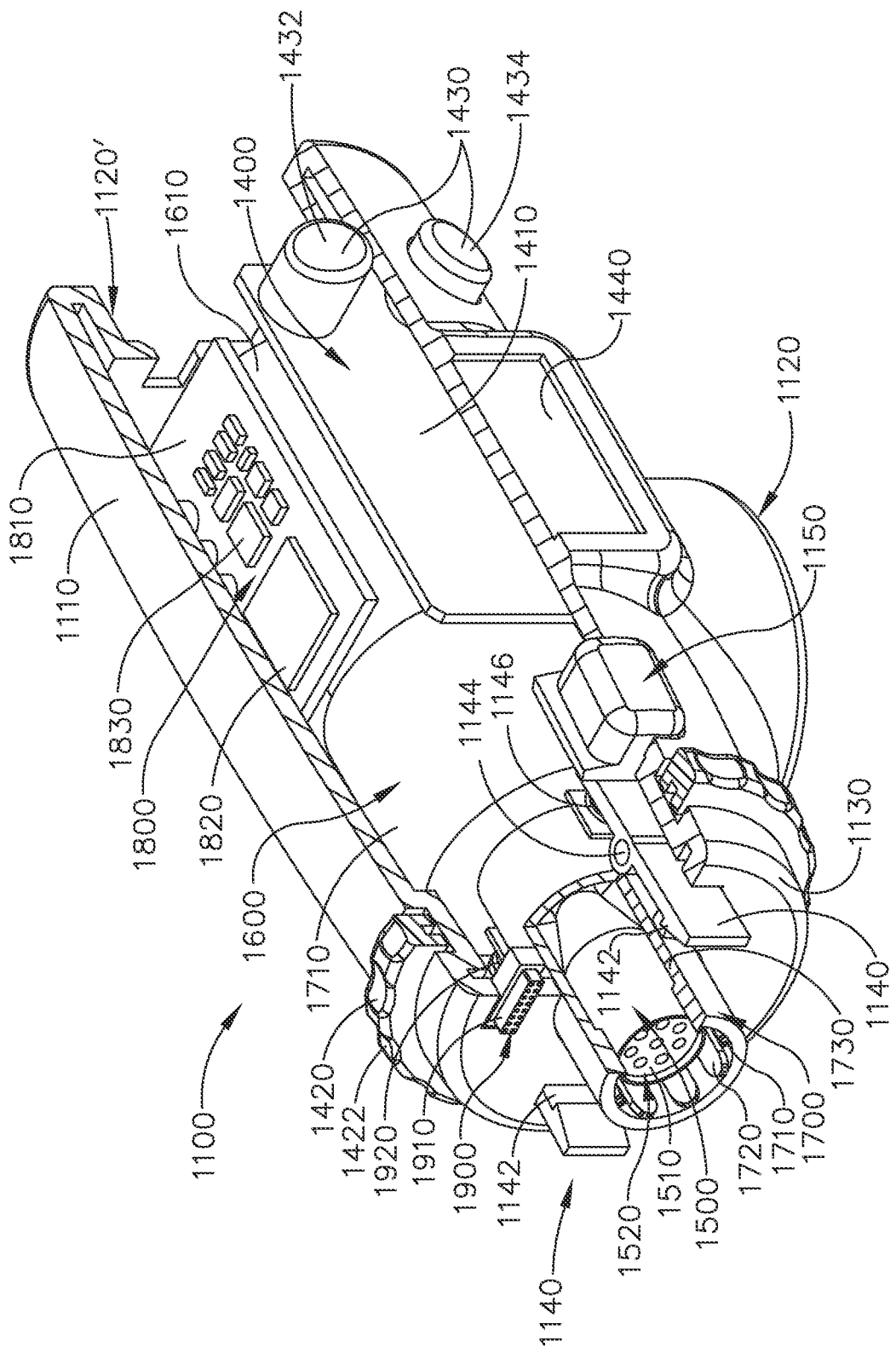
FIG. 8 is a cross-sectional perspective view of the drive module of FIG. 7.
Figure 9:
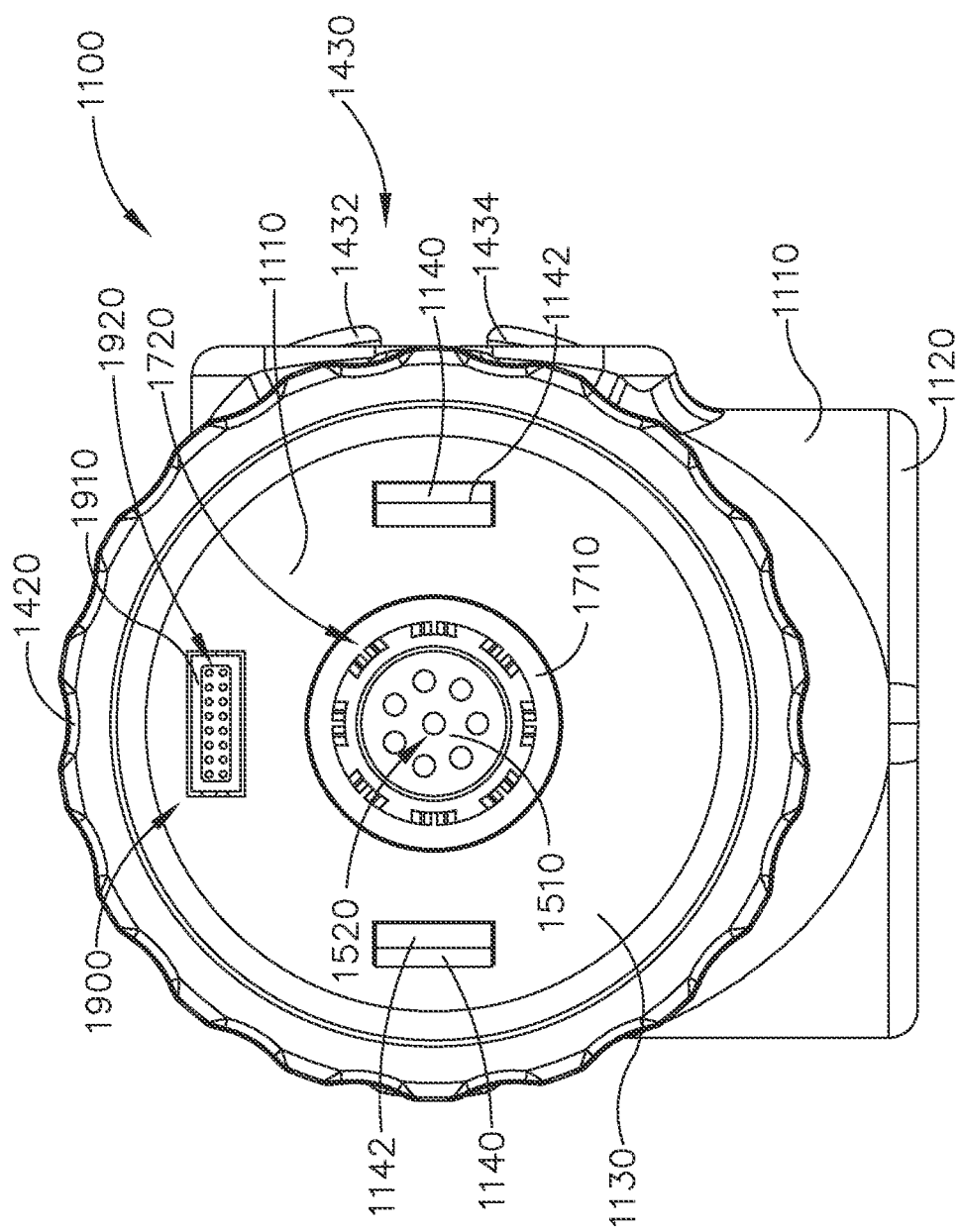
FIG. 9 is an end view of the drive module of FIG. 7.

Referring to FIGS. 7 and 8, the handle drive module 1100 further comprises a frame 1500, a motor assembly 1600, a drive system 1700 operably engaged with the motor assembly 1600, and a control system 1800. The frame 1500 comprises an elongate shaft that extends through the motor assembly 1600. The elongate shaft comprises a distal end 1510 and electrical contacts, or sockets, 1520 defined in the distal end 1510. The electrical contacts 1520 are in electrical communication with the control system 1800 of the drive module 1100 via one or more electrical circuits and are configured to convey signals and/or power between the control system 1800 and the shaft assembly, such as the shaft assembly 2000, 3000, 4000, or 5000, for example, attached to the drive module 1100. The control system 1800 comprises a printed circuit board (PCB) 1810, at least one microprocessor 1820, and at least one memory device 1830. The board 1810 can be rigid and/or flexible and can comprise any suitable number of layers. The microprocessor 1820 and the memory device 1830 are part of a control circuit defined on the board 1810 which controls the operation of the motor assembly 1600, as described in greater detail below.

Figure 12:
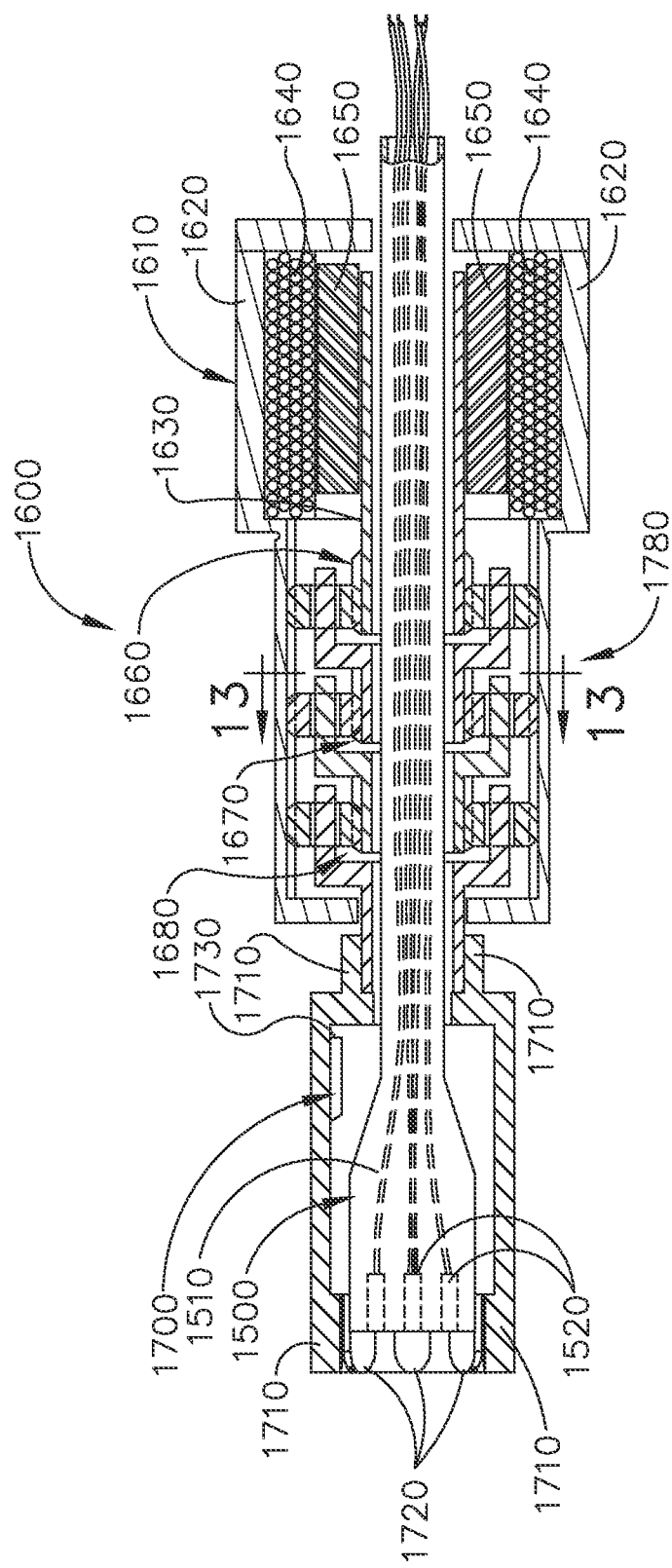
FIG. 12 is a cross-sectional perspective view of a motor and a speed reduction gear assembly of the drive module of FIG. 7.
Figure 13:
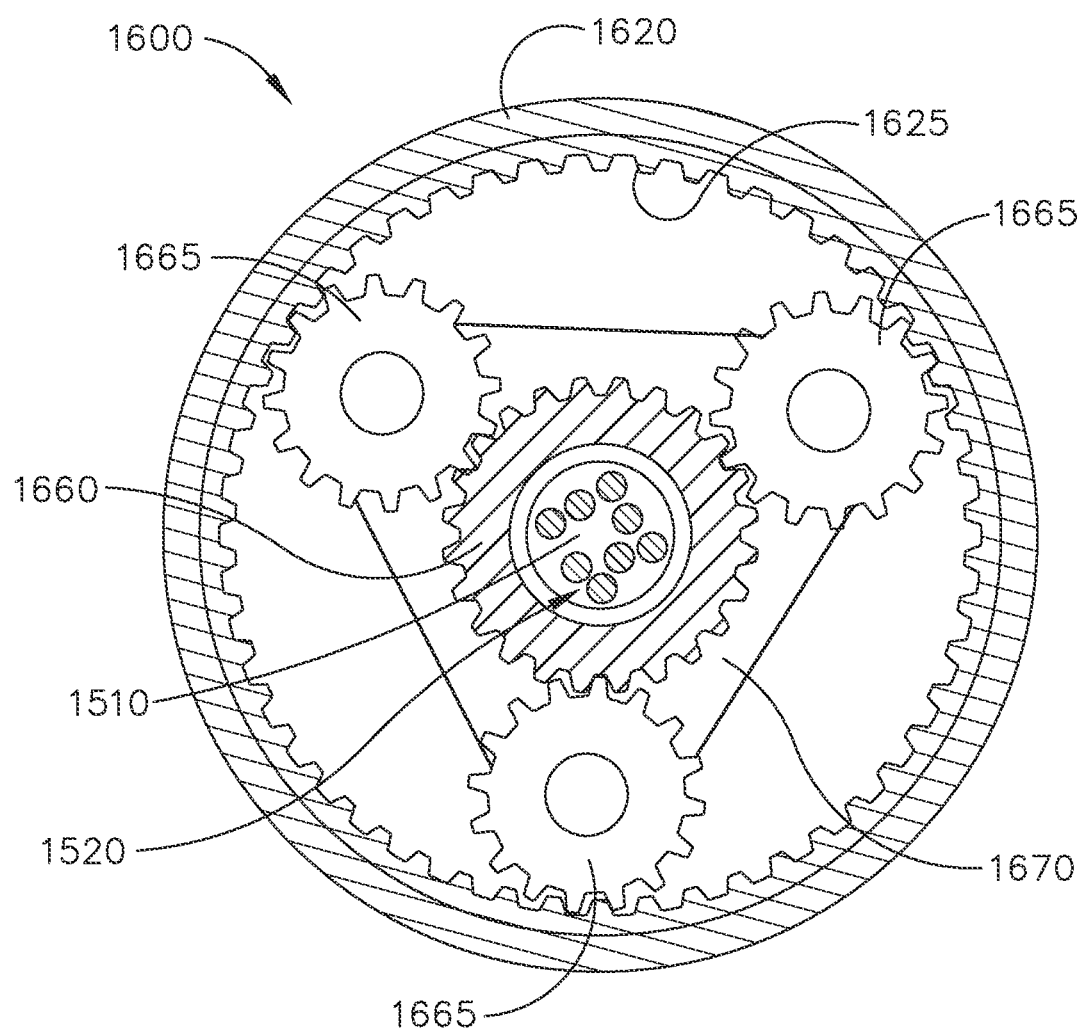
FIG. 13 is an end view of the speed reduction gear assembly of FIG. 12.
Figure 14:
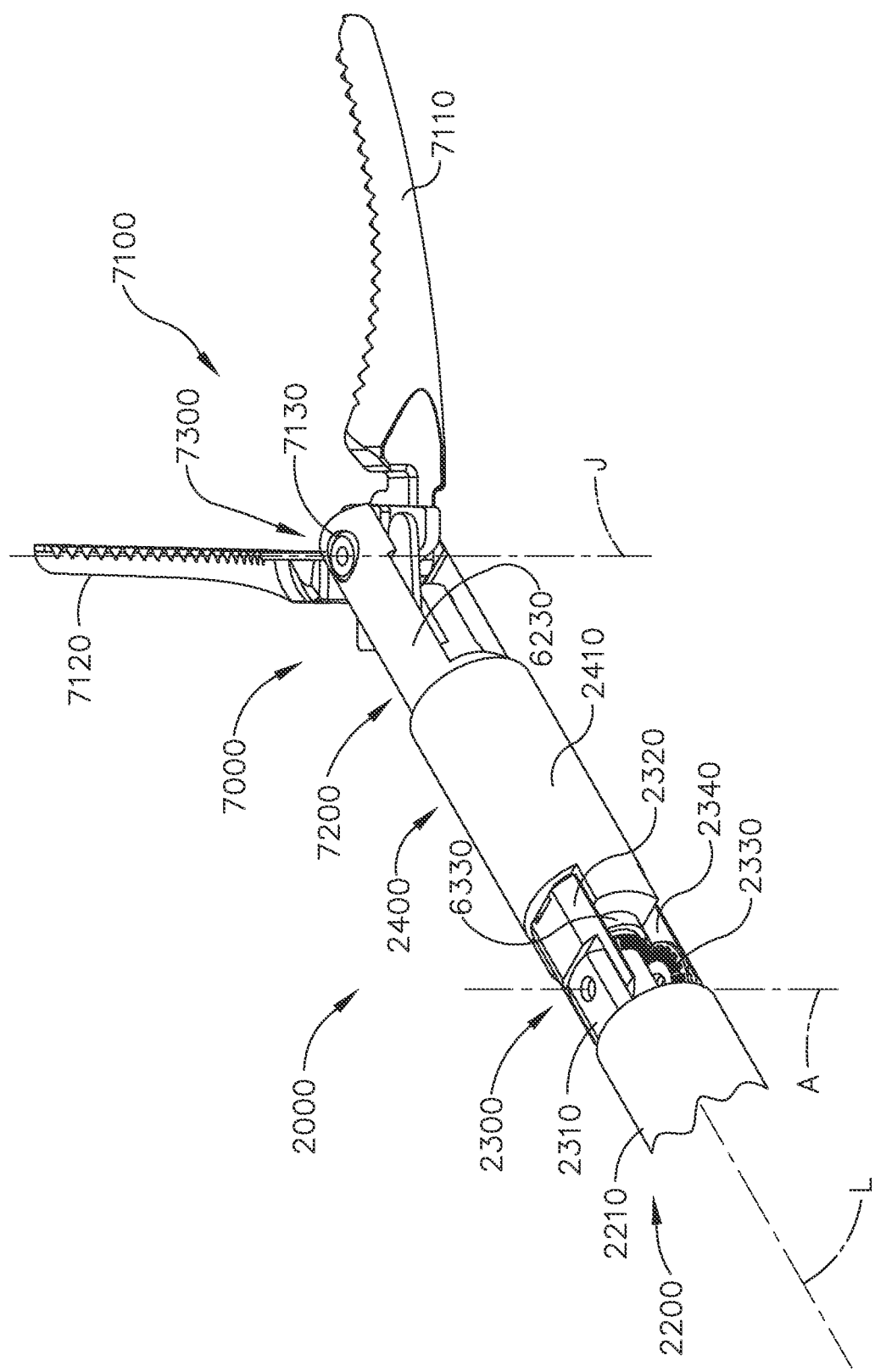
FIG. 14 is a partial perspective view of an end effector of the shaft assembly of FIG. 2 in an open configuration.

Referring to FIGS. 12 and 13, the motor assembly 1600 comprises an electric motor 1610 including a housing 1620, a drive shaft 1630, and a gear reduction system. The electric motor 1610 further comprises a stator including windings 1640 and a rotor including magnetic elements 1650. The stator windings 1640 are supported in the housing 1620 and the rotor magnetic elements 1650 are mounted to the drive shaft 1630. When the stator windings 1640 are energized with an electric current controlled by the control system 1800, the drive shaft 1630 is rotated about a longitudinal axis. The drive shaft 1630 is operably engaged with a first planetary gear system 1660 which includes a central sun gear and several planetary gears operably intermeshed with the sun gear. The sun gear of the first planetary gear system 1660 is fixedly mounted to the drive shaft 1630 such that it rotates with the drive shaft 1630. The planetary gears of the first planetary gear system 1660 are rotatably mounted to the sun gear of a second planetary gear system 1670 and, also, intermeshed with a geared or splined inner surface 1625 of the motor housing 1620. As a result of the above, the rotation of the first sun gear rotates the first planetary gears which rotate the second sun gear. Similar to the above, the second planetary gear system 1670 further comprises planetary gears 1665 (FIG. 13) which drive a third planetary gear system and, ultimately, the drive shaft 1710. The planetary gear systems 1660, 1670, and 1680 co-operate to gear down the speed applied to the drive shaft 1710 by the motor shaft 1620. Various alternative embodiments are envisioned without a speed reduction system. Such embodiments are suitable when it is desirable to drive the end effector functions quickly. Notably, the drive shaft 1630 comprises an aperture, or hollow core, extending therethrough through which wires and/or electrical circuits can extend.

The control system 1800 is in communication with the motor assembly 1600 and the electrical power circuit of the drive module 1100. The control system 1800 is configured to control the power delivered to the motor assembly 1600 from the electrical power circuit. The electrical power circuit is configured to supply a constant, or at least nearly constant, direct current (DC) voltage. In at least one instance, the electrical power circuit supplies 3 VDC to the control system 1800. The control system 1800 comprises a pulse width modulation (PWM) circuit which is configured to deliver voltage pulses to the motor assembly 1600. The duration or width of the voltage pulses, and/or the duration or width between the voltage pulses, supplied by the PWM circuit can be controlled in order to control the power applied to the motor assembly 1600. By controlling the power applied to the motor assembly 1600, the PWM circuit can control the speed of the output shaft of the motor assembly 1600. In addition to or in lieu of a PWM circuit, the control system 1800 can include a frequency modulation (FM) circuit. As discussed in greater detail below, the control system 1800 is operable in more than one operating mode and, depending on the operating mode being used, the control system 1800 can operate the motor assembly 1600 at a speed, or a range of speeds, which is determined to be appropriate for that operating mode.

Further to the above, referring again to FIGS. 7 and 8, the drive system 1700 comprises a rotatable shaft 1710 comprising a splined distal end 1720 and a longitudinal aperture 1730 defined therein. The rotatable shaft 1710 is operably mounted to the output shaft of the motor assembly 1600 such that the rotatable shaft 1710 rotates with the motor output shaft. The handle frame 1510 extends through the longitudinal aperture 1730 and rotatably supports the rotatable shaft 1710. As a result, the handle frame 1510 serves as a bearing for the rotatable shaft 1710. The handle frame 1510 and the rotatable shaft 1710 extend distally from a mounting interface 1130 of the drive module 1110 and are coupled with corresponding components on the shaft assembly 2000 when the shaft assembly 2000 is assembled to the drive module 1100. Referring primarily to FIGS. 3-6, the shaft assembly 2000 further comprises a frame 2500 and a drive system 2700. The frame 2500 comprises a longitudinal shaft 2510 extending through the shaft assembly 2000 and a plurality of electrical contacts, or pins, 2520 extending proximally from the shaft 2510. When the shaft assembly 2000 is attached to the drive module 1100, the electrical contacts 2520 on the shaft frame 2510 engage the electrical contacts 1520 on the handle frame 1510 and create electrical pathways therebetween.

Similar to the above, the drive system 2700 comprises a rotatable drive shaft 2710 which is operably coupled to the rotatable drive shaft 1710 of the handle 1000 when the shaft assembly 2000 is assembled to the drive module 1100 such that the drive shaft 2710 rotates with the drive shaft 1710. To this end, the drive shaft 2710 comprises a splined proximal end 2720 which mates with the splined distal end 1720 of the drive shaft 1710 such that the drive shafts 1710 and 2710 rotate together when the drive shaft 1710 is rotated by the motor assembly 1600. Given the nature of the splined interconnection between the drive shafts 1710 and 2710 and the electrical interconnection between the frames 1510 and 2510, the shaft assembly 2000 is assembled to the handle 1000 along a longitudinal axis; however, the operable interconnection between the drive shafts 1710 and 2710 and the electrical interconnection between the frames 1510 and 2510 can comprise any suitable configuration which can allow a shaft assembly to be assembled to the handle 1000 in any suitable manner.

Figure 10:
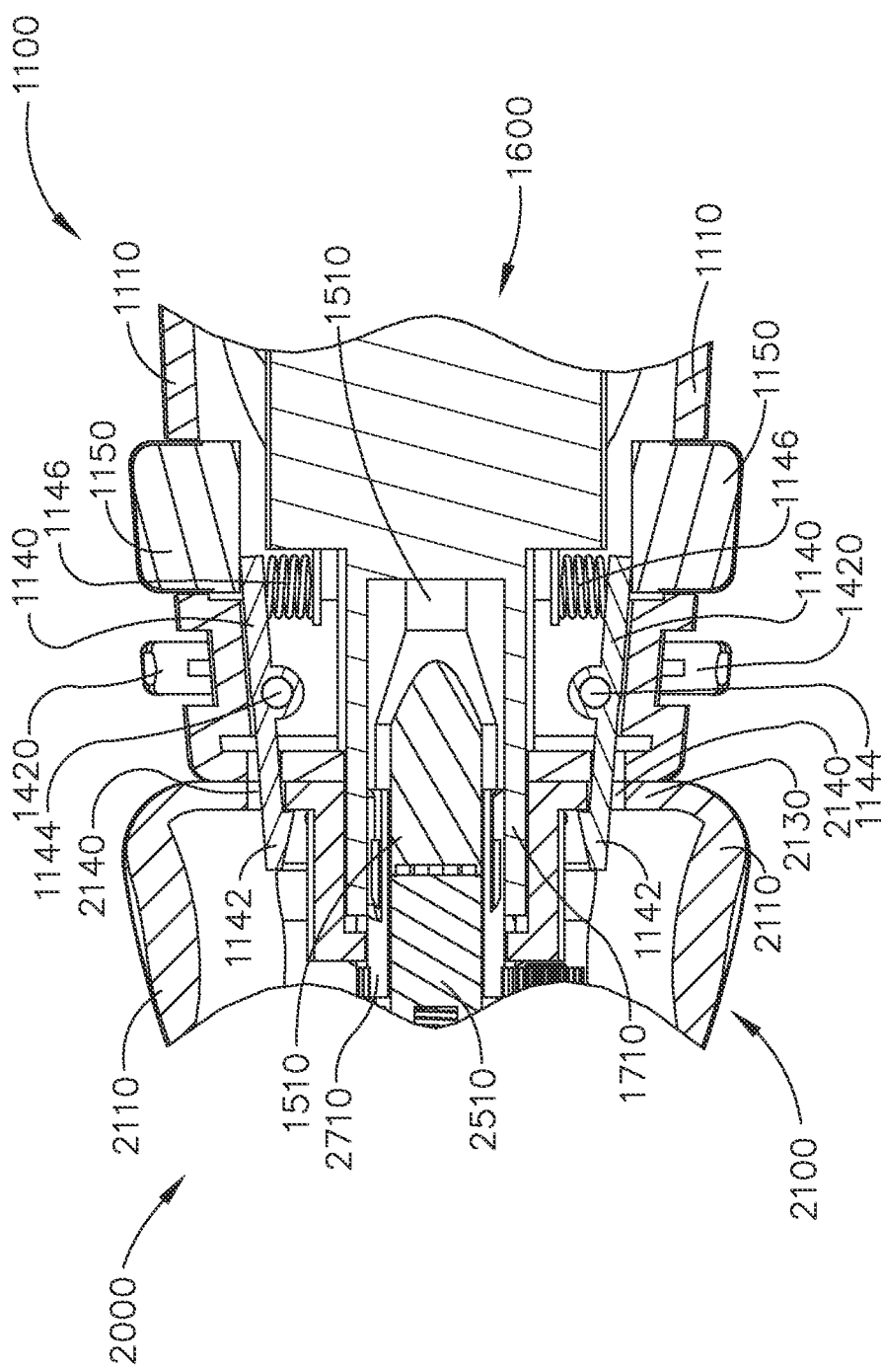
FIG. 10 is a partial cross-sectional view of the interconnection between the handle and shaft assembly of FIG. 2 in a locked configuration.
Figure 11:
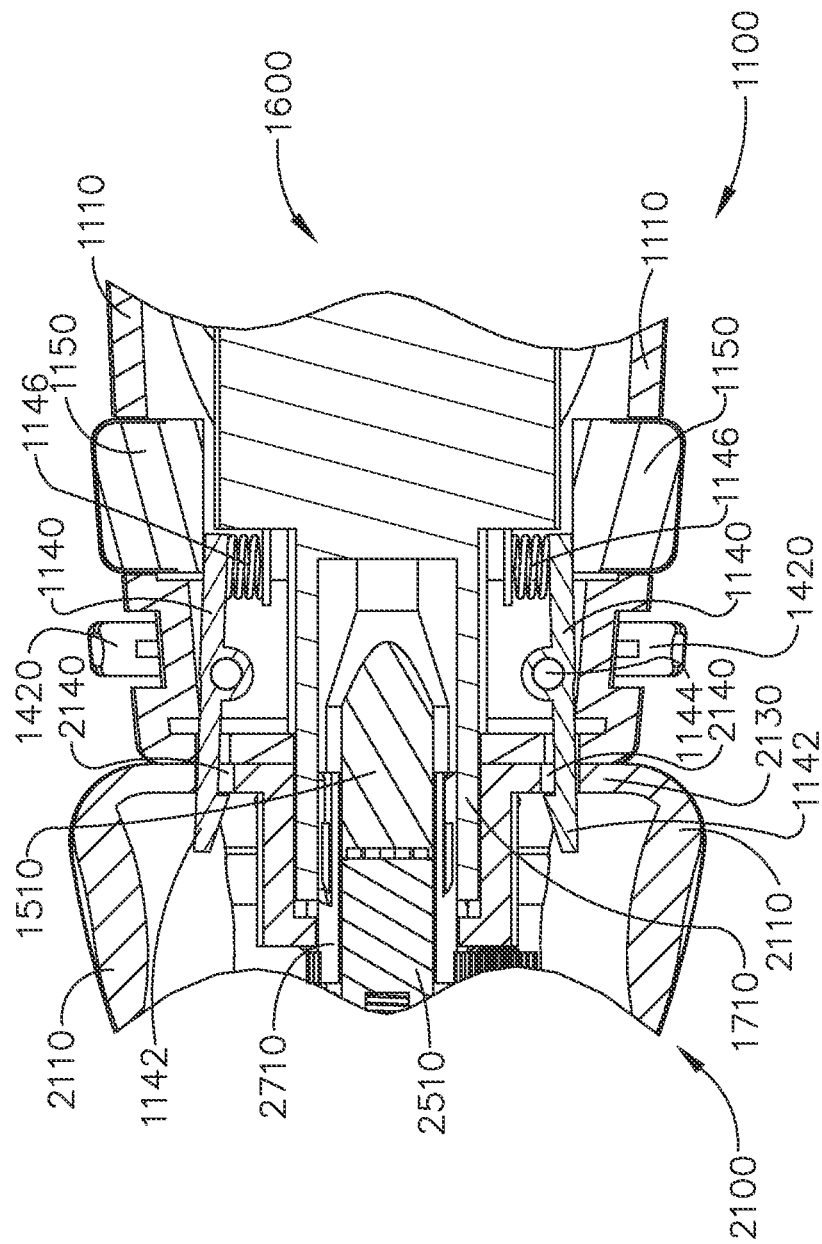
FIG. 11 is a partial cross-sectional view of the interconnection between the handle and shaft assembly of FIG. 2 in an unlocked configuration.

As discussed above, referring to FIGS. 3-8, the mounting interface 1130 of the drive module 1110 is configured to be coupled to a corresponding mounting interface on the shaft assemblies 2000, 3000, 4000, and 5000, for example. For instance, the shaft assembly 2000 comprises a mounting interface 2130 configured to be coupled to the mounting interface 1130 of the drive module 1100. More specifically, the proximal portion 2100 of the shaft assembly 2000 comprises a housing 2110 which defines the mounting interface 2130. Referring primarily to FIG. 8, the drive module 1100 comprises latches 1140 which are configured to releasably hold the mounting interface 2130 of the shaft assembly 2000 against the mounting interface 1130 of the drive module 1100. When the drive module 1100 and the shaft assembly 2000 are brought together along a longitudinal axis, as described above, the latches 1140 contact the mounting interface 2130 and rotate outwardly into an unlocked position. Referring primarily to FIGS. 8, 10, and 11, each latch 1140 comprises a lock end 1142 and a pivot portion 1144. The pivot portion 1144 of each latch 1140 is rotatably coupled to the housing 1110 of the drive module 1100 and, when the latches 1140 are rotated outwardly, as mentioned above, the latches 1140 rotate about the pivot portions 1144. Notably, each latch 1140 further comprises a biasing spring 1146 configured to bias the latches 1140 inwardly into a locked position. Each biasing spring 1146 is compressed between a latch 1140 and the housing 1110 of the drive module 1100 such that the biasing springs 1146 apply biasing forces to the latches 1140; however, such biasing forces are overcome when the latches 1140 are rotated outwardly into their unlocked positions by the shaft assembly 2000. That said, when the latches 1140 rotate outwardly after contacting the mounting interface 2130, the lock ends 1142 of the latches 1140 can enter into latch windows 2140 defined in the mounting interface 2130. Once the lock ends 1142 pass through the latch windows 2140, the springs 1146 can bias the latches 1140 back into their locked positions. Each lock end 1142 comprises a lock shoulder, or surface, which securely holds the shaft assembly 2000 to the drive module 1100.

Further to the above, the biasing springs 1146 hold the latches 1140 in their locked positions. The distal ends 1142 are sized and configured to prevent, or at least inhibit, relative longitudinal movement, i.e., translation along a longitudinal axis, between the shaft assembly 2000 and the drive module 1100 when the latches 1140 are in their locked positions. Moreover, the latches 1140 and the latch windows 1240 are sized and configured to prevent relative lateral movement, i.e., translation transverse to the longitudinal axis, between the shaft assembly 2000 and the drive module 1100. In addition, the latches 1140 and the latch windows 2140 are sized and configured to prevent the shaft assembly 2000 from rotating relative to the drive module 1100. The drive module 1100 further comprises release actuators 1150 which, when depressed by a clinician, move the latches 1140 from their locked positions into their unlocked positions. The drive module 1100 comprises a first release actuator 1150 slideably mounted in an opening defined in the first side of the handle housing 1110 and a second release actuator 1150 slideably mounted in an opening defined in a second, or opposite, side of the handle housing 1110. Although the release actuators 1150 are actuatable separately, both release actuators 1150 typically need to be depressed to completely unlock the shaft assembly 2000 from the drive module 1100 and allow the shaft assembly 2000 to be detached from the drive module 1100. That said, it is possible that the shaft assembly 2000 could be detached from the drive module 1100 by depressing only one release actuator 1150.

Once the shaft assembly 2000 has been secured to the handle 1000 and the end effector 7000, for example, has been assembled to the shaft 2000, the clinician can maneuver the handle 1000 to insert the end effector 7000 into a patient. In at least one instance, the end effector 7000 is inserted into the patient through a trocar and then manipulated in order to position the jaw assembly 7100 of the end effector assembly 7000 relative to the patient's tissue. Oftentimes, the jaw assembly 7100 must be in its closed, or clamped, configuration in order to fit through the trocar. Once through the trocar, the jaw assembly 7100 can be opened so that the patient tissue fit between the jaws of the jaw assembly 7100. At such point, the jaw assembly 7100 can be returned to its closed configuration to clamp the patient tissue between the jaws. The clamping force applied to the patient tissue by the jaw assembly 7100 is sufficient to move or otherwise manipulate the tissue during a surgical procedure. Thereafter, the jaw assembly 7100 can be re-opened to release the patient tissue from the end effector 7000. This process can be repeated until it is desirable to remove the end effector 7000 from the patient. At such point, the jaw assembly 7100 can be returned to its closed configuration and retracted through the trocar. Other surgical techniques are envisioned in which the end effector 7000 is inserted into a patient through an open incision, or without the use of the trocar. In any event, it is envisioned that the jaw assembly 7100 may have to be opened and closed several times throughout a surgical technique.

Referring again to FIGS. 3-6, the shaft assembly 2000 further comprises a clamping trigger system 2600 and a control system 2800. The clamping trigger system 2600 comprises a clamping trigger 2610 rotatably connected to the proximal housing 2110 of the shaft assembly 2000. As discussed below, the clamping trigger 2610 actuates the motor 1610 to operate the jaw drive of the end effector 7000 when the clamping trigger 2610 is actuated. The clamping trigger 2610 comprises an elongate portion which is graspable by the clinician while holding the handle 1000. The clamping trigger 2610 further comprises a mounting portion 2620 which is pivotably connected to a mounting portion 2120 of the proximal housing 2110 such that the clamping trigger 2610 is rotatable about a fixed, or an at least substantially fixed, axis. The closure trigger 2610 is rotatable between a distal position and a proximal position, wherein the proximal position of the closure trigger 2610 is closer to the pistol grip of the handle 1000 than the distal position. The closure trigger 2610 further comprises a tab 2615 extending therefrom which rotates within the proximal housing 2110. When the closure trigger 2610 is in its distal position, the tab 2615 is positioned above, but not in contact with, a switch 2115 mounted on the proximal housing 2110. The switch 2115 is part of an electrical circuit configured to detect the actuation of the closure trigger 2610 which is in an open condition the closure trigger 2610 is in its open position. When the closure trigger 2610 is moved into its proximal position, the tab 2615 comes into contact with the switch 2115 and closes the electrical circuit. In various instances, the switch 2115 can comprise a toggle switch, for example, which is mechanically switched between open and closed states when contacted by the tab 2615 of the closure trigger 2610. In certain instances, the switch 2115 can comprise a proximity sensor, for example, and/or any suitable type of sensor. In at least one instance, the switch 2115 comprises a Hall Effect sensor which can detect the amount in which the closure trigger 2610 has been rotated and, based on the amount of rotation, control the speed in which the motor 1610 is operated. In such instances, larger rotations of the closure trigger 2610 result in faster speeds of the motor 1610 while smaller rotations result in slower speeds, for example. In any event, the electrical circuit is in communication with the control system 2800 of the shaft assembly 2000, which is discussed in greater detail below.

Further to the above, the control system 2800 of the shaft assembly 2000 comprises a printed circuit board (PCB) 2810, at least one microprocessor 2820, and at least one memory device 2830. The board 2810 can be rigid and/or flexible and can comprise any suitable number of layers. The microprocessor 2820 and the memory device 2830 are part of a control circuit defined on the board 2810 which communicates with the control system 1800 of the handle 1000. The shaft assembly 2000 further comprises a signal communication system 2900 and the handle 1000 further comprises a signal communication system 1900 which are configured to convey data between the shaft control system 2800 and the handle control system 1800. The signal communication system 2900 is configured to transmit data to the signal communication system 1900 utilizing any suitable analog and/or digital components. In various instances, the communication systems 2900 and 1900 can communicate using a plurality of discrete channels which allows the input gates of the microprocessor 1820 to be directly controlled, at least in part, by the output gates of the microprocessor 2820. In some instances, the communication systems 2900 and 1900 can utilize multiplexing. In at least one such instance, the control system 2900 includes a multiplexing device that sends multiple signals on a carrier channel at the same time in the form of a single, complex signal to a multiplexing device of the control system 1900 that recovers the separate signals from the complex signal.

The communication system 2900 comprises an electrical connector 2910 mounted to the circuit board 2810. The electrical connector 2910 comprises a connector body and a plurality of electrically-conductive contacts mounted to the connector body. The electrically-conductive contacts comprise male pins, for example, which are soldered to electrical traces defined in the circuit board 2810. In other instances, the male pins can be in communication with circuit board traces through zero-insertion-force (ZIF) sockets, for example. The communication system 1900 comprises an electrical connector 1910 mounted to the circuit board 1810. The electrical connector 1910 comprises a connector body and a plurality of electrically-conductive contacts mounted to the connector body. The electrically-conductive contacts comprise female pins, for example, which are soldered to electrical traces defined in the circuit board 1810. In other instances, the female pins can be in communication with circuit board traces through zero-insertion-force (ZIF) sockets, for example. When the shaft assembly 2000 is assembled to the drive module 1100, the electrical connector 2910 is operably coupled to the electrical connector 1910 such that the electrical contacts form electrical pathways therebetween. The above being said, the connectors 1910 and 2910 can comprise any suitable electrical contacts. Moreover, the communication systems 1900 and 2900 can communicate with one another in any suitable manner. In various instances, the communication systems 1900 and 2900 communicate wirelessly. In at least one such instance, the communication system 2900 comprises a wireless signal transmitter and the communication system 1900 comprises a wireless signal receiver such that the shaft assembly 2000 can wirelessly communicate data to the handle 1000. Likewise, the communication system 1900 can comprise a wireless signal transmitter and the communication system 2900 can comprise a wireless signal receiver such that the handle 1000 can wirelessly communicate data to the shaft assembly 2000.

As discussed above, the control system 1800 of the handle 1000 is in communication with, and is configured to control, the electrical power circuit of the handle 1000. The handle control system 1800 is also powered by the electrical power circuit of the handle 1000. The handle communication system 1900 is in signal communication with the handle control system 1800 and is also powered by the electrical power circuit of the handle 1000. The handle communication system 1900 is powered by the handle electrical power circuit via the handle control system 1800, but could be directly powered by the electrical power circuit. As also discussed above, the handle communication system 1900 is in signal communication with the shaft communication system 2900. That said, the shaft communication system 2900 is also powered by the handle electrical power circuit via the handle communication system 1900. To this end, the electrical connectors 1910 and 2010 connect both one or more signal circuits and one or more power circuits between the handle 1000 and the shaft assembly 2000. Moreover, the shaft communication system 2900 is in signal communication with the shaft control system 2800, as discussed above, and is also configured to supply power to the shaft control system 2800. Thus, the control systems 1800 and 2800 and the communication systems 1900 and 2900 are all powered by the electrical power circuit of the handle 1000; however, alternative embodiments are envisioned in which the shaft assembly 2000 comprises its own power source, such as one or more batteries, for example, an an electrical power circuit configured to supply power from the batteries to the handle systems 2800 and 2900. In at least one such embodiment, the handle control system 1800 and the handle communication system 1900 are powered by the handle electrical power system and the shaft control system 2800 and the handle communication system 2900 are powered by the shaft electrical power system.

Further to the above, the actuation of the clamping trigger 2610 is detected by the shaft control system 2800 and communicated to the handle control system 1800 via the communication systems 2900 and 1900. Upon receiving a signal that the clamping trigger 2610 has been actuated, the handle control system 1800 supplies power to the electric motor 1610 of the motor assembly 1600 to rotate the drive shaft 1710 of the handle drive system 1700, and the drive shaft 2710 of the shaft drive system 2700, in a direction which closes the jaw assembly 7100 of the end effector 7000. The mechanism for converting the rotation of the drive shaft 2710 to a closure motion of the jaw assembly 7100 is discussed in greater detail below. So long as the clamping trigger 2610 is held in its actuated position, the electric motor 1610 will rotate the drive shaft 1710 until the jaw assembly 7100 reaches its fully-clamped position. When the jaw assembly 7100 reaches its fully-clamped position, the handle control system 1800 cuts the electrical power to the electric motor 1610. The handle control system 1800 can determine when the jaw assembly 7100 has reached its fully-clamped position in any suitable manner. For instance, the handle control system 1800 can comprise an encoder system which monitors the rotation of, and counts the rotations of, the output shaft of the electric motor 1610 and, once the number of rotations reaches a predetermined threshold, the handle control system 1800 can discontinue supplying power to the electric motor 1610. In at least one instance, the end effector assembly 7000 can comprise one or more sensors configured to detect when the jaw assembly 7100 has reached its fully-clamped position. In at least one such instance, the sensors in the end effector 7000 are in signal communication with the handle control system 1800 via electrical circuits extending through the shaft assembly 2000 which can include the electrical contacts 1520 and 2520, for example.

When the clamping trigger 2610 is rotated distally out of its proximal position, the switch 2115 is opened which is detected by the shaft control system 2800 and communicated to the handle control system 1800 via the communication systems 2900 and 1900. Upon receiving a signal that the clamping trigger 2610 has been moved out of its actuated position, the handle control system 1800 reverses the polarity of the voltage differential being applied to the electric motor 1610 of the motor assembly 1600 to rotate the drive shaft 1710 of the handle drive system 1700, and the drive shaft 2710 of the shaft drive system 2700, in an opposite direction which, as a result, opens the jaw assembly 7100 of the end effector 7000. When the jaw assembly 7100 reaches its fully-open position, the handle control system 1800 cuts the electrical power to the electric motor 1610. The handle control system 1800 can determine when the jaw assembly 7100 has reached its fully-open position in any suitable manner. For instance, the handle control system 1800 can utilize the encoder system and/or the one or more sensors described above to determine the configuration of the jaw assembly 7100. In view of the above, the clinician needs to be mindful about holding the clamping trigger 2610 in its actuated position in order to maintain the jaw assembly 7100 in its clamped configuration as, otherwise, the control system 1800 will open jaw assembly 7100. With this in mind, the shaft assembly 2000 further comprises an actuator latch 2630 configured to releasably hold the clamping trigger 2610 in its actuated position to prevent the accidental opening of the jaw assembly 7100. The actuator latch 2630 can be manually released, or otherwise defeated, by the clinician to allow the clamping trigger 2610 to be rotated distally and open the jaw assembly 7100.

The clamping trigger system 2600 further comprises a resilient biasing member, such as a torsion spring, for example, configured to resist the closure of the clamping trigger system 2600. The torsion spring can also assist in reducing and/or mitigating sudden movements and/or jitter of the clamping trigger 2610. Such a torsion spring can also automatically return the clamping trigger 2610 to its unactuated position when the clamping trigger 2610 is released. The actuator latch 2630 discussed above can suitably hold the clamping trigger 2610 in its actuated position against the biasing force of the torsion spring.

As discussed above, the control system 1800 operates the electric motor 1610 to open and close the jaw assembly 7100. The control system 1800 is configured to open and close the jaw assembly 7100 at the same speed. In such instances, the control system 1800 applies the same voltage pulses to the electric motor 1610, albeit with different voltage polarities, when opening and closing the jaw assembly 7100. That said, the control system 1800 can be configured to open and close the jaw assembly 7100 at different speeds. For instance, the jaw assembly 7100 can be closed at a first speed and opened at a second speed which is faster than the first speed. In such instances, the slower closing speed affords the clinician an opportunity to better position the jaw assembly 7100 while clamping the tissue. Alternatively, the control system 1800 can open the jaw assembly 7100 at a slower speed. In such instances, the slower opening speed reduces the possibility of the opening jaws colliding with adjacent tissue. In either event, the control system 1800 can decrease the duration of the voltage pulses and/or increase the duration between the voltage pulses to slow down and/or speed up the movement of the jaw assembly 7100.

As discussed above, the control system 1800 is configured to interpret the position of the clamping trigger 2610 as a command to position the jaw assembly 7100 in a specific configuration. For instance, the control system 1800 is configured to interpret the proximal-most position of the clamping trigger 2610 as a command to close the jaw assembly 7100 and any other position of the clamping trigger as a command to open the jaw assembly 7100. That said, the control system 1800 can be configured to interpret the position of the clamping trigger 2610 in a proximal range of positions, instead of a single position, as a command to close the jaw assembly 7100. Such an arrangement can allow the jaw assembly 7000 to be better responsive to the clinician's input. In such instances, the range of motion of the clamping trigger 2610 is divided into ranges—a proximal range which is interpreted as a command to close the jaw assembly 7100 and a distal range which is interpreted as a command to open the jaw assembly 7100. In at least one instance, the range of motion of the clamping trigger 2610 can have an intermediate range between the proximal range and the distal range. When the clamping trigger 2610 is in the intermediate range, the control system 1800 can interpret the position of the clamping trigger 2610 as a command to neither open nor close the jaw assembly 7100. Such an intermediate range can prevent, or reduce the possibility of, jitter between the opening and closing ranges. In the instances described above, the control system 1800 can be configured to ignore cumulative commands to open or close the jaw assembly 7100. For instance, if the closure trigger 2610 has already been fully retracted into its proximal-most position, the control assembly 1800 can ignore the motion of the clamping trigger 2610 in the proximal, or clamping, range until the clamping trigger 2610 enters into the distal, or opening, range wherein, at such point, the control system 1800 can then actuate the electric motor 1610 to open the jaw assembly 7100.

In certain instances, further to the above, the position of the clamping trigger 2610 within the clamping trigger range, or at least a portion of the clamping trigger range, can allow the clinician to control the speed of the electric motor 1610 and, thus, the speed in which the jaw assembly 7100 is being opened or closed by the control assembly 1800. In at least one instance, the sensor 2115 comprises a Hall Effect sensor, and/or any other suitable sensor, configured to detect the position of the clamping trigger 2610 between its distal, unactuated position and its proximal, fully-actuated position. The Hall Effect sensor is configured to transmit a signal to the handle control system 1800 via the shaft control system 2800 such that the handle control system 1800 can control the speed of the electric motor 1610 in response to the position of the clamping trigger 2610. In at least one instance, the handle control system 1800 controls the speed of the electric motor 1610 proportionately, or in a linear manner, to the position of the clamping trigger 2610. For example, if the clamping trigger 2610 is moved half way through its range, then the handle control system 1800 will operate the electric motor 1610 at half of the speed in which the electric motor 1610 is operated when the clamping trigger 2610 is fully-retracted. Similarly, if the clamping trigger 2610 is moved a quarter way through its range, then the handle control system 1800 will operate the electric motor 1610 at a quarter of the speed in which the electric motor 1610 is operated when the clamping trigger 2610 is fully-retracted. Other embodiments are envisioned in which the handle control system 1800 controls the speed of the electric motor 1610 in a non-linear manner to the position of the clamping trigger 2610. In at least one instance, the control system 1800 operates the electric motor 1610 slowly in the distal portion of the clamping trigger range while quickly accelerating the speed of the electric motor 1610 in the proximal portion of the clamping trigger range.

As described above, the clamping trigger 2610 is movable to operate the electric motor 1610 to open or close the jaw assembly 7100 of the end effector 7000. The electric motor 1610 is also operable to rotate the end effector 7000 about a longitudinal axis and articulate the end effector 7000 relative to the elongate shaft 2200 about the articulation joint 2300 of the shaft assembly 2000. Referring primarily to FIGS. 7 and 8, the drive module 1100 comprises an input system 1400 including a rotation actuator 1420 and an articulation actuator 1430. The input system 1400 further comprises a printed circuit board (PCB) 1410 which is in signal communication with the printed circuit board (PCB) 1810 of the control system 1800. The drive module 1100 comprises an electrical circuit, such as a flexible wiring harness or ribbon, for example, which permits the input system 1400 to communicate with the control system 1800. The rotation actuator 1420 is rotatably supported on the housing 1110 and is in signal communication with the input board 1410 and/or control board 1810, as described in greater detail below. The articulation actuator 1430 is supported by and in signal communication with the input board 1410 and/or control board 1810, as also described in greater detail below.

Referring primarily to FIGS. 8, 10, and 11, further to the above, the handle housing 1110 comprises an annular groove or slot defined therein adjacent the distal mounting interface 1130. The rotation actuator 1420 comprises an annular ring 1422 rotatably supported within the annular groove and, owing to the configuration of the sidewalls of the annular groove, the annular ring 1422 is constrained from translating longitudinally and/or laterally with respect to the handle housing 1110. The annular ring 1422 is rotatable in a first, or clockwise, direction and a second, or counter-clockwise, direction, about a longitudinal axis extending through the frame 1500 of the drive module 1100. The rotation actuator 1420 comprises one or more sensors configured to detect the rotation of the annular ring 1422. In at least one instance, the rotation actuator 1420 comprises a first sensor positioned on a first side of the drive module 1100 and a second sensor positioned on a second, or opposite, side of the drive module 1100 and the annular ring 1422 comprises a detectable element which is detectable by the first and second sensors. The first sensor is configured to detect when the annular ring 1422 is rotated in the first direction and the second sensor is configured to detect when the annular ring 1422 is rotated in the second direction. When the first sensor detects that the annular ring 1422 is rotated in the first direction, the handle control system 1800 rotates the handle drive shaft 1710, the drive shaft 2710, and the end effector 7000 in the first direction, as described in greater detail below. Similarly, the handle control system 1800 rotates the handle drive shaft 1710, the drive shaft 2710, and the end effector 7000 in the second direction when the second sensor detects that the annular ring 1422 is rotated in the second direction. In view of the above, the reader should appreciate that the clamping trigger 2610 and the rotation actuator 1420 are both operable to rotate the drive shaft 2710.

In various embodiments, further to the above, the first and second sensors comprise switches which are mechanically closable by the detectable element of the annular ring 1422. When the annular ring 1422 is rotated in the first direction from a center position, the detectable element closes the switch of the first sensor. When the switch of the first sensor is closed, the control system 1800 operates the electric motor 1610 to rotate the end effector 7000 in the first direction. When the annular ring 1422 is rotated in the second direction toward the center position, the detectable element is disengaged from the first switch and the first switch is re-opened. Once the first switch is re-opened, the control system 1800 cuts the power to the electric motor 1610 to stop the rotation of the end effector 7000. Similarly, the detectable element closes the switch of the second sensor when the annular ring 1422 is rotated in the second direction from the center position. When the switch of the second sensor is closed, the control system 1800 operates the electric motor 1610 to rotate the end effector 7000 in the second direction. When the annular ring 1422 is rotated in the first direction toward the center position, the detectable element is disengaged from the second switch and the second switch is re-opened. Once the second switch is re-opened, the control system 1800 cuts the power to the electric motor 1610 to stop the rotation of the end effector 7000.

In various embodiments, further to the above, the first and second sensors of the rotation actuator 1420 comprise proximity sensors, for example. In certain embodiments, the first and second sensors of the rotation actuator 1420 comprise Hall Effect sensors, and/or any suitable sensors, configured to detect the distance between the detectable element of the annular ring 1422 and the first and second sensors. If the first Hall Effect sensor detects that the annular ring 1422 has been rotated in the first direction, then, as discussed above, the control system 1800 will rotate the end effector 7000 in the first direction. In addition, the control system 1800 can rotate the end effector 7000 at a faster speed when the detectable element is closer to the first Hall Effect sensor than when the detectable element is further away from the first Hall Effect sensor. If the second Hall Effect sensor detects that the annular ring 1422 has been rotated in the second direction, then, as discussed above, the control system 1800 will rotate the end effector 7000 in the second direction. In addition, the control system 1800 can rotate the end effector 7000 at a faster speed when the detectable element is closer to the second Hall Effect sensor than when the detectable element is further away from the second Hall Effect sensor. As a result, the speed in which the end effector 7000 is rotated is a function of the amount, or degree, in which the annular ring 1422 is rotated. The control system 1800 is further configured to evaluate the inputs from both the first and second Hall Effect sensors when determining the direction and speed in which to rotate the end effector 7000. In various instances, the control system 1800 can use the closest Hall Effect sensor to the detectable element of the annular ring 1422 as a primary source of data and the Hall Effect sensor furthest away from the detectable element as a confirmational source of data to double-check the data provided by the primary source of data. The control system 1800 can further comprise a data integrity protocol to resolve situations in which the control system 1800 is provided with conflicting data. In any event, the handle control system 1800 can enter into a neutral state in which the handle control system 1800 does not rotate the end effector 7000 when the Hall Effect sensors detect that the detectable element is in its center position, or in a position which is equidistant between the first Hall Effect sensor and the second Hall Effect sensor. In at least one such instance, the control system 1800 can enter into its neutral state when the detectable element is in a central range of positions. Such an arrangement would prevent, or at least reduce the possibility of, rotational jitter when the clinician is not intending to rotate the end effector 7000.

Further to the above, the rotation actuator 1420 can comprise one or more springs configured to center, or at least substantially center, the rotation actuator 1420 when it is released by the clinician. In such instances, the springs can act to shut off the electric motor 1610 and stop the rotation of the end effector 7000. In at least one instance, the rotation actuator 1420 comprises a first torsion spring configured to rotate the rotation actuator 1420 in the first direction and a second torsion spring configured to rotate the rotation actuator 1420 in the second direction. The first and second torsion springs can have the same, or at least substantially the same, spring constant such that the forces and/or torques applied by the first and second torsion springs balance, or at least substantially balance, the rotation actuator 1420 in its center position.

In view of the above, the reader should appreciate that the clamping trigger 2610 and the rotation actuator 1420 are both operable to rotate the drive shaft 2710 and either, respectively, operate the jaw assembly 7100 or rotate the end effector 7000. The system that uses the rotation of the drive shaft 2710 to selectively perform these functions is described in greater detail below.

Referring to FIGS. 7 and 8, the articulation actuator 1430 comprises a first push button 1432 and a second push button 1434. The first push button 1432 is part of a first articulation control circuit and the second push button 1434 is part of a second articulation circuit of the input system 1400. The first push button 1432 comprises a first switch that is closed when the first push button 1432 is depressed. The handle control system 1800 is configured to sense the closure of the first switch and, moreover, the closure of the first articulation control circuit. When the handle control system 1800 detects that the first articulation control circuit has been closed, the handle control system 1800 operates the electric motor 1610 to articulate the end effector 7000 in a first articulation direction about the articulation joint 2300. When the first push button 1432 is released by the clinician, the first articulation control circuit is opened which, once detected by the control system 1800, causes the control system 1800 to cut the power to the electric motor 1610 to stop the articulation of the end effector 7000.

In various instances, further to the above, the articulation range of the end effector 7000 is limited and the control system 1800 can utilize the encoder system discussed above for monitoring the rotational output of the electric motor 1610, for example, to monitor the amount, or degree, in which the end effector 7000 is rotated in the first direction. In addition to or in lieu of the encoder system, the shaft assembly 2000 can comprise a first sensor configured to detect when the end effector 7000 has reached the limit of its articulation in the first direction. In any event, when the control system 1800 determines that the end effector 7000 has reached the limit of articulation in the first direction, the control system 1800 can cut the power to the electric motor 1610 to stop the articulation of the end effector 7000.

Similar to the above, the second push button 1434 comprises a second switch that is closed when the second push button 1434 is depressed. The handle control system 1800 is configured to sense the closure of the second switch and, moreover, the closure of the second articulation control circuit. When the handle control system 1800 detects that the second articulation control circuit has been closed, the handle control system 1800 operates the electric motor 1610 to articulate the end effector 7000 in a second direction about the articulation joint 2300. When the second push button 1434 is released by the clinician, the second articulation control circuit is opened which, once detected by the control system 1800, causes the control system 1800 to cut the power to the electric motor 1610 to stop the articulation of the end effector 7000.

In various instances, the articulation range of the end effector 7000 is limited and the control system 1800 can utilize the encoder system discussed above for monitoring the rotational output of the electric motor 1610, for example, to monitor the amount, or degree, in which the end effector 7000 is rotated in the second direction. In addition to or in lieu of the encoder system, the shaft assembly 2000 can comprise a second sensor configured to detect when the end effector 7000 has reached the limit of its articulation in the second direction. In any event, when the control system 1800 determines that the end effector 7000 has reached the limit of articulation in the second direction, the control system 1800 can cut the power to the electric motor 1610 to stop the articulation of the end effector 7000.

Figure 15:
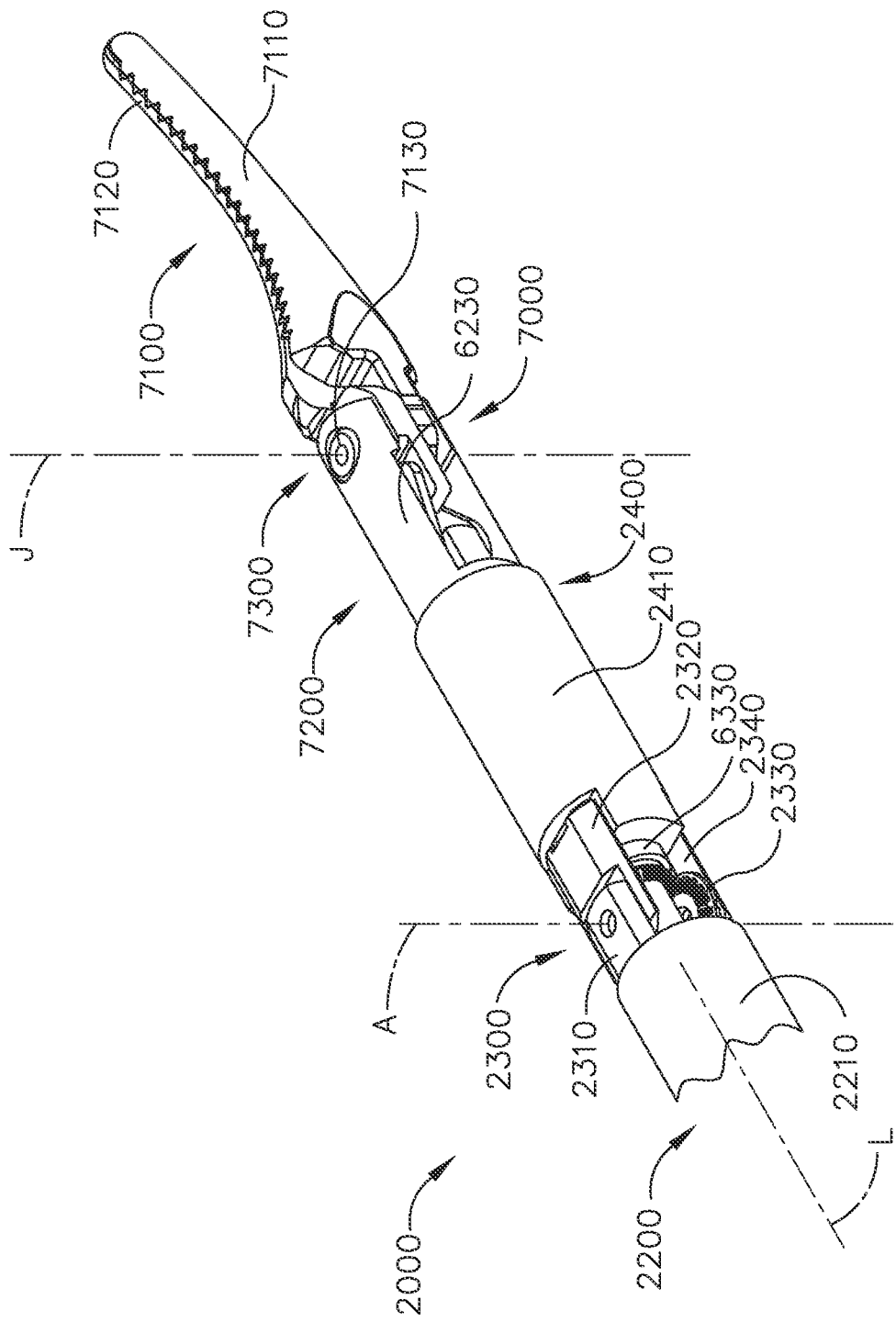
FIG. 15 is a partial perspective view of the end effector of FIG. 14 in a closed configuration.

As described above, the end effector 7000 is articulatable in a first direction (FIG. 16) and/or a second direction (FIG. 17) from a center, or unarticulated, position (FIG. 15). Once the end effector 7000 has been articulated, the clinician can attempt to re-center the end effector 7000 by using the first and second articulation push buttons 1432 and 1434. As the reader can appreciate, the clinician may struggle to re-center the end effector 7000 as, for instance, the end effector 7000 may not be entirely visible once it is positioned in the patient. In some instances, the end effector 7000 may not fit back through a trocar if the end effector 7000 is not re-centered, or at least substantially re-centered. With that in mind, the control system 1800 is configured to provide feedback to the clinician when the end effector 7000 is moved into its unarticulated, or centered, position. In at least one instance, the feedback comprises audio feedback and the handle control system 1800 can comprise a speaker which emits a sound, such as a beep, for example, when the end effector 7000 is centered. In certain instances, the feedback comprises visual feedback and the handle control system 1800 can comprise a light emitting diode (LED), for example, positioned on the handle housing 1110 which flashes when the end effector 7000 is centered. In various instances, the feedback comprises haptic feedback and the handle control system 1800 can comprise an electric motor comprising an eccentric element which vibrates the handle 1000 when the end effector 7000 is centered. Manually re-centering the end effector 7000 in this way can be facilitated by the control system 1800 slowing the motor 1610 when the end effector 7000 is approaching its centered position. In at least one instance, the control system 1800 slows the articulation of the end effector 7000 when the end effector 7000 is within approximately 5 degrees of center in either direction, for example.

In addition to or in lieu of the above, the handle control system 1800 can be configured to re-center the end effector 7000. In at least one such instance, the handle control system 1800 can re-center the end effector 7000 when both of the articulation buttons 1432 and 1434 of the articulation actuator 1430 are depressed at the same time. When the handle control system 1800 comprises an encoder system configured to monitor the rotational output of the electric motor 1610, for example, the handle control system 1800 can determine the amount and direction of articulation needed to re-center, or at least substantially re-center, the end effector 7000. In various instances, the input system 1400 can comprise a home button, for example, which, when depressed, automatically centers the end effector 7000.

Figure 5:
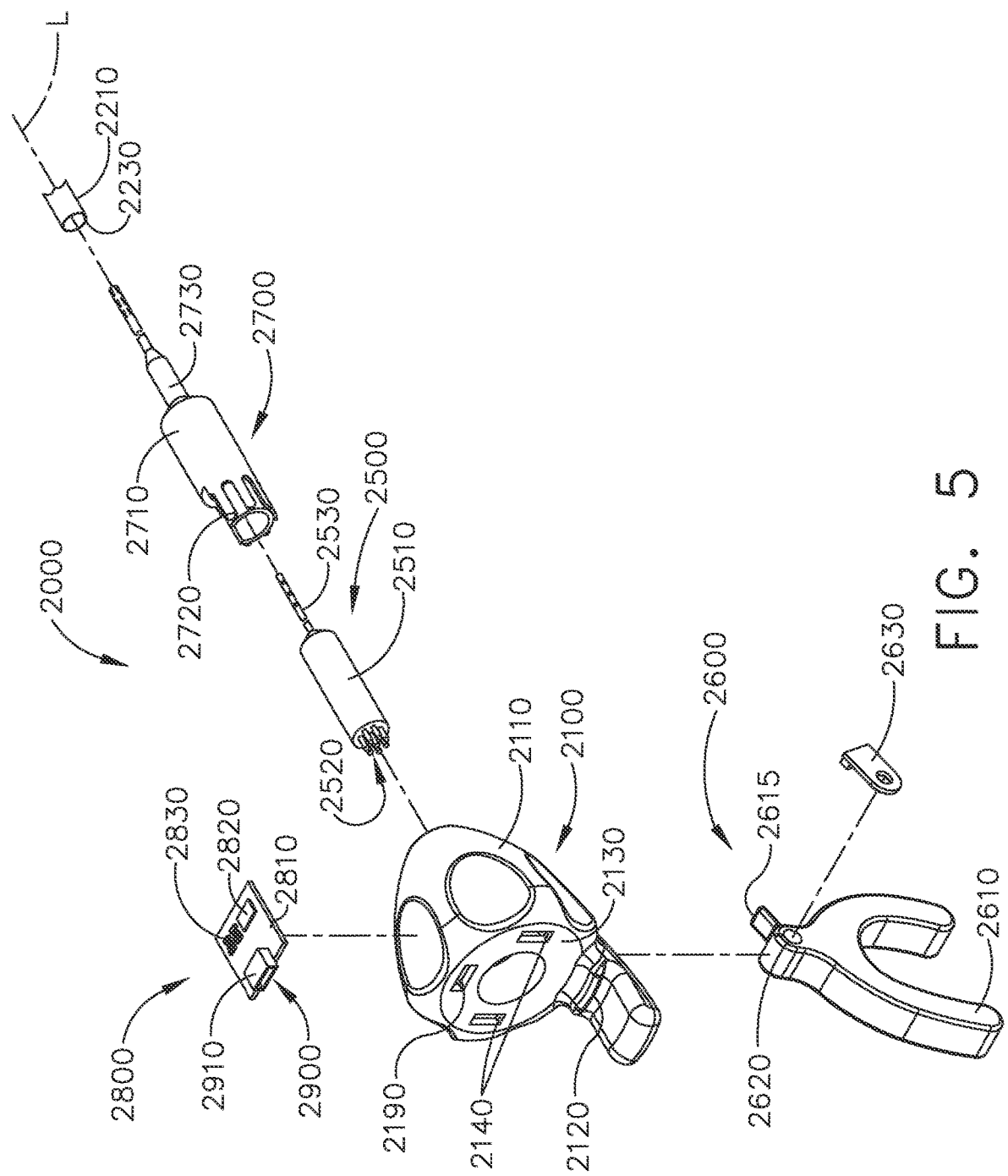
FIG. 5 is a partial exploded view of the shaft assembly of FIG. 2.
Figure 6:
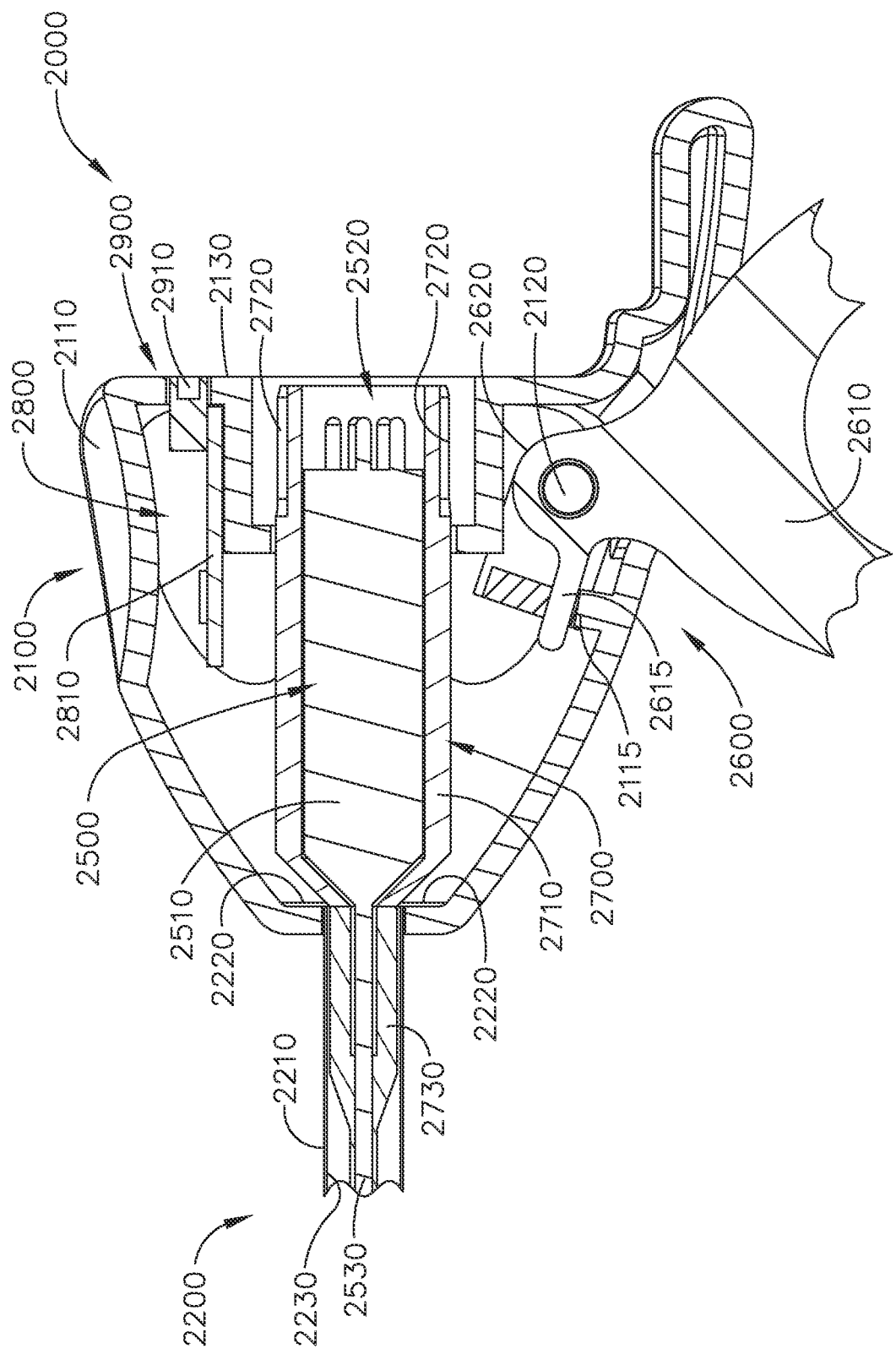
FIG. 6 is a partial cross-sectional elevational view of the shaft assembly of FIG. 2.

Referring primarily to FIGS. 5 and 6, the elongate shaft 2200 of the shaft assembly 2000 comprises an outer housing, or tube, 2210 mounted to the proximal housing 2110 of the proximal portion 2100. The outer housing 2210 comprises a longitudinal aperture 2230 extending therethrough and a proximal flange 2220 which secures the outer housing 2210 to the proximal housing 2110. The frame 2500 of the shaft assembly 2000 extends through the longitudinal aperture 2230 of the elongate shaft 2200. More specifically, the shaft 2510 of the shaft frame 2500 necks down into a smaller shaft 2530 which extends through the longitudinal aperture 2230. That said, the shaft frame 2500 can comprise any suitable arrangement. The drive system 2700 of the shaft assembly 2000 also extends through the longitudinal aperture 2230 of the elongate shaft 2200. More specifically, the drive shaft 2710 of the shaft drive system 2700 necks down into a smaller drive shaft 2730 which extends through the longitudinal aperture 2230. That said, the shaft drive system 2700 can comprise any suitable arrangement.

Figure 20:
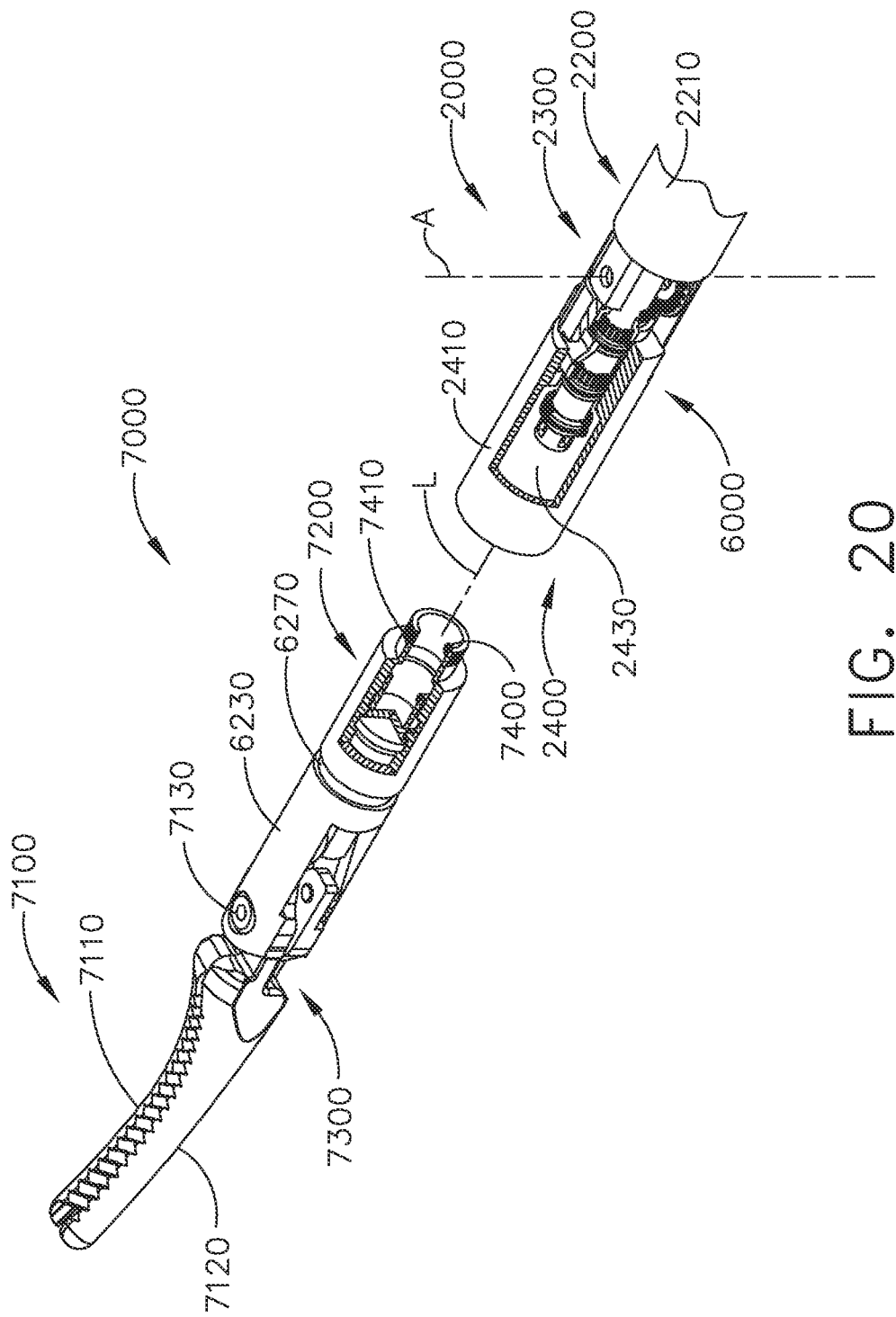
FIG. 20 is a partial cross-sectional perspective view of the end effector of FIG. 14 detached from the shaft assembly of FIG. 2.
Figure 22:
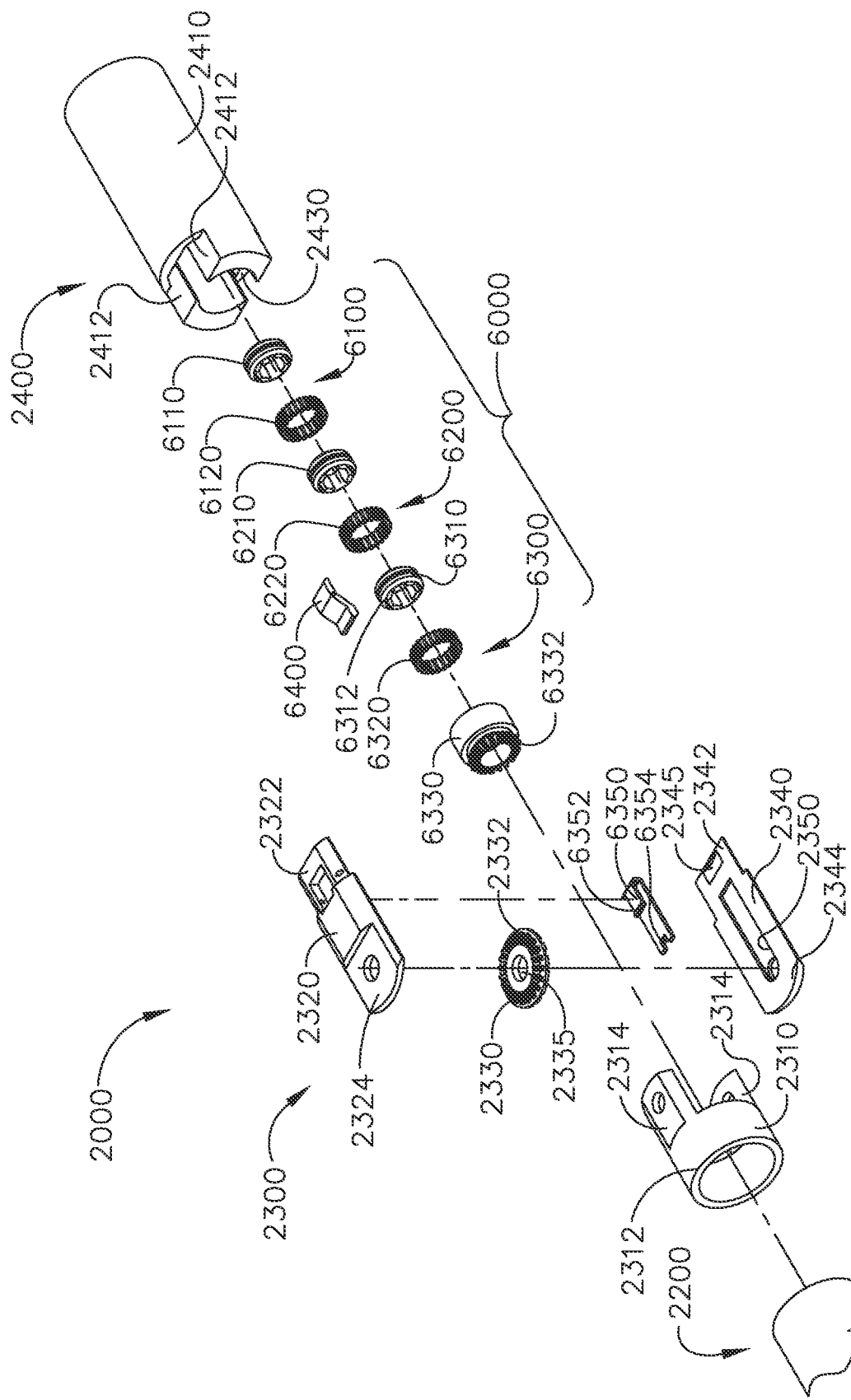
FIG. 22 is an exploded view of a distal attachment portion of the shaft assembly of FIG. 2.
Figure 23:
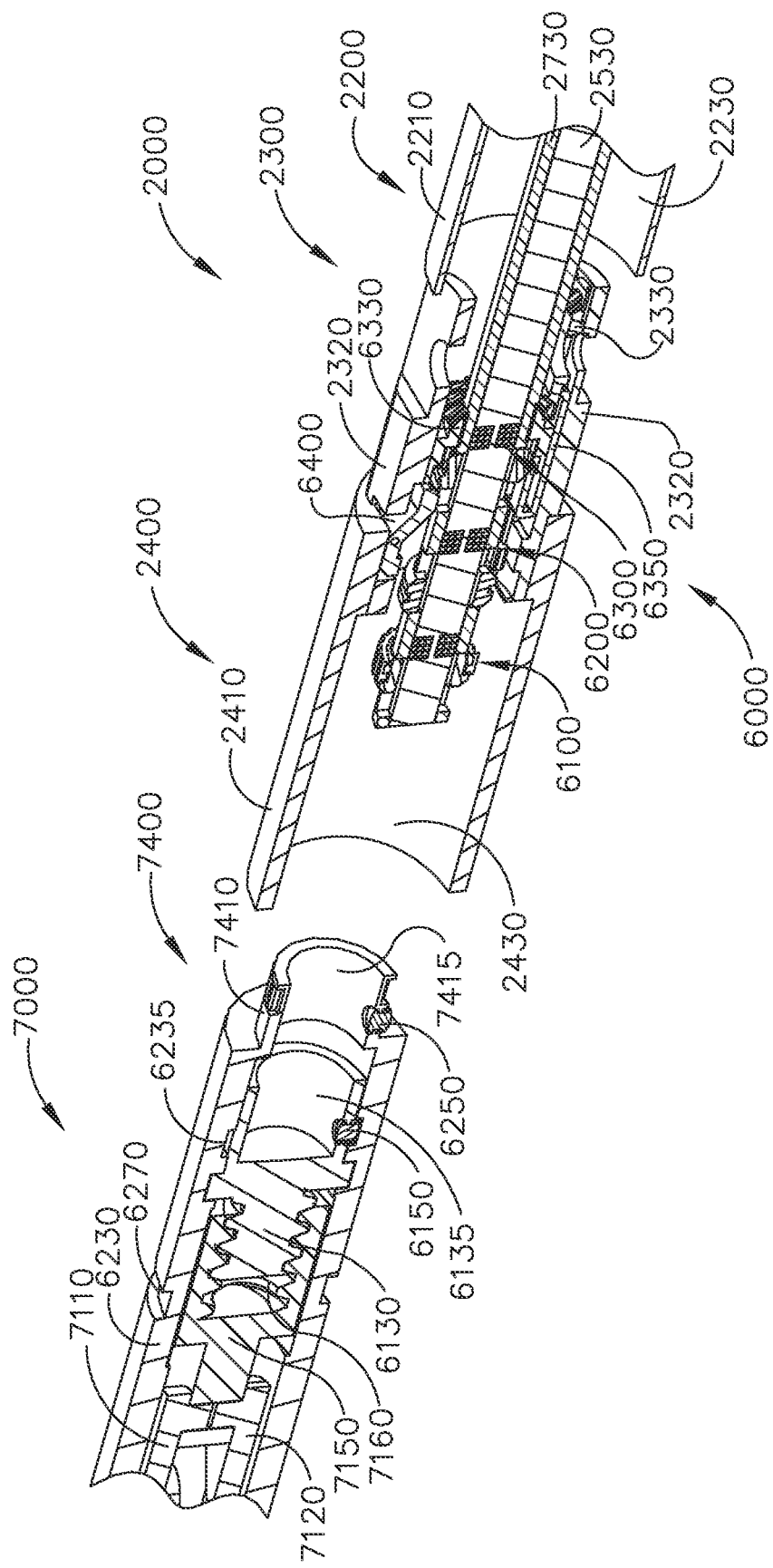
FIG. 23 is another partial cross-sectional perspective view of the end effector of FIG. 14 detached from the shaft assembly of FIG. 2.
Figure 24:
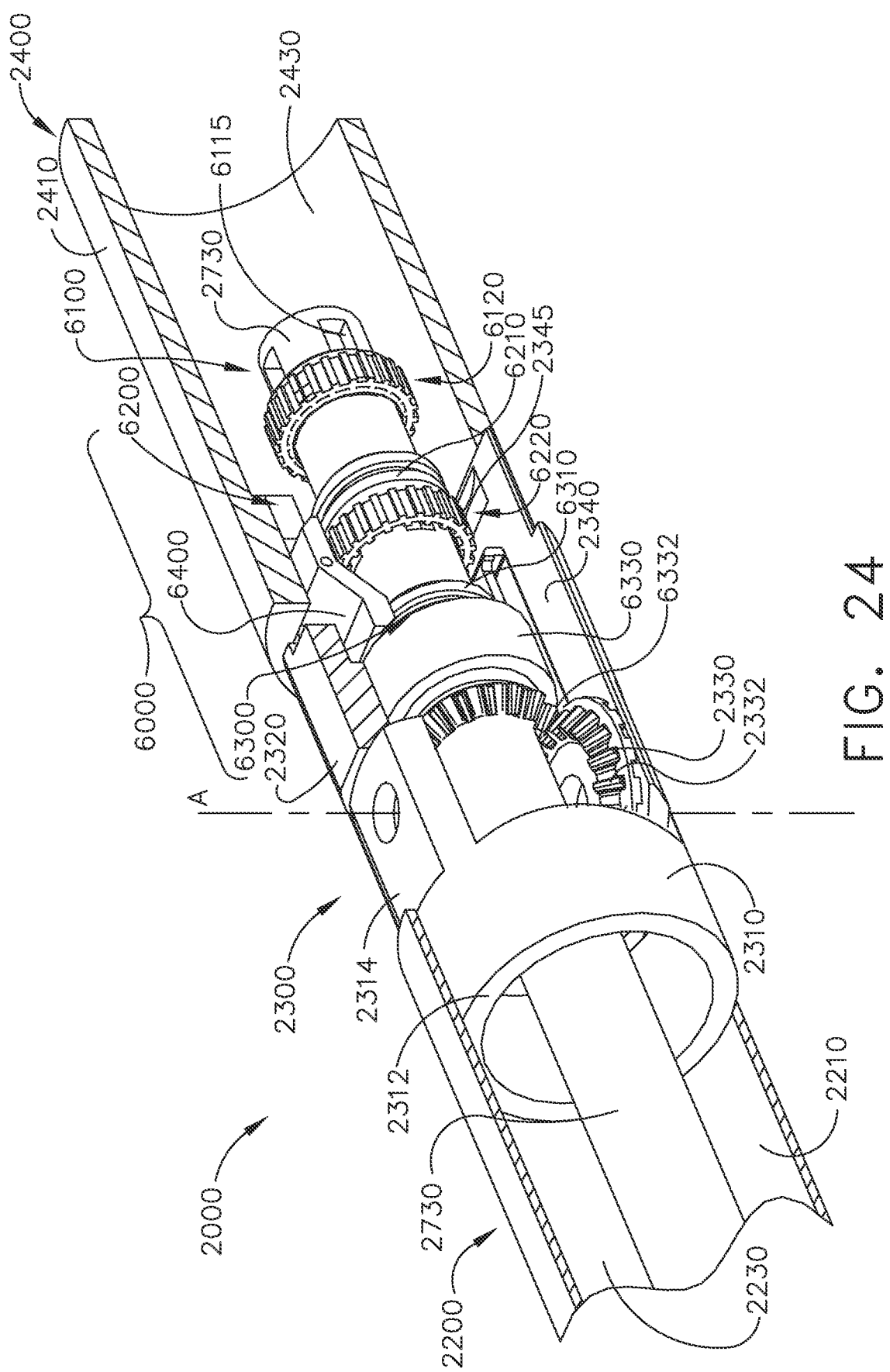
FIG. 24 is a partial cross-sectional perspective view of the end effector of FIG. 14 attached to the shaft assembly of FIG. 2.

Referring primarily to FIGS. 20, 23, and 24, the outer housing 2210 of the elongate shaft 2200 extends to the articulation joint 2300. The articulation joint 2300 comprises a proximal frame 2310 mounted to the outer housing 2210 such that there is little, if any, relative translation and/or rotation between the proximal frame 2310 and the outer housing 2210. Referring primarily to FIG. 22, the proximal frame 2310 comprises an annular portion 2312 mounted to the sidewall of the outer housing 2210 and tabs 2314 extending distally from the annular portion 2312. The articulation joint 2300 further comprises links 2320 and 2340 which are rotatably mounted to the frame 2310 and mounted to an outer housing 2410 of the distal attachment portion 2400. The link 2320 comprises a distal end 2322 mounted to the outer housing 2410. More specifically, the distal end 2322 of the link 2320 is received and fixedly secured within a mounting slot 2412 defined in the outer housing 2410. Similarly, the link 2340 comprises a distal end 2342 mounted to the outer housing 2410. More specifically, the distal end 2342 of the link 2340 is received and fixedly secured within a mounting slot defined in the outer housing 2410. The link 2320 comprises a proximal end 2324 rotatably coupled to a tab 2314 of the proximal articulation frame 2310. Although not illustrated in FIG. 22, a pin extends through apertures defined in the proximal end 2324 and the tab 2314 to define a pivot axis therebetween. Similarly, the link 2340 comprises a proximal end 2344 rotatably coupled to a tab 2314 of the proximal articulation frame 2310. Although not illustrated in FIG. 22, a pin extends through apertures defined in the proximal end 2344 and the tab 2314 to define a pivot axis therebetween. These pivot axes are collinear, or at least substantially collinear, and define an articulation axis A of the articulation joint 2300.

Referring primarily to FIGS. 20, 23, and 24, the outer housing 2410 of the distal attachment portion 2400 comprises a longitudinal aperture 2430 extending therethrough. The longitudinal aperture 2430 is configured to receive a proximal attachment portion 7400 of the end effector 7000. The end effector 7000 comprises an outer housing 6230 which is closely received within the longitudinal aperture 2430 of the distal attachment portion 2400 such that there is little, if any, relative radial movement between the proximal attachment portion 7400 of the end effector 7000 and the distal attachment portion 2400 of the shaft assembly 2000. The proximal attachment portion 7400 further comprises an annular array of lock notches 7410 defined on the outer housing 6230 which is releasably engaged by an end effector lock 6400 in the distal attachment portion 2400 of the shaft assembly 2000. When the end effector lock 6400 is engaged with the array of lock notches 7410, the end effector lock 6400 prevents, or at least inhibits, relative longitudinal movement between the proximal attachment portion 7400 of the end effector 7000 and the distal attachment portion 2400 of the shaft assembly 2000. As a result of the above, only relative rotation between the proximal attachment portion 7400 of the end effector 7000 and the distal attachment portion 2400 of the shaft assembly 2000 is permitted. To this end, the outer housing 6230 of the end effector 7000 is closely received within the longitudinal aperture 2430 defined in the distal attachment portion 2400 of the shaft assembly 2000.

Figure 21:
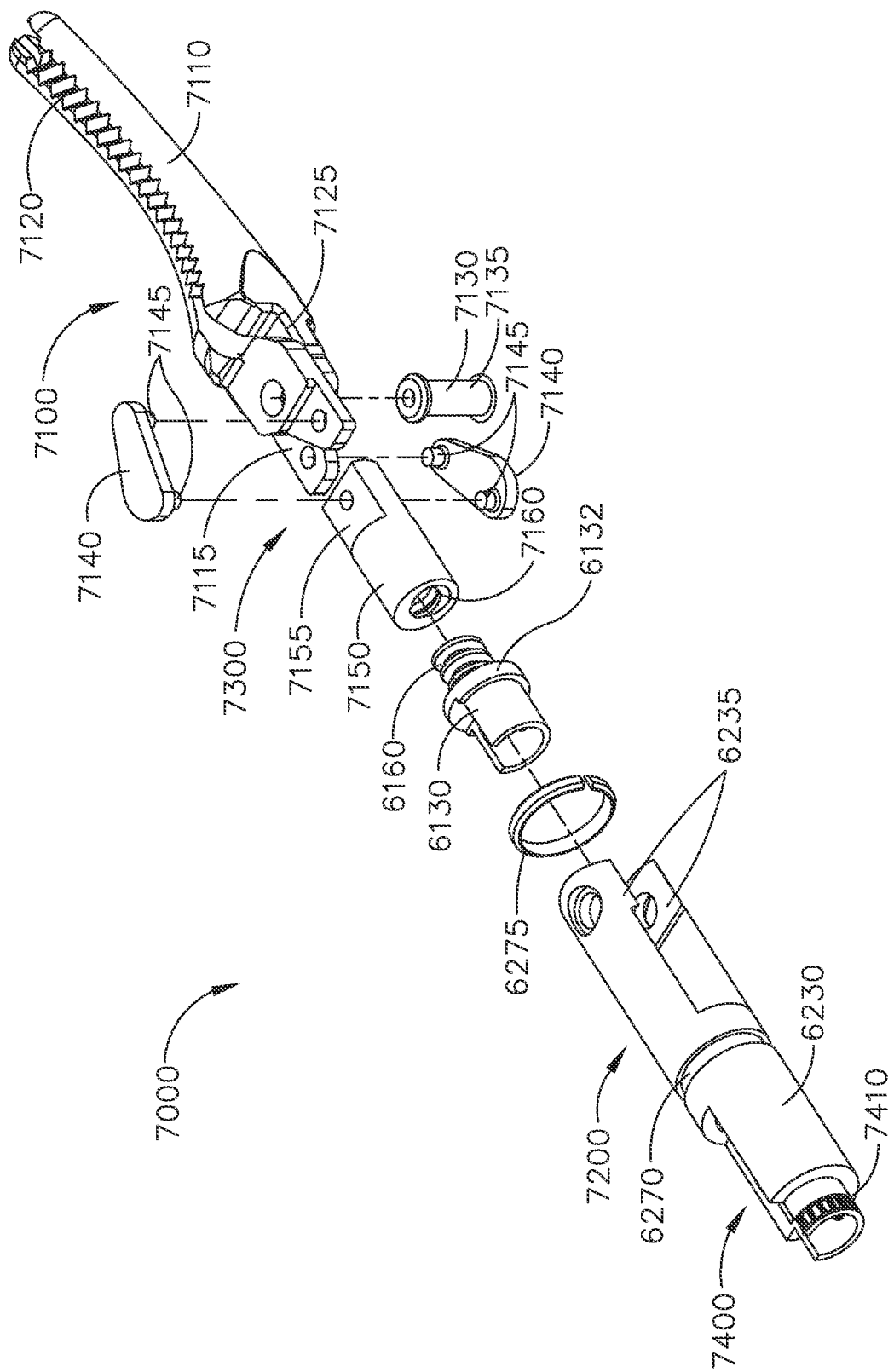
FIG. 21 is an exploded view of the end effector of FIG. 14 illustrated with some components removed.

Further to the above, referring to FIG. 21, the outer housing 6230 further comprises an annular slot, or recess, 6270 defined therein which is configured to receive an O-ring 6275 therein. The O-ring 6275 is compressed between the outer housing 6230 and the sidewall of the longitudinal aperture 2430 when the end effector 7000 is inserted into the distal attachment portion 2400. The O-ring 6275 is configured to resist, but permit, relative rotation between the end effector 7000 and the distal attachment portion 2400 such that the O-ring 6275 can prevent, or reduce the possibility of, unintentional relative rotation between the end effector 7000 and the distal attachment portion 2400. In various instances, the O-ring 6275 can provide a seal between the end effector 7000 and the distal attachment portion 2400 to prevent, or at least reduce the possibility of, fluid ingress into the shaft assembly 2000, for example.

Referring to FIGS. 14-21, the jaw assembly 7100 of the end effector 7000 comprises a first jaw 7110 and a second jaw 7120. Each jaw 7110, 7120 comprises a distal end which is configured to assist a clinician in dissecting tissue with the end effector 7000. Each jaw 7110, 7120 further comprises a plurality of teeth which are configured to assist a clinician in grasping and holding onto tissue with the end effector 7000. Moreover, referring primarily to FIG. 21, each jaw 7110, 7120 comprises a proximal end, i.e., proximal ends 7115, 7125, respectively, which rotatably connect the jaws 7110, 7120 together. Each proximal end 7115, 7125 comprises an aperture extending therethrough which is configured to closely receive a pin 7130 therein. The pin 7130 comprises a central body 7135 closely received within the apertures defined in the proximal ends 7115, 7125 of the jaws 7110, 7120 such that there is little, if any, relative translation between the jaws 7110, 7120 and the pin 7130. The pin 7130 defines a jaw axis J about which the jaws 7110, 7120 can be rotated and, also, rotatably mounts the jaws 7110, 7120 to the outer housing 6230 of the end effector 7000. More specifically, the outer housing 6230 comprises distally-extending tabs 6235 having apertures defined therein which are also configured to closely receive the pin 7130 such that the jaw assembly 7100 does not translate relative to a shaft portion 7200 of the end effector 7000. The pin 7130 further comprises enlarged ends which prevent the jaws 7110, 7120 from becoming detached from the pin 7130 and also prevents the jaw assembly 7100 from becoming detached from the shaft portion 7200. This arrangement defines a rotation joint 7300.

Referring primarily to FIGS. 21 and 23, the jaws 7110 and 7120 are rotatable between their open and closed positions by a jaw assembly drive including drive links 7140, a drive nut 7150, and a drive screw 6130. As described in greater detail below, the drive screw 6130 is selectively rotatable by the drive shaft 2730 of the shaft drive system 2700. The drive screw 6130 comprises an annular flange 6132 which is closely received within a slot, or groove, 6232 (FIG. 25) defined in the outer housing 6230 of the end effector 7000. The sidewalls of the slot 6232 are configured to prevent, or at least inhibit, longitudinal and/or radial translation between the drive screw 6130 and the outer housing 6230, but yet permit relative rotational motion between the drive screw 6130 and the outer housing 6230. The drive screw 6130 further comprises a threaded end 6160 which is threadably engaged with a threaded aperture 7160 defined in the drive nut 7150. The drive nut 7150 is constrained from rotating with the drive screw 6130 and, as a result, the drive nut 7150 is translated when the drive screw 6130 is rotated. In use, the drive screw 6130 is rotated in a first direction to displace the drive nut 7150 proximally and in a second, or opposite, direction to displace the drive nut 7150 distally. The drive nut 7150 further comprises a distal end 7155 comprising an aperture defined therein which is configured to closely receive pins 7145 extending from the drive links 7140. Referring primarily to FIG. 21, a first drive link 7140 is attached to one side of the distal end 7155 and a second drive link 7140 is attached to the opposite side of the distal end 7155. The first drive link 7140 comprises another pin 7145 extending therefrom which is closely received in an aperture defined in the proximal end 7115 of the first jaw 7110 and, similarly, the second drive link 7140 comprises another pin extending therefrom which is closely received in an aperture defined in the proximal end 7125 of the second jaw 7120. As a result of the above, the drive links 7140 operably connect the jaws 7110 and 7120 to the drive nut 7150. When the drive nut 7150 is driven proximally by the drive screw 6130, as described above, the jaws 7110, 7120 are rotated into the closed, or clamped, configuration. Correspondingly, the jaws 7110, 7120 are rotated into their open configuration when the drive nut 7150 is driven distally by the drive screw 6130.

Figure 16:
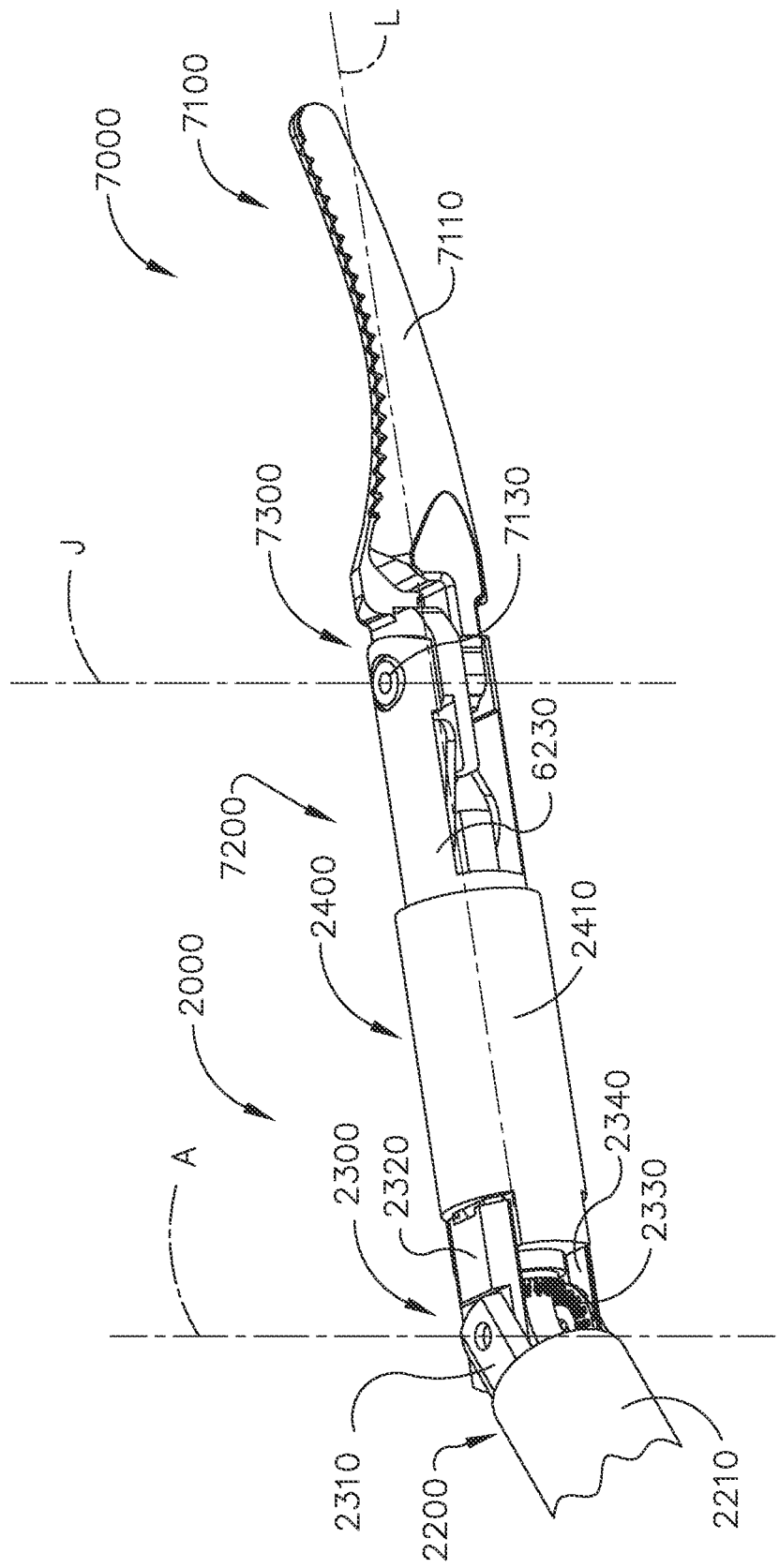
FIG. 16 is a partial perspective view of the end effector of FIG. 14 articulated in a first direction.
Figure 17:
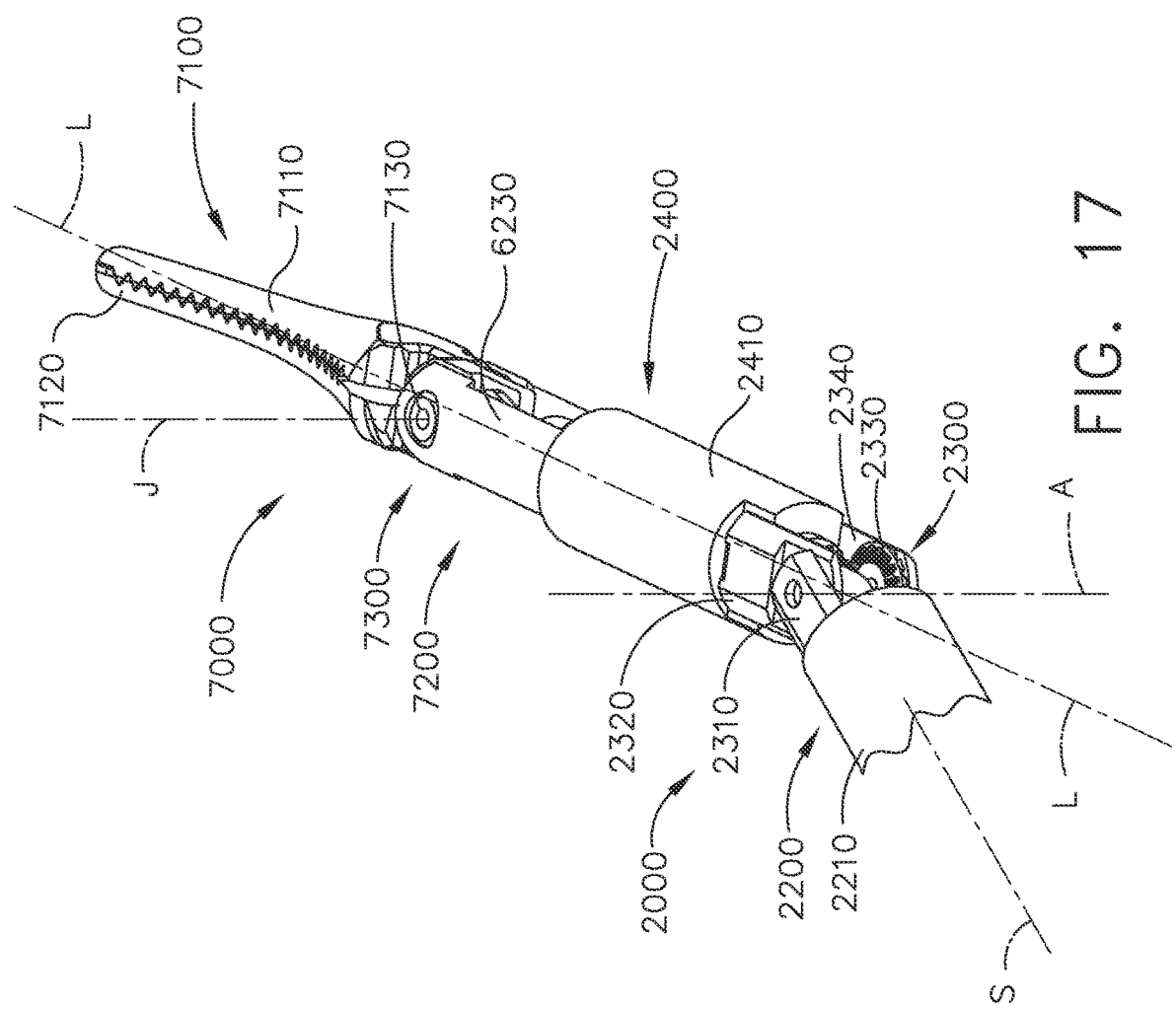
FIG. 17 is a partial perspective view of the end effector of FIG. 14 articulated in a second direction.
Figure 18:
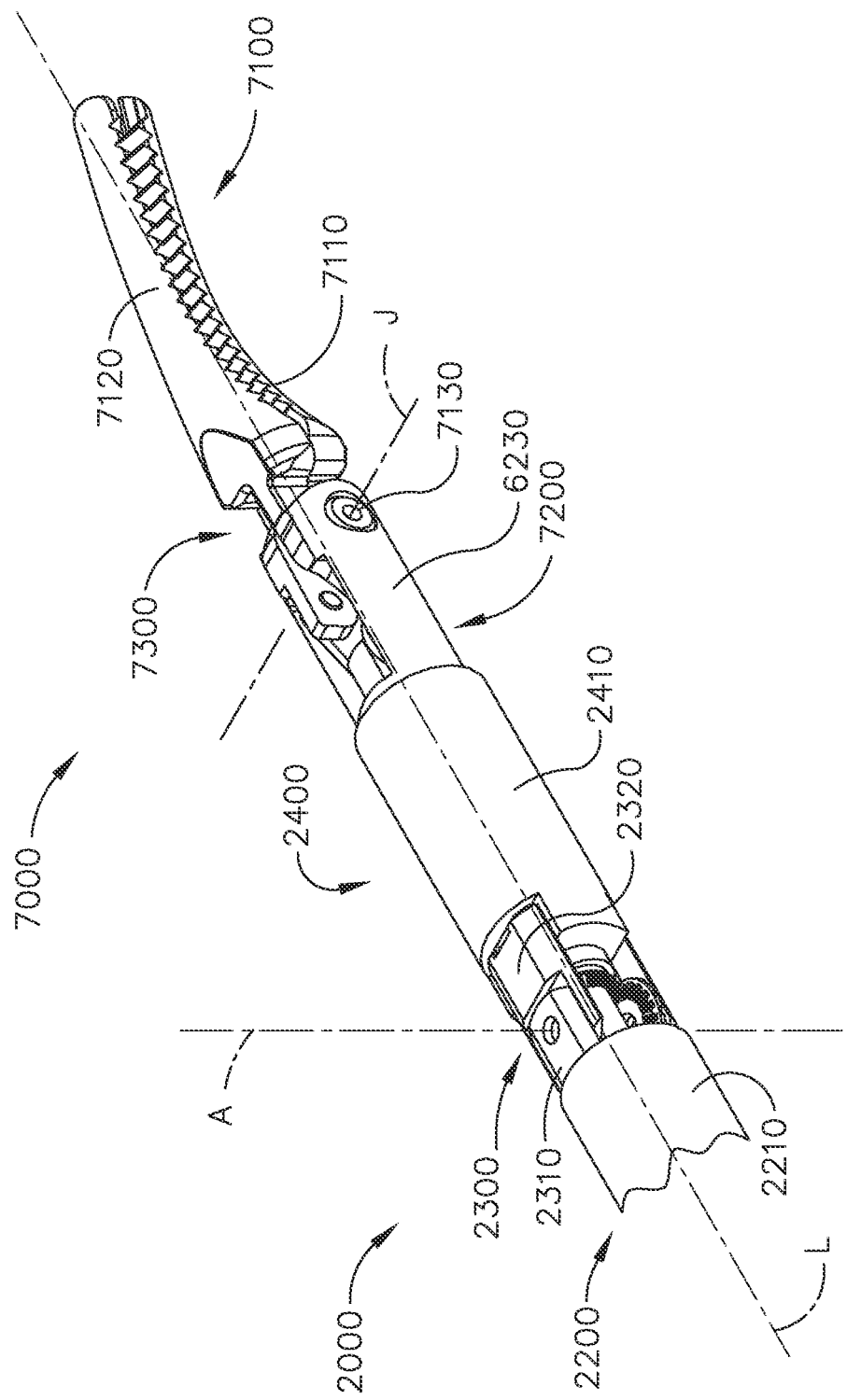
FIG. 18 is a partial perspective view of the end effector of FIG. 14 rotated in a first direction.
Figure 19:
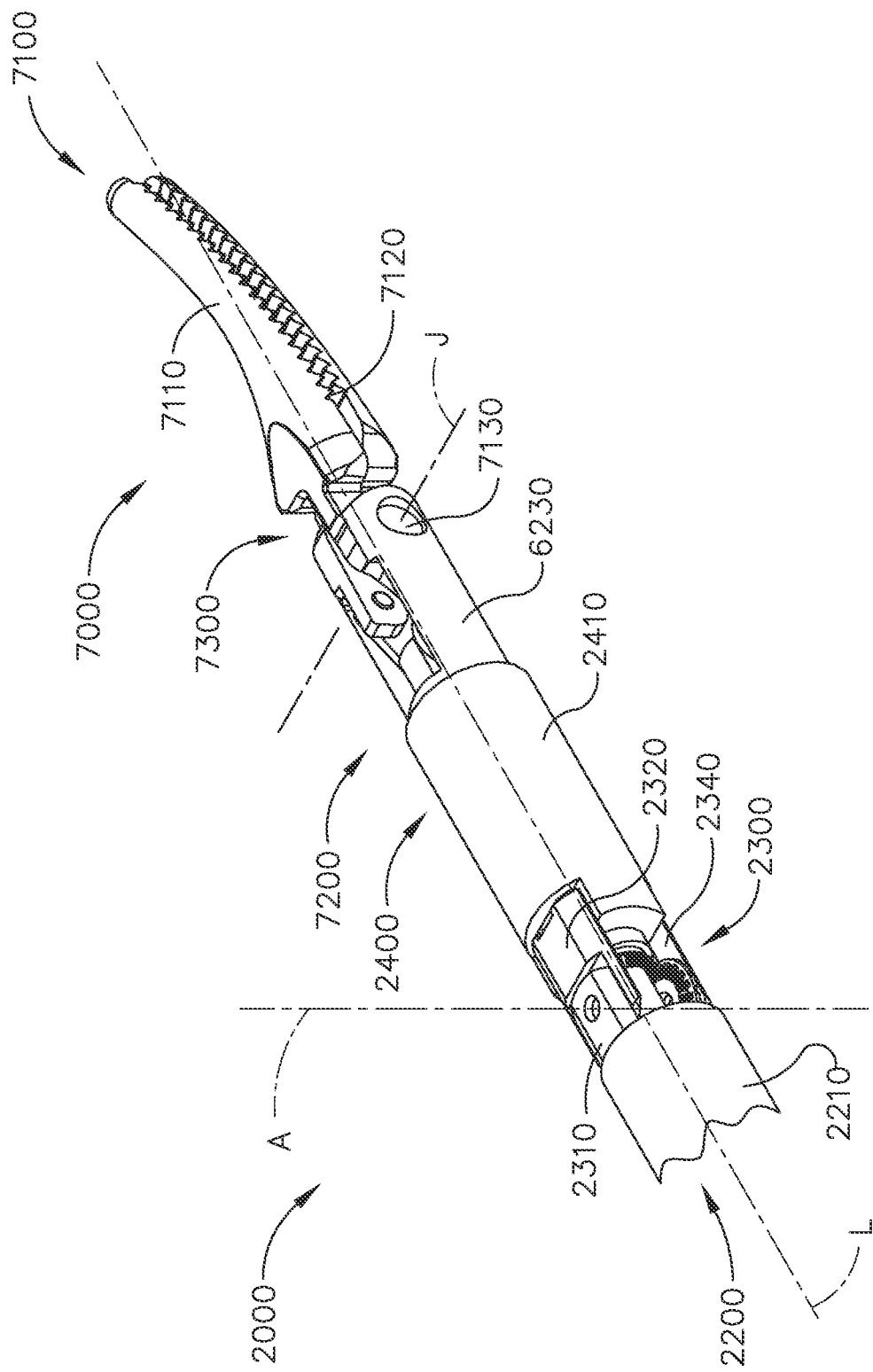
FIG. 19 is a partial perspective view of the end effector of FIG. 14 rotated in a second direction.
Figure 26:
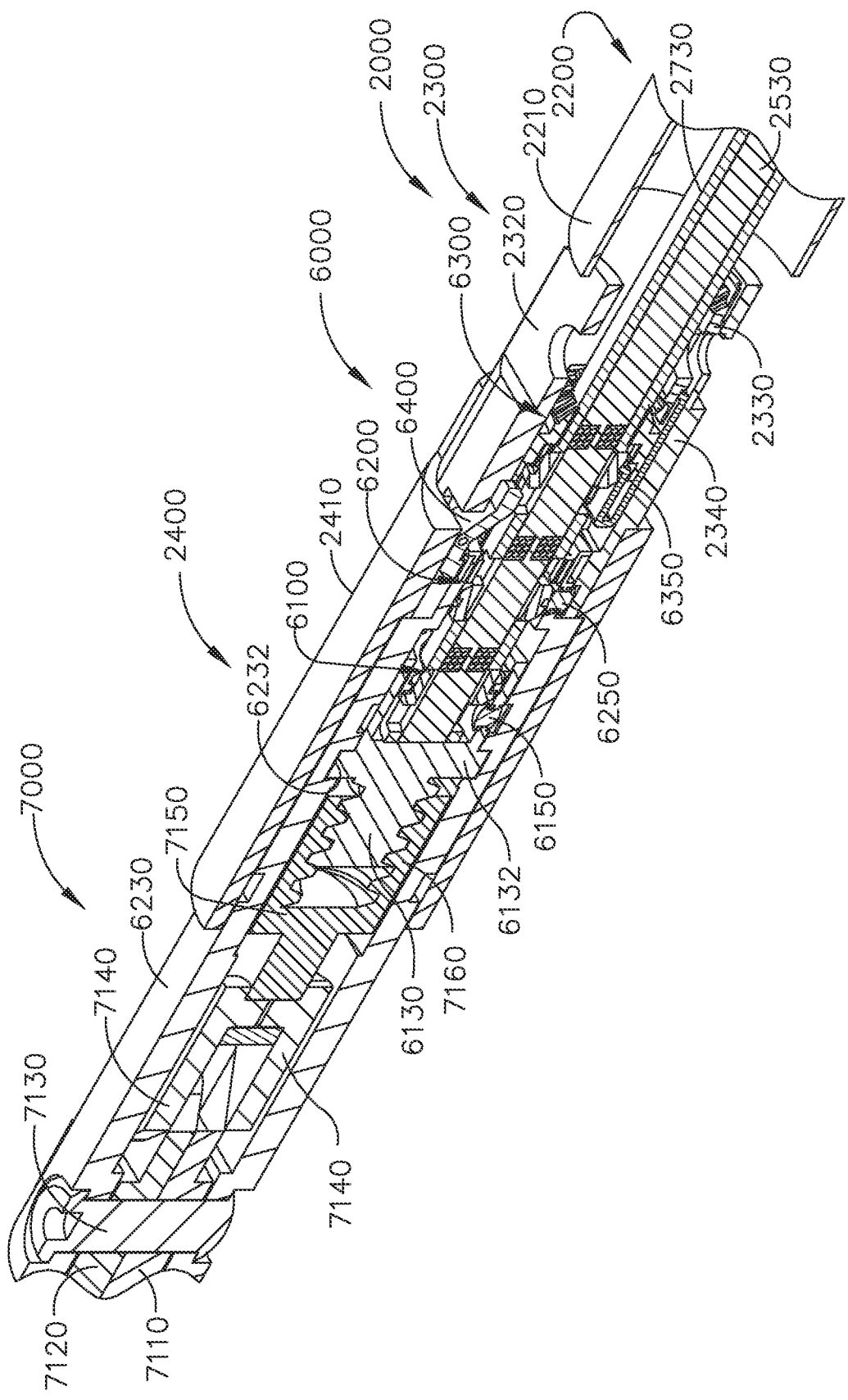
FIG. 26 is another partial cross-sectional perspective view of the end effector of FIG. 14 attached to the shaft assembly of FIG. 2.
Figure 27:
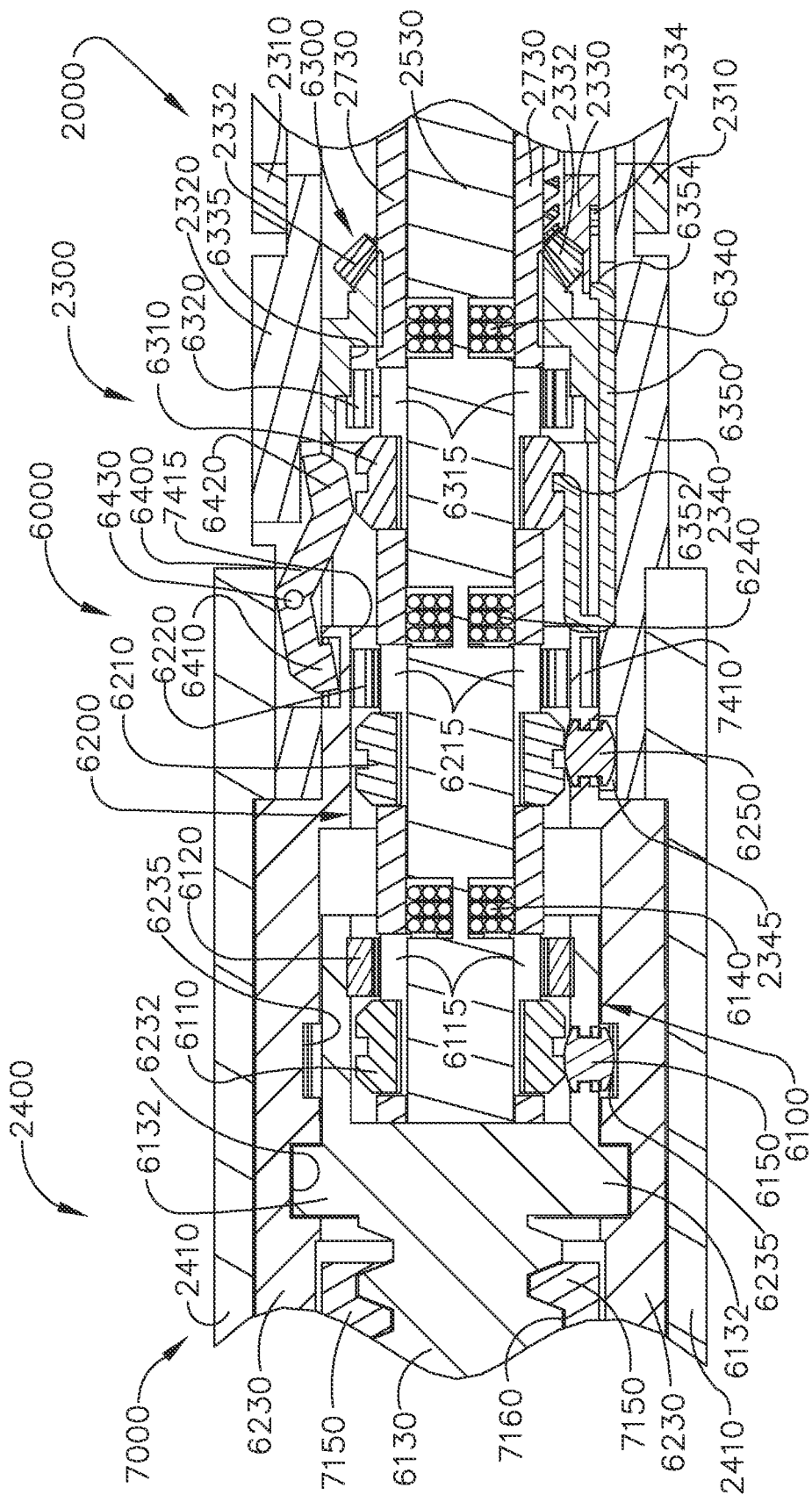
FIG. 27 is a partial cross-sectional view of the end effector of FIG. 14 attached to the shaft assembly of FIG. 2 depicting a first, second, and third clutch of the end effector.

As discussed above, the control system 1800 is configured to actuate the electric motor 1610 to perform three different end effector functions—clamping/opening the jaw assembly 7100 (FIGS. 14 and 15), rotating the end effector 7000 about a longitudinal axis (FIGS. 18 and 19), and articulating the end effector 7000 about an articulation axis (FIGS. 16 and 17). Referring primarily to FIGS. 26 and 27, the control system 1800 is configured to operate a transmission 6000 to selectively perform these three end effector functions. The transmission 6000 comprises a first clutch system 6100 configured to selectively transmit the rotation of the drive shaft 2730 to the drive screw 6130 of the end effector 7000 to open or close the jaw assembly 7100, depending on the direction in which the drive shaft 2730 is rotated. The transmission 6000 further comprises a second clutch system 6200 configured to selectively transmit the rotation of the drive shaft 2730 to the outer housing 6230 of the end effector 7000 to rotate the end effector 7000 about the longitudinal axis L. The transmission 6000 also comprises a third clutch system 6300 configured to selectively transmit the rotation of the drive shaft 2730 to the articulation joint 2300 to articulate the distal attachment portion 2400 and the end effector 7000 about the articulation axis A. The clutch systems 6100, 6200, and 6300 are in electrical communication with the control system 1800 via electrical circuits extending through the shaft 2510, the connector pins 2520, the connector pins 1520, and the shaft 1510, for example. In at least one instance, each of these clutch control circuits comprises two connector pins 2520 and two connector pins 1520, for example.

In various instances, further to the above, the shaft 2510 and/or the shaft 1510 comprise a flexible circuit including electrical traces which form part of the clutch control circuits. The flexible circuit can comprise a ribbon, or substrate, with conductive pathways defined therein and/or thereon. The flexible circuit can also comprise sensors and/or any solid state component, such as signal smoothing capacitors, for example, mounted thereto. In at least one instance, each of the conductive pathways can comprise one or more signal smoothing capacitors which can, among other things, even out fluctuations in signals transmitted through the conductive pathways. In various instances, the flexible circuit can be coated with at least one material, such as an elastomer, for example, which can seal the flexible circuit against fluid ingress.

Figure 22A:
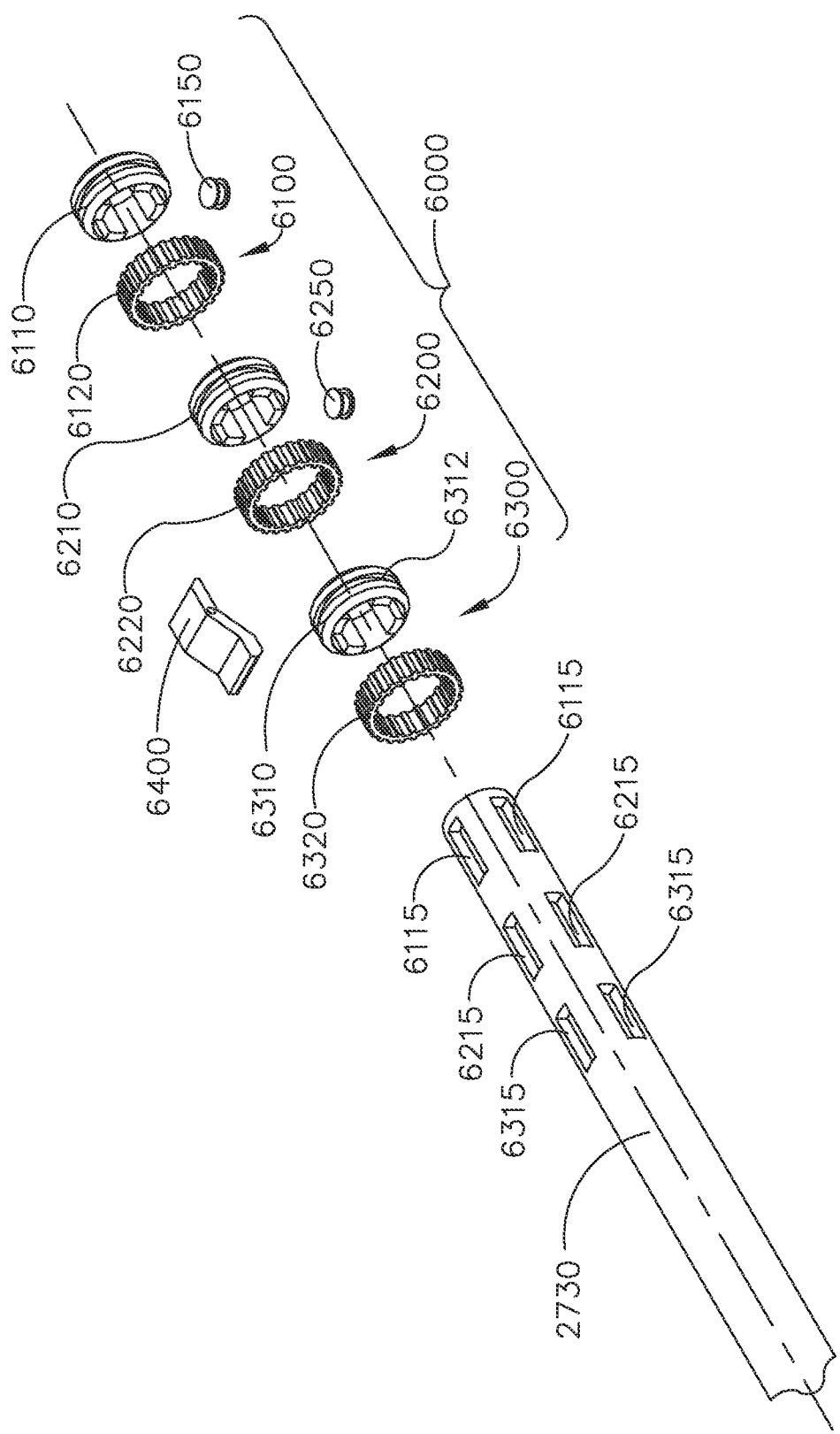
FIG. 22A is an exploded view of the distal portion of the shaft assembly of FIG. 2 illustrated with some components removed.
Figure 28:
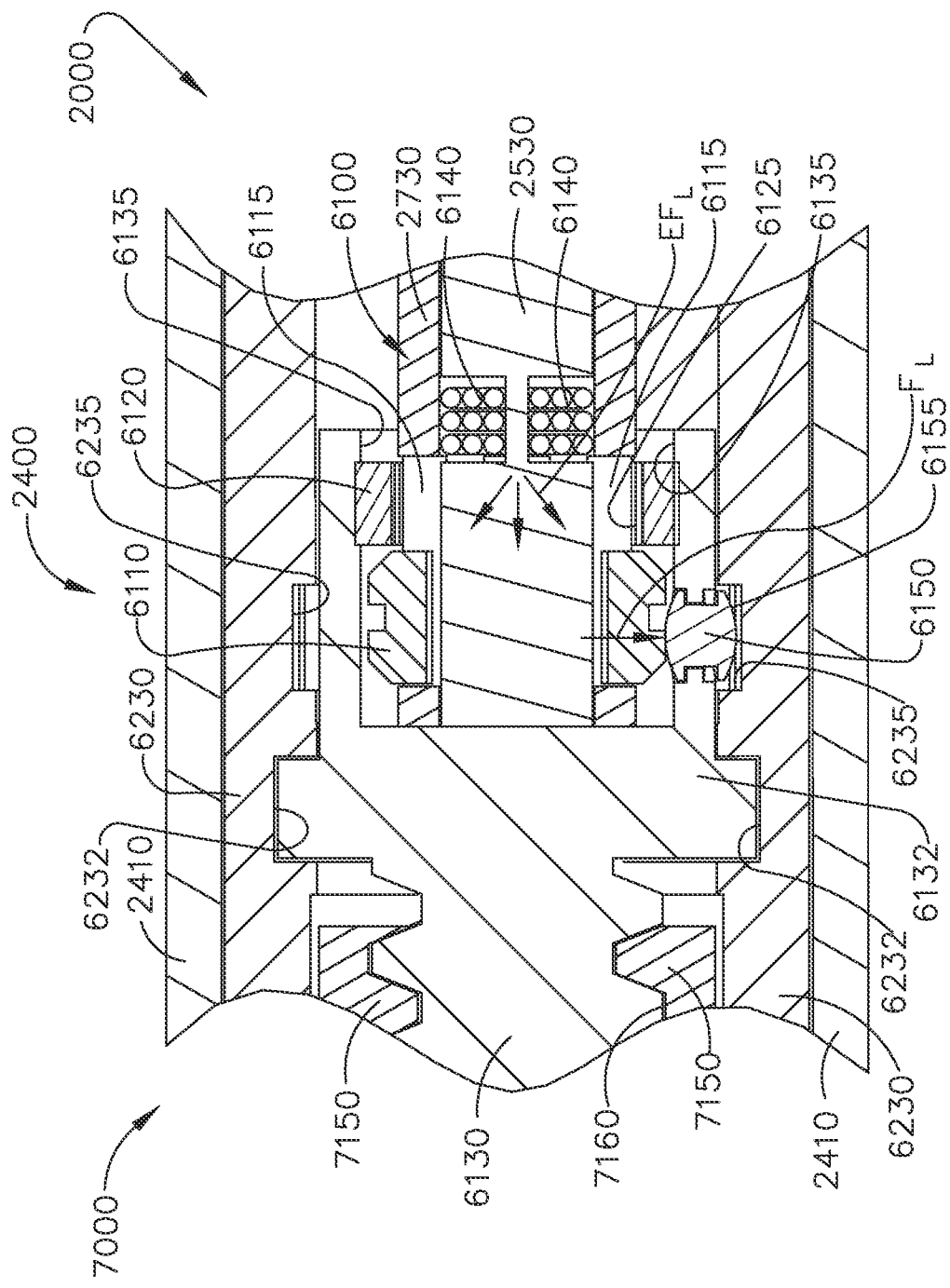
FIG. 28 depicts the first clutch of FIG. 27 in an unactuated condition.

Referring primarily to FIG. 28, the first clutch system 6100 comprises a first clutch 6110, an expandable first drive ring 6120, and a first electromagnetic actuator 6140. The first clutch 6110 comprises an annular ring and is slideably disposed on the drive shaft 2730. The first clutch 6110 is comprised of a magnetic material and is movable between a disengaged, or unactuated, position (FIG. 28) and an engaged, or actuated, position (FIG. 29) by electromagnetic fields EF generated by the first electromagnetic actuator 6140. In various instances, the first clutch 6110 is at least partially comprised of iron and/or nickel, for example. In at least one instance, the first clutch 6110 comprises a permanent magnet. As illustrated in FIG. 22A, the drive shaft 2730 comprises one or more longitudinal key slots 6115 defined therein which are configured to constrain the longitudinal movement of the clutch 6110 relative to the drive shaft 2730. More specifically, the clutch 6110 comprises one or more keys extending into the key slots 6115 such that the distal ends of the key slots 6115 stop the distal movement of the clutch 6110 and the proximal ends of the key slots 6115 stop the proximal movement of the clutch 6110.

Figure 29:
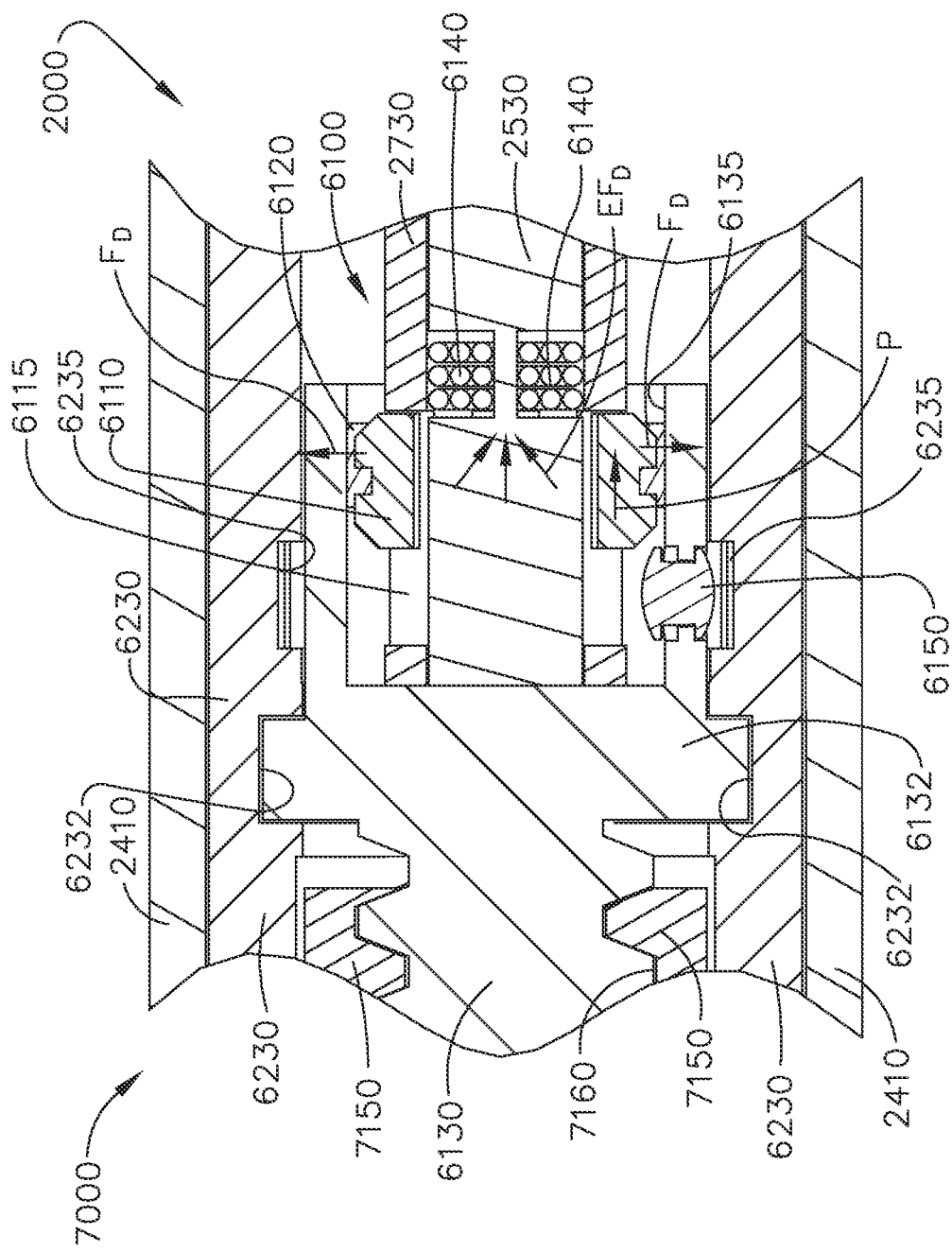
FIG. 29 depicts the first clutch of FIG. 27 in an actuated condition.

When the first clutch 6110 is in its disengaged position (FIG. 28), the first clutch 6110 rotates with the drive shaft 2130 but does not transmit rotational motion to the first drive ring 6120. As can be seen in FIG. 28, the first clutch 6110 is separated from, or not in contact with, the first drive ring 6120. As a result, the rotation of the drive shaft 2730 and the first clutch 6110 is not transmitted to the drive screw 6130 when the first clutch assembly 6100 is in its disengaged state. When the first clutch 6110 is in its engaged position (FIG. 29), the first clutch 6110 is engaged with the first drive ring 6120 such that the first drive ring 6120 is expanded, or stretched, radially outwardly into contact with the drive screw 6130. In at least one instance, the first drive ring 6120 comprises an elastomeric band, for example. As can be seen in FIG. 29, the first drive ring 6120 is compressed against an annular inner sidewall 6135 of the drive screw 6130. As a result, the rotation of the drive shaft 2730 and the first clutch 6110 is transmitted to the drive screw 6130 when the first clutch assembly 6100 is in its engaged state. Depending on the direction in which the drive shaft 2730 is rotated, the first clutch assembly 6100 can move the jaw assembly 7100 into its open and closed configurations when the first clutch assembly 6100 is in its engaged state.

As described above, the first electromagnetic actuator 6140 is configured to generate magnetic fields to move the first clutch 6110 between its disengaged (FIG. 28) and engaged (FIG. 29) positions. For instance, referring to FIG. 28, the first electromagnetic actuator 6140 is configured to emit a magnetic field EFL which repulses, or drives, the first clutch 6110 away from the first drive ring 6120 when the first clutch assembly 6100 is in its disengaged state. The first electromagnetic actuator 6140 comprises one or more wound coils in a cavity defined in the shaft frame 2530 which generate the magnetic field EFL when current flows in a first direction through a first electrical clutch circuit including the wound coils. The control system 1800 is configured to apply a first voltage polarity to the first electrical clutch circuit to create the current flowing in the first direction. The control system 1800 can continuously apply the first voltage polarity to the first electric shaft circuit to continuously hold the first clutch 6110 in its disengaged position. While such an arrangement can prevent the first clutch 6110 from unintentionally engaging the first drive ring 6120, such an arrangement can also consume a lot of power. Alternatively, the control system 1800 can apply the first voltage polarity to the first electrical clutch circuit for a sufficient period of time to position the first clutch 6110 in its disengaged position and then discontinue applying the first voltage polarity to the first electric clutch circuit, thereby resulting in a lower consumption of power. That being said, the first clutch assembly 6100 further comprises a first clutch lock 6150 mounted in the drive screw 6130 which is configured to releasably hold the first clutch 6110 in its disengaged position. The first clutch lock 6150 is configured to prevent, or at least reduce the possibility of, the first clutch 6110 from becoming unintentionally engaged with the first drive ring 6120. When the first clutch 6110 is in its disengaged position, as illustrated in FIG. 28, the first clutch lock 6150 interferes with the free movement of the first clutch 6110 and holds the first clutch 6110 in position via a friction force and/or an interference force therebetween. In at least one instance, the first clutch lock 6150 comprises an elastomeric plug, seat, or detent, comprised of rubber, for example. In certain instances, the first clutch lock 6150 comprises a permanent magnet which holds the first clutch 6110 in its disengaged position by an electromagnetic force. In any event, the first electromagnetic actuator 6140 can apply an electromagnetic pulling force to the first clutch 6110 that overcomes these forces, as described in greater detail below.

Further to the above, referring to FIG. 29, the first electromagnetic actuator 6140 is configured to emit a magnetic field EFD which pulls, or drives, the first clutch 6110 toward the first drive ring 6120 when the first clutch assembly 6100 is in its engaged state. The coils of the first electromagnetic actuator 6140 generate the magnetic field EFD when current flows in a second, or opposite, direction through the first electrical clutch circuit. The control system 1800 is configured to apply an opposite voltage polarity to the first electrical clutch circuit to create the current flowing in the opposite direction. The control system 1800 can continuously apply the opposite voltage polarity to the first electrical clutch circuit to continuously hold the first clutch 6110 in its engaged position and maintain the operable engagement between the first drive ring 6120 and the drive screw 6130. Alternatively, the first clutch 6110 can be configured to become wedged within the first drive ring 6120 when the first clutch 6110 is in its engaged position and, in such instances, the control system 1800 may not need to continuously apply a voltage polarity to the first electrical clutch circuit to hold the first clutch assembly 6100 in its engaged state. In such instances, the control system 1800 can discontinue applying the voltage polarity once the first clutch 6110 has been sufficiently wedged in the first drive ring 6120.

Notably, further to the above, the first clutch lock 6150 is also configured to lockout the jaw assembly drive when the first clutch 6110 is in its disengaged position. More specifically, referring again to FIG. 28, the first clutch 6110 pushes the first clutch lock 6150 in the drive screw 6130 into engagement with the outer housing 6230 of the end effector 7000 when the first clutch 6110 is in its disengaged position such that the drive screw 6130 does not rotate, or at least substantially rotate, relative to the outer housing 6230. The outer housing 6230 comprises a slot 6235 defined therein which is configured to receive the first clutch lock 6150. When the first clutch 6110 is moved into its engaged position, referring to FIG. 29, the first clutch 6110 is no longer engaged with the first clutch lock 6150 and, as a result, the first clutch lock 6150 is no longer biased into engagement with the outer housing 6230 and the drive screw 6130 can rotate freely with respect to the outer housing 6230. As a result of the above, the first clutch 6110 can do at least two things—operate the jaw drive when the first clutch 6110 is in its engaged position and lock out the jaw drive when the first clutch 6110 is in its disengaged position.

Moreover, further to the above, the threads of the threaded portions 6160 and 7160 can be configured to prevent, or at least resist, backdriving of the jaw drive. In at least one instance, the thread pitch and/or angle of the threaded portions 6160 and 7160, for example, can be selected to prevent the backdriving, or unintentional opening, of the jaw assembly 7100. As a result of the above, the possibility of the jaw assembly 7100 unintentionally opening or closing is prevented, or at least reduced.

Figure 30:
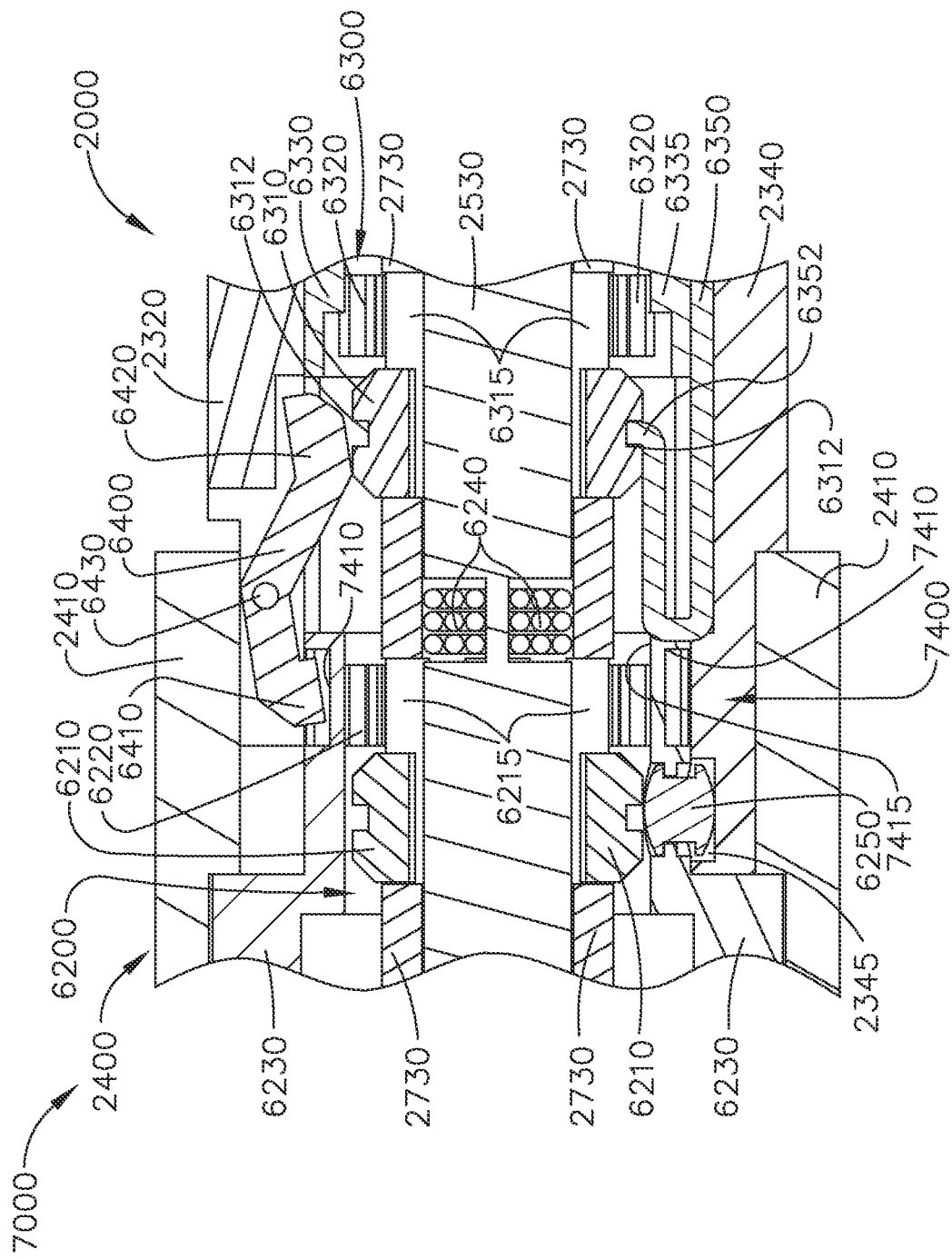
FIG. 30 depicts the second clutch of FIG. 27 in an unactuated condition.

Referring primarily to FIG. 30, the second clutch system 6200 comprises a second clutch 6210, an expandable second drive ring 6220, and a second electromagnetic actuator 6240. The second clutch 6210 comprises an annular ring and is slideably disposed on the drive shaft 2730. The second clutch 6210 is comprised of a magnetic material and is movable between a disengaged, or unactuated, position (FIG. 30) and an engaged, or actuated, position (FIG. 31) by electromagnetic fields EF generated by the second electromagnetic actuator 6240. In various instances, the second clutch 6210 is at least partially comprised of iron and/or nickel, for example. In at least one instance, the second clutch 6210 comprises a permanent magnet. As illustrated in FIG. 22A, the drive shaft 2730 comprises one or more longitudinal key slots 6215 defined therein which are configured to constrain the longitudinal movement of the second clutch 6210 relative to the drive shaft 2730. More specifically, the second clutch 6210 comprises one or more keys extending into the key slots 6215 such that the distal ends of the key slots 6215 stop the distal movement of the second clutch 6210 and the proximal ends of the key slots 6215 stop the proximal movement of the second clutch 6210.

Figure 31:
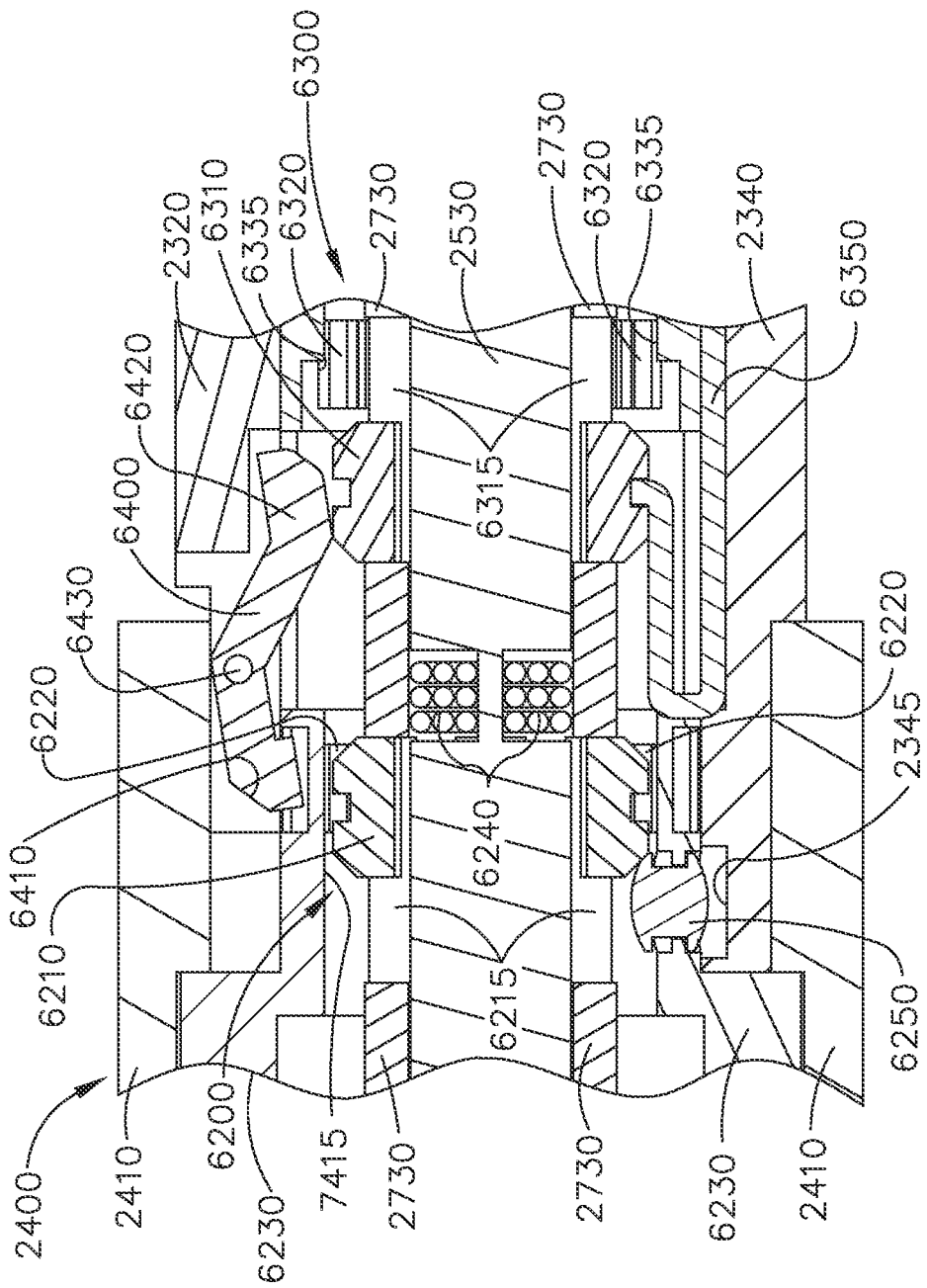
FIG. 31 depicts the second clutch of FIG. 27 in an actuated condition.

When the second clutch 6210 is in its disengaged position, referring to FIG. 30, the second clutch 6210 rotates with the drive shaft 2730 but does not transmit rotational motion to the second drive ring 6220. As can be seen in FIG. 30, the second clutch 6210 is separated from, or not in contact with, the second drive ring 6220. As a result, the rotation of the drive shaft 2730 and the second clutch 6210 is not transmitted to the outer housing 6230 of the end effector 7000 when the second clutch assembly 6200 is in its disengaged state. When the second clutch 6210 is in its engaged position (FIG. 31), the second clutch 6210 is engaged with the second drive ring 6220 such that the second drive ring 6220 is expanded, or stretched, radially outwardly into contact with the outer housing 6230. In at least one instance, the second drive ring 6220 comprises an elastomeric band, for example. As can be seen in FIG. 31, the second drive ring 6220 is compressed against an annular inner sidewall 7415 of the outer housing 6230. As a result, the rotation of the drive shaft 2730 and the second clutch 6210 is transmitted to the outer housing 6230 when the second clutch assembly 6200 is in its engaged state. Depending on the direction in which the drive shaft 2730 is rotated, the second clutch assembly 6200 can rotate the end effector 7000 in a first direction or a second direction about the longitudinal axis L when the second clutch assembly 6200 is in its engaged state.

As described above, the second electromagnetic actuator 6240 is configured to generate magnetic fields to move the second clutch 6210 between its disengaged (FIG. 30) and engaged (FIG. 31) positions. For instance, the second electromagnetic actuator 6240 is configured to emit a magnetic field EFL which repulses, or drives, the second clutch 6210 away from the second drive ring 6220 when the second clutch assembly 6200 is in its disengaged state. The second electromagnetic actuator 6240 comprises one or more wound coils in a cavity defined in the shaft frame 2530 which generate the magnetic field EFL when current flows in a first direction through a second electrical clutch circuit including the wound coils. The control system 1800 is configured to apply a first voltage polarity to the second electrical clutch circuit to create the current flowing in the first direction. The control system 1800 can continuously apply the first voltage polarity to the second electric clutch circuit to continuously hold the second clutch 6120 in its disengaged position. While such an arrangement can prevent the second clutch 6210 from unintentionally engaging the second drive ring 6220, such an arrangement can also consume a lot of power. Alternatively, the control system 1800 can apply the first voltage polarity to the second electrical clutch circuit for a sufficient period of time to position the second clutch 6210 in its disengaged position and then discontinue applying the first voltage polarity to the second electric clutch circuit, thereby resulting in a lower consumption of power. That being said, the second clutch assembly 6200 further comprises a second clutch lock 6250 mounted in the outer housing 6230 which is configured to releasably hold the second clutch 6210 in its disengaged position. Similar to the above, the second clutch lock 6250 can prevent, or at least reduce the possibility of, the second clutch 6210 from becoming unintentionally engaged with the second drive ring 6220. When the second clutch 6210 is in its disengaged position, as illustrated in FIG. 30, the second clutch lock 6250 interferes with the free movement of the second clutch 6210 and holds the second clutch 6210 in position via a friction and/or interference force therebetween. In at least one instance, the second clutch lock 6250 comprises an elastomeric plug, seat, or detent, comprised of rubber, for example. In certain instances, the second clutch lock 6250 comprises a permanent magnet which holds the second clutch 6210 in its disengaged position by an electromagnetic force. That said, the second electromagnetic actuator 6240 can apply an electromagnetic pulling force to the second clutch 6210 that overcomes these forces, as described in greater detail below.

Further to the above, referring to FIG. 31, the second electromagnetic actuator 6240 is configured to emit a magnetic field EFD which pulls, or drives, the second clutch 6210 toward the second drive ring 6220 when the second clutch assembly 6200 is in its engaged state. The coils of the second electromagnetic actuator 6240 generate the magnetic field EFD when current flows in a second, or opposite, direction through the second electrical shaft circuit. The control system 1800 is configured to apply an opposite voltage polarity to the second electrical shaft circuit to create the current flowing in the opposite direction. The control system 1800 can continuously apply the opposite voltage polarity to the second electric shaft circuit to continuously hold the second clutch 6210 in its engaged position and maintain the operable engagement between the second drive ring 6220 and the outer housing 6230. Alternatively, the second clutch 6210 can be configured to become wedged within the second drive ring 6220 when the second clutch 6210 is in its engaged position and, in such instances, the control system 1800 may not need to continuously apply a voltage polarity to the second shaft electrical circuit to hold the second clutch assembly 6200 in its engaged state. In such instances, the control system 1800 can discontinue applying the voltage polarity once the second clutch 6210 has been sufficiently wedged in the second drive ring 6220.

Notably, further to the above, the second clutch lock 6250 is also configured to lockout the rotation of the end effector 7000 when the second clutch 6210 is in its disengaged position. More specifically, referring again to FIG. 30, the second clutch 6210 pushes the second clutch lock 6250 in the outer shaft 6230 into engagement with the articulation link 2340 when the second clutch 6210 is in its disengaged position such that the end effector 7000 does not rotate, or at least substantially rotate, relative to the distal attachment portion 2400 of the shaft assembly 2000. As illustrated in FIG. 27, the second clutch lock 6250 is positioned or wedged within a slot, or channel, 2345 defined in the articulation link 2340 when the second clutch 6210 is in its disengaged position. As a result of the above, the possibility of the end effector 7000 unintentionally rotating is prevented, or at least reduced. Moreover, as a result of the above, the second clutch 6210 can do at least two things—operate the end effector rotation drive when the second clutch 6210 is in its engaged position and lock out the end effector rotation drive when the second clutch 6210 is in its disengaged position.

Figure 25:
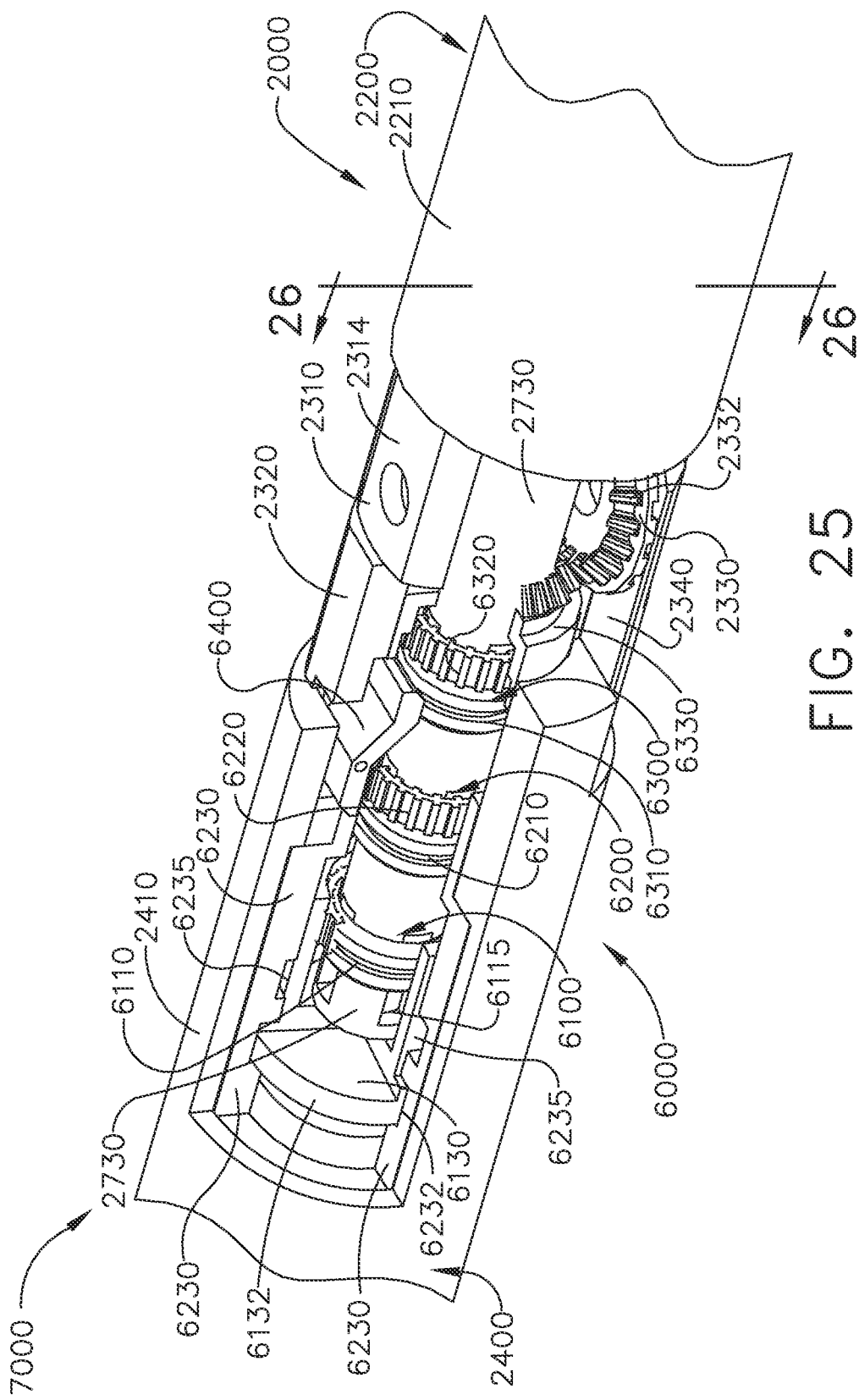
FIG. 25 is a partial cross-sectional perspective view of the end effector of FIG. 14 attached to the shaft assembly of FIG. 2.

Referring primarily to FIGS. 22, 24, and 25, the shaft assembly 2000 further comprises an articulation drive system configured to articulate the distal attachment portion 2400 and the end effector 7000 about the articulation joint 2300. The articulation drive system comprises an articulation drive 6330 rotatably supported within the distal attachment portion 2400. That said, the articulation drive 6330 is closely received within the distal attachment portion 2400 such that the articulation drive 6330 does not translate, or at least substantially translate, relative to the distal attachment portion 2400. The articulation drive system of the shaft assembly 2000 further comprises a stationary gear 2330 fixedly mounted to the articulation frame 2310. More specifically, the stationary gear 2330 is fixedly mounted to a pin connecting a tab 2314 of the articulation frame 2310 and the articulation link 2340 such that the stationary gear 2330 does not rotate relative to the articulation frame 2310. The stationary gear 2330 comprises a central body 2335 and an annular array of stationary teeth 2332 extending around the perimeter of the central body 2335. The articulation drive 6330 comprises an annular array of drive teeth 6332 which is meshingly engaged with the stationary teeth 2332. When the articulation drive 6330 is rotated, the articulation drive 6330 pushes against the stationary gear 2330 and articulates the distal attachment portion 2400 of the shaft assembly 2000 and the end effector 7000 about the articulation joint 2300.

Figure 32:
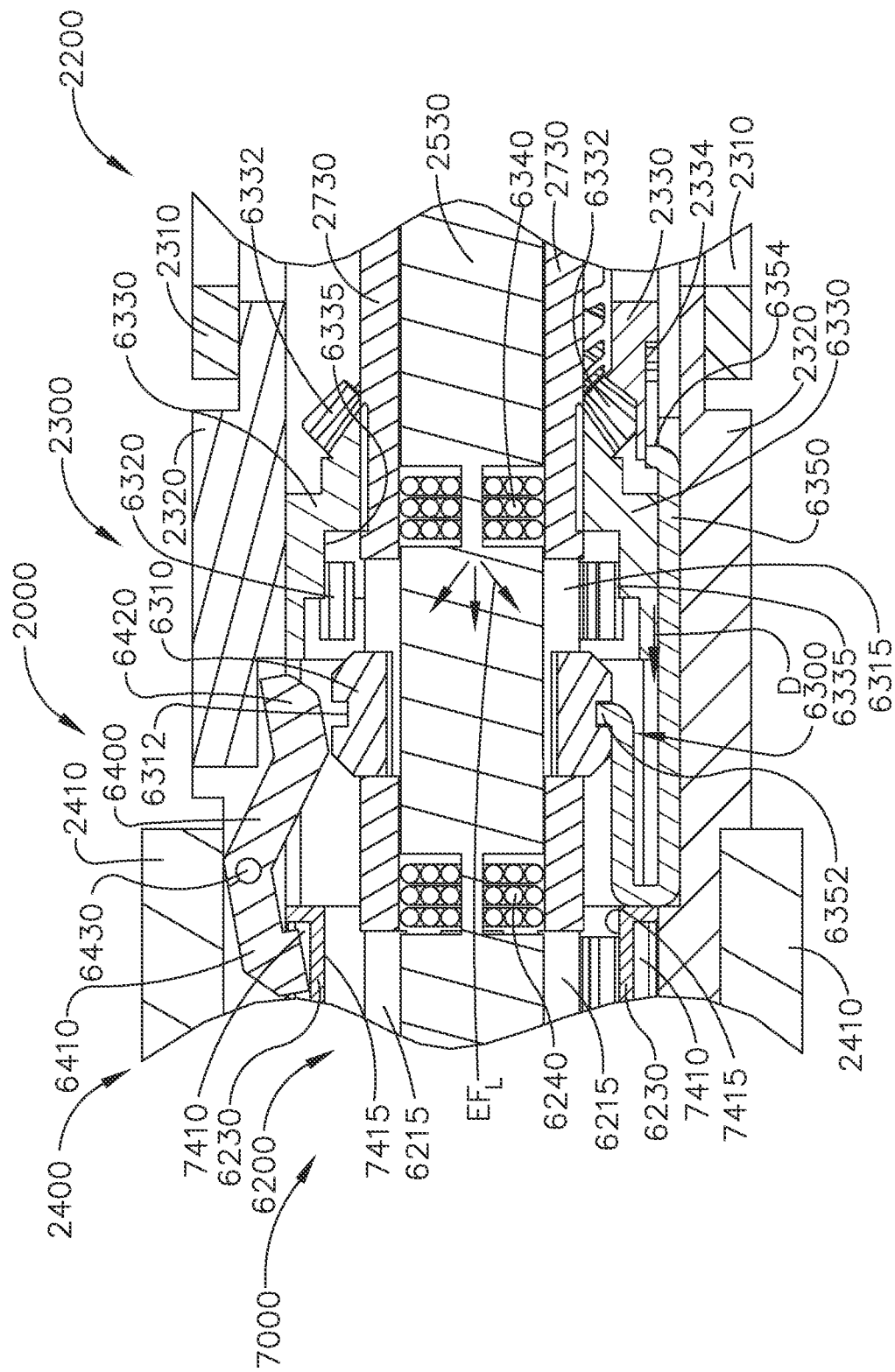
FIG. 32 depicts the third clutch of FIG. 27 in an unactuated condition.

Referring primarily to FIG. 32, the third clutch system 6300 comprises a third clutch 6310, an expandable third drive ring 6320, and a third electromagnetic actuator 6340. The third clutch 6310 comprises an annular ring and is slideably disposed on the drive shaft 2730. The third clutch 6310 is comprised of a magnetic material and is movable between a disengaged, or unactuated, position (FIG. 32) and an engaged, or actuated, position (FIG. 33) by electromagnetic fields EF generated by the third electromagnetic actuator 6340. In various instances, the third clutch 6310 is at least partially comprised of iron and/or nickel, for example. In at least one instance, the third clutch 6310 comprises a permanent magnet. As illustrated in FIG. 22A, the drive shaft 2730 comprises one or more longitudinal key slots 6315 defined therein which are configured to constrain the longitudinal movement of the third clutch 6310 relative to the drive shaft 2730. More specifically, the third clutch 6310 comprises one or more keys extending into the key slots 6315 such that the distal ends of the key slots 6315 stop the distal movement of the third clutch 6310 and the proximal ends of the key slots 6315 stop the proximal movement of the third clutch 6310.

Figure 33:
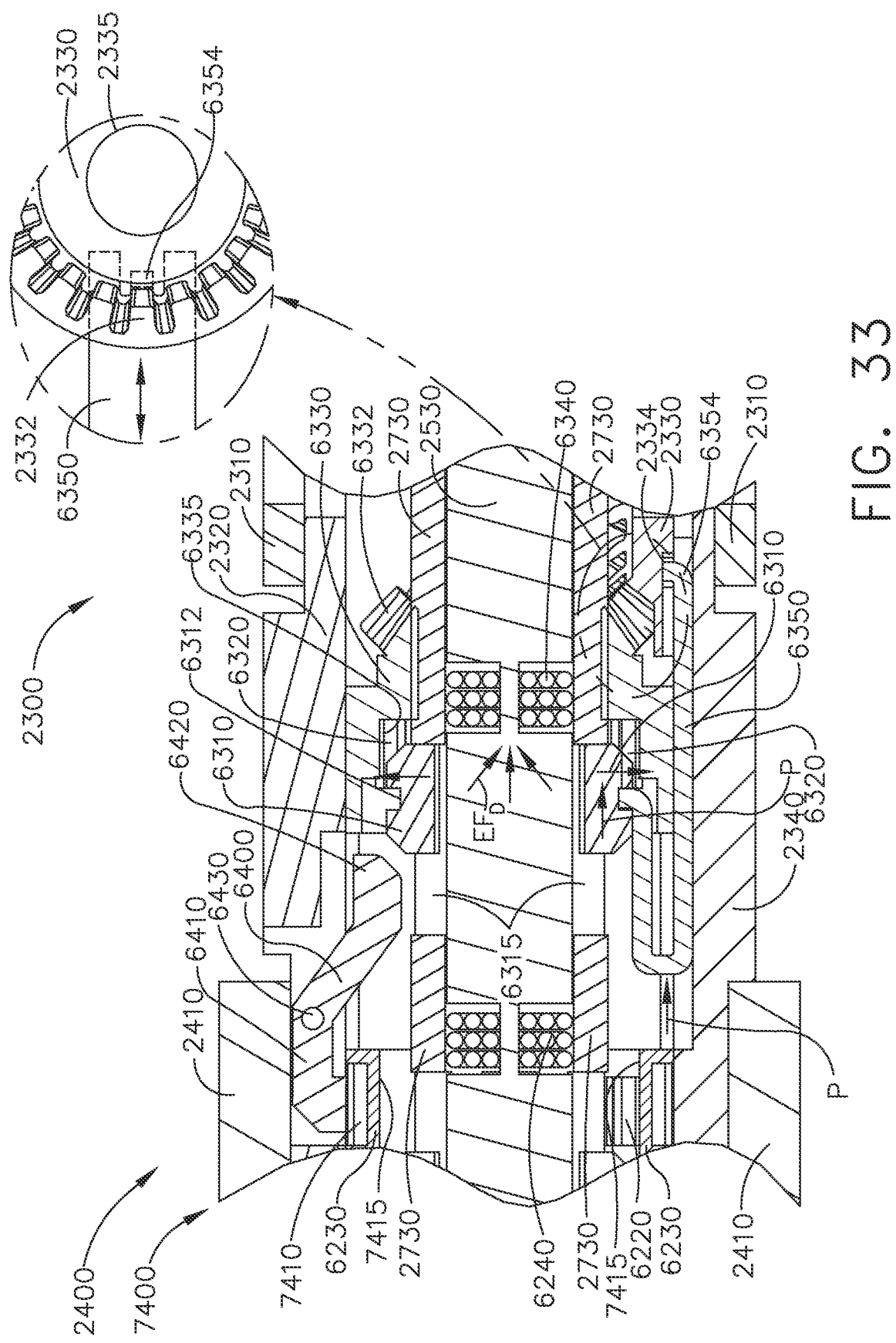
FIG. 33 depicts the third clutch of FIG. 27 in an actuated condition.

When the third clutch 6310 is in its disengaged position, referring to FIG. 32, the third clutch 6310 rotates with the drive shaft 2730 but does not transmit rotational motion to the third drive ring 6320. As can be seen in FIG. 32, the third clutch 6310 is separated from, or not in contact with, the third drive ring 6320. As a result, the rotation of the drive shaft 2730 and the third clutch 6310 is not transmitted to the articulation drive 6330 when the third clutch assembly 6300 is in its disengaged state. When the third clutch 6310 is in its engaged position, referring to FIG. 33, the third clutch 6310 is engaged with the third drive ring 6320 such that the third drive ring 6320 is expanded, or stretched, radially outwardly into contact with the articulation drive 6330. In at least one instance, the third drive ring 6320 comprises an elastomeric band, for example. As can be seen in FIG. 33, the third drive ring 6320 is compressed against an annular inner sidewall 6335 of the articulation drive 6330. As a result, the rotation of the drive shaft 2730 and the third clutch 6310 is transmitted to the articulation drive 6330 when the third clutch assembly 6300 is in its engaged state. Depending on the direction in which the drive shaft 2730 is rotated, the third clutch assembly 6300 can articulate the distal attachment portion 2400 of the shaft assembly 2000 and the end effector 7000 in a first or second direction about the articulation joint 2300.

As described above, the third electromagnetic actuator 6340 is configured to generate magnetic fields to move the third clutch 6310 between its disengaged (FIG. 32) and engaged (FIG. 33) positions. For instance, referring to FIG. 32, the third electromagnetic actuator 6340 is configured to emit a magnetic field EFL which repulses, or drives, the third clutch 6310 away from the third drive ring 6320 when the third clutch assembly 6300 is in its disengaged state. The third electromagnetic actuator 6340 comprises one or more wound coils in a cavity defined in the shaft frame 2530 which generate the magnetic field EFL when current flows in a first direction through a third electrical clutch circuit including the wound coils. The control system 1800 is configured to apply a first voltage polarity to the third electrical clutch circuit to create the current flowing in the first direction. The control system 1800 can continuously apply the first voltage polarity to the third electric clutch circuit to continuously hold the third clutch 6310 in its disengaged position. While such an arrangement can prevent the third clutch 6310 from unintentionally engaging the third drive ring 6320, such an arrangement can also consume a lot of power. Alternatively, the control system 1800 can apply the first voltage polarity to the third electrical clutch circuit for a sufficient period of time to position the third clutch 6310 in its disengaged position and then discontinue applying the first voltage polarity to the third electric clutch circuit, thereby resulting in a lower consumption of power.

Further to the above, the third electromagnetic actuator 6340 is configured to emit a magnetic field EFD which pulls, or drives, the third clutch 6310 toward the third drive ring 6320 when the third clutch assembly 6300 is in its engaged state. The coils of the third electromagnetic actuator 6340 generate the magnetic field EFD when current flows in a second, or opposite, direction through the third electrical clutch circuit. The control system 1800 is configured to apply an opposite voltage polarity to the third electrical shaft circuit to create the current flowing in the opposite direction. The control system 1800 can continuously apply the opposite voltage polarity to the third electric shaft circuit to continuously hold the third clutch 6310 in its engaged position and maintain the operable engagement between the third drive ring 6320 and the articulation drive 6330. Alternatively, the third clutch 6210 can be configured to become wedged within the third drive ring 6320 when the third clutch 6310 is in its engaged position and, in such instances, the control system 1800 may not need to continuously apply a voltage polarity to the third shaft electrical circuit to hold the third clutch assembly 6300 in its engaged state. In such instances, the control system 1800 can discontinue applying the voltage polarity once the third clutch 6310 has been sufficiently wedged in the third drive ring 6320. In any event, the end effector 7000 is articulatable in a first direction or a second direction, depending on the direction in which the drive shaft 2730 is rotated, when the third clutch assembly 6300 is in its engaged state.

Further to the above, referring to FIGS. 22, 32, and 33, the articulation drive system further comprises a lockout 6350 which prevents, or at least inhibits, the articulation of the distal attachment portion 2400 of the shaft assembly 2000 and the end effector 7000 about the articulation joint 2300 when the third clutch 6310 is in its disengaged position (FIG. 32). Referring primarily to FIG. 22, the articulation link 2340 comprises a slot, or groove, 2350 defined therein wherein the lockout 6350 is slideably positioned in the slot 2350 and extends at least partially under the stationary articulation gear 2330. The lockout 6350 comprises at attachment hook 6352 engaged with the third clutch 6310. More specifically, the third clutch 6310 comprises an annular slot, or groove, 6312 defined therein and the attachment hook 6352 is positioned in the annular slot 6312 such that the lockout 6350 translates with the third clutch 6310. Notably, however, the lockout 6350 does not rotate, or at least substantially rotate, with the third clutch 6310. Instead, the annular groove 6312 in the third clutch 6310 permits the third clutch 6310 to rotate relative to the lockout 6350. The lockout 6350 further comprises a lockout hook 6354 slideably positioned in a radially-extending lockout slot 2334 defined in the bottom of the stationary gear 2330. When the third clutch 6310 is in its disengaged position, as illustrated in FIG. 32, the lockout 6350 is in a locked position in which the lockout hook 6354 prevents the end effector 7000 from rotating about the articulation joint 2300. When the third clutch 6310 is in its engaged position, as illustrated in FIG. 33, the lockout 6350 is in an unlocked position in which the lockout hook 6354 is no longer positioned in the lockout slot 2334. Instead, the lockout hook 6354 is positioned in a clearance slot defined in the middle or body 2335 of the stationary gear 2330. In such instances, the lockout hook 6354 can rotate within the clearance slot when the end effector 7000 rotates about the articulation joint 2300.

Further to the above, the radially-extending lockout slot 2334 depicted in FIGS. 32 and 33 extends longitudinally, i.e., along an axis which is parallel to the longitudinal axis of the elongate shaft 2200. Once the end effector 7000 has been articulated, however, the lockout hook 6354 is no longer aligned with the longitudinal lockout slot 2334. With this in mind, the stationary gear 2330 comprises a plurality, or an array, of radially-extending lockout slots 2334 defined in the bottom of the stationary gear 2330 such that, when the third clutch 6310 is deactuated and the lockout 6350 is pulled distally after the end effector 7000 has been articulated, the lockout hook 6354 can enter one of the lockout slots 2334 and lock the end effector 7000 in its articulated position. Thus, as a result, the end effector 7000 can be locked in an unarticulated and an articulated position. In various instances, the lockout slots 2334 can define discrete articulated positions for the end effector 7000. For instance, the lockout slots 2334 can be defined at 10 degree intervals, for example, which can define discrete articulation orientations for the end effector 7000 at 10 degree intervals. In other instances, these orientations can be at 5 degree intervals, for example. In alternative embodiments, the lockout 6350 comprises a brake that engages a circumferential shoulder defined in the stationary gear 2330 when the third clutch 6310 is disengaged from the third drive ring 6320. In such an embodiment, the end effector 7000 can be locked in any suitable orientation. In any event, the lockout 6350 prevents, or at least reduces the possibility of, the end effector 7000 unintentionally articulating. As a result of the above, the third clutch 6310 can do things—operate the articulation drive when it is in its engaged position and lock out the articulation drive when it is in its disengaged position.

Referring primarily to FIGS. 24 and 25, the shaft frame 2530 and the drive shaft 2730 extend through the articulation joint 2300 into the distal attachment portion 2400. When the end effector 7000 is articulated, as illustrated in FIGS. 16 and 17, the shaft frame 2530 and the drive shaft 2730 bend to accommodate the articulation of the end effector 7000. Thus, the shaft frame 2530 and the drive shaft 2730 are comprised of any suitable material which accommodates the articulation of the end effector 7000. Moreover, as discussed above, the shaft frame 2530 houses the first, second, and third electromagnetic actuators 6140, 6240, and 6340. In various instances, the first, second, and third electromagnetic actuators 6140, 6240, and 6340 each comprise wound wire coils, such as copper wire coils, for example, and the shaft frame 2530 is comprised of an insulative material to prevent, or at least reduce the possibility of, short circuits between the first, second, and third electromagnetic actuators 6140, 6240, and 6340. In various instances, the first, second, and third electrical clutch circuits extending through the shaft frame 2530 are comprised of insulated electrical wires, for example. Further to the above, the first, second, and third electrical clutch circuits place the electromagnetic actuators 6140, 6240, and 6340 in communication with the control system 1800 in the drive module 1100.

As described above, the clutches 6110, 6210, and/or 6310 can be held in their disengaged positions so that they do not unintentionally move into their engaged positions. In various arrangements, the clutch system 6000 comprises a first biasing member, such as a spring, for example, configured to bias the first clutch 6110 into its disengaged position, a second biasing member, such as a spring, for example, configured to bias the second clutch 6210 into its disengaged position, and/or a third biasing member, such as a spring, for example, configured to bias the third clutch 6110 into its disengaged position. In such arrangements, the biasing forces of the springs can be selectively overcome by the electromagnetic forces generated by the electromagnetic actuators when energized by an electrical current. Further to the above, the clutches 6110, 6210, and/or 6310 can be retained in their engaged positions by the drive rings 6120, 6220, and/or 6320, respectively. More specifically, in at least one instance, the drive rings 6120, 6220, and/or 6320 are comprised of an elastic material which grips or frictionally holds the clutches 6110, 6210, and/or 6310, respectively, in their engaged positions. In various alternative embodiments, the clutch system 6000 comprises a first biasing member, such as a spring, for example, configured to bias the first clutch 6110 into its engaged position, a second biasing member, such as a spring, for example, configured to bias the second clutch 6210 into its engaged position, and/or a third biasing member, such as a spring, for example, configured to bias the third clutch 6110 into its engaged position. In such arrangements, the biasing forces of the springs can be overcome by the electromagnetic forces applied by the electromagnetic actuators 6140, 6240, and/or 6340, respectively, as needed to selectively hold the clutches 6110, 6210, and 6310 in their disengaged positions. In any one operational mode of the surgical system, the control assembly 1800 can energize one of the electromagnetic actuators to engage one of the clutches while energizing the other two electromagnetic actuators to disengage the other two clutches.

Although the clutch system 6000 comprises three clutches to control three drive systems of the surgical system, a clutch system can comprise any suitable number of clutches to control any suitable number of systems. Moreover, although the clutches of the clutch system 6000 slide proximally and distally between their engaged and disengaged positions, the clutches of a clutch system can move in any suitable manner. In addition, although the clutches of the clutch system 6000 are engaged one at a time to control one drive motion at a time, various instances are envisioned in which more than one clutch can be engaged to control more than one drive motion at a time.

In view of the above, the reader should appreciate that the control system 1800 is configured to, one, operate the motor system 1600 to rotate the drive shaft system 2700 in an appropriate direction and, two, operate the clutch system 6000 to transfer the rotation of the drive shaft system 2700 to the appropriate function of the end effector 7000. Moreover, as discussed above, the control system 1800 is responsive to inputs from the clamping trigger system 2600 of the shaft assembly 2000 and the input system 1400 of the handle 1000. When the clamping trigger system 2600 is actuated, as discussed above, the control system 1800 activates the first clutch assembly 6100 and deactivates the second clutch assembly 6200 and the third clutch assembly 6300. In such instances, the control system 1800 also supplies power to the motor system 1600 to rotate the drive shaft system 2700 in a first direction to clamp the jaw assembly 7100 of the end effector 7000. When the control system 1800 detects that the jaw assembly 7100 is in its clamped configuration, the control system 1800 stops the motor assembly 1600 and deactivates the first clutch assembly 6100. When the control system 1800 detects that the clamping trigger system 2600 has been moved to, or is being moved to, its unactuated position, the control system 1800 activates, or maintains the activation of, the first clutch assembly 6100 and deactivates, or maintains the deactivation of, the second clutch assembly 6200 and the third clutch assembly 6300. In such instances, the control system 1800 also supplies power to the motor system 1600 to rotate the drive shaft system 2700 in a second direction to open the jaw assembly 7100 of the end effector 7000.

When the rotation actuator 1420 is actuated in a first direction, further to the above, the control system 1800 activates the second clutch assembly 6200 and deactivates the first clutch assembly 6100 and the third clutch assembly 6300. In such instances, the control system 1800 also supplies power to the motor system 1600 to rotate the drive shaft system 2700 in a first direction to rotate the end effector 7000 in a first direction. When the control system 1800 detects that the rotation actuator 1420 has been actuated in a second direction, the control system 1800 activates, or maintains the activation of, the second clutch assembly 6200 and deactivates, or maintains the deactivation of, the first clutch assembly 6100 and the third clutch assembly 6300. In such instances, the control system 1800 also supplies power to the motor system 1600 to rotate the drive shaft system 2700 in a second direction to rotate the drive shaft system 2700 in a second direction to rotate the end effector 7000 in a second direction. When the control system 1800 detects that the rotation actuator 1420 is not actuated, the control system 1800 deactivates the second clutch assembly 6200.

When the first articulation actuator 1432 is depressed, further to the above, the control system 1800 activates the third clutch assembly 6300 and deactivates the first clutch assembly 6100 and the second clutch assembly 6200. In such instances, the control system 1800 also supplies power to the motor system 1600 to rotate the drive shaft system 2700 in a first direction to articulate the end effector 7000 in a first direction. When the control system 1800 detects that the second articulation actuator 1434 is depressed, the control system 1800 activates, or maintains the activation of, the third clutch assembly 6200 and deactivates, or maintains the deactivation of, the first clutch assembly 6100 and the second clutch assembly 6200. In such instances, the control system 1800 also supplies power to the motor system 1600 to rotate the drive shaft system 2700 in a second direction to articulate the end effector 7000 in a second direction. When the control system 1800 detects that neither the first articulation actuator 1432 nor the second articulation actuator 1434 are actuated, the control system 1800 deactivates the third clutch assembly 6200.

Further to the above, the control system 1800 is configured to change the operating mode of the stapling system based on the inputs it receives from the clamping trigger system 2600 of the shaft assembly 2000 and the input system 1400 of the handle 1000. The control system 1800 is configured to shift the clutch system 6000 before rotating the shaft drive system 2700 to perform the corresponding end effector function. Moreover, the control system 1800 is configured to stop the rotation of the shaft drive system 2700 before shifting the clutch system 6000. Such an arrangement can prevent the sudden movements in the end effector 7000. Alternatively, the control system 1800 can shift the clutch system 600 while the shaft drive system 2700 is rotating. Such an arrangement can allow the control system 1800 to shift quickly between operating modes.

Figure 34:
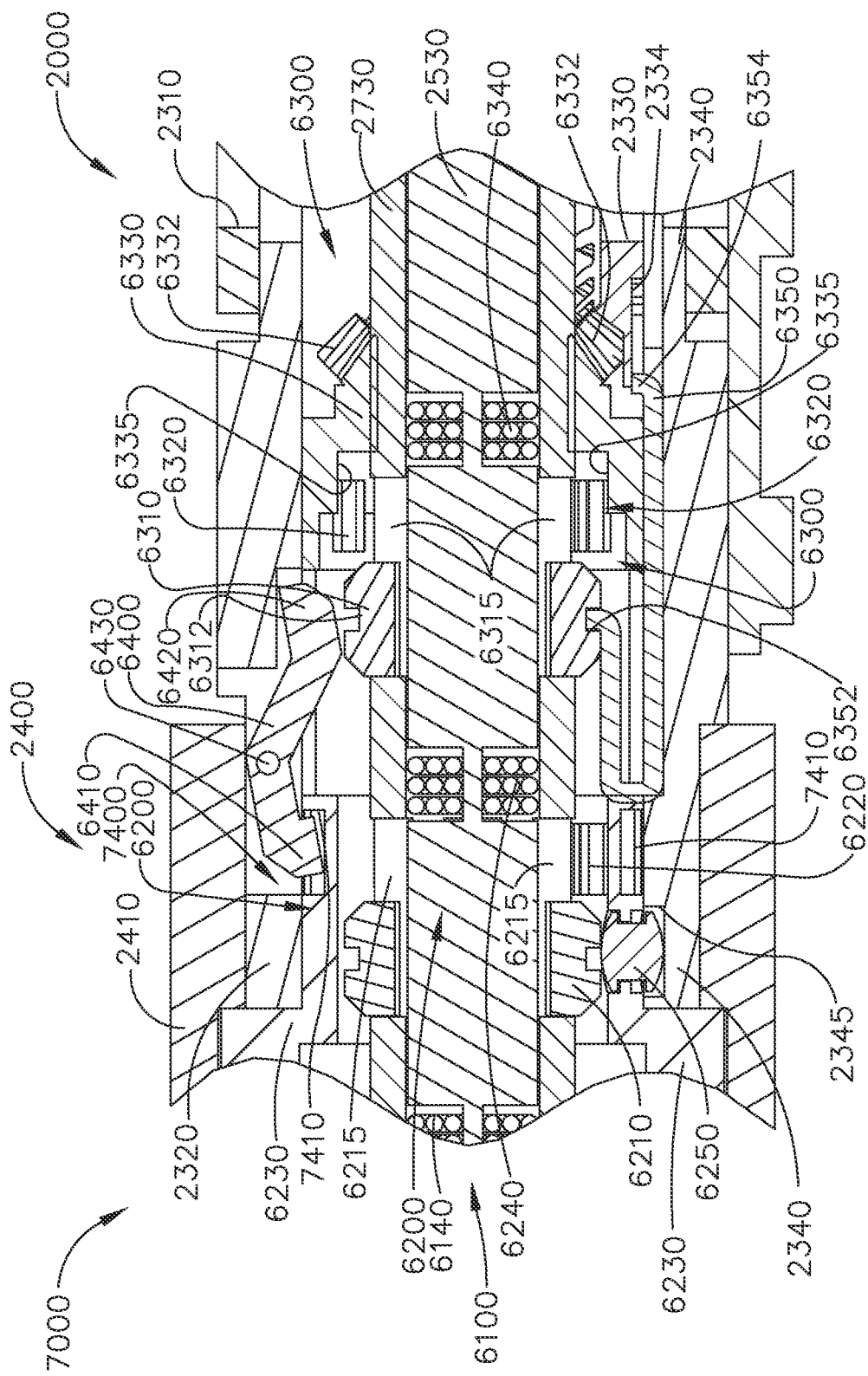
FIG. 34 depicts the second and third clutches of FIG. 27 in their unactuated conditions and the end effector of FIG. 14 locked to the shaft assembly of FIG. 2.
Figure 35:
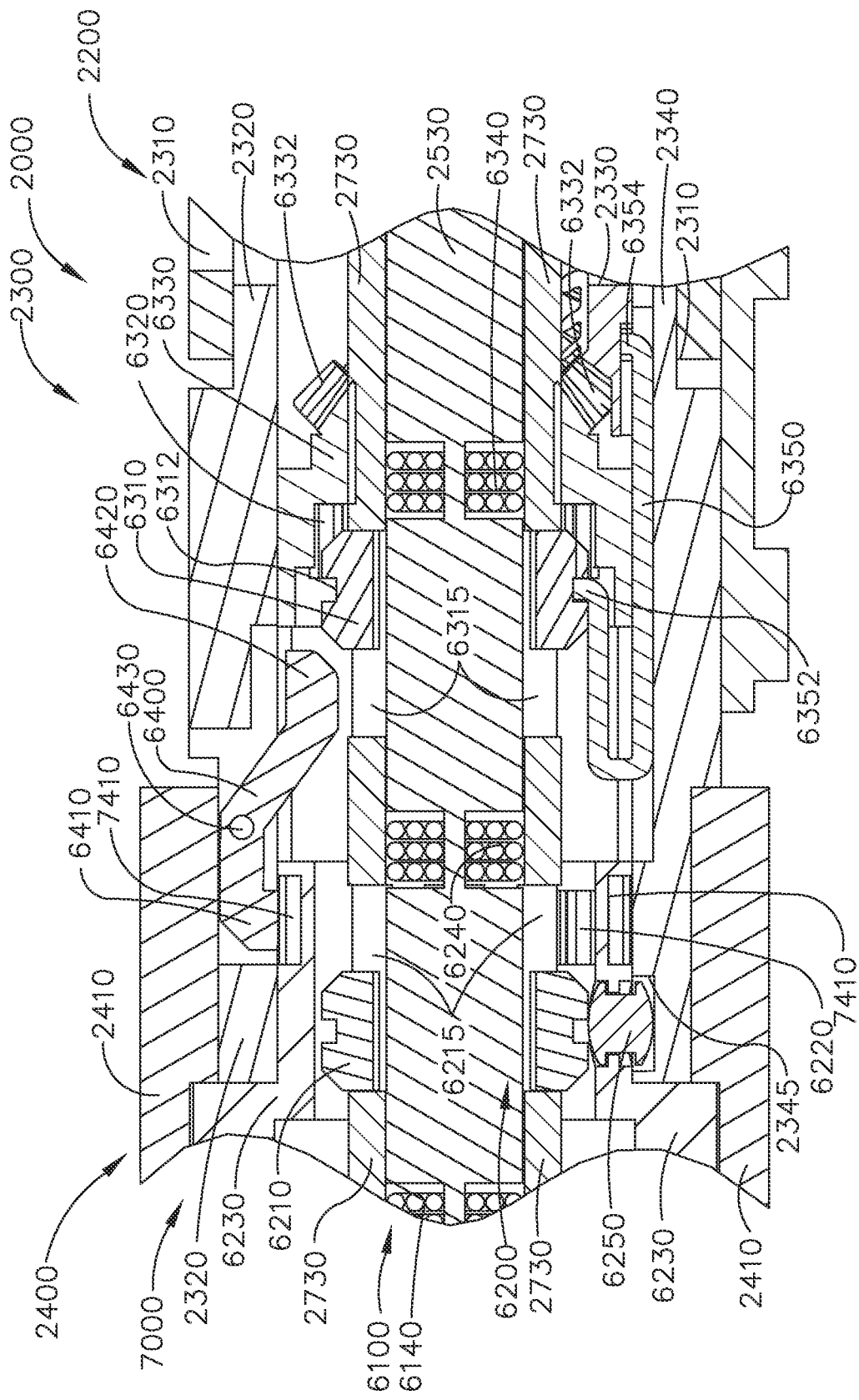
FIG. 35 depicts the second clutch of FIG. 27 in its unactuated condition and the third clutch of FIG. 27 in its actuated condition.
Figure 36:
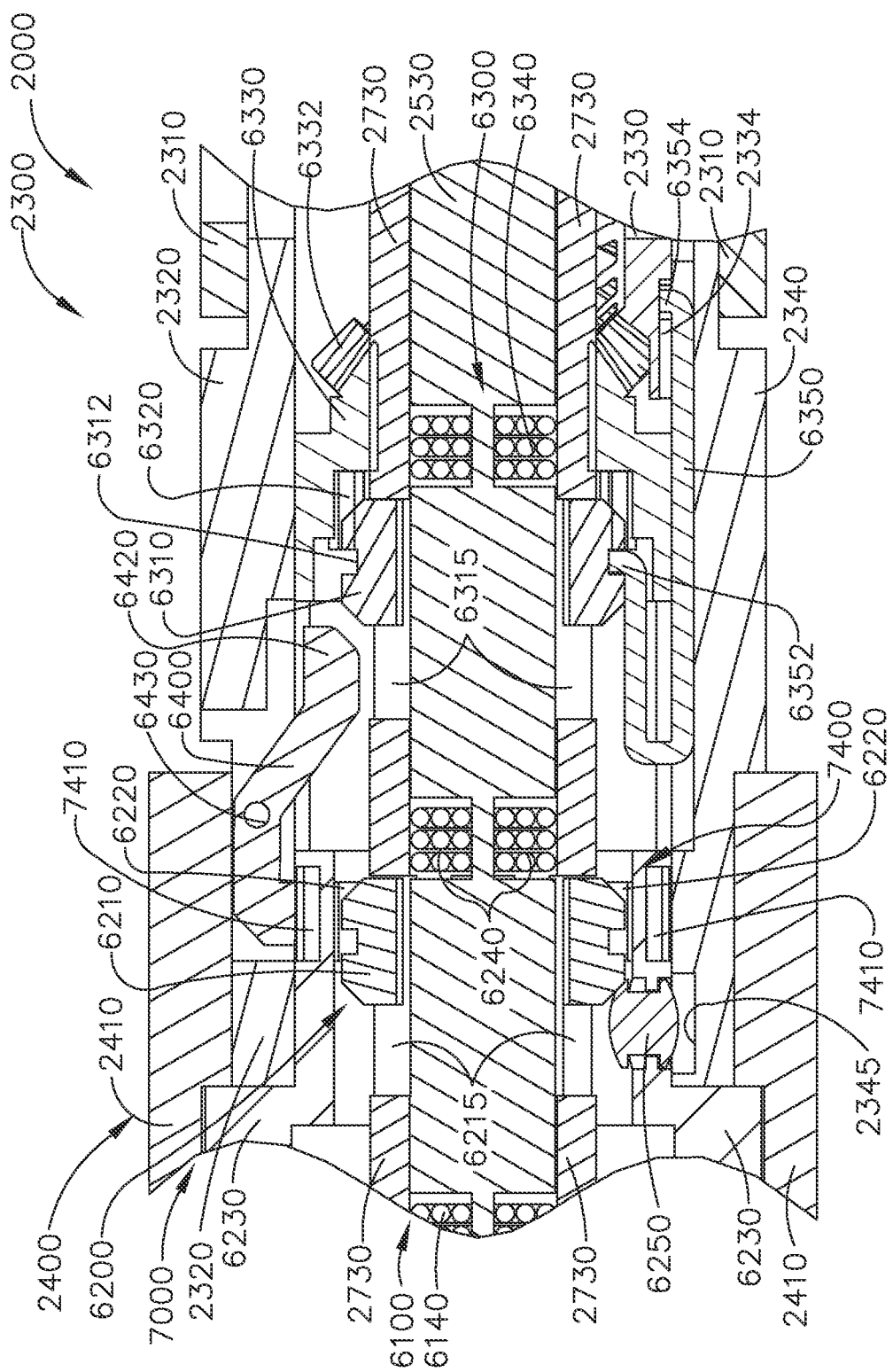
FIG. 36 depicts the second and third clutches of FIG. 27 in their actuated conditions and the end effector of FIG. 14 unlocked from the shaft assembly of FIG. 2.

As discussed above, referring to FIG. 34, the distal attachment portion 2400 of the shaft assembly 2000 comprises an end effector lock 6400 configured to prevent the end effector 7000 from being unintentionally decoupled from the shaft assembly 2000. The end effector lock 6400 comprises a lock end 6410 selectively engageable with the annular array of lock notches 7410 defined on the proximal attachment portion 7400 of the end effector 7000, a proximal end 6420, and a pivot 6430 rotatably connecting the end effector lock 6400 to the articulation link 2320. When the third clutch 6310 of the third clutch assembly 6300 is in its disengaged position, as illustrated in FIG. 34, the third clutch 6310 is contact with the proximal end 6420 of the end effector lock 6400 such that the lock end 6410 of the end effector lock 6400 is engaged with the array of lock notches 7410. In such instances, the end effector 7000 can rotate relative to the end effector lock 6400 but cannot translate relative to the distal attachment portion 2400. When the third clutch 6310 is moved into its engaged position, as illustrated in FIG. 35, the third clutch 6310 is no longer engaged with the proximal end 6420 of the end effector lock 6400. In such instances, the end effector lock 6400 is free to pivot upwardly and permit the end effector 7000 to be detached from the shaft assembly 2000.

The above being said, referring again to FIG. 34, it is possible that the second clutch 6210 of the second clutch assembly 6200 is in its disengaged position when the clinician detaches, or attempts to detach, the end effector 7000 from the shaft assembly 2000. As discussed above, the second clutch 6210 is engaged with the second clutch lock 6250 when the second clutch 6210 is in its disengaged position and, in such instances, the second clutch lock 6250 is pushed into engagement with the articulation link 2340. More specifically, the second clutch lock 6250 is positioned in the channel 2345 defined in the articulation 2340 when the second clutch 6210 is engaged with the second clutch lock 6250 which may prevent, or at least impede, the end effector 7000 from being detached from the shaft assembly 2000. To facilitate the release of the end effector 7000 from the shaft assembly 2000, the control system 1800 can move the second clutch 6210 into its engaged position in addition to moving the third clutch 6310 into its engaged position. In such instances, the end effector 7000 can clear both the end effector lock 6400 and the second clutch lock 6250 when the end effector 7000 is removed.

In at least one instance, further to the above, the drive module 1100 comprises an input switch and/or sensor in communication with the control system 1800 via the input system 1400, and/or the control system 1800 directly, which, when actuated, causes the control system 1800 to unlock the end effector 7000. In various instances, the drive module 1100 comprises an input screen 1440 in communication with the board 1410 of the input system 1400 which is configured to receive an unlock input from the clinician. In response to the unlock input, the control system 1800 can stop the motor system 1600, if it is running, and unlock the end effector 7000 as described above. The input screen 1440 is also configured to receive a lock input from the clinician in which the input system 1800 moves the second clutch assembly 6200 and/or the third clutch assembly 6300 into their unactuated states to lock the end effector 7000 to the shaft assembly 2000.

Figure 37:
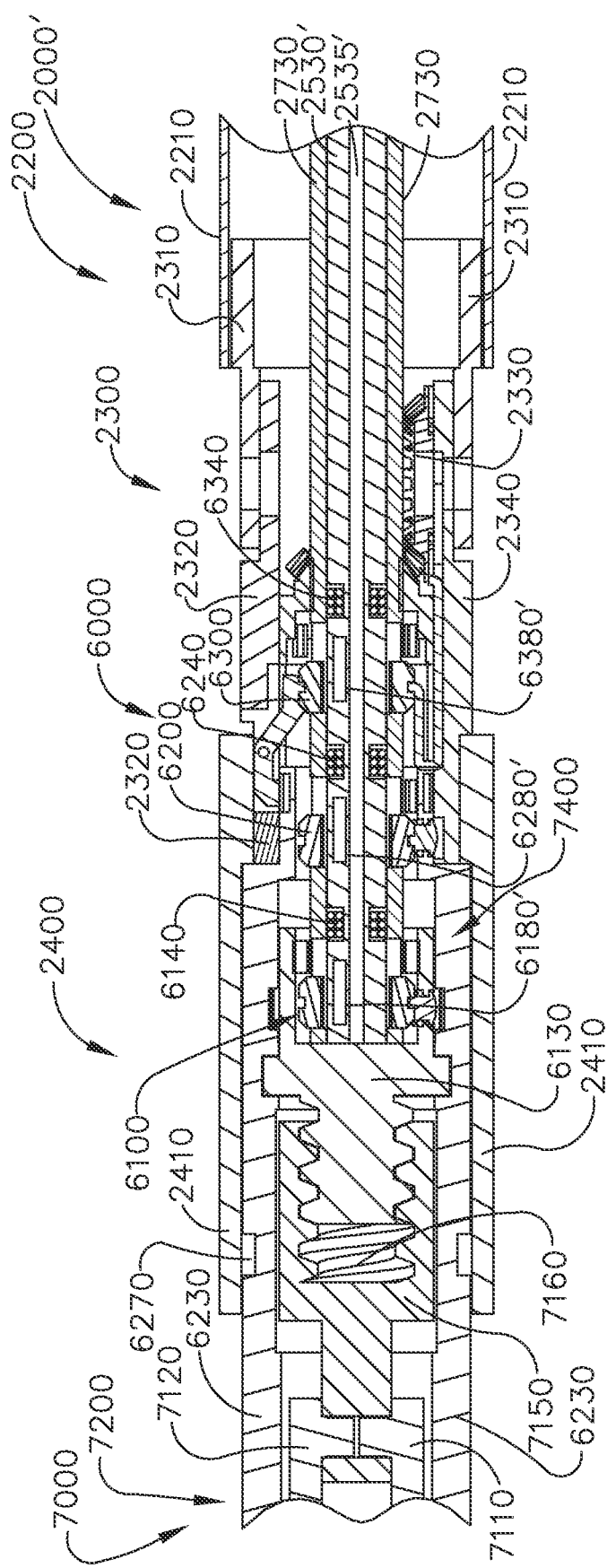
FIG. 37 is a partial cross-sectional view of a shaft assembly in accordance with at least one alternative embodiment comprising sensors configured to detect the conditions of the first, second, and third clutches of FIG. 27.

FIG. 37 depicts a shaft assembly 2000' in accordance with at least one alternative embodiment. The shaft assembly 2000' is similar to the shaft assembly 2000 in many respects, most of which will not be repeated herein for the sake of brevity. Similar to the shaft assembly 2000, the shaft assembly 2000' comprises a shaft frame, i.e., shaft frame 2530'. The shaft frame 2530' comprises a longitudinal passage 2535' and, in addition, a plurality of clutch position sensors, i.e., a first sensor 6180', a second sensor 6280', and a third sensor 6380' positioned in the shaft frame 2530'. The first sensor 6180' is in signal communication with the control system 1800 as part of a first sensing circuit. The first sensing circuit comprises signal wires extending through the longitudinal passage 2535'; however, the first sensing circuit can comprise a wireless signal transmitter and receiver to place the first sensor 6180' in signal communication with the control system 1800. The first sensor 6180' is positioned and arranged to detect the position of the first clutch 6110 of the first clutch assembly 6100. Based on data received from the first sensor 6180', the control system 1800 can determine whether the first clutch 6110 is in its engaged position, its disengaged position, or somewhere in-between. With this information, the control system 1800 can assess whether or not the first clutch 6110 is in the correct position given the operating state of the surgical instrument. For instance, if the surgical instrument is in its jaw clamping/opening operating state, the control system 1800 can verify whether the first clutch 6110 is properly positioned in its engaged position. In such instances, further to the below, the control system 1800 can also verify that the second clutch 6210 is in its disengaged position via the second sensor 6280' and that the third clutch 6310 is in its disengaged position via the third sensor 6380'. Correspondingly, the control system 1800 can verify whether the first clutch 6110 is properly positioned in its disengaged position if the surgical instrument is not in its jaw clamping/opening state. To the extent that the first clutch 6110 is not in its proper position, the control system 1800 can actuate the first electromagnetic actuator 6140 in an attempt to properly position the first clutch 6110. Likewise, the control system 1800 can actuate the electromagnetic actuators 6240 and/or 6340 to properly position the clutches 6210 and/or 6310, if necessary.

The second sensor 6280' is in signal communication with the control system 1800 as part of a second sensing circuit. The second sensing circuit comprises signal wires extending through the longitudinal passage 2535'; however, the second sensing circuit can comprise a wireless signal transmitter and receiver to place the second sensor 6280' in signal communication with the control system 1800. The second sensor 6280' is positioned and arranged to detect the position of the second clutch 6210 of the first clutch assembly 6200. Based on data received from the second sensor 6280', the control system 1800 can determine whether the second clutch 6210 is in its engaged position, its disengaged position, or somewhere in-between. With this information, the control system 1800 can assess whether or not the second clutch 6210 is in the correct position given the operating state of the surgical instrument. For instance, if the surgical instrument is in its end effector rotation operating state, the control system 1800 can verify whether the second clutch 6210 is properly positioned in its engaged position. In such instances, the control system 1800 can also verify that the first clutch 6110 is in its disengaged position via the first sensor 6180' and, further to the below, the control system 1800 can also verify that the third clutch 6310 is in its disengaged position via the third sensor 6380'. Correspondingly, the control system 1800 can verify whether the second clutch 6110 is properly positioned in its disengaged position if the surgical instrument is not in its end effector rotation state. To the extent that the second clutch 6210 is not in its proper position, the control system 1800 can actuate the second electromagnetic actuator 6240 in an attempt to properly position the second clutch 6210. Likewise, the control system 1800 can actuate the electromagnetic actuators 6140 and/or 6340 to properly position the clutches 6110 and/or 6310, if necessary.

The third sensor 6380' is in signal communication with the control system 1800 as part of a third sensing circuit. The third sensing circuit comprises signal wires extending through the longitudinal passage 2535'; however, the third sensing circuit can comprise a wireless signal transmitter and receiver to place the third sensor 6380' in signal communication with the control system 1800. The third sensor 6380' is positioned and arranged to detect the position of the third clutch 6310 of the third clutch assembly 6300. Based on data received from the third sensor 6380', the control system 1800 can determine whether the third clutch 6310 is in its engaged position, its disengaged position, or somewhere in-between. With this information, the control system 1800 can assess whether or not the third clutch 6310 is in the correct position given the operating state of the surgical instrument. For instance, if the surgical instrument is in its end effector articulation operating state, the control system 1800 can verify whether the third clutch 6310 is properly positioned in its engaged position. In such instances, the control system 1800 can also verify that the first clutch 6110 is in its disengaged position via the first sensor 6180' and that the second clutch 6210 is in its disengaged position via the second sensor 6280'. Correspondingly, the control system 1800 can verify whether the third clutch 6310 is properly positioned in its disengaged position if the surgical instrument is not in its end effector articulation state. To the extent that the third clutch 6310 is not in its proper position, the control system 1800 can actuate the third electromagnetic actuator 6340 in an attempt to properly position the third clutch 6310. Likewise, the control system 1800 can actuate the electromagnetic actuators 6140 and/or 6240 to properly position the clutches 6110 and/or 6210, if necessary.

Further to the above, the clutch position sensors, i.e., the first sensor 6180', the second sensor 6280', and the third sensor 6380' can comprise any suitable type of sensor. In various instances, the first sensor 6180', the second sensor 6280', and the third sensor 6380' each comprise a proximity sensor. In such an arrangement, the sensors 6180', 6280', and 6380' are configured to detect whether or not the clutches 6110, 6210, and 6310, respectively, are in their engaged positions. In various instances, the first sensor 6180', the second sensor 6280', and the third sensor 6380' each comprise a Hall Effect sensor, for example. In such an arrangement, the sensors 6180', 6280', and 6380' can not only detect whether or not the clutches 6110, 6210, and 6310, respectively, are in their engaged positions but the sensors 6180', 6280', and 6380' can also detect how close the clutches 6110, 6210, and 6310 are with respect to their engaged or disengaged positions.

Figure 38:
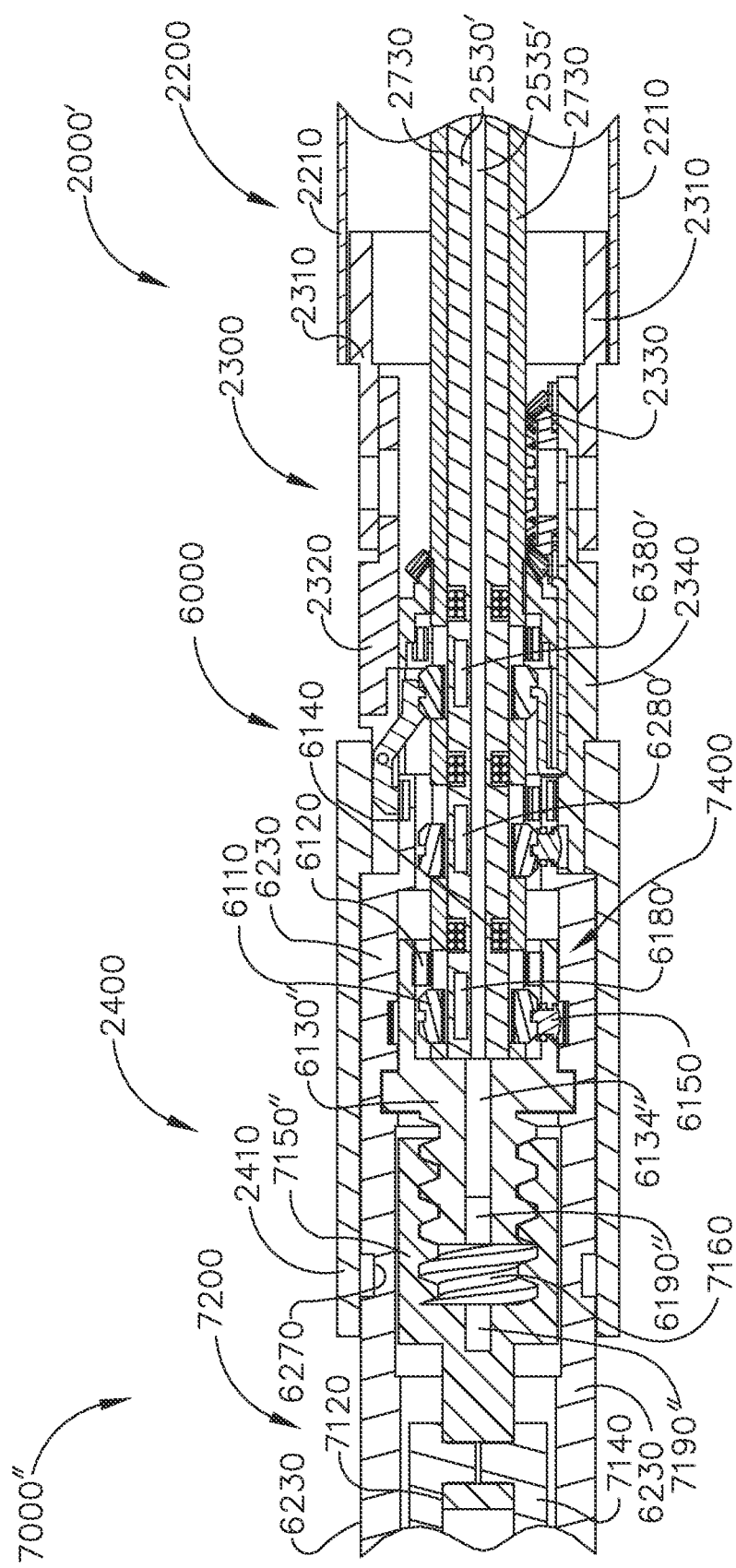
FIG. 38 is a partial cross-sectional view of a shaft assembly in accordance with at least one alternative embodiment comprising sensors configured to detect the conditions of the first, second, and third clutches of FIG. 27.

FIG. 38 depicts the shaft assembly 2000' and an end effector 7000" in accordance with at least one alternative embodiment. The end effector 7000" is similar to the end effector 7000 in many respects, most of which will not be repeated herein for the sake of brevity. Similar to the end effector 7000, the shaft assembly 7000" comprises a jaw assembly 7100 and a jaw assembly drive configured to move the jaw assembly 7100 between its open and closed configurations. The jaw assembly drive comprises drive links 7140, a drive nut 7150", and a drive screw 6130". The drive nut 7150" comprises a sensor 7190" positioned therein which is configured to detect the position of a magnetic element 6190" positioned in the drive screw 6130". The magnetic element 6190" is positioned in an elongate aperture 6134" defined in the drive screw 6130" and can comprise a permanent magnet and/or can be comprised of iron, nickel, and/or any suitable metal, for example. In various instances, the sensor 7190" comprises a proximity sensor, for example, which is in signal communication with the control system 1800. In certain instances, the sensor 7190" comprises a Hall Effect sensor, for example, in signal communication with the control system 1800. In certain instances, the sensor 7190" comprises an optical sensor, for example, and the detectable element 6190" comprises an optically detectable element, such as a reflective element, for example. In either event, the sensor 7190" is configured to communicate wirelessly with the control system 1800 via a wireless signal transmitter and receiver and/or via a wired connection extending through the shaft frame passage 2532', for example.

The sensor 7190", further to the above, is configured to detect when the magnetic element 6190" is adjacent to the sensor 7190" such that the control system 1800 can use this data to determine that the jaw assembly 7100 has reached the end of its clamping stroke. At such point, the control system 1800 can stop the motor assembly 1600. The sensor 7190" and the control system 1800 are also configured to determine the distance between where the drive screw 6130" is currently positioned and where the drive screw 6130" should be positioned at the end of its closure stroke in order to calculate the amount of closure stroke of the drive screw 6130" that is still needed to close the jaw assembly 7100. Moreover, such information can be used by the control system 1800 to assess the current configuration of the jaw assembly 7100, i.e., whether the jaw assembly 7100 is in its open configuration, its closed configuration, or a partially closed configuration. The sensor system could be used to determine when the jaw assembly 7100 has reached its fully open position and stop the motor assembly 1600 at that point. In various instances, the control system 1800 could use this sensor system to confirm that the first clutch assembly 6100 is in its actuated state by confirming that the jaw assembly 7100 is moving while the motor assembly 1600 is turning. Similarly, the control system 1800 could use this sensor system to confirm that the first clutch assembly 6100 is in its unactuated state by confirming that the jaw assembly 7100 is not moving while the motor assembly 1600 is turning.

Figure 39:
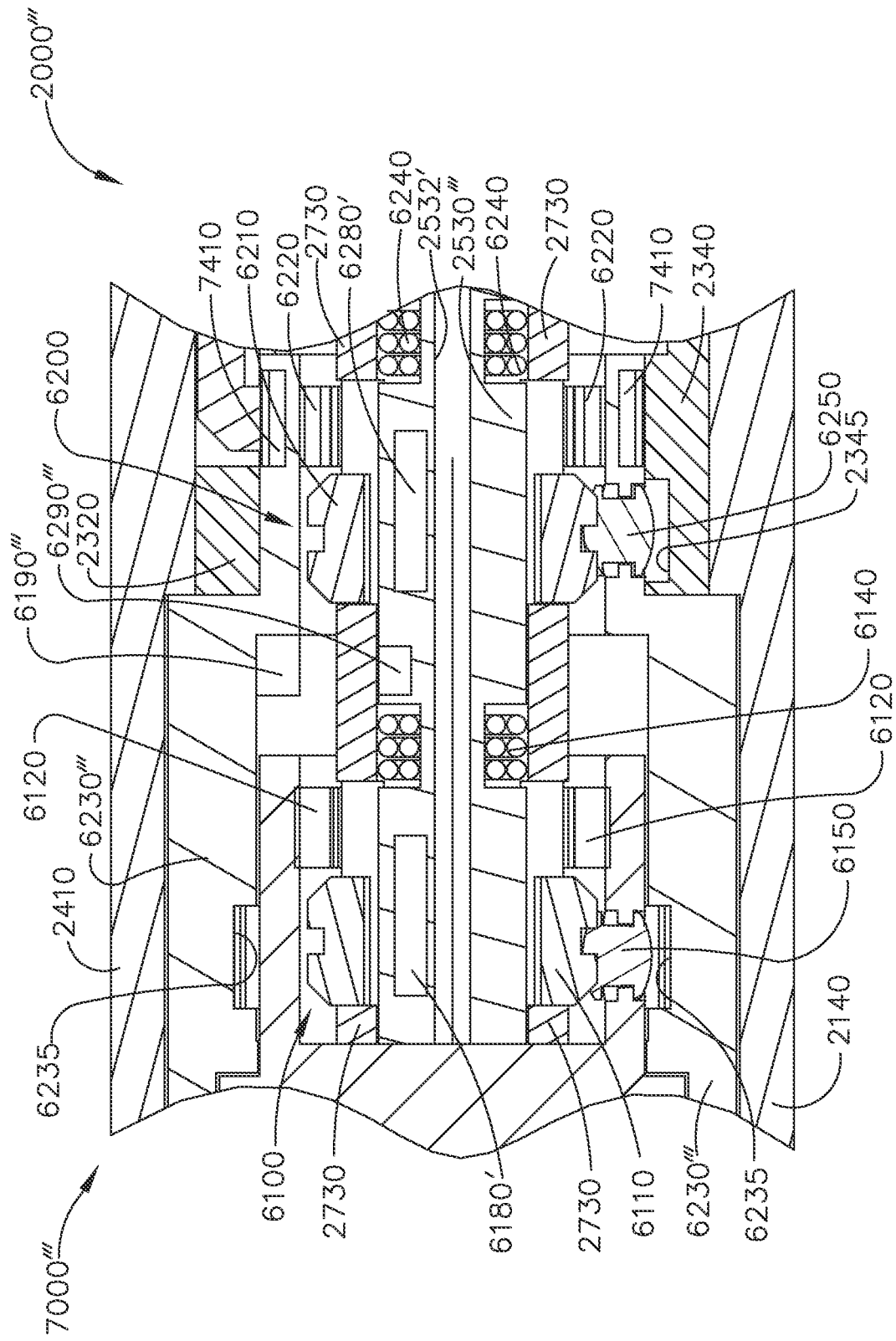
FIG. 39 depicts the first and second clutches of FIG. 38 in their unactuated conditions and a sensor in accordance with at least one alternative embodiment.

FIG. 39 depicts a shaft assembly 2000''' and an end effector 7000''' in accordance with at least one alternative embodiment. The shaft assembly 2000''' is similar to the shaft assemblies 2000 and 2000' in many respects, most of which will not be repeated herein for the sake of brevity. The end effector 7000''' is similar to the end effectors 7000 and 7000" in many respects, most of which will not be repeated herein for the sake of brevity. Similar to the end effector 7000, the end effector 7000''' comprises a jaw assembly 7100 and a jaw assembly drive configured to move the jaw assembly 7100 between its open and closed configurations and, in addition, an end effector rotation drive that rotates the end effector 7000''' relative to the distal attachment portion 2400 of the shaft assembly 2000'. The end effector rotation drive comprises an outer housing 6230''' that is rotated relative to a shaft frame 2530''' of the end effector 7000''' by the second clutch assembly 6200. The shaft frame 2530''' comprises a sensor 6290''' positioned therein which is configured to detect the position of a magnetic element 6190''' positioned in and/or on the outer housing 6230'''. The magnetic element 6190''' can comprise a permanent magnet and/or can be comprised of iron, nickel, and/or any suitable metal, for example. In various instances, the sensor 6290''' comprises a proximity sensor, for example, in signal communication with the control system 1800. In certain instances, the sensor 6290''' comprises a Hall Effect sensor, for example, in signal communication with the control system 1800. In either event, the sensor 6290''' is configured to communicate wirelessly with the control system 1800 via a wireless signal transmitter and receiver and/or via a wired connection extending through the shaft frame passage 2532', for example. In various instances, the control system 1800 can use the sensor 6290''' to confirm whether the magnetic element 6190''' is rotating and, thus, confirm that the second clutch assembly 6200 is in its actuated state. Similarly, the control system 1800 can use the sensor 6290''' to confirm whether the magnetic element 6190''' is not rotating and, thus, confirm that the second clutch assembly 6200 is in its unactuated state. The control system 1800 can also use the sensor 6290''' to confirm that the second clutch assembly 6200 is in its unactuated state by confirming that the second clutch 6210 is positioned adjacent the sensor 6290'''.

Figure 40:
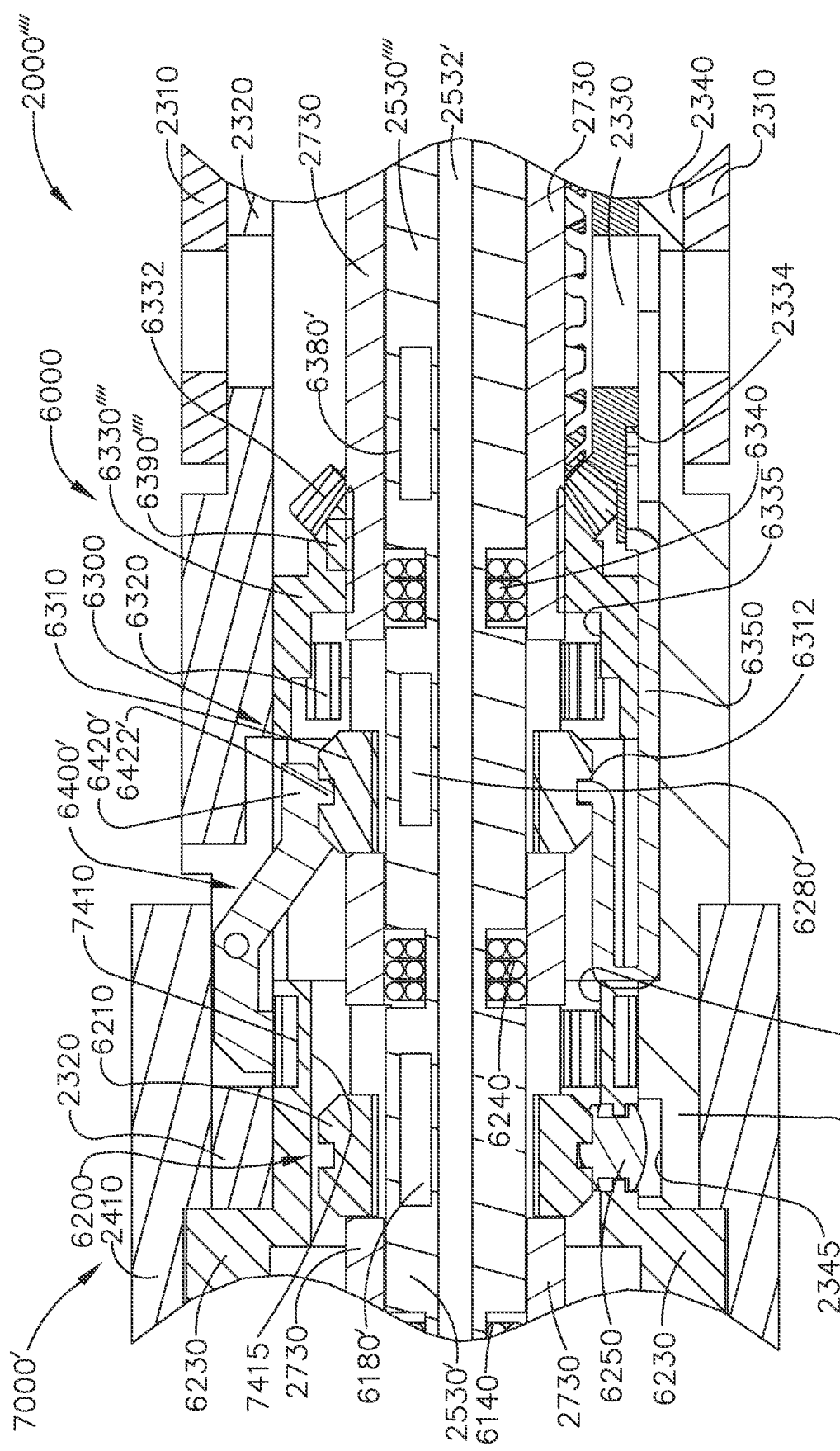
FIG. 40 depicts the second and third clutches of FIG. 38 in their unactuated conditions and a sensor in accordance with at least one alternative embodiment.

FIG. 40 depicts a shaft assembly 2000'''' in accordance with at least one alternative embodiment. The shaft assembly 2000'''' is similar to the shaft assemblies 2000, 2000', and 2000''' in many respects, most of which will not be repeated herein for the sake of brevity. Similar to the shaft assembly 2000, the shaft assembly 2000'''' comprises, among other things, an elongate shaft 2200, an articulation joint 2300, and a distal attachment portion 2400 configured to receive an end effector, such as end effector 7000', for example. Similar to the shaft assembly 2000, the shaft assembly 2000'''' comprises an articulation drive, i.e., articulation drive 6330'''' configured to rotate the distal attachment portion 2400 and the end effector 7000' about the articulation joint 2300. Similar to the above, a shaft frame 2530'''' comprises a sensor positioned therein configured to detect the position, and/or rotation, of a magnetic element 6390'''' positioned in and/or on the articulation drive 6330''''. The magnetic element 6390'''' can comprise a permanent magnet and/or can be comprised of iron, nickel, and/or any suitable metal, for example. In various instances, the sensor comprises a proximity sensor, for example, in signal communication with the control system 1800. In certain instances, the sensor comprises a Hall Effect sensor, for example, in signal communication with the control system 1800. In either event, the sensor is configured to communicate wirelessly with the control system 1800 via a wireless signal transmitter and receiver and/or via a wired connection extending through the shaft frame passage 2532', for example. In various instances, the control system 1800 can use the sensor to confirm whether the magnetic element 6390'''' is rotating and, thus, confirm that the third clutch assembly 6300 is in its actuated state. Similarly, the control system 1800 can use the sensor to confirm whether the magnetic element 6390'''' is not rotating and, thus, confirm that the third clutch assembly 6300 is in its unactuated state. In certain instances, the control system 1800 can use the sensor to confirm that the third clutch assembly 6300 is in its unactuated state by confirming that the third clutch 6310 is positioned adjacent the sensor.

Referring to FIG. 40 once again, the shaft assembly 2000'''' comprises an end effector lock 6400' configured to releasably lock the end effector 7000', for example, to the shaft assembly 2000''''. The end effector lock 6400' is similar to the end effector lock 6400 in many respects, most of which will not be discussed herein for the sake of brevity. Notably, though, a proximal end 6420' of the lock 6400' comprises a tooth 6422' configured to engage the annular slot 6312 of the third clutch 6310 and releasably hold the third clutch 6310 in its disengaged position. That said, the actuation of the third electromagnetic assembly 6340 can disengage the third clutch 6310 from the end effector lock 6400'. Moreover, in such instances, the proximal movement of the third clutch 6310 into its engaged position rotates the end effector lock 6400' into a locked position and into engagement with the lock notches 7410 to lock the end effector 7000' to the shaft assembly 2000''''. Correspondingly, the distal movement of the third clutch 6310 into its disengaged position unlocks the end effector 7000' and allows the end effector 7000' to be disassembled from the shaft assembly 2000''''.

Further to the above, an instrument system including a handle and a shaft assembly attached thereto can be configured to perform a diagnostic check to assess the state of the clutch assemblies 6100, 6200, and 6300. In at least one instance, the control system 1800 sequentially actuates the electromagnetic actuators 6140, 6240, and/or 6340—in any suitable order—to verify the positions of the clutches 6110, 6210, and/or 6310, respectively, and/or verify that the clutches are responsive to the electromagnetic actuators and, thus, not stuck. The control system 1800 can use sensors, including any of the sensors disclosed herein, to verify the movement of the clutches 6110, 6120, and 6130 in response to the electromagnetic fields created by the electromagnetic actuators 6140, 6240, and/or 6340. In addition, the diagnostic check can also include verifying the motions of the drive systems. In at least one instance, the control system 1800 sequentially actuates the electromagnetic actuators 6140, 6240, and/or 6340—in any suitable order—to verify that the jaw drive opens and/or closes the jaw assembly 7100, the rotation drive rotates the end effector 7000, and/or the articulation drive articulates the end effector 7000, for example. The control system 1800 can use sensors to verify the motions of the jaw assembly 7100 and end effector 7000.

The control system 1800 can perform the diagnostic test at any suitable time, such as when a shaft assembly is attached to the handle and/or when the handle is powered on, for example. If the control system 1800 determines that the instrument system passed the diagnostic test, the control system 1800 can permit the ordinary operation of the instrument system. In at least one instance, the handle can comprise an indicator, such as a green LED, for example, which indicates that the diagnostic check has been passed. If the control system 1800 determines that the instrument system failed the diagnostic test, the control system 1800 can prevent and/or modify the operation of the instrument system. In at least one instance, the control system 1800 can limit the functionality of the instrument system to only the functions necessary to remove the instrument system from the patient, such as straightening the end effector 7000 and/or opening and closing the jaw assembly 7100, for example. In at least one respect, the control system 1800 enters into a limp mode. The limp mode of the control system 1800 can reduce a current rotational speed of the motor 1610 by any percentage selected from a range of about 75% to about 25%, for example. In one example, the limp mode reduces a current rotational speed of the motor 1610 by 50%. In one example, the limp mode reduces a current rotational speed of the motor 1610 by 75%. The limp mode may cause a current torque of the motor 1610 to be reduced by any percentage selected from a range of about 75% to about 25%, for example. In one example, the limp mode reduces a current torque of the motor 1610 by 50%. The handle can comprise an indicator, such as a red LED, for example, which indicates that the instrument system failed the diagnostic check and/or that the instrument system has entered into a limp mode. The above being said, any suitable feedback can be used to warn the clinician that the instrument system is not operating properly such as, for example, an audible warning and/or a tactile or vibratory warning, for example.

Figure 41:
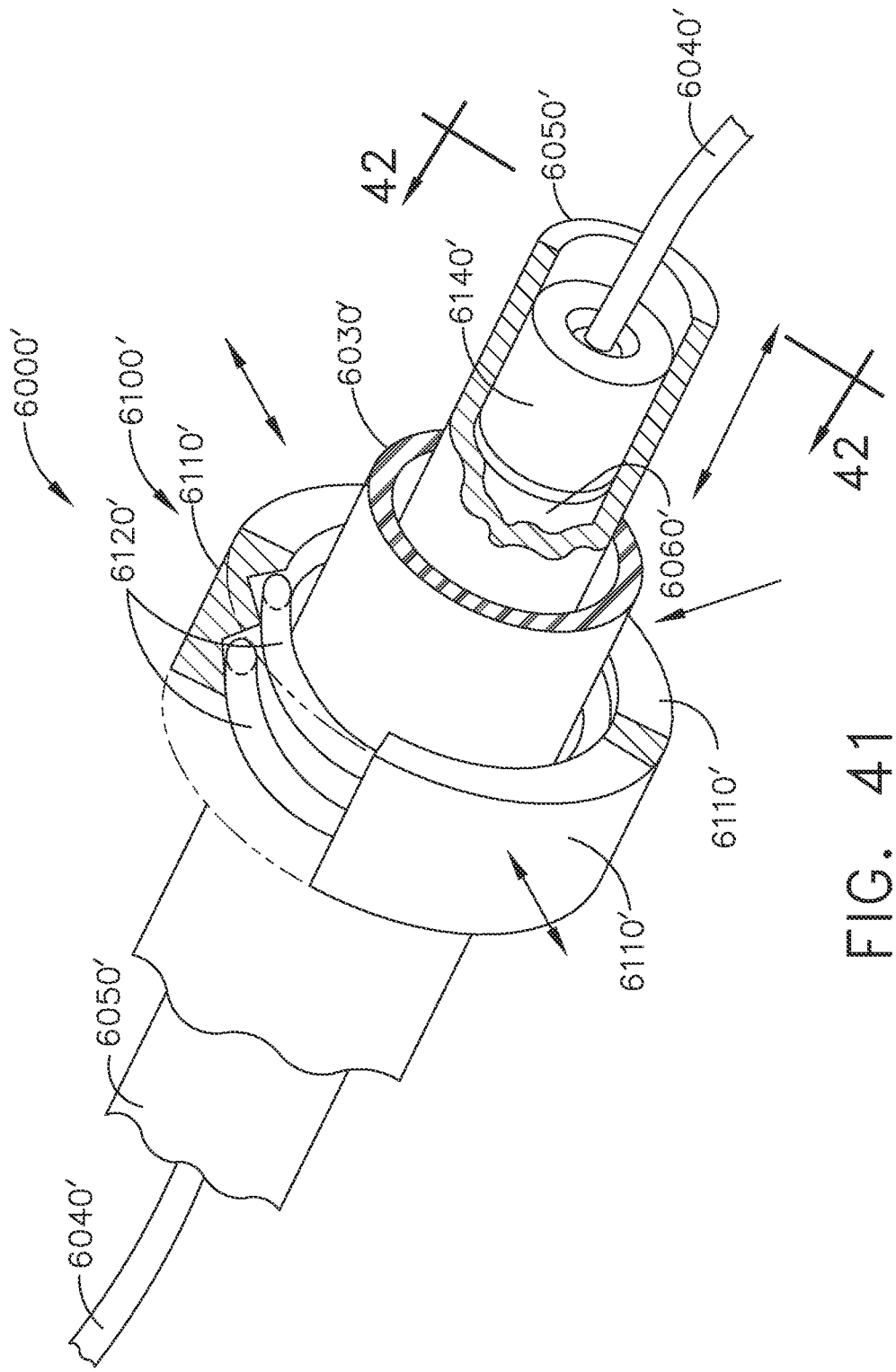
FIG. 41 is a partial cross-sectional view of a shaft assembly in accordance with at least one embodiment.
Figure 42:
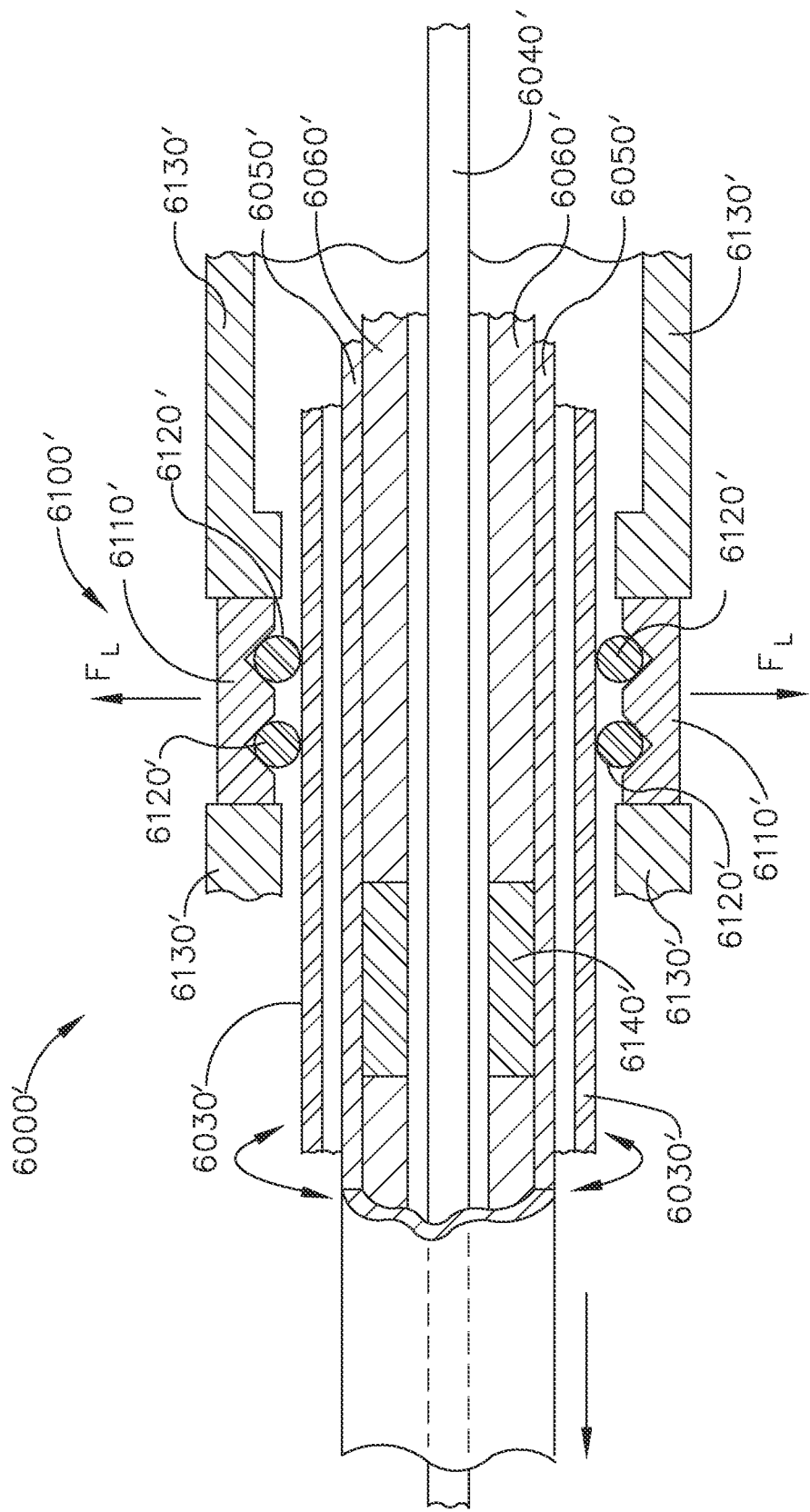
FIG. 42 is a partial cross-sectional view of the shaft assembly of FIG. 41 comprising a clutch illustrated in an unactuated condition.
Figure 43:
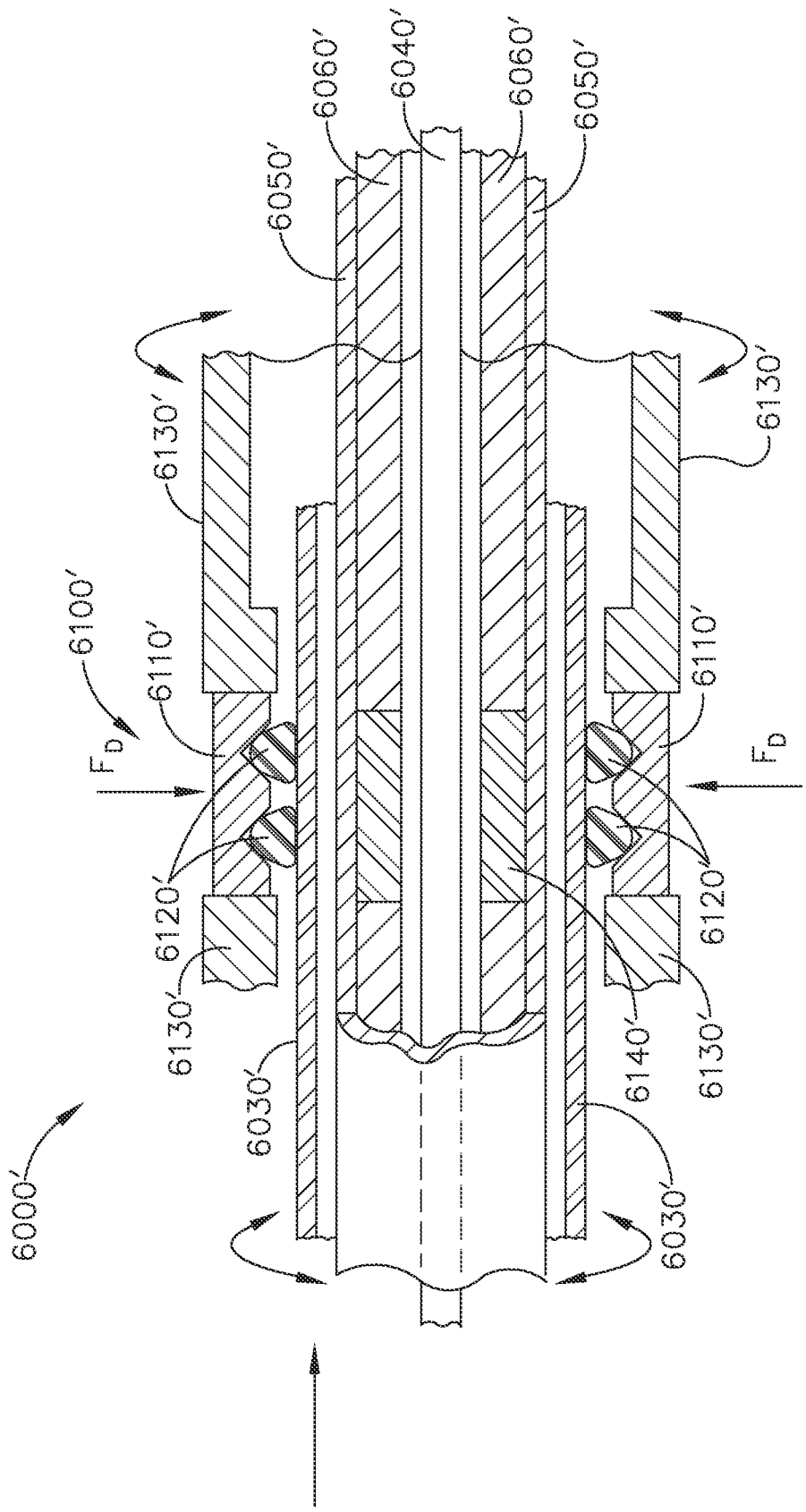
FIG. 43 is a partial cross-sectional view of the shaft assembly of FIG. 41 illustrating the clutch in an actuated condition.

FIGS. 41-43 depict a clutch system 6000' in accordance with at least one alternative embodiment. The clutch system 6000' is similar to the clutch system 6000 in many respects, most of which will not be repeated herein for the sake of brevity. Similar to the clutch system 6000, the clutch system 6000' comprises a clutch assembly 6100' which is actuatable to selectively couple a rotatable drive input 6030' with a rotatable drive output 6130'. The clutch assembly 6100' comprises clutch plates 6110' and drive rings 6120'. The clutch plates 6110' are comprised of a magnetic material, such as iron and/or nickel, for example, and can comprise a permanent magnet. As described in greater detail below, the clutch plates 6110' are movable between unactuated positions (FIG. 42) and actuated positions (FIG. 43) within the drive output 6130'. The clutch plates 6110' are slideably positioned in apertures defined in the drive output 6130' such that the clutch plates 6110' rotate with the drive output 6130' regardless of whether the clutch plates 6110' are in their unactuated or actuated positions.

When the clutch plates 6110' are in their unactuated positions, as illustrated in FIG. 42, the rotation of the drive input 6030' is not transferred to the drive output 6130'. More specifically, when the drive input 6030' is rotated, in such instances, the drive input 6030' slides past and rotates relative to the drive rings 6120' and, as a result, the drive rings 6120' do not drive the clutch plates 6110' and the drive output 6130'. When the clutch plates 6110' are in their actuated positions, as illustrated in FIG. 43, the clutch plates 6110' resiliently compress the drive rings 6120' against the drive input 6030'. The drive rings 6120' are comprised of any suitable compressible material, such as rubber, for example. In any event, in such instances, the rotation of the drive input 6030' is transferred to the drive output 6130' via the drive rings 6120' and the clutch plates 6110'. The clutch system 6000' comprises a clutch actuator 6140' configured to move the clutch plates 6110' into their actuated positions. The clutch actuator 6140' is comprised of a magnetic material such as iron and/or nickel, for example, and can comprise a permanent magnet. The clutch actuator 6140' is slideably positioned in a longitudinal shaft frame 6050' extending through the drive input 6030' and can be moved between an unactuated position (FIG. 42) and an actuated position (FIG. 43) by a clutch shaft 6060'. In at least one instance, the clutch shaft 6060' comprises a polymer cable, for example. When the clutch actuator 6140' is in its actuated position, as illustrated in FIG. 43, the clutch actuator 6140' pulls the clutch plates 6110' inwardly to compress the drive rings 6120', as discussed above. When the clutch actuator 6140' is moved into its unactuated position, as illustrated in FIG. 42, the drive rings 6120' resiliently expand and push the clutch plates 6110' away from the drive input 6030'. In various alternative embodiments, the clutch actuator 6140' can comprise an electromagnet. In such an arrangement, the clutch actuator 6140' can be actuated by an electrical circuit extending through a longitudinal aperture defined in the clutch shaft 6060', for example. In various instances, the clutch system 6000' further comprises electrical wires 6040', for example, extending through the longitudinal aperture.

Figure 44:
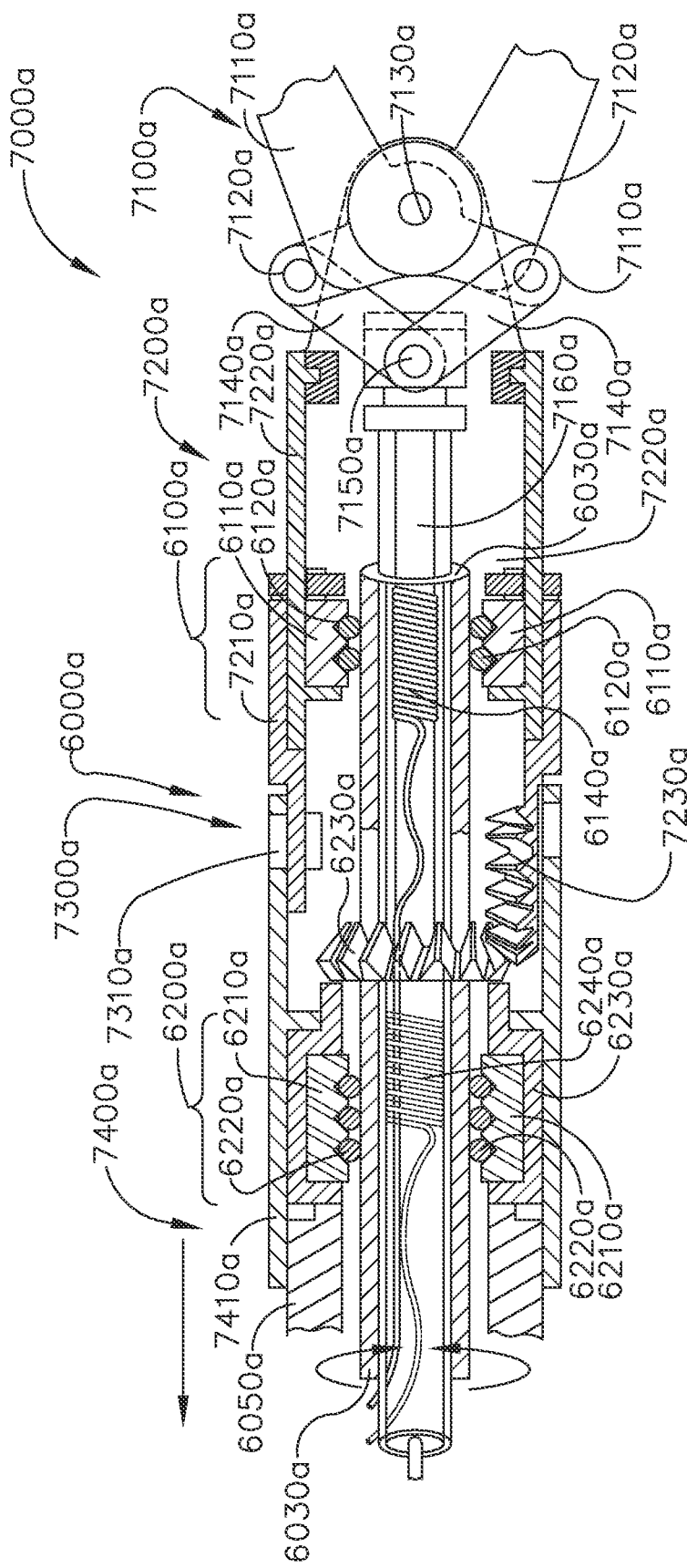
FIG. 44 is a partial cross-sectional view of a shaft assembly in accordance with at least one embodiment comprising first and second clutches illustrated in an unactuated condition.

FIG. 44 depicts an end effector 7000a including a jaw assembly 7100a, a jaw assembly drive, and a clutch system 6000a in accordance with at least one alternative embodiment. The jaw assembly 7100a comprises a first jaw 7110a and a second jaw 7120a which are selectively rotatable about a pivot 7130a. The jaw assembly drive comprises a translatable actuator rod 7160a and drive links 7140a which are pivotably coupled to the actuator rod 7160a about a pivot 7150a. The drive links 7140a are also pivotably coupled to the jaws 7110a and 7120a such that the jaws 7110a and 7120a are rotated closed when the actuator rod 7160a is pulled proximally and rotated open when the actuator rod 7160a is pushed distally. The clutch system 6000a is similar to the clutch systems 6000 and 6000' in many respects, most of which will not be repeated herein for the sake of brevity. The clutch system 6000a comprises a first clutch assembly 6100a and a second clutch assembly 6200a which are configured to selectively transmit the rotation of a drive input 6030a to rotate the jaw assembly 7100a about a longitudinal axis and articulate the jaw assembly 7100a about an articulation joint 7300a, respectively, as described in greater detail below.

The first clutch assembly 6100a comprises clutch plates 6110a and drive rings 6120a and work in a manner similar to the clutch plates 6110' and drive rings 6120' discussed above. When the clutch pates 6110a are actuated by an electromagnetic actuator 6140a, the rotation of the drive input 6030a is transferred to an outer shaft housing 7200a. More specifically, the outer shaft housing 7200a comprises a proximal outer housing 7210a and a distal outer housing 7220a which is rotatably supported by the proximal outer housing 7210a and is rotated relative to the proximal outer housing 7210a by the drive input 6030a when the clutch plates 6110a are in their actuated position. The rotation of the distal outer housing 7220a rotates the jaw assembly 7100a about the longitudinal axis owing to fact that the pivot 7130a of the jaw assembly 7100a is mounted to the distal outer housing 7220a. As a result, the outer shaft housing 7200a rotates the jaw assembly 7100a in a first direction when the outer shaft housing 7200a is rotated in a first direction by the drive input 6030a. Similarly, the outer shaft housing 7200a rotates the jaw assembly 7100a in a second direction when the outer shaft housing 7200a is rotated in a second direction by the drive input 6030a. When the electromagnetic actuator 6140a is de-energized, the drive rings 6120a expand and the clutch plates 6110a are moved into their unactuated positions, thereby decoupling the end effector rotation drive from the drive input 6030a.

The second clutch assembly 6200a comprises clutch plates 6210a and drive rings 6220a and work in a manner similar to the clutch plates 6110' and drive rings 6120' discussed above. When the clutch pates 6210a are actuated by an electromagnetic actuator 6240a, the rotation of the drive input 6030a is transferred to an articulation drive 6230a. The articulation drive 6230a is rotatably supported within an outer shaft housing 7410a of an end effector attachment portion 7400a and is rotatably supported by a shaft frame 6050a extending through the outer shaft housing 7410a. The articulation drive 6230a comprises a gear face defined thereon which is operably intermeshed with a stationary gear face 7230a defined on the proximal outer housing 7210a of the outer shaft housing 7200a. As a result, the articulation drive 6230a articulates the outer shaft housing 7200a and the jaw assembly 7100a in a first direction when the articulation drive 6230a is rotated in a first direction by the drive input 6030a. Similarly, the articulation drive 6230a articulates the outer shaft housing 7200a and the jaw assembly 7100a in a second direction when the articulation drive 6230a is rotated in a second direction by the drive input 6030a. When the electromagnetic actuator 6240a is de-energized, the drive rings 6220a expand and the clutch plates 6210a are moved into their unactuated positions, thereby decoupling the end effector articulation drive from the drive input 6030a.

Further to the above, the shaft assembly 4000 is illustrated in FIGS. 45-49. The shaft assembly 4000 is similar to the shaft assemblies 2000, 2000', 2000''', and 2000'''' in many respects, most of which will not be repeated herein for the sake of brevity. The shaft assembly 4000 comprises a proximal portion 4100, an elongate shaft 4200, a distal attachment portion 2400, and an articulate joint 2300 which rotatably connects the distal attachment portion 2040 to the elongate shaft 4200. The proximal portion 4100, similar to the proximal portion 2100, is operably attachable to the drive module 1100 of the handle 1000. The proximal portion 4100 comprises a housing 4110 including an attachment interface 4130 configured to mount the shaft assembly 4000 to the attachment interface 1130 of the handle 1000. The shaft assembly 4000 further comprises a frame 4500 including a shaft 4510 configured to be coupled to the shaft 1510 of the handle frame 1500 when the shaft assembly 4000 is attached to the handle 1000. The shaft assembly 4000 also comprises a drive system 4700 including a rotatable drive shaft 4710 configured to be operably coupled to the drive shaft 1710 of the handle drive system 1700 when the shaft assembly 4000 is attached to the handle 1000. The distal attachment portion 2400 is configured to receive an end effector, such as end effector 8000, for example. The end effector 8000 is similar to the end effector 7000 in many respects, most of which will not be repeated herein for the sake of brevity. That said, the end effector 8000 comprises a jaw assembly 8100 configured to, among other things, grasp tissue.

Figure 48:
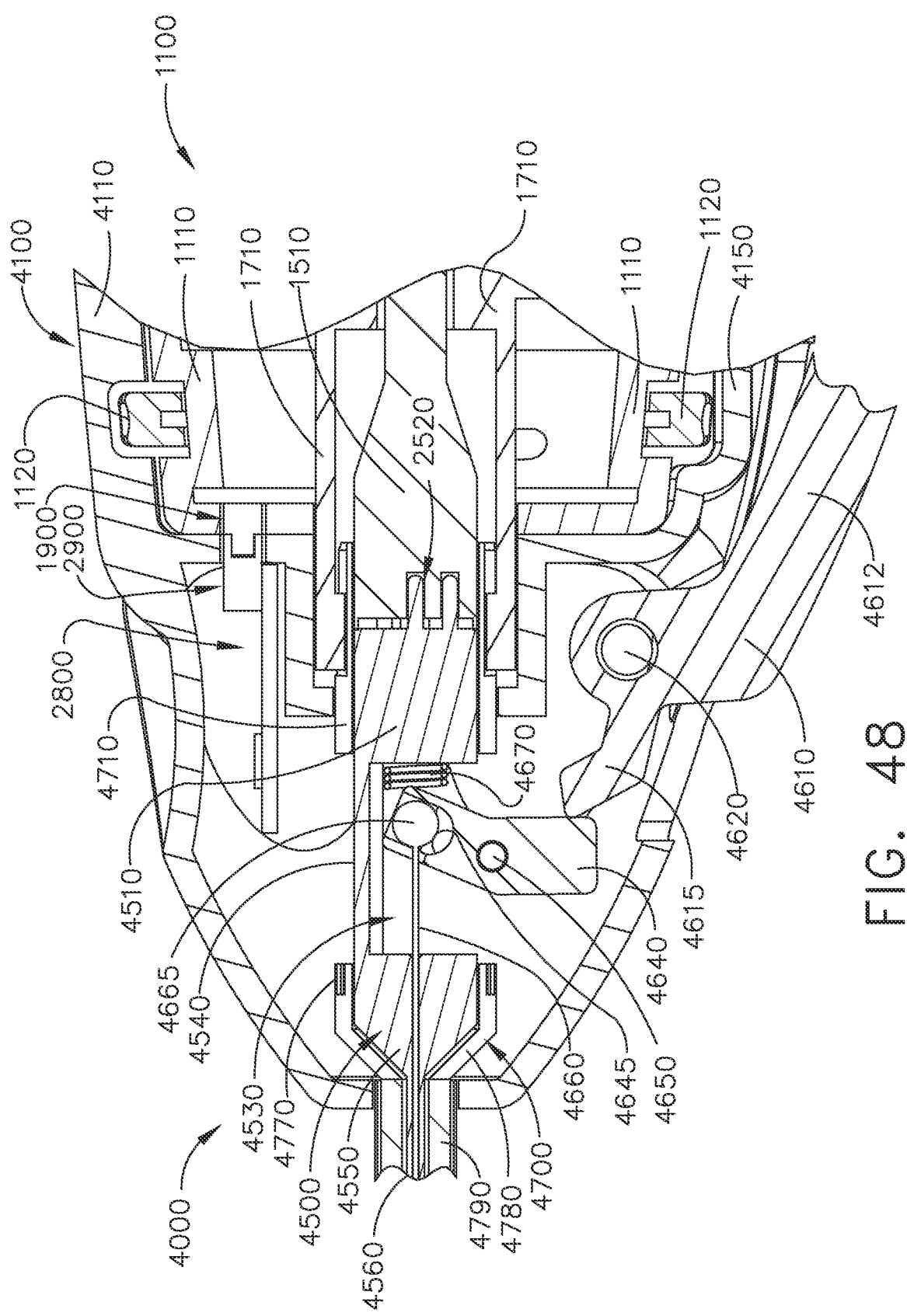
FIG. 48 is another partial cross-sectional view of the shaft assembly of FIG. 45 attached to the handle of FIG. 1.
Figure 49:
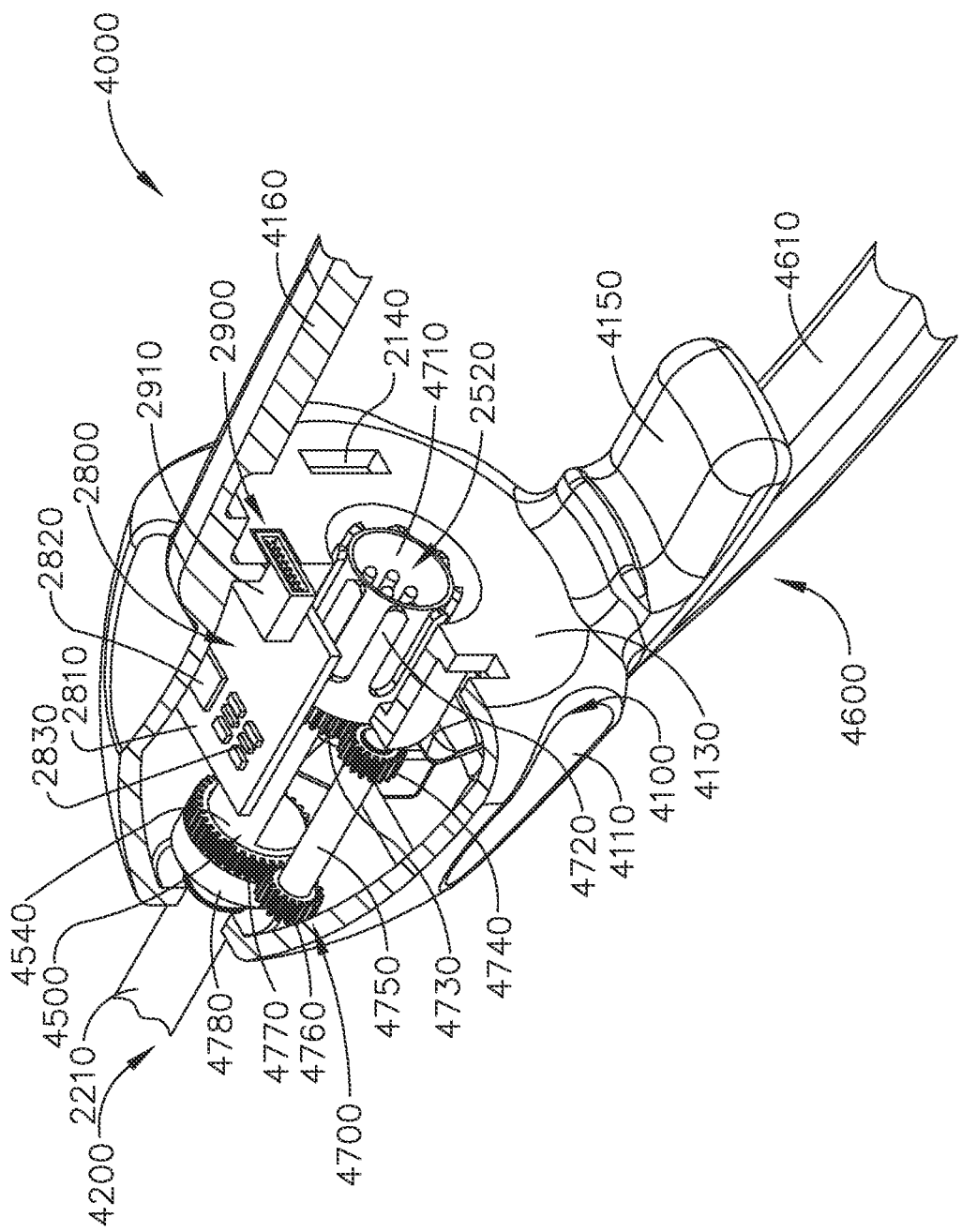
FIG. 49 is a partial cross-sectional perspective view of the shaft assembly of FIG. 45.

As discussed above, referring primarily to FIGS. 47-49, the frame 4500 of the shaft assembly 4000 comprises a frame shaft 4510. The frame shaft 4510 comprises a notch, or cut-out, 4530 defined therein. As discussed in greater detail below, the cut-out 4530 is configured to provide clearance for a jaw closure actuation system 4600. The frame 4500 further comprises a distal portion 4550 and a bridge 4540 connecting the distal portion 4550 to the frame shaft 4510. The frame 4500 further comprises a longitudinal portion 4560 extending through the elongate shaft 4200 to the distal attachment portion 2400. Similar to the above, the frame shaft 4510 comprises one or more electrical traces defined thereon and/or therein. The electrical traces extend through the longitudinal portion 4560, the distal portion 4550, the bridge 4540, and/or any suitable portion of the frame shaft 4510 to the electrical contacts 2520. Referring primarily to FIG. 48, the distal portion 4550 and longitudinal portion 4560 comprise a longitudinal aperture defined therein which is configured to receive a rod 4660 of the jaw closure actuation system 4600, as described in greater detail below.

As also discussed above, referring primarily to FIGS. 48 and 49, the drive system 4700 of the shaft assembly 4000 comprises a drive shaft 4710. The drive shaft 4710 is rotatably supported within the proximal shaft housing 4110 by the frame shaft 4510 and is rotatable about a longitudinal axis extending through the frame shaft 4510. The drive system 4700 further comprises a transfer shaft 4750 and an output shaft 4780. The transfer shaft 4750 is also rotatably supported within the proximal shaft housing 4110 and is rotatable about a longitudinal axis extending parallel to, or at least substantially parallel to, the frame shaft 4510 and the longitudinal axis defined therethrough. The transfer shaft 4750 comprises a proximal spur gear 4740 fixedly mounted thereto such that the proximal spur gear 4740 rotates with the transfer shaft 4750. The proximal spur gear 4740 is operably intermeshed with an annular gear face 4730 defined around the outer circumference of the drive shaft 4710 such that the rotation of the drive shaft 4710 is transferred to the transfer shaft 4750. The transfer shaft 4750 further comprises a distal spur gear 4760 fixedly mounted thereto such that the distal spur gear 4760 rotates with the transfer shaft 4750. The distal spur gear 4760 is operably intermeshed with an annular gear 4770 defined around the outer circumference of the output shaft 4780 such that the rotation of the transfer shaft 4750 is transferred to the output shaft 4780. Similar to the above, the output shaft 4780 is rotatably supported within the proximal shaft housing 4110 by the distal portion 4550 of the shaft frame 4500 such that the output shaft 4780 rotates about the longitudinal shaft axis. Notably, the output shaft 4780 is not directly coupled to the input shaft 4710; rather, the output shaft 4780 is operably coupled to the input shaft 4710 by the transfer shaft 4750. Such an arrangement provides room for the manually-actuated jaw closure actuation system 4600 discussed below.

Further to the above, referring primarily to FIGS. 47 and 48, the jaw closure actuation system 4600 comprises an actuation, or scissors, trigger 4610 rotatably coupled to the proximal shaft housing 4110 about a pivot 4620. The actuation trigger 4610 comprises an elongate portion 4612, a proximal end 4614, and a grip ring aperture 4616 defined in the proximal end 4614 which is configured to be gripped by the clinician. The shaft assembly 4000 further comprises a stationary grip 4160 extending from the proximal housing 4110. The stationary grip 4160 comprises an elongate portion 4162, a proximal end 4164, and a grip ring aperture 4166 defined in the proximal end 4164 which is configured to be gripped by the clinician. In use, as described in greater detail below, the actuation trigger 4610 is rotatable between an unactuated position and an actuated position (FIG. 48), i.e., toward the stationary grip 4160, to close the jaw assembly 8100 of the end effector 8000.

Referring primarily to FIG. 48, the jaw closure actuation system 4600 further comprises a drive link 4640 rotatably coupled to the proximal shaft housing 4110 about a pivot 4650 and, in addition, an actuation rod 4660 operably coupled to the drive link 4640. The actuation rod 4660 extends through an aperture defined in the longitudinal frame portion 4560 and is translatable along the longitudinal axis of the shaft frame 4500. The actuation rod 4660 comprises a distal end operably coupled to the jaw assembly 8100 and a proximal end 4665 positioned in a drive slot 4645 defined in the drive link 4640 such that the actuation rod 4660 is translated longitudinally when the drive link 4640 is rotated about the pivot 4650. Notably, the proximal end 4665 is rotatably supported within the drive slot 4645 such that the actuation rod 4660 can rotate with the end effector 8000.

Further to the above, the actuation trigger 4610 further comprises a drive arm 4615 configured to engage and rotate the drive link 4640 proximally, and translate the actuation rod 4660 proximally, when the actuation trigger 4610 is actuated, i.e., moved closer to the proximal shaft housing 4110. In such instances, the proximal rotation of the drive link 4640 resiliently compresses a biasing member, such as a coil spring 4670, for example, positioned intermediate the drive link 4640 and the frame shaft 4510. When the actuation trigger 4610 is released, the compressed coil spring 4670 re-expands and pushes the drive link 4640 and the actuation rod 4660 distally to open the jaw assembly 8100 of the end effector 8000. Moreover, the distal rotation of the drive link 4640 drives, and automatically rotates, the actuation trigger 4610 back into its unactuated position. That being said, the clinician could manually return the actuation trigger 4610 back into its unactuated position. In such instances, the actuation trigger 4610 could be opened slowly. In either event, the shaft assembly 4000 further comprises a lock configured to releasably hold the actuation trigger 4610 in its actuated position such that the clinician can use their hand to perform another task without the jaw assembly 8100 opening unintentionally.

In various alternative embodiments, further to the above, the actuation rod 4660 can be pushed distally to close the jaw assembly 8100. In at least one such instance, the actuation rod 4660 is mounted directly to the actuation trigger 4610 such that, when the actuation trigger 4610 is actuated, the actuation trigger 4610 drives the actuation rod 4660 distally. Similar to the above, the actuation trigger 4610 can compress a spring when the actuation trigger 4610 is closed such that, when the actuation trigger 4610 is released, the actuation rod 4660 is pushed proximally.

Further to the above, the shaft assembly 4000 has three functions—opening/closing the jaw assembly of an end effector, rotating the end effector about a longitudinal axis, and articulating the end effector about an articulation axis. The end effector rotation and articulation functions of the shaft assembly 4000 are driven by the motor assembly 1600 and the control system 1800 of the drive module 1100 while the jaw actuation function is manually-driven by the jaw closure actuation system 4600. The jaw closure actuation system 4600 could be a motor-driven system but, instead, the jaw closure actuation system 4600 has been kept a manually-driven system such that the clinician can have a better feel for the tissue being clamped within the end effector. While motorizing the end effector rotation and actuation systems provides certain advantages for controlling the position of the end effector, motorizing the jaw closure actuation system 4600 may cause the clinician to lose a tactile sense of the force being applied to the tissue and may not be able to assess whether the force is insufficient or excessive. Thus, the jaw closure actuation system 4600 is manually-driven even though the end effector rotation and articulation systems are motor-driven.

Figure 50:
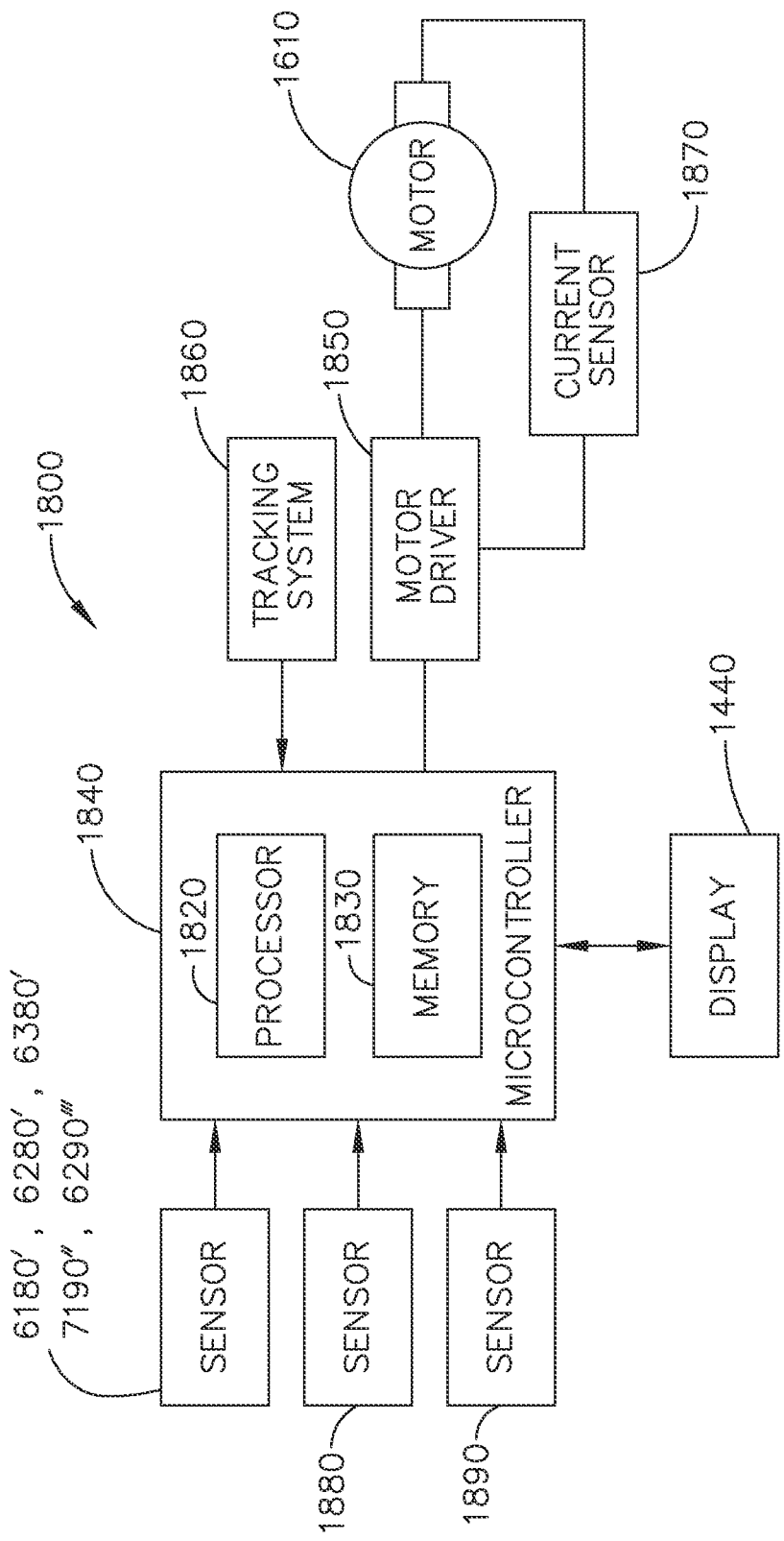
FIG. 50 is a schematic of the control system of the surgical system of FIG. 1.

FIG. 50 is a logic diagram of the control system 1800 of the surgical system depicted in FIG. 1 in accordance with at least one embodiment. The control system 1800 comprises a control circuit. The control circuit includes a microcontroller 1840 comprising a processor 1820 and a memory 1830. One or more sensors, such as sensors 1880, 1890, 6180', 6280', 6380', 7190", and/or 6290''', for example, provide real time feedback to the processor 1820. The control system 1800 further comprises a motor driver 1850 configured to control the electric motor 1610 and a tracking system 1860 configured to determine the position of one or more longitudinally movable components in the surgical instrument, such as the clutches 6110, 6120, and 6130 and/or the longitudinally-movable drive nut 7150 of the jaw assembly drive, for example. The tracking system 1860 is also configured to determine the position of one or more rotational components in the surgical instrument, such as the drive shaft 2530, the outer shaft 6230, and/or the articulation drive 6330, for example. The tracking system 1860 provides position information to the processor 1820, which can be programmed or configured to, among other things, determine the position of the clutches 6110, 6120, and 6130 and the drive nut 7150 as well as the orientation of the jaws 7110 and 7120. The motor driver 1850 may be an A3941 available from Allegro Microsystems, Inc., for example; however, other motor drivers may be readily substituted for use in the tracking system 1860. A detailed description of an absolute positioning system is described in U.S. Patent Application Publication No. 2017/0296213, entitled SYSTEMS AND METHODS FOR CONTROLLING A SURGICAL STAPLING AND CUTTING INSTRUMENT, the entire disclosure of which is hereby incorporated herein by reference.

The microcontroller 1840 may be any single core or multicore processor such as those known under the trade name ARM Cortex by Texas Instruments, for example. In at least one instance, the microcontroller 1840 is a LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EE-PROM), one or more pulse width modulation (PWM) modules and/or frequency modulation (FM) modules, one or more quadrature encoder inputs (QEI) analog, one or more 12-bit Analog-to-Digital Converters (ADC) with 12 analog input channels, for example, details of which are available from the product datasheet.

In various instances, the microcontroller 1840 comprises a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 1840 is programmed to perform various functions such as precisely controlling the speed and/or position of the drive nut 7150 of the jaw closure assembly, for example. The microcontroller 1840 is also programmed to precisely control the rotational speed and position of the end effector 7000 and the articulation speed and position of the end effector 7000. In various instances, the microcontroller 1840 computes a response in the software of the microcontroller 1840. The computed response is compared to a measured response of the actual system to obtain an "observed" response, which is used for actual feedback decisions. The observed response is a favorable, tuned, value that balances the smooth, continuous nature of the simulated response with the measured response, which can detect outside influences on the system.

The motor 1610 is controlled by the motor driver 1850. In various forms, the motor 1610 is a DC brushed driving motor having a maximum rotational speed of approximately 25,000 RPM, for example. In other arrangements, the motor 1610 includes a brushless motor, a cordless motor, a synchronous motor, a stepper motor, or any other suitable electric motor. The motor driver 1850 may comprise an H-bridge driver comprising field-effect transistors (FETs), for example. The motor driver 1850 may be an A3941 available from Allegro Microsystems, Inc., for example. The A3941 driver 1850 is a full-bridge controller for use with external N-channel power metal oxide semiconductor field effect transistors (MOSFETs) specifically designed for inductive loads, such as brush DC motors. In various instances, the driver 1850 comprises a unique charge pump regulator provides full (>10 V) gate drive for battery voltages down to 7 V and allows the A3941 to operate with a reduced gate drive, down to 5.5 V. A bootstrap capacitor may be employed to provide the above-battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the highside or the lowside FETs. The power FETs are protected from shoot-through by resistor adjustable dead time. Integrated diagnostics provide indication of undervoltage, overtemperature, and power bridge faults, and can be configured to protect the power MOSFETs under most short circuit conditions. Other motor drivers may be readily substituted.

The tracking system 1860 comprises a controlled motor drive circuit arrangement comprising one or more position sensors, such as sensors 1880, 1890, 6180', 6280', 6380', 7190", and/or 6290''', for example. The position sensors for an absolute positioning system provide a unique position signal corresponding to the location of a displacement member. As used herein, the term displacement member is used generically to refer to any movable member of the surgical system. In various instances, the displacement member may be coupled to any position sensor suitable for measuring linear displacement. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall Effect sensors, a magnetic sensing system comprising a fixed magnet and a series of movable linearly arranged Hall Effect sensors, an optical sensing system comprising a movable light source and a series of linearly arranged photo diodes or photo detectors, or an optical sensing system comprising a fixed light source and a series of movable linearly arranged photo diodes or photo detectors, or any combination thereof.

The position sensors 1880, 1890, 6180', 6280', 6380', 7190", and/or 6290''', for example, may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-Effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

In various instances, one or more of the position sensors of the tracking system 1860 comprise a magnetic rotary absolute positioning system. Such position sensors may be implemented as an AS5055EQFT single-chip magnetic rotary position sensor available from Austria Microsystems, AG and can be interfaced with the controller 1840 to provide an absolute positioning system. In certain instances, a position sensor comprises a low-voltage and low-power component and includes four Hall-Effect elements in an area of the position sensor that is located adjacent a magnet. A high resolution ADC and a smart power management controller are also provided on the chip. A CORDIC processor (for Coordinate Rotation Digital Computer), also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface such as an SPI interface to the controller 1840. The position sensors can provide 12 or 14 bits of resolution, for example. The position sensors can be an AS5055 chip provided in a small QFN 16-pin 4×4×0.85 mm package, for example.

The tracking system 1860 may comprise and/or be programmed to implement a feedback controller, such as a PID, state feedback, and adaptive controller. A power source converts the signal from the feedback controller into a physical input to the system, in this case voltage. Other examples include pulse width modulation (PWM) and/or frequency modulation (FM) of the voltage, current, and force. Other sensor(s) may be provided to measure physical parameters of the physical system in addition to position. In various instances, the other sensor(s) can include sensor arrangements such as those described in U.S. Pat. No. 9,345,481, entitled STAPLE CARTRIDGE TISSUE THICKNESS SENSOR SYSTEM, which is hereby incorporated herein by reference in its entirety; U.S. Patent Application Publication No. 2014/0263552, entitled STAPLE CARTRIDGE TISSUE THICKNESS SENSOR SYSTEM, which is hereby incorporated herein by reference in its entirety; and U.S. patent application Ser. No. 15/628,175, entitled TECHNIQUES FOR ADAPTIVE CONTROL OF MOTOR VELOCITY OF A SURGICAL STAPLING AND CUTTING INSTRUMENT, which is hereby incorporated herein by reference in its entirety. In a digital signal processing system, absolute positioning system is coupled to a digital data acquisition system where the output of the absolute positioning system will have finite resolution and sampling frequency. The absolute positioning system may comprise a compare and combine circuit to combine a computed response with a measured response using algorithms such as weighted average and theoretical control loop that drives the computed response towards the measured response. The computed response of the physical system takes into account properties like mass, inertial, viscous friction, inductance resistance, etc., to predict what the states and outputs of the physical system will be by knowing the input.

The absolute positioning system provides an absolute position of the displacement member upon power up of the instrument without retracting or advancing the displacement member to a reset (zero or home) position as may be required with conventional rotary encoders that merely count the number of steps forwards or backwards that the motor 1610 has taken to infer the position of a device actuator, drive bar, knife, and the like.

A sensor 1880 comprising a strain gauge or a micro-strain gauge, for example, is configured to measure one or more parameters of the end effector, such as, for example, the strain experienced by the jaws 7110 and 7120 during a clamping operation. The measured strain is converted to a digital signal and provided to the processor 1820. In addition to or in lieu of the sensor 1880, a sensor 1890 comprising a load sensor, for example, can measure the closure force applied by the closure drive system to the jaws 7110 and 7120. In various instances, a current sensor 1870 can be employed to measure the current drawn by the motor 1610.

The force required to clamp the jaw assembly 7100 can correspond to the current drawn by the motor 1610, for example. The measured force is converted to a digital signal and provided to the processor 1820. A magnetic field sensor can be employed to measure the thickness of the captured tissue. The measurement of the magnetic field sensor can also be converted to a digital signal and provided to the processor 1820.

The measurements of the tissue compression, the tissue thickness, and/or the force required to close the end effector on the tissue as measured by the sensors can be used by the controller 1840 to characterize the position and/or speed of the movable member being tracked. In at least one instance, a memory 1830 may store a technique, an equation, and/or a look-up table which can be employed by the controller 1840 in the assessment. In various instances, the controller 1840 can provide the user of the surgical instrument with a choice as to the manner in which the surgical instrument should be operated. To this end, the display 1440 can display a variety of operating conditions of the instrument and can include touch screen functionality for data input. Moreover, information displayed on the display 1440 may be overlaid with images acquired via the imaging modules of one or more endoscopes and/or one or more additional surgical instruments used during the surgical procedure.

As discussed above, the drive module 1100 of the handle 1000 and/or the shaft assemblies 2000, 3000, 4000, and/or 5000, for example, attachable thereto comprise control systems. Each of the control systems can comprise a circuit board having one or more processors and/or memory devices. Among other things, the control systems are configured to store sensor data, for example. They are also configured to store data which identifies the shaft assembly to the handle 1000. Moreover, they are also configured to store data including whether or not the shaft assembly has been previously used and/or how many times the shaft assembly has been used. This information can be obtained by the handle 1000 to assess whether or not the shaft assembly is suitable for use and/or has been used less than a predetermined number of times, for example.

Figure 51:
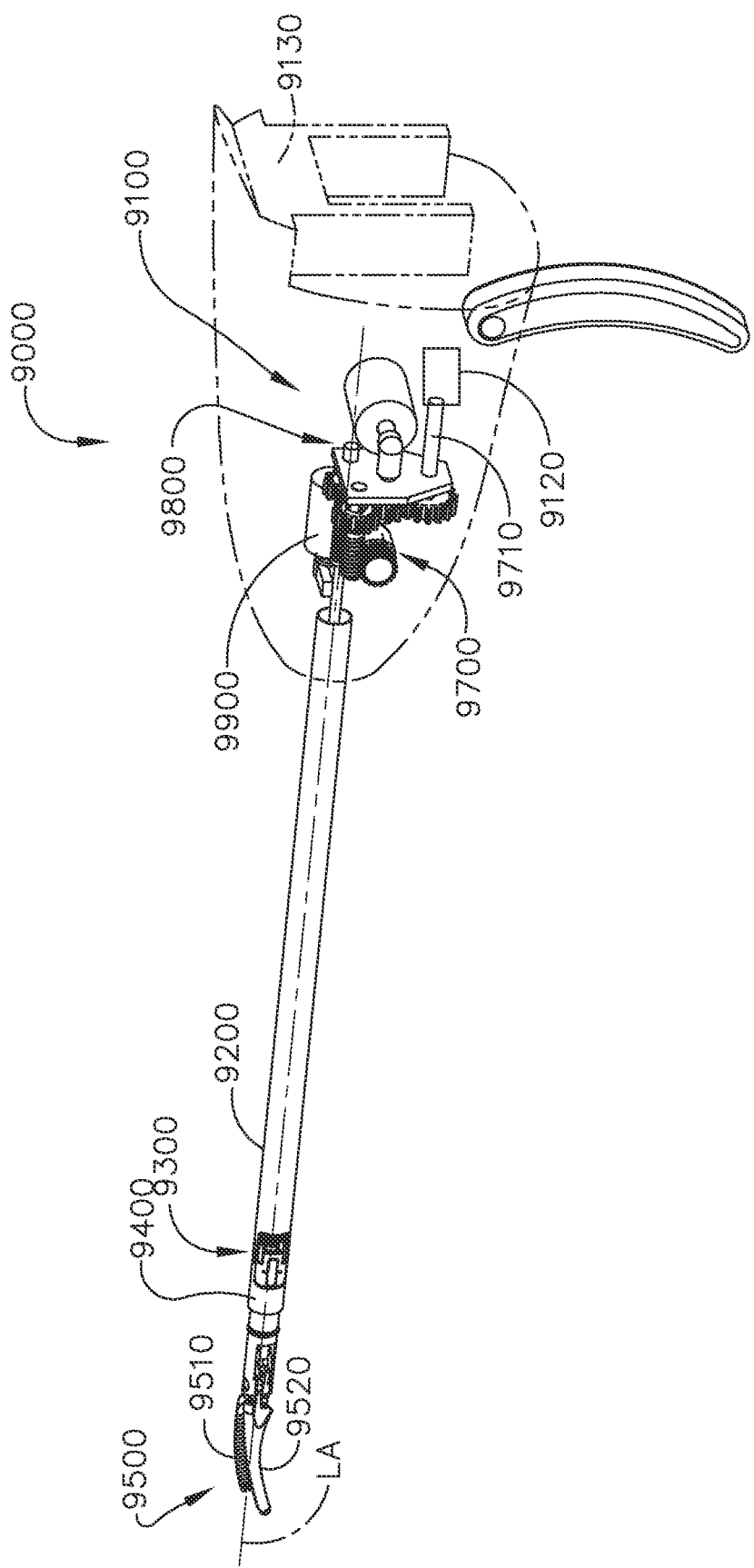
FIG. 51 is a perspective view of a shaft assembly in accordance with at least one embodiment.

A shaft assembly 9000 is illustrated in FIGS. 51-69. The shaft assembly 9000 is similar to the shaft assemblies 2000, 3000, 4000, and 5000 in many respects, most of which will not be discussed herein for the sake of brevity. As illustrated in FIG. 51, the shaft assembly 9000 comprises a proximal portion 9100, an elongate shaft 9200 extending from the proximal portion 9100, a distal attachment portion 9400, and an articulation joint 9300. The proximal portion 9100 comprises an interface 9130 configured to be attached to a handle, such as the handle 1000, for example. The articulation joint 9300 rotatably connects the distal attachment portion 9400 to the elongate shaft 9200. The shaft assembly 9000 further comprises an end effector assembly 9500 attached to the distal attachment portion 9400. The end effector assembly 9500 comprises a first jaw 9510 and a second jaw 9520 configured to be opened and closed to clamp and/or manipulate the tissue of a patient. In use, the end effector assembly 9500 can be articulated about the articulation joint 9300 and/or rotated relative to the distal attachment portion 9400 about a longitudinal axis LA to better situate the jaws 9510 and 9520 within a patient in order to perform various end effector functions, as will be described in greater detail below.

Figure 52:
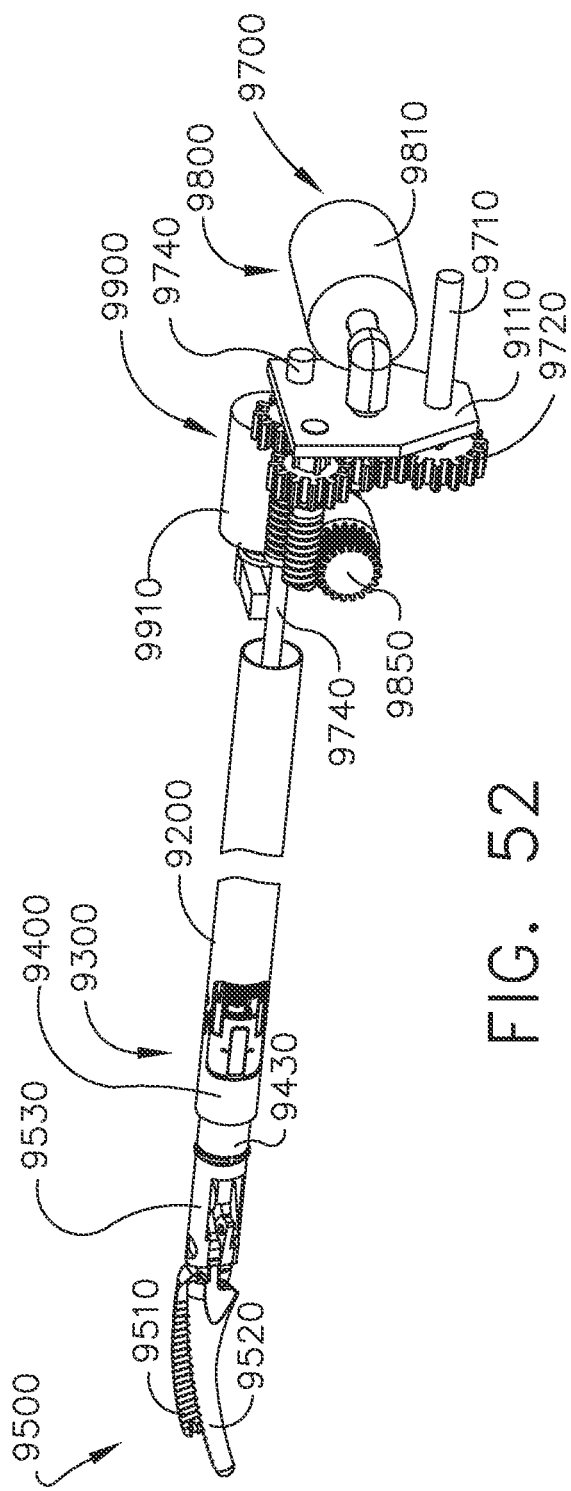
FIG. 52 is a perspective view of the shaft assembly of FIG. 51 illustrated with some components removed.
Figure 53:
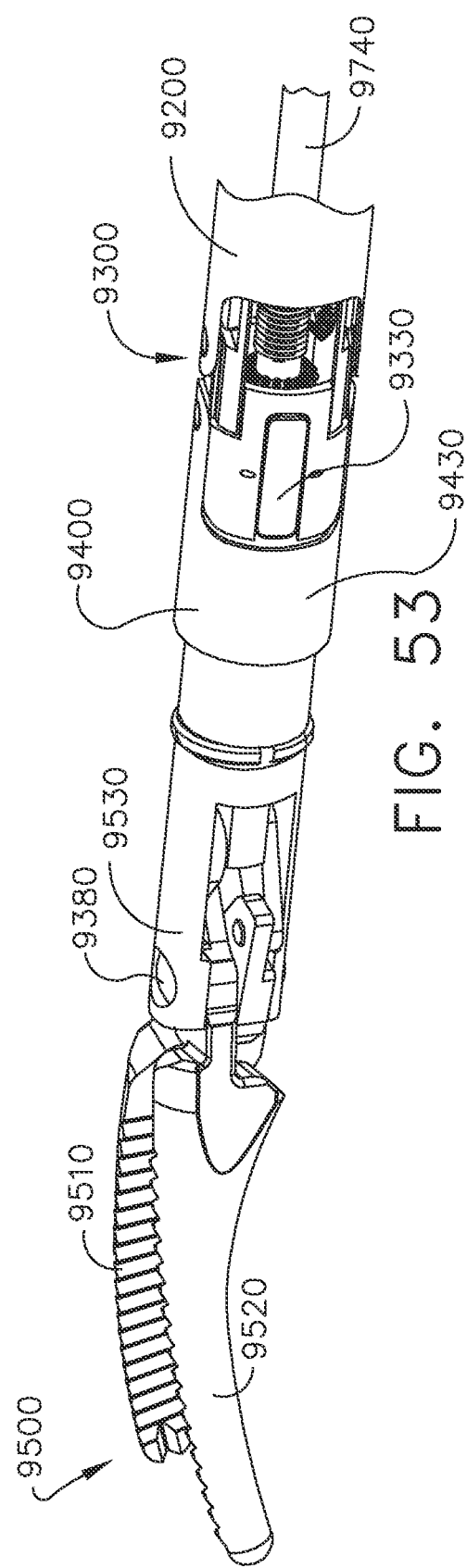
FIG. 53 is a perspective view of an end effector of the shaft assembly of FIG. 51.
Figure 54:
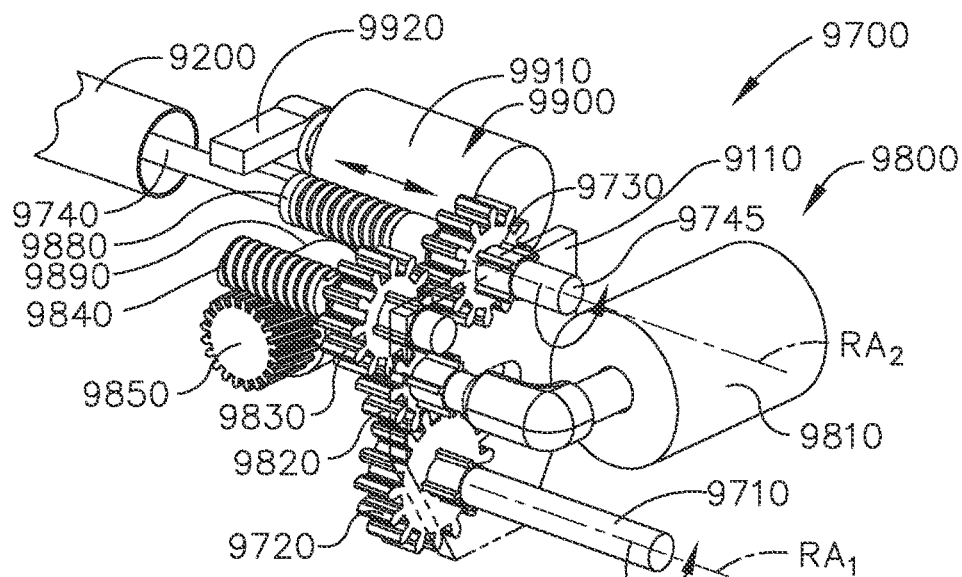
FIG. 54 is a perspective view of a drive assembly of the shaft assembly of FIG. 51.
Figure 55:
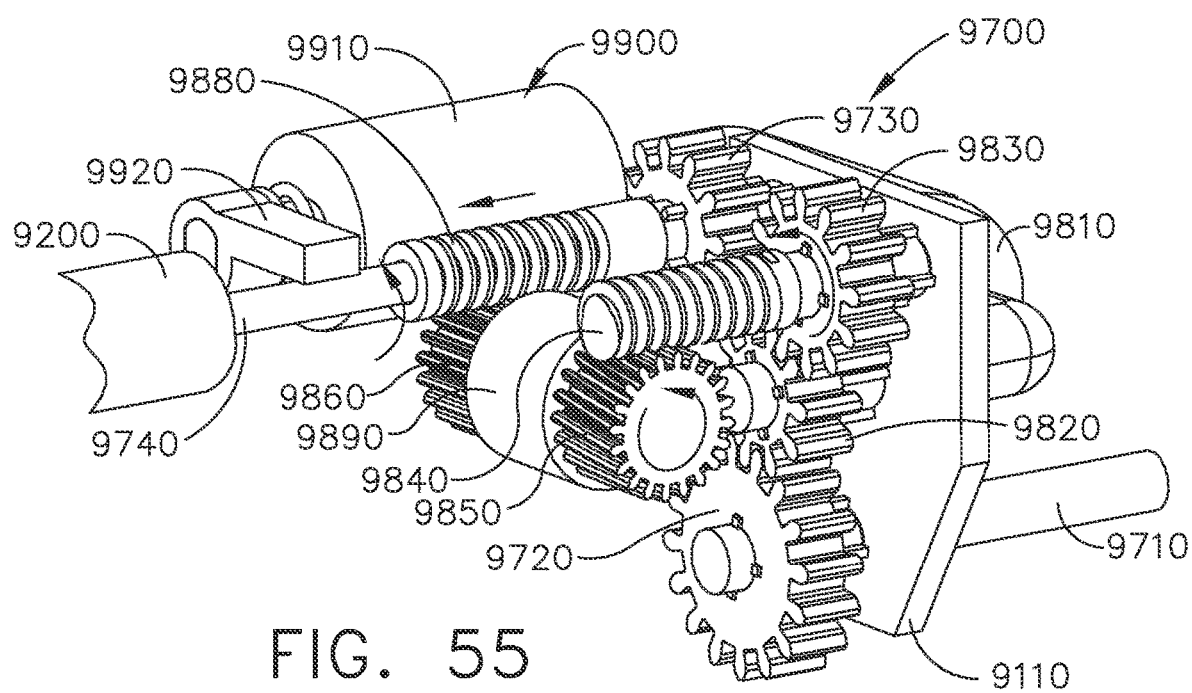
FIG. 55 is another perspective view of the drive assembly of FIG. 54.

Referring to FIG. 52, the shaft assembly 9000 comprises a drive assembly 9700 supported on a frame 9110 in the proximal shaft portion 9100. The drive assembly 9700 is capable of being operated in two configurations—a shifting configuration and a drive configuration. Moreover, as discussed in greater detail below, the drive assembly 9700 is configured to provide three end effector functions by way of one rotary input. The drive assembly 9700 comprises a first, or input, rotatable drive shaft 9710 configured to transfer rotational motions from a drive motor 9120 (illustrated in FIG. 51) to a main gear 9720 of the drive assembly 9700. Referring to FIGS. 54 and 55, the input drive shaft 9710 is rotatable about a first rotation axis $RA_1$ and is rotatably supported by the frame 9110. The main gear 9720 is mounted to the input drive shaft 9710 such that the main gear 9720 rotates with the input drive shaft 9710. The drive assembly 9700 further comprises a second, or output, rotatable drive shaft 9740. The output drive shaft 9740 is rotatable about a second rotation axis $RA_2$ and is also rotatably supported by the frame 9110. As described in greater detail below, the drive assembly 9700 also comprises a first rotatable gear 9730 and a second rotatable gear 9830 which are selectively engageable with the main gear 9720.

Referring to FIG. 52, the shaft assembly 9000 further comprises a shifting assembly 9800 configured to shift the drive assembly 9700. The shifting assembly 9800 comprises a solenoid 9810 which translates a shifter gear 9820 to place the drive assembly 9700 in its shifting configuration or its drive configuration. Referring to FIGS. 58 and 59, the shifter gear 9820 is operably intermeshed with the main gear 9720 of the drive assembly 9700 when the shifter gear 9820 is in its shifting configuration (FIG. 58) and, also, its drive configuration (FIG. 59). That being said, the shifter gear 9820 rotatably drives either the first rotatable gear 9730 or the second rotatable gear 9830 depending on whether the drive assembly 9700 is in its shifting configuration (FIG. 58) or its drive configuration (FIG. 59). Ultimately, the first and second rotatable gears 9730 and 9830 both drive the output drive shaft 9740, but in different ways. More specifically, the output drive shaft 9740 is rotated by the shifter gear 9820 via the first rotatable gear 9730 when the drive assembly 9700 is in its drive configuration and, on the other hand, the output drive shaft 9740 is translated by the shifter gear 9820 via the second rotatable gear 9830 when the drive assembly 9700 is in its shifting configuration.

Referring primarily to FIGS. 58 and 59, the frame 9110 comprises a slot 9115 defined therein which is configured to guide and/or constrain the movement of the shifter gear 9820. The slot 9115 comprises a first end configured to stop the shifter gear 9820 in its first position and a second end configured to stop the shifter gear 9820 in its second position. More specifically, the shifter gear 9820 is rotatably mounted to a shifter shaft 9825 extending through the slot 9115 which slides within the slot 9115 and moves the shifter gear 9820 between its first and second positions when the solenoid 9810 is actuated. The slot 9115 comprises arcuate sidewalls extending between the first and second ends thereof which define an arcuate path for the shifter gear 9820. The arcuate path is centered about the axis $RA_1$ extending through the input shaft 9710. That said, the slot 9115 can comprise any suitable configuration and define any suitable path for the shifter gear 9820. In at least one instance, the slot 9115 is straight and defines a straight path for the shifter gear 9820.

Figure 56:
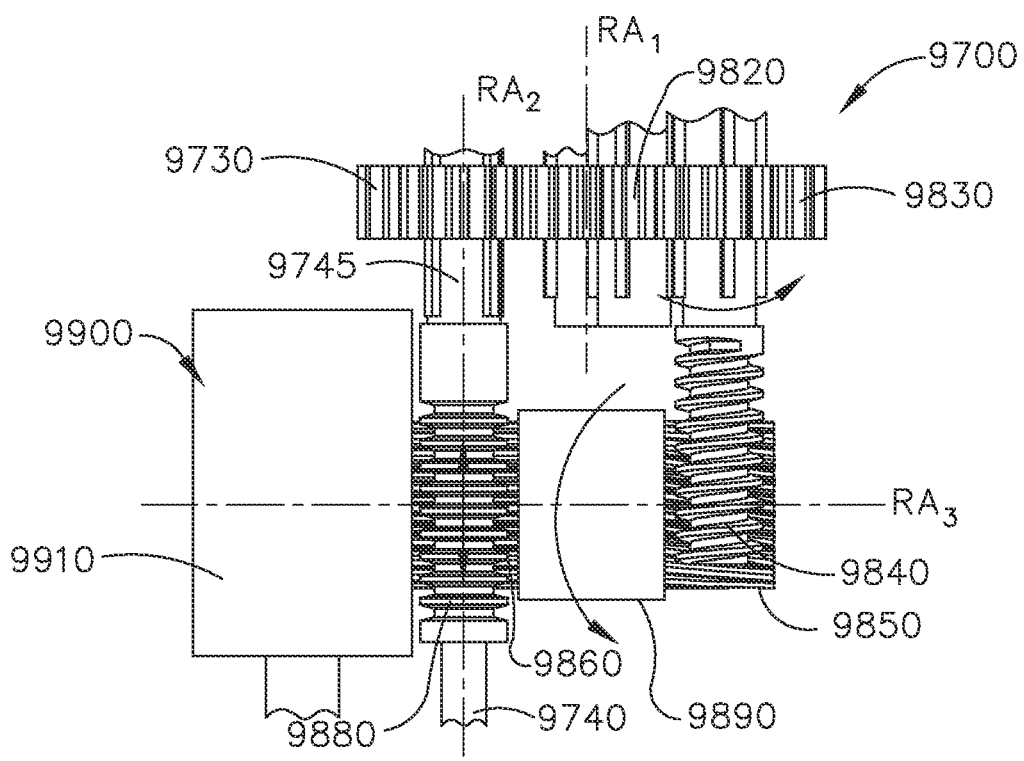
FIG. 56 is a partial plan view of the drive assembly of FIG. 54.

Referring to FIGS. 55 and 56, the shifting assembly 9800 further comprises a threaded transfer shaft 9840 mounted to the second rotatable gear 9830 such that the transfer shaft 9840 turns with the second rotatable gear 9830. Similar to the input shaft 9710, the transfer shaft 9840 is rotatably supported by the frame 9110. The shifting assembly 9800 further comprises a lateral shaft 9890 rotatably supported within the proximal portion 9100 which comprises a pinion gear 9850 operably intermeshed with the transfer shaft 9840 such that the rotation of the transfer shaft 9840 is transferred to the lateral shaft 9890. The lateral shaft 9890 further comprises a rack gear 9860 defined thereon which is meshingly engaged with a rack 9880 defined on the output drive shaft 9740. The lateral shaft 9890 is rotatable about a third rotation axis $RA_3$. As illustrated in FIG. 56, the first rotation axis $RA_1$ and the second rotation axis $RA_2$ are parallel, or at least substantially parallel, to one another, and the third rotation axis $RA_3$ is perpendicular, or at least substantially perpendicular, to the first rotation axis $RA_1$ and the second rotation axis $RA_2$.

As outlined above, referring to FIG. 56, the shifter gear 9820 is intermeshed with the rotatable gear 9830 when the drive assembly 9700 is in its shifting configuration. As the motor 9120 powers the input shaft 9710 to rotate the main gear 9720, the shifter gear 9820 also rotates. As the shifter gear 9820 rotates while engaged with the rotatable gear 9830, the transfer shaft 9840 rotates in the same direction as the rotatable gear 9830 and the lateral shaft 9890 rotates about the axis $RA_3$. When the main gear 9720 is rotated in a first direction, in this configuration, the rack gear 9860 drives the drive shaft 9740 distally via the rack 9880, as illustrated in FIG. 61. When the main gear 9720 is rotated in a second, or opposite, direction, the rack gear 9860 drives the drive shaft 9740 proximally, as illustrated in FIG. 60. As discussed in greater detail below, the drive shaft 9740 is shiftable proximally and distally to place the drive shaft 9740 in a first, or proximal, drive configuration, a second, or intermediate, drive configuration, and a third, or distal, drive configuration.

Further to the above, the shaft assembly 9000 and/or handle 1000, for example, comprise a control system configured to operate the drive motor 9120 and the solenoid 9810. The control system of the shaft assembly 9000 is similar to the control system 1800 and/or 2800 in many respects, most of which will not be discussed herein for the sake of brevity. The control system is configured to receive inputs from the clinician and, in response to those inputs, shift the shaft assembly 9000 into a first, or articulation, operating mode, a second, or rotation, operating mode, or a third, or jaw drive, operating mode. The first, second, and third operating modes of the shaft assembly 9000 correspond to the first, second, and third positions of the output shaft 9740. When the shaft assembly 9000 is instructed to switch between operating modes, the solenoid 9810 moves the shifter gear 9820 into its second position and then rotates the input shaft 9710 to translate the output shaft 9740. The control system is configured to correlate the amount in which the input shaft 9710 is rotated to the amount in which the output shaft 9740 is translated. The control system is configured to monitor the rotations of the drive motor 9120 and then stop the drive motor 9120 once the drive motor 9120 has been rotated the appropriate number of rotations to shift the output shaft 9740. The control system comprises a memory device which stores the number of rotations needed to translate the output shaft 9740 between its first, second, and third positions. For instance, the memory device stores the number of rotations of the drive motor 9120 to translate the output shaft 9740 between the first position and the second position, the first position and the third position, and the second position and the third position. The control system is also configured to know what position the output shaft 9740 is currently in before operating the drive motor 9120. In various instances, the control system can comprise a sensor system configured to detect the current position of the output shaft 9740 and then determine the number of rotations, and the direction of those rotations, in which the drive motor 9120 should be operated.

Once the output shaft 9740 has been positioned in the first, second, or third position, as described above, the control system operates the solenoid 9810 to place the shifter gear 9820 in the drive configuration. In such instances, the shifter gear 9820 is disengaged from the second gear 9830 and then engaged with the first gear 9730. The first gear 9730 is mounted to the output shaft 9740 such that the rotation of the first gear 9730 is transmitted to the output shaft 9740. More specifically, the first gear 9730 is disposed on the splined proximal end 9745 of the output shaft 9740 such that the first gear 9730 and the output shaft 9740 rotate together. That said, the output shaft 9740 can translate relative to the first gear 9730 owing to the splined proximal end 9745 such that the first gear 9730 remains aligned with the shifter gear 9820 when the output shaft 9740 is being translated as described above. As discussed in greater detail below, the input shaft 9710 is rotatable in a first direction to rotate the output shaft 9740 in a first direction and a second direction to rotate the output shaft 9740 in a second direction.

FIGS. 58 and 61 illustrate the drive assembly 9700 in the shifting configuration. The main gear 9720 is rotatably engaged with the shifter gear 9820 in the shifting configuration to transfer motion from the input drive shaft 9710 to the second rotatable gear 9830. FIGS. 59 and 60 illustrate the drive assembly 9700 in the drive configuration. In the drive configuration, the main gear 9720 is rotatably engaged with the shifter gear 9820 to transfer motion from the input drive shaft 9710 to the first rotatable gear 9730. As discussed above, the output drive shaft 9740 is translatable. In fact, the output drive shaft 9740 is translatable between three different operational positions—a first, or proximal, position in which the output drive shaft 9740 drives an articulation system, a second, or intermediate, position in which the output drive shaft 9740 drives an end effector rotation system, and a third, or distal, position in which the output shaft 9740 drives a jaw drive system.

Figure 63:
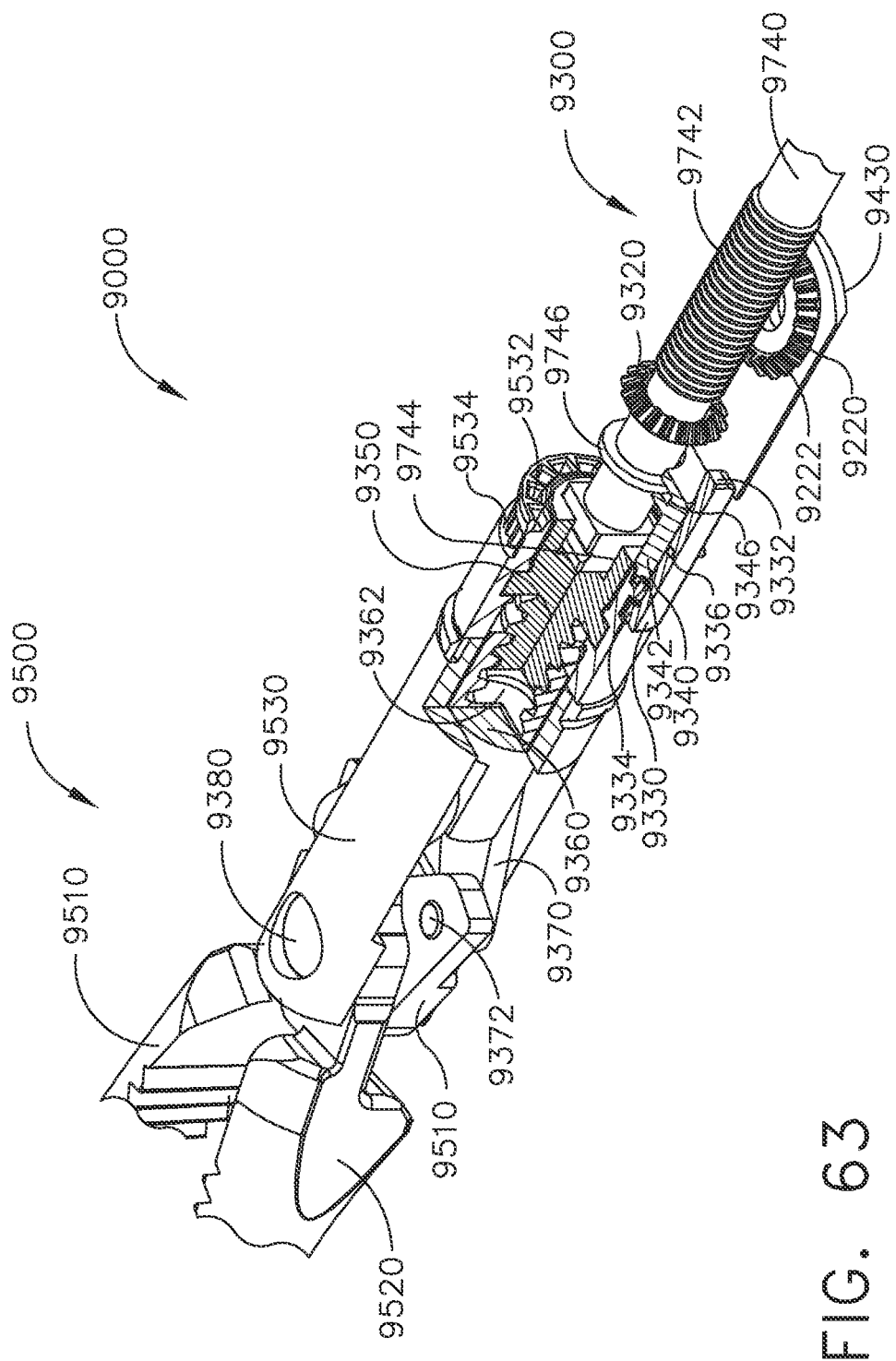
FIG. 63 is a partial perspective cross-sectional view of the end effector of FIG. 53.

Turning now to FIGS. 62 and 63, the articulation joint 9300 comprises an articulation system configured to articulate the distal attachment portion 9400 and the end effector 9500 in a first direction and a second direction. The articulation system comprises a fixed gear 9220 mounted on an outer housing 9530 of the end effector 9500 and, also, an articulation drive gear 9320 fixedly mounted to the output shaft 9740 such that the articulation drive gear 9320 rotates with the output shaft 9740. When the output shaft 9740 is in its first, or proximal position, as illustrated in FIGS. 64 and 65, the articulation drive gear 9320 is operably intermeshed with the fixed gear 9220. As the output drive shaft 9740 is rotated in the first direction, in such instances, the articulation drive gear 9320 rotates in conjunction with the output shaft 9740 which articulates the end effector 9500 in a first articulation direction due to the meshing engagement of the articulation drive gear 9320 and the fixed gear 9220. As the output shaft 9740 is rotated in the second direction, the articulation drive gear 9320 rotates in conjunction with the output drive shaft 9740 which articulates the end effector 9500 in a second, or opposite, articulation direction, also due to the meshing engagement of the articulation drive gear 9320 and the fixed gear 9220. When the end effector 9500 is articulated, the output drive shaft 9740 is configured to bend in order to accommodate the articulation motion of the end effector 9500. Thus, the output drive shaft 9740 is comprised of suitable materials which compliment the bending movement of the output shaft 9740 during an articulation motion, as illustrated in FIG. 65.

As discussed above, referring again to FIGS. 64 and 65, the end effector 9500 is in its articulation mode when the output shaft 9740 is in its first, or proximal, position. In such instances, as also discussed above, the rotation of the output shaft 9740 articulates the end effector 9500. That said, in such instances, the rotation of the output shaft 9740 does not rotate the end effector 9500 about the longitudinal axis and/or operate the jaw drive to open and close the jaws 9510 and 9520. Stated another way, the jaw opening/closure mode and the end effector rotation mode are inactive when the end effector 9500 is in the articulation mode. As illustrated in FIGS. 64 and 65, the distal end 9744 of the output shaft 9740 is not engaged with a drive screw 9350 of the jaw drive when the end effector 9500 is in the articulation mode and, as such, the output shaft 9740 cannot drive the drive screw 9350 until the output shaft 9740 has been shifted distally, as described in greater detail below. Moreover, the end effector 9500 can't be rotated about the longitudinal axis because the end effector 9500 is locked to the distal attachment portion 9400 of the shaft assembly 9000 by a rotation lock 9330 when the end effector 9500 is in the articulation mode. In such instances, the housing 9530 of the end effector 9500 is locked to a housing 9430 of the distal attachment portion 9400 by the rotation lock 9330 such that the end effector 9500 cannot rotate relative to the shaft assembly 9000 until the output shaft 9740 has been shifted distally, as described in greater detail below.

Further to the above, referring again to FIGS. 64 and 65, the rotation lock 9330 is pivotably coupled to the housing 9430 of the distal attachment portion 9400 about a center attachment portion 9336. The rotation lock 9330 further comprises a proximal end 9332 and a distal lock end 9334. When the output shaft 9740 is in its first, or proximal, drive position, and the end effector 9500 is in its articulation mode, the distal lock end 9334 of the rotation lock 9330 is wedged into engagement with an annular array of lock apertures 9534 defined around the outer housing 9530 of the end effector 9500. More specifically, the proximal end 9332 of the rotation lock 9330 is wedged outwardly by a drive lock 9340 coupled to the output shaft 9740 which, in turn, wedges the distal lock end 9334 inwardly. The drive lock 9340, which is described in greater detail below, comprises a slot 9346 defined therein and is translated proximally and distally with the output shaft 9740 by a flange 9746 extending into the slot 9346. When the output shaft 9740 is moved distally out of its first, or proximal, drive position, the drive lock 9340 is moved out of engagement with the proximal end 9332 of the rotation lock 9330, as illustrated in FIGS. 66-69.

When the output shaft 9740 is not in its first, or proximal, drive position, the articulation drive gear 9320 is not operably intermeshed with the fixed gear 9220. In such instances, the rotation of the output shaft 9740 does not articulate the end effector 9500. That said, the end effector 9500 is held in its articulated position by the drive shaft 9740 when the drive shaft 9740 is translated distally from its first position. More specifically, the drive shaft 9740 comprises articulation lock teeth 9742 defined thereon which engage, or mesh with, the teeth 9222 of the fixed gear 9220 when the drive shaft 9740 is advanced distally and, owing to the engagement between the teeth 9742 and 9222, the end effector 9500 is locked in position. This articulation lock works when the end effector 9500 is articulated in the first direction, articulated in the second direction, and when the end effector 9500 is unarticulated. Moreover, this articulation lock is engaged as soon as the drive shaft 9740 is displaced distally from its first position. Thus, the articulation lock is engaged when the drive shaft 9740 is in its second position and third position. In order to unlock the articulation lock, the drive shaft 9740 is moved back into its first position to disengage the teeth 9742 from the teeth 9222. At such point, the end effector 9500 can be articulated once again.

Figure 66:
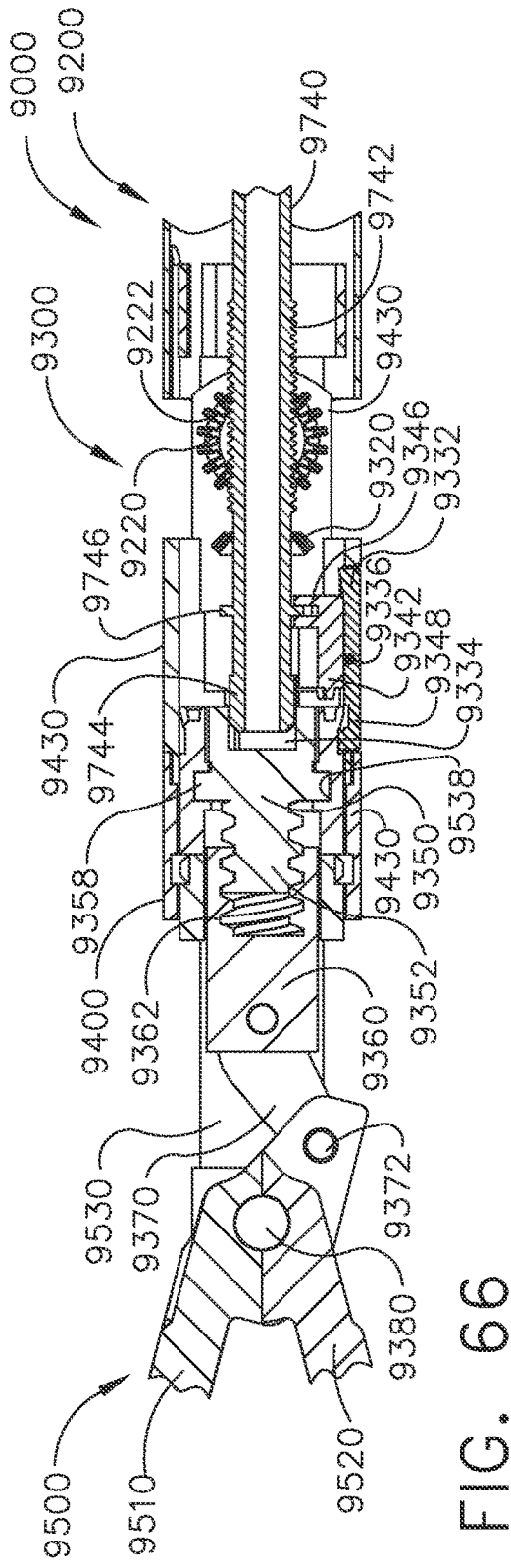
FIG. 66 is a partial top cross-sectional view of the end effector of FIG. 53 in a rotation drive mode.
Figure 67:
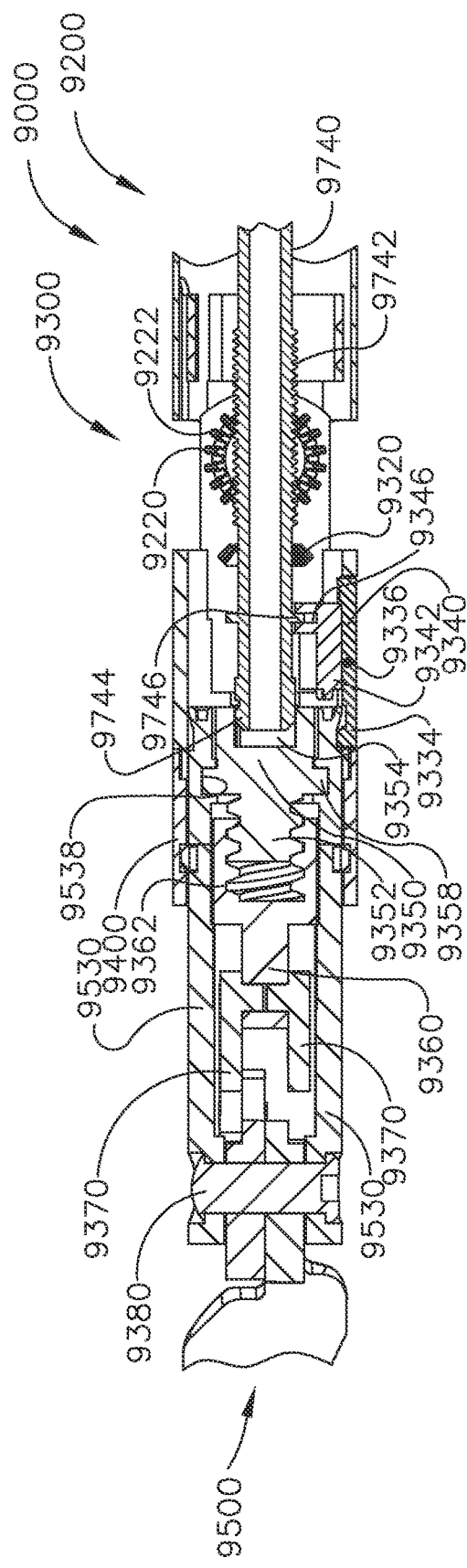
FIG. 67 is a partial top cross-sectional view of the end effector of FIG. 53 in a rotated configuration.

When the output drive shaft 9740 is in its second, or intermediate, position, referring to FIGS. 66 and 67, the end effector 9500 is in its rotation drive mode. In such instances, the articulation drive gear 9320 mounted to the output shaft 9740 is not engaged with the fixed gear 9220 and, as a result, the rotation of the output shaft 9740 does not articulate the distal attachment portion 9400 and the end effector 9500. That said, the distal end 9744 of the output shaft 9740 is positioned within the drive socket 9354 of the drive screw 9350 when the output shaft 9740 is in its second position. Notably, though, the distal end 9744 is not fully seated in the drive socket 9354—this happens when the output shaft 9740 is translated distally into its third, or distal, position (FIGS. 68 and 69), as discussed in greater detail below. That being said, the rotation of the output shaft 9740 is transferred to the drive screw 9350 when the output shaft 9740 is in its second, or intermediate, position. Owing to a close, or friction, fit between the drive screw 9350 and the outer housing 9530 of the end effector 9500, however, the rotation of the drive screw 9350 is transferred to the outer housing 9350. More specifically, the drive screw 9350 comprises a flange 9358 closely received within a slot 9538 defined in the outer housing 9530 and, as such, the drive screw 9350 and the outer housing 9530 rotate together when the end effector 9500 is in its rotation drive mode. Moreover, the entire end effector 9500, including the jaws 9510 and 9520 rotatably coupled to the outer housing 9530 by a pivot pin 9380, is rotated about a longitudinal axis when the end effector 9500 is in its rotation drive mode and the output shaft 9740 is rotated.

When the output shaft 9740 is rotated in a first direction when the end effector 9500 is in its rotation drive mode, further to the above, the end effector 9500 is rotated relative to the distal attachment portion 9400 of the shaft assembly 9000 in the first direction. Correspondingly, the end effector 9500 is rotated relative to the distal attachment portion 9400 in a second, or opposite, direction when the output shaft 9740 is rotated in the second, or opposite, direction. Notably, the rotation of the drive screw 9350 does not open and/or close the jaws 9510 and 9520 in such instances as the drive screw 9350 does not rotate relative to the outer housing 9530 and/or jaws 9510 and 9520. Also, notably, the outer housing 9530 of the end effector 9500 rotates relative to the outer housing 9430 of the distal attachment portion 9400 when the end effector 9500 is in its rotation drive mode. This is due to the distal displacement of the drive lock 9340 away from the proximal end 9332 of the rotation lock 9330 when the drive shaft 9740 is moved into its second position such that, as a result, the outer housing 9530 of the end effector 9500 can rotate relative to the outer housing 9430 of the distal attachment portion 9400.

Figure 68:
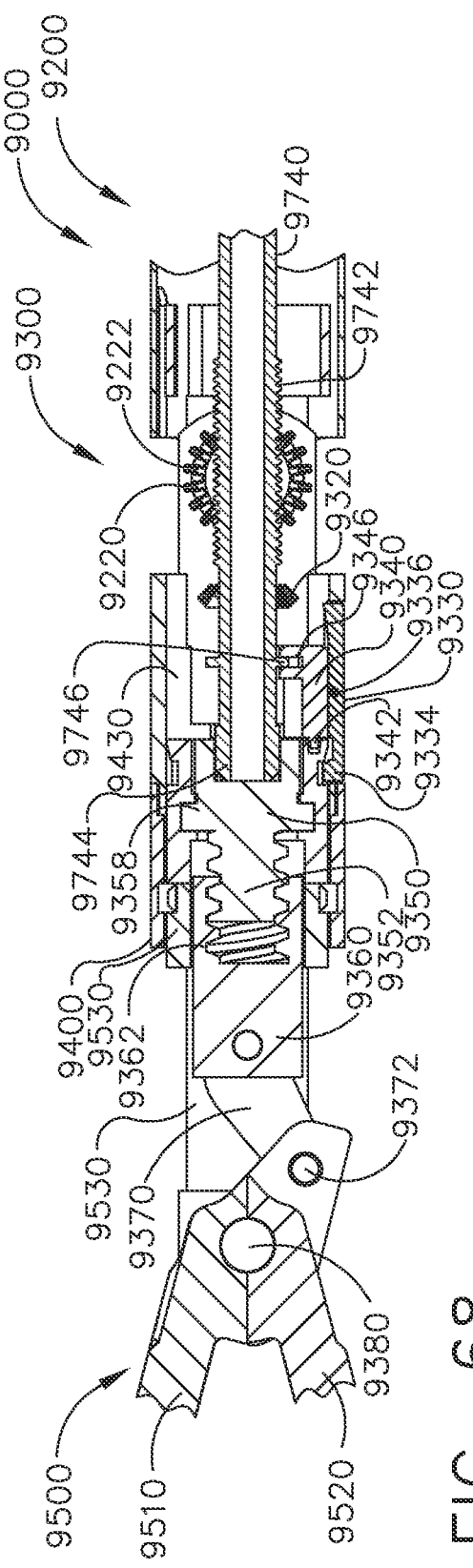
FIG. 68 is a partial top cross-sectional view of the end effector of FIG. 53 in a jaw open/closure drive mode.
Figure 69:
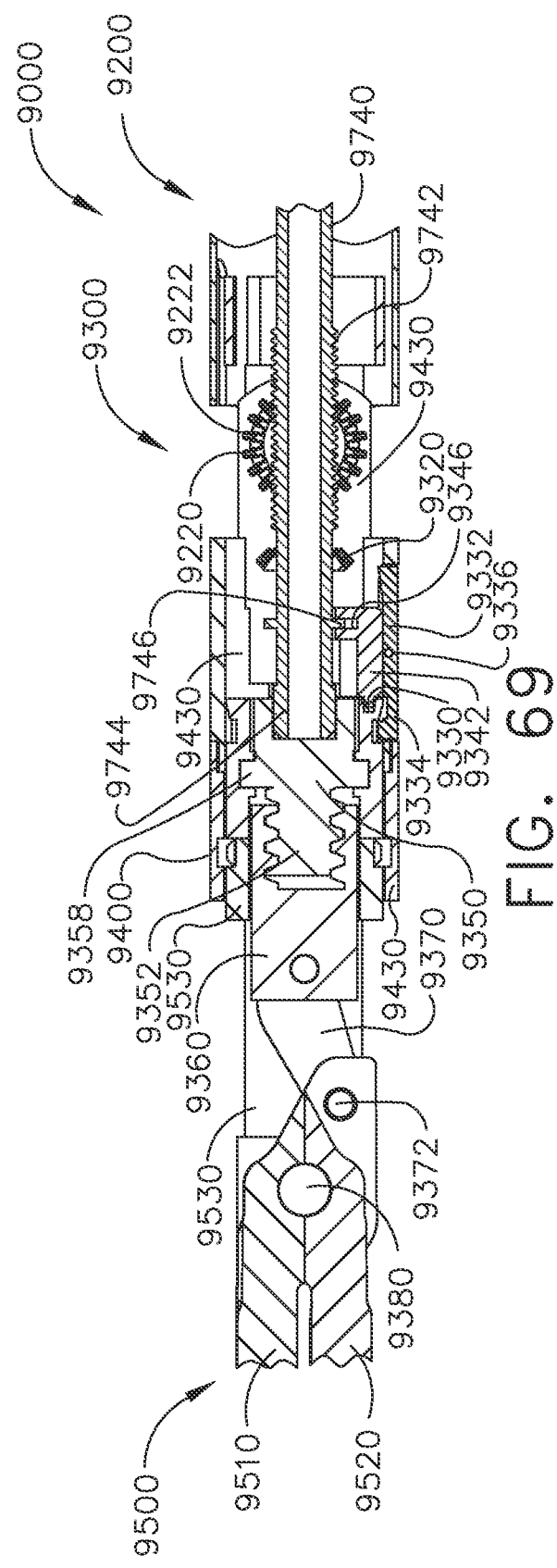
FIG. 69 is a partial top cross-sectional view of the end effector of FIG. 53 in a closed configuration.

When the output drive shaft 9740 is in its third, or distal, position, referring to FIGS. 68 and 69, the end effector 9500 is in its jaw drive mode. In such instances, the articulation drive gear 9320 mounted to the output shaft 9740 is not engaged with the fixed gear 9220 and, as a result, the rotation of the output shaft 9740 does not articulate the distal attachment portion 9400 and the end effector 9500. That said, further to the above, the distal end 9744 of the drive shaft 9740 is fully seated in the drive socket 9354 of the drive screw 9350 when the end effector 9500 is in its distal position. As a result, the drive screw 9350 rotates with the output shaft 9740. Moreover, the drive screw 9350 rotates relative to the outer housing 9530 when the end effector 9500 is in its jaw drive mode. This is because the drive lock 9340 coupled to the drive shaft 9740 is driven distally into engagement with the outer housing 9530 when the drive shaft 9740 is moved into its third, or distal, drive position and, as a result, prevents the outer housing 9530 from rotating with the drive screw 9350. More specifically, referring to FIG. 63, the drive lock 9340 comprises a distal lock end 9342 configured to engage an annular array of lock apertures 9532 defined in the proximal end of the outer housing 9530 and, once the distal lock end 9342 is engaged with the apertures 9532, the outer housing 9530 is held in position by the drive lock 9340.

Further to the above, the end effector 9500 further comprises a drive nut 9360 threadably engaged with the drive screw 9350 and, in addition, two drive links 9370 pivotably coupled to the drive nut 9360—each of which is also pivotably coupled to a jaw 9510 and 9520. The drive nut 9360 comprises a threaded aperture 9362 defined therein threadably engaged with a threaded end 9352 of the drive shaft 9350. The drive nut 9360 is constrained from rotating relative to the outer housing 9530 and, as a result, the drive nut 9360 is translated proximally or distally when the drive screw 9350 is rotated, depending on the direction in which the drive screw 9350 is rotated. When the drive screw 9350 is rotated in a first direction by the drive shaft 9740, the drive screw 9350 pushes the drive nut 9360 and the drive links 9370 distally to open the jaws 9510 and 9520. When the drive screw 9350 is rotated in a second direction by the drive shaft 9740, the drive screw 9350 pulls the drive nut and the drive links 9370 proximally to close the jaws 9510 and 9520. That being said, a different thread could be used to reverse these motions.

In view of the above, the end effector 9500 cannot be rotated about its longitudinal axis and the jaws 9510 and 9520 cannot be opened and closed during the articulation mode. Moreover, the end effector 9500 cannot be articulated about the articulation joint 9300 and the jaws 9510 and 9520 cannot be opened and closed during the end effector rotation mode. Similarly, the end effector 9500 cannot be rotated or articulated during the jaw drive mode.

Further to the above, the shaft assembly 9000 comprises a braking system 9900 configured to hold the drive shaft 9740 in its first, or articulation, drive position, its second, or rotation, drive position, and/or its third, or jaw drive, position. The braking system 9900 comprises a solenoid 9910, a brake arm 9920 operably connected to a rotatable output shaft of the solenoid 9910, and a biasing member. The brake arm 9920 is rotatable between a first position in which the brake arm 9920 is engaged with the drive shaft 9740 and a second position in which the brake arm 9920 is disengaged from the drive shaft 9740. The biasing member biases the brake arm 9920 into its first position, but this bias is overcome when the solenoid 9910 is actuated. When the brake arm 9920 is in its first position, the brake arm 9920 opposes, through friction, the movement of the drive shaft 9740. In such instances, the brake arm 9920 can reduce the possibility of the drive shaft 9740 being accidentally pushed longitudinally out of position. When the brake arm 9920 is in its second position, the brake arm 9920 does not oppose the motion of the drive shaft 9740. In various instances, the solenoid 9910 can be actuated to lift the brake arm 9920 when the shaft assembly 9000 has been shifted into its drive configuration by the solenoid 9810, as discussed above. In at least one such instance, the solenoid 9910 can be actuated to lift the brake arm 9920 when the shaft assembly 9000 is in its drive configuration and the input motor 9120 is being operated. The shifting solenoid 9810 and the brake solenoid 9910 are in communication with the control system of the shaft assembly 9000 and/or the control system of the handle 1000, for example, and can be selectively actuated by the control system. The control system can actuate the solenoid 9910 to inhibit the movement of the drive shaft 9740 at any suitable time. In at least one instance, the control system is configured to always apply a braking force to the drive shaft 9740 except when the shaft assembly 9000 and/or handle are in a limp mode, for example. In certain alternative embodiments, a static friction member, for example, can be used to inhibit unintended displacement of the drive shaft 9740.

The shaft assembly 9000 further comprises a sensor system configured to detect the longitudinal position of the drive shaft 9740. In at least one instance, the drive shaft 9740 comprises a magnetic element, such as a permanent magnet, iron, and/or nickel, for example, which is detectable by one or more sensors of the sensor system. In at least one instance, a sensor of the sensor system comprises a Hall Effect sensor, for example. The sensor system is in communication with the control system of the shaft assembly 9000 and/or the handle 1000, for example, and is configured to confirm whether the drive shaft 9740 is in its proximal drive position, its intermediate drive position, its distal drive position, or somewhere in-between. With this information, the control system can monitor the position of the drive shaft 9740 in real-time and adjust the longitudinal position of the drive shaft 9740, if necessary.

Figure 70:
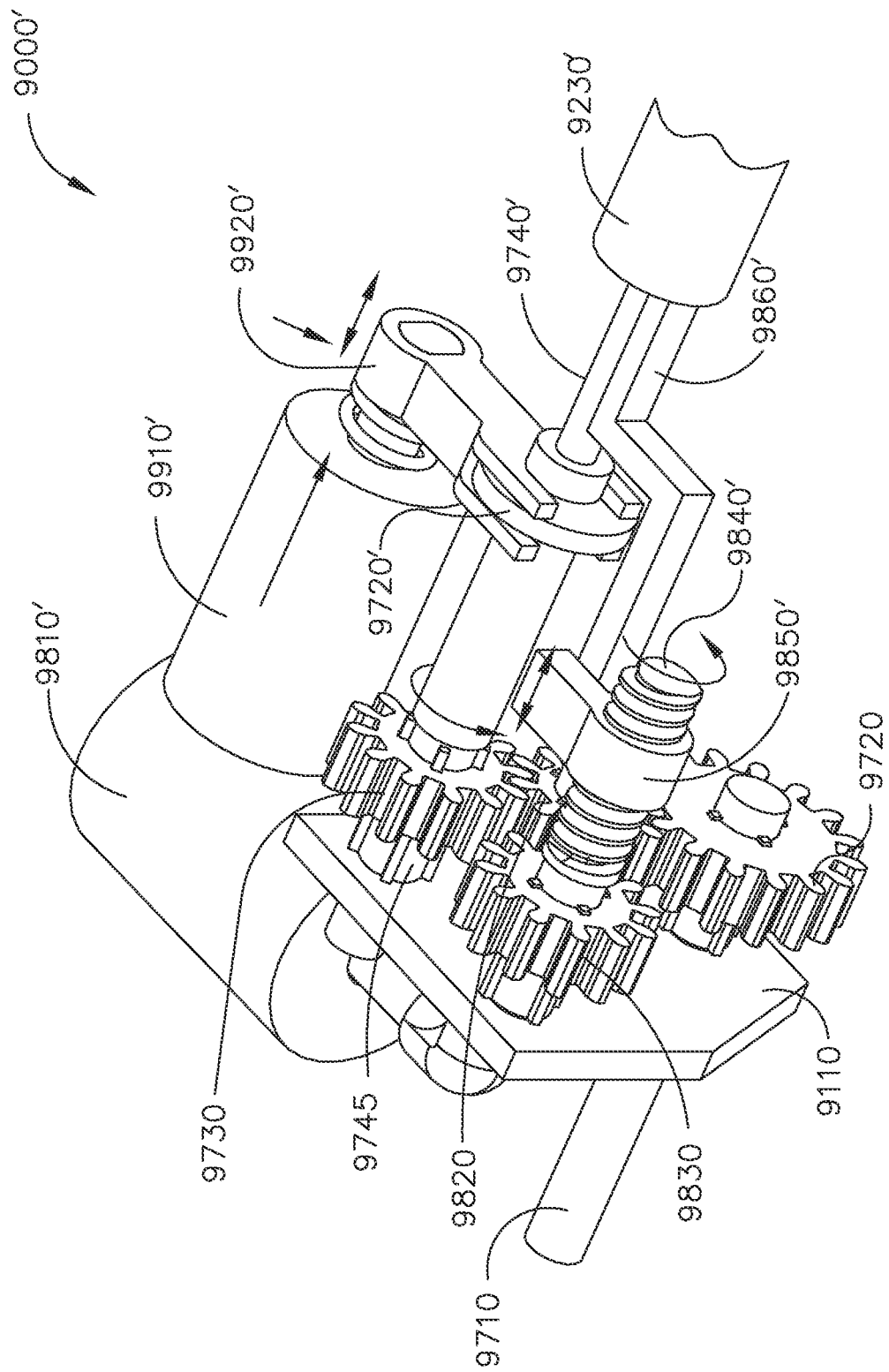
FIG. 70 is a perspective view of a drive assembly of a shaft assembly in accordance with at least one embodiment.
Figure 71:
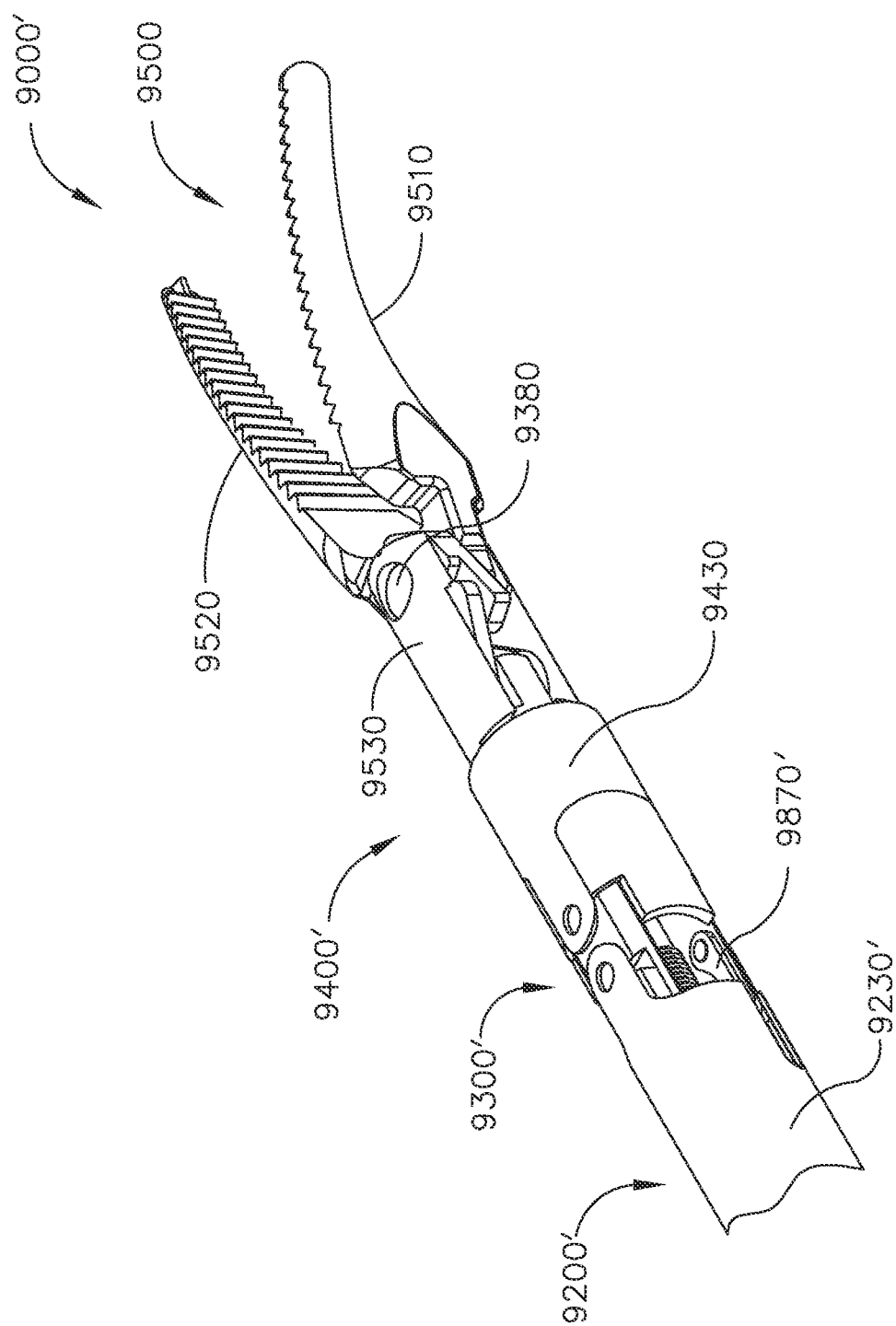
FIG. 71 is a perspective view of an end effector of the shaft assembly of FIG. 70 in an open configuration.
Figure 72:
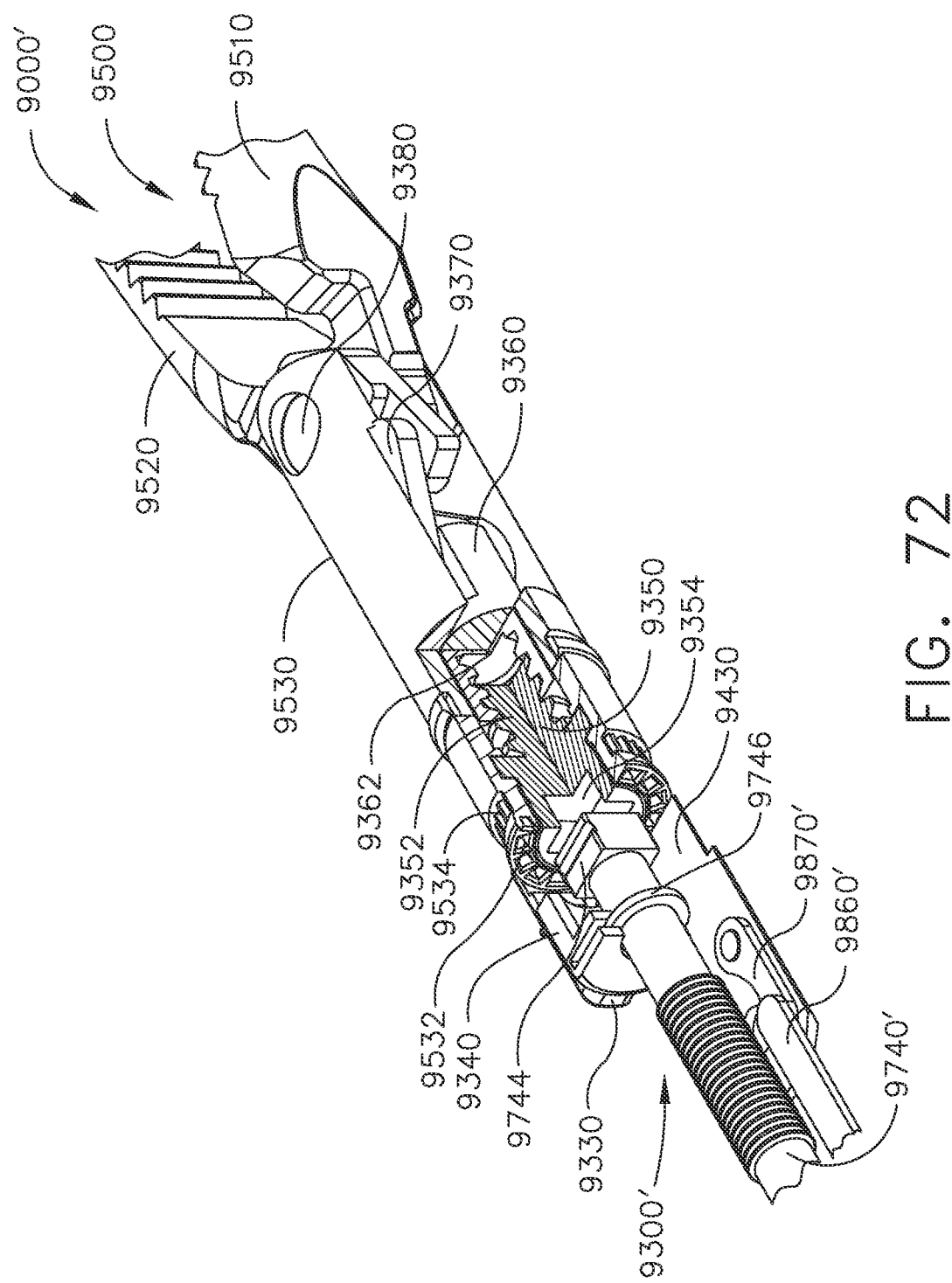
FIG. 72 is a partial perspective cross-sectional view of the end effector of FIG. 71.
Figure 73:
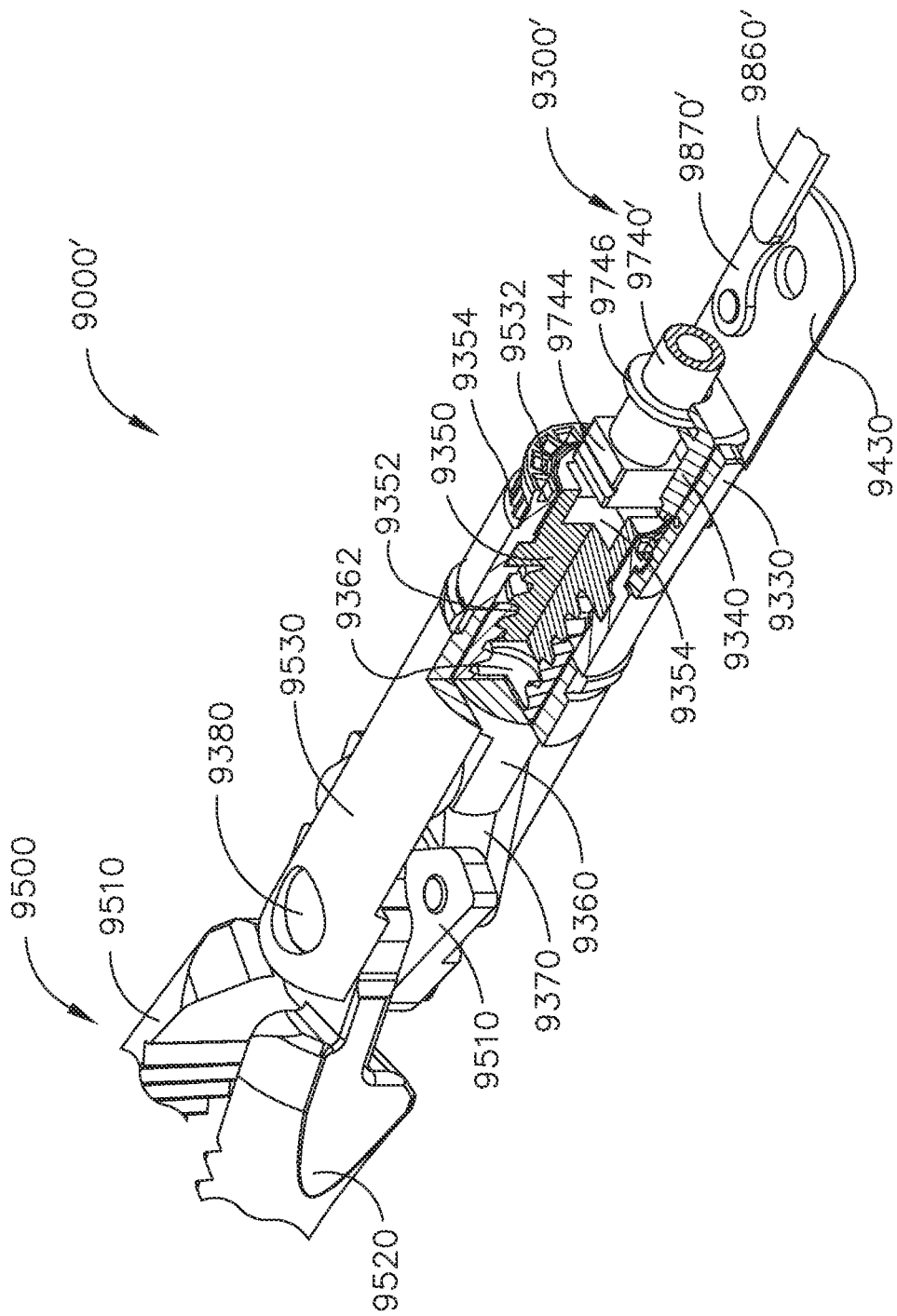
FIG. 73 is another partial perspective cross-sectional view of the end effector of FIG. 71.

A shaft assembly 9000' is depicted tin FIGS. 70-79 which is similar to the shaft assembly 9000 in many respects, most of which will not be discussed herein for the sake of brevity. Referring primarily to FIG. 71, the shaft assembly 9000' comprises an elongate shaft 9200', a distal attachment portion 9400', and an articulation joint 9300' rotatably connecting the distal attachment portion 9400' to the elongate shaft 9200'. The shaft assembly 9000' further comprises an end effector 9500 rotatably supported within an outer housing 9430 of the distal attachment portion 9400'. The shaft assembly 9000' also comprises a drive system configured to rotate the end effector 9500 about a longitudinal axis, articulate the end effector 9500 about the articulation joint 9300', and open and close the jaws 9510 and 9520 of the end effector 9500.

Referring primarily to FIG. 70, the drive system comprises, among other things, a rotatable input shaft 9710, a first output shaft 9740', and a second output shaft 9860'. The drive system further comprises a shifter solenoid 9810' configured to selectively couple the input shaft 9710 with the first output shaft 9740' in a first drive configuration and the second output shaft 9860' in a second drive configuration. In the first drive configuration, the rotatable input shaft 9710 rotates the main gear 9720 which, in turn, rotates the shifter gear 9820. In such instances, the shifter gear 9820 rotates the first drive gear 9730 which, in turn, rotates the first output shaft 9740'. Similar to the output shaft 9740, the first drive gear 9730 is engaged with a splined proximal end 9745 of the first output shaft 9740' such that the first output shaft 9740' rotates with, but can translate relative to, the first drive gear 9730. The drive system of the shaft assembly 9000' further comprises a second shifter solenoid 9910' configured to translate the first output shaft 9740' between a disengaged position (FIGS. 74 and 75), a first drive position (FIGS. 76 and 77), and a second drive position (FIGS. 78 and 79). The second shifter solenoid 9910' comprises a shift arm 9920' engaged with a flange 9720' defined on the first output shaft 9740' which is configured to push the first output shaft 9740' between its disengaged position, first drive positon, and second drive position.

In the second drive configuration, further to the above, the rotatable input shaft 9710 rotates the main gear 9720 which, in turn, rotates the shifter gear 9820. In such instances, the shifter gear 9820 rotates the second drive gear 9830 which, in turn, rotates a threaded shaft 9840'. The drive system further comprises a drive nut 9850' threadably engaged with the threaded shaft 9840' such that, when the threaded shaft 9840' is rotated in a first direction by the input shaft 9710, the drive nut 9850' is translated proximally and, when the threaded shaft 9840' is rotated in a second, or opposite, direction by the input shaft 9710, the drive nut 9850' is translated distally. The second output shaft 9860' comprises a bar fixedly mounted to the drive nut 9850' such that the second output shaft 9860' translates with the drive nut 9850'. Thus, the rotation of the rotatable input shaft 9710 translates the second output shaft 9860'. The translatable second output shaft 9860' extends through an outer housing 9230' of the elongate shaft 9200' alongside the rotatable/translatable first output shaft 9740'. As described in greater detail below, the first output shaft 9740' drives a first end effector function and a second end effector function while the second output shaft 9860' drives a third end effector function.

Further to the above, referring to FIGS. 72-75, the drive system further comprises a drive link 9870' pivotably coupled to the second output shaft 9860'. The drive link 9870' extends across the articulation joint 9300' and is pivotably coupled to the outer housing 9430 of the distal attachment portion 9400'. When the input shaft 9710 is rotated in the first direction and the drive link 9870' is pulled proximally by the drive nut 9850', the distal attachment portion 9400' and the end effector 9500 are articulated in a first articulation direction. When the input shaft 9710 is rotated in the second direction and the drive link 9870' is pushed distally by the drive nut 9850', referring to FIG. 75, the distal attachment portion 9400' and the end effector 9500 are articulated in a second, or opposite, articulation direction. The threaded interface between the threaded shaft 9840' and the drive nut 9850' prevents, or at least inhibits, the articulation drive from being back-driven, or unintentionally articulated. As a result, the end effector 9500 is held in position when the shifter gear 9820 is shifted out of engagement with the second gear 9830 and into engagement with the first gear 9730. Notably, the first output shaft 9740' is not involved in the articulation of the end effector 9500. In fact, the first output shaft 9740' is in its disengaged position such that the distal end 9744 of the first output shaft 9740' is not engaged with the drive screw 9750 when the end effector 9500 is being articulated.

Figure 76:
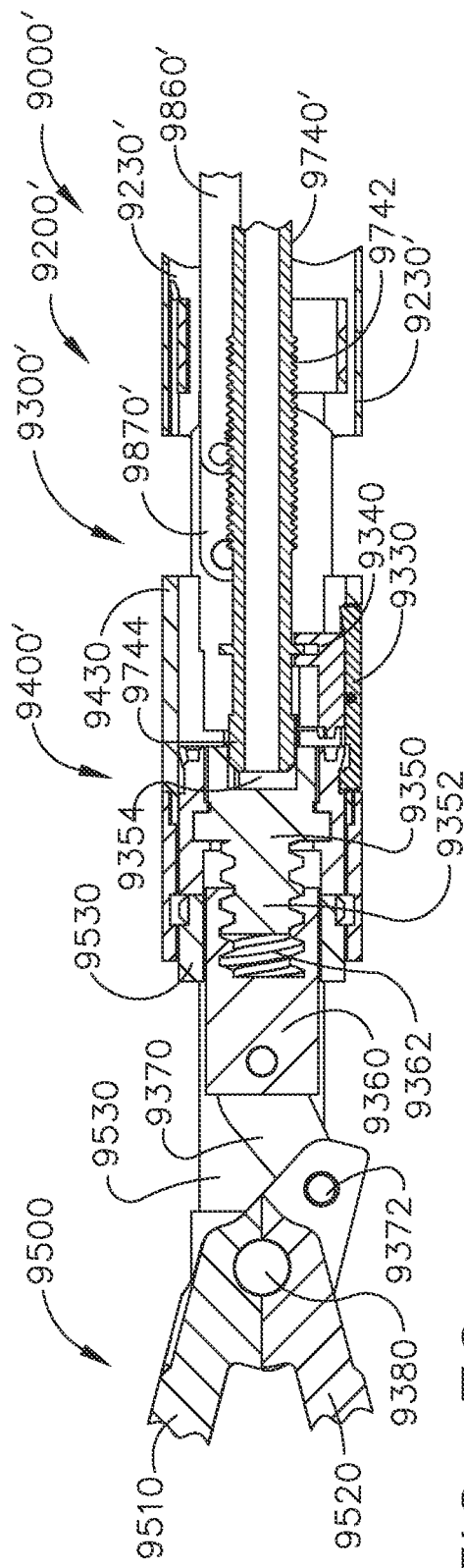
FIG. 76 is a partial top cross-sectional view of the end effector of FIG. 71 in a rotation drive mode.
Figure 77:
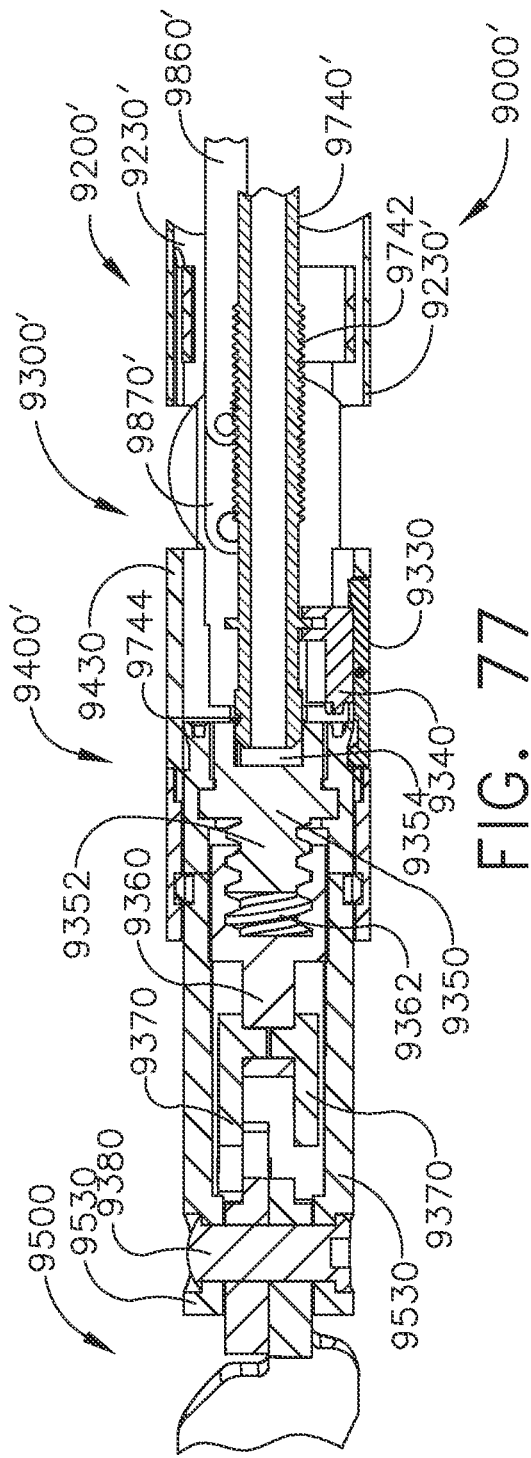
FIG. 77 is a partial top cross-sectional view of the end effector of FIG. 71 in a rotated configuration.

Further to the above, the first output shaft 9740' is used to selectively rotate the end effector 9500 about a longitudinal axis. The first output shaft 9740' is also used to selectively operate the jaw drive to open and close the end effector 9500. The first drive position of the first rotatable output shaft 9740' is used to rotate the end effector 9500 of the shaft assembly 9000' about a longitudinal axis. As illustrated in FIGS. 76 and 77, the distal end 9744 of the first output shaft 9740' is seated, but not completely seated, within the drive socket 9354 defined in the drive screw 9350 when the first output shaft 9740' is in its first drive position. Notably, however, the drive lock 9340 is not engaged with the outer housing 9530 of the end effector 9500 and, as a result, the outer housing 9530 rotates with the drive screw 9350. In such instances, the rotation of the first output shaft 9740' is transferred to the drive screw 9350 to rotate the entire end effector 9500, as described above. The second drive position of the first rotatable output shaft 9740' is used to open and close the jaws 9510 and 9520. As illustrated in FIGS. 78 and 79, the distal end 9744 of the first output shaft 9740' is completely seated within the drive socket 9354 defined in the drive screw 9350 when the first output shaft 9740' is in its second drive position. Notably, the drive lock 9340 is engaged with the outer housing 9530 of the end effector 9500 and, as a result, the drive screw 9350 rotates relative to the outer housing 9530. In such instances, the rotation of the first output shaft 9740' opens and closes the jaws 9510 and 9520—depending on the direction in which the first output shaft 9740' is rotated.

The reader should appreciate that the proximal, intermediate, and distal drive positions of the output shaft 9740 of the shaft assembly 9000 are analogous to the proximal, intermediate, and distal drive positions of the first output shaft 9740'. More specifically, the output shaft 9740 is operable to articulate the end effector 9500 when the output shaft 9740 is in its proximal position, while the end effector 9500 is articulated, by the second output shaft 9860', when the first output shaft 9740' is in its proximal position. Moreover, the output shaft 9740 is operable to rotate the end effector 9500 when the output shaft 9740 is in its intermediate position while, likewise, the first output shaft 9740' is operable to rotate the end effector 9500 when the first output shaft 9740' is in its intermediate position. Similarly, the output shaft 9740 is operable to open and close the end effector 9500 when the output shaft 9740 is in its distal position while, likewise, the first output shaft 9740' is operable to open and close the end effector 9500 when the first output shaft 9740' is in its distal position.

Figure 80:
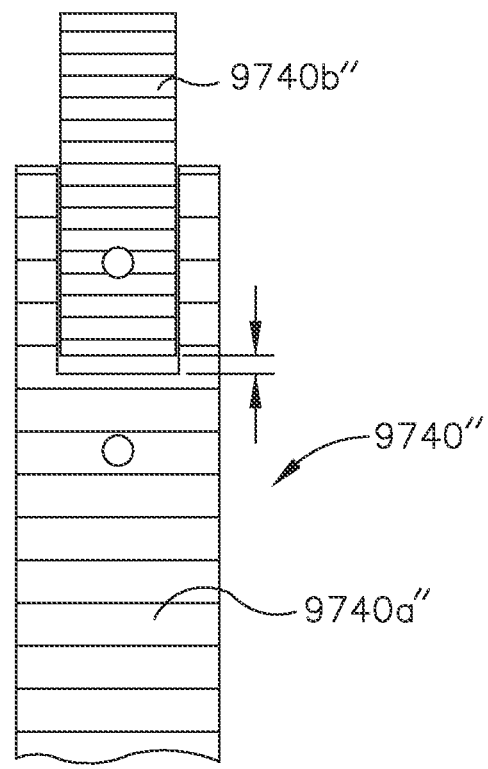
FIG. 80 is a partial top cross-sectional view of a drive shaft in accordance with at least one embodiment.
Figure 81:
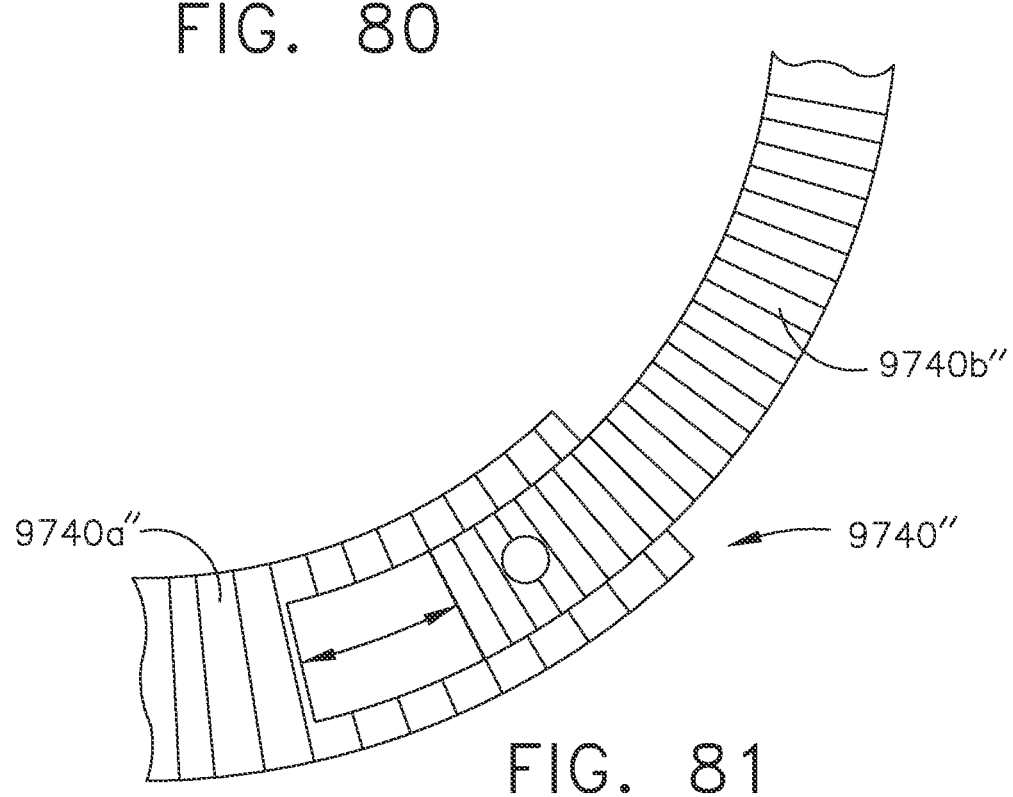
FIG. 81 is a partial top cross-sectional view of the drive shaft of FIG. 80 in an articulated configuration.

The output shaft 9740 of the shaft assembly 9000 and/or the first output shaft 9740' of the shaft assembly 9000' are comprised of a unitary piece of material. Such an arrangement reduces the possibility of the output shafts 9740 and 9740' failing under load. That said, alternative embodiments are envisioned in which the output shafts 9740 and/or 9740' are comprised of two or more components. Referring to FIGS. 80 and 81, a drive shaft 9740" comprises a first shaft component 9740a" and a second shaft component 9740b". The first shaft component 9740a" comprises a drive aperture defined therein and the second shaft component 9740b" is positioned in the drive aperture. The drive aperture comprises a configuration which is configured to transmit torque between the first shaft component 9740a" and the second shaft component 9740b", yet permit relative translational movement between the first shaft component 9740a" and the second shaft component 9740b". Such an arrangement is useful to accommodate the articulation of an end effector when the drive shaft 9740" extends through an articulation joint, for example. In such instances, the interconnection between the first shaft component 9740a" and the second shaft component 9740b" can comprise an extension joint which allows the drive shaft 9740" to extend in length when the end effector is articulated.

Figure 57:
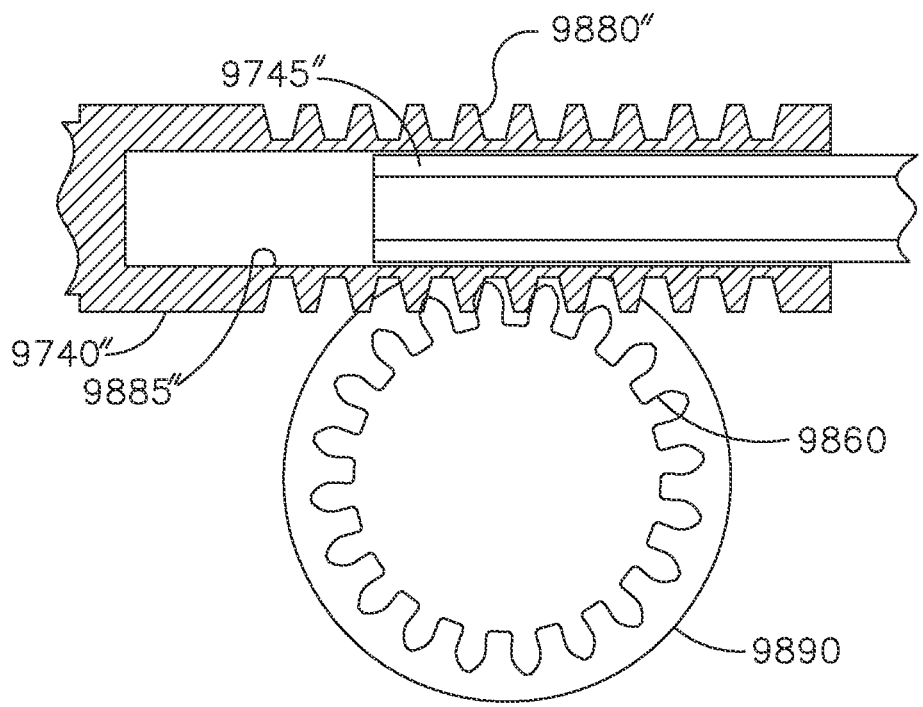
FIG. 57 is a partial cross-sectional view of a drive assembly in accordance with at least one alternative embodiment.

Referring to FIG. 57, the drive shaft 9740" is similar to the drive shaft 9740 in many respects, most of which will not be discussed herein for the sake of brevity. Similar to the drive shaft 9740, the drive shaft 9740" is translated proximally and distally to shift an end effector between drive modes and then rotated to drive the end effector in the selected drive mode. That said, the drive shaft 9740" comprises an extension joint in the proximal drive system which facilitates the translation and rotation of the drive shaft 9740". This extension joint of the drive shaft 9740" comprises a drive aperture 9885" defined in a proximal rack portion 9880" of the drive shaft 9740" and, in addition, a proximal splined portion 9745" slideably positioned in the drive aperture 9885". Similar to the above, the drive aperture 9885" comprises a configuration configured to transmit torque between the proximal splined portion 9745" and the distal portion of the shaft 9740" yet permit relative translation therebetween. In such an arrangement, the proximal splined portion 9745" does not need to move relative to the gear 9730 in order to accommodate the distal displacement of the shaft 9740". Such an arrangement reduces the possibility that the gear 9730 may be pulled out of engagement with the shifter gear 9820, for example.

Further to the above, the rotation lock 9330, which is configured to engage the end effector 9500 to prevent the end effector 9500 from rotating about its longitudinal axis as described above, is also configured to releasably attach the end effector 9500 to the shaft assembly 9000 and/or shaft assembly 9000'. When the end effector 9500 is assembled to the shaft assembly 9000, for example, the rotation lock 9330 engages the annular array of teeth 9534 defined around the perimeter of the end effector housing 9530 to releasably hold the end effector 9500 in position. When the drive shaft 9740 is in its first position, the drive lock 9340 blocks the rotation lock 9330 from being rotated to release the end effector 9500. In order to release the end effector 9500 from the shaft assembly 9000, the drive shaft 9740 can be advanced distally to move the drive lock 9340 distally and allow the rotation lock 9330 to rotate so that the end effector 9500 can be pulled longitudinally away from the shaft assembly 9000. In at least one instance, the drive shaft 9740 must be moved into its third, or distal, drive position in order to release the end effector 9500.

The surgical instrument systems described herein are motivated by an electric motor; however, the surgical instrument systems described herein can be motivated in any suitable manner. In certain instances, the motors disclosed herein may comprise a portion or portions of a robotically controlled system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail, the entire disclosure of which is incorporated by reference herein.

The surgical instrument systems described herein can be used in connection with the deployment and deformation of staples. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue. In addition, various embodiments are envisioned which utilize a suitable cutting means to cut the tissue.

The entire disclosures of:

U.S. patent application Ser. No. 11/013,924, entitled TROCAR SEAL ASSEMBLY, now U.S. Pat. No. 7,371,227;

U.S. patent application Ser. No. 11/162,991, entitled ELECTROACTIVE POLYMER-BASED ARTICULATION MECHANISM FOR GRASPER, now U.S. Pat. No. 7,862,579;

U.S. patent application Ser. No. 12/364,256, entitled SURGICAL DISSECTOR, now U.S. Patent Application Publication No. 2010/0198248;

U.S. patent application Ser. No. 13/536,386, entitled EMPTY CLIP CARTRIDGE LOCKOUT, now U.S. Pat. No. 9,282,974;

U.S. patent application Ser. No. 13/832,786, entitled CIRCULAR NEEDLE APPLIER WITH OFFSET NEEDLE AND CARRIER TRACKS, now U.S. Pat. No. 9,398,905;

U.S. patent application Ser. No. 12/592,174, entitled APPARATUS AND METHOD FOR MINIMALLY INVASIVE SUTURING, now U.S. Pat. No. 8,123,764;

U.S. patent application Ser. No. 12/482,049, entitled ENDOSCOPIC STITCHING DEVICES, now U.S. Pat. No. 8,628,545;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 14/200,111, entitled CONTROL SYSTEMS FOR SURGICAL INSTRUMENTS, now U.S. Pat. No. 9,629,629;

U.S. patent application Ser. No. 14/248,590, entitled MOTOR DRIVEN SURGICAL INSTRUMENTS WITH LOCKABLE DUAL DRIVE SHAFTS, now U.S. Pat. No. 9,826,976;

U.S. patent application Ser. No. 14/813,242, entitled SURGICAL INSTRUMENT COMPRISING SYSTEMS FOR ASSURING THE PROPER SEQUENTIAL OPERATION OF THE SURGICAL INSTRUMENT, now U.S. Patent Application Publication No. 2017/0027571;

U.S. patent application Ser. No. 14/248,587, entitled POWERED SURGICAL STAPLER, now U.S. Pat. No. 9,867,612;

U.S. patent application Ser. No. 12/945,748, entitled SURGICAL TOOL WITH A TWO DEGREE OF FREEDOM WRIST, now U.S. Pat. No. 8,852,174;

U.S. patent application Ser. No. 13/297,158, entitled METHOD FOR PASSIVELY DECOUPLING TORQUE APPLIED BY A REMOTE ACTUATOR INTO AN INDEPENDENTLY ROTATING MEMBER, now U.S. Pat. No. 9,095,362;

International Application No. PCT/US2015/023636, entitled SURGICAL INSTRUMENT WITH SHIFTABLE TRANSMISSION, now International Patent Publication No. WO 2015/153642 A1;

International Application No. PCT/US2015/051837, entitled HANDHELD ELECTROMECHANICAL SURGICAL SYSTEM, now International Patent Publication No. WO 2016/057225 A1;

U.S. patent application Ser. No. 14/657,876, entitled SURGICAL GENERATOR FOR ULTRASONIC AND ELECTROSURGICAL DEVICES, U.S. Patent Application Publication No. 2015/0182277;

U.S. patent application Ser. No. 15/382,515, entitled MODULAR BATTERY POWERED HANDHELD SURGICAL INSTRUMENT AND METHODS THEREFOR, U.S. Patent Application Publication No. 2017/0202605;

U.S. patent application Ser. No. 14/683,358, entitled SURGICAL GENERATOR SYSTEMS AND RELATED METHODS, U.S. Patent Application Publication No. 2016/0296271;

U.S. patent application Ser. No. 14/149,294, entitled HARVESTING ENERGY FROM A SURGICAL GENERATOR, U.S. Pat. No. 9,795,436;

U.S. patent application Ser. No. 15/265,293, entitled TECHNIQUES FOR CIRCUIT TOPOLOGIES FOR COMBINED GENERATOR, U.S. Patent Application Publication No. 2017/0086910; and U.S. patent application Ser. No. 15/265,279, entitled TECHNIQUES FOR OPERATING GENERATOR FOR DIGITALLY GENERATING ELECTRICAL SIGNAL WAVEFORMS AND SURGICAL INSTRUMENTS, U.S. Patent Application Publication No. 2017/0086914, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical instrument, comprising:
    a shaft;
    an end effector coupled to the shaft, the end effector being configured to perform a first end effector function and a second end effector function;
    a rotatable input shaft;
    an output shaft;
    a transmission operable in a drive configuration and a shifting configuration, wherein the output shaft is translatable between a first position and a second position by the rotation of the input shaft when the transmission is in the shifting configuration, and wherein the output shaft is rotated by the rotation of the input shaft when the transmission is in the drive configuration; and
    a brake configured to hold the output shaft in the first position and the second position but permit the output shaft to rotate in the first position and the second position,
    wherein the first end effector function is drivable by the output shaft when the output shaft is in its first position, and wherein the second end effector function is drivable by the output shaft when the output shaft is in its second position.

2. The surgical instrument of claim 1, wherein the end effector comprises a jaw assembly, and wherein the output shaft is configured to drive the jaw assembly when the output shaft is in its first position and the transmission is in its drive configuration.

3. The surgical instrument of claim 2, wherein the end effector is rotatable about a longitudinal axis, and wherein the output shaft is configured to rotate the end effector when the output shaft is in its second position and the transmission is in its drive configuration.

4. The surgical instrument of claim 3, further comprising an articulation joint connecting the end effector to the shaft, wherein the output shaft is translatable into a third position by the rotation of the input shaft when the transmission is in the shifting configuration, and wherein the output shaft is configured to articulate the end effector when the output shaft is in its third position and the transmission is in its drive configuration.

5. The surgical instrument of claim 1, wherein the output shaft comprises a rack portion, and wherein the transmission comprises a rack gear engaged with the rack portion configured to drive the output shaft between its first and second positions.

6. The surgical instrument of claim 1, wherein the transmission comprises:
    a first drive path which rotates the output shaft;

a second drive path which translates the output shaft; and a solenoid shifter comprising a shifter gear movable between a first position and a second position, wherein the shifter gear is configured to selectively couple the rotatable input shaft with the first drive path when the shifter gear is in its first position and the second drive path when the shifter gear is in its second position.

7. The surgical instrument of claim 1, further comprising a brake actuator configured to disengage the brake from the output shaft when the output shaft is being shifted between its first position and its second position.

8. The surgical instrument of claim 1, further comprising:
a first lockout configured to lockout the first end effector function when the output shaft is in its second position; and
a second lockout configured to lockout the second end effector function when the output shaft is in its first position.

9. The surgical instrument of claim 8, wherein the movement of the output shaft from its first position to its second position engages the first lockout, and wherein the movement of the output shaft from its second position to its first position engages the second lockout.

10. The surgical instrument of claim 8, wherein the movement of the output shaft from its first position to its second position disengages the second lockout, and wherein the movement of the output shaft from its second position to its first position disengages the first lockout.

11. The surgical instrument of claim 8, wherein the end effector is configured to perform a third end effector function, and wherein the third end effector function is drivable by the output shaft when the output shaft is in a third position.

12. The surgical instrument of claim 11, further comprising a third lockout configured to lockout the third end effector function when the output shaft is in its first position or its second position.

13. The surgical instrument of claim 12, wherein the movement of the output shaft into its first position or its second position engages the third lockout.

14. The surgical instrument of claim 12, wherein the movement of the output shaft into its third position disengages the third lockout.

15. The surgical instrument of claim 1, wherein the end effector comprises a suturing instrument configured to stitch thread into the tissue of a patient.

16. The surgical instrument of claim 1, wherein the end effector comprises a clipping instrument configured to apply a clip to the tissue of a patient.

17. The surgical instrument of claim 1, wherein the end effector comprises a grasping instrument comprising jaws closable onto the tissue of a patient.

18. The surgical instrument of claim 1, wherein the end effector comprises a dissecting instrument comprising jaws openable to separate the tissue of a patient.

19. A surgical instrument, comprising:
a shaft;
an end effector coupled to the shaft and comprising a jaw assembly;
a rotatable input shaft;
an output shaft comprising a rack portion; and
a transmission operable in a drive configuration and a shifting configuration and comprising a rack gear engaged with the rack portion, wherein the output shaft is translatable between a first position and a second position by the rotation of the input shaft when the transmission is in the shifting configuration, and wherein the output shaft is rotated by the rotation of the input shaft when the transmission is in the drive configuration, the rack gear being configured to drive the output shaft between its first and second positions,
wherein the output shaft is configured to drive the jaw assembly when the output shaft is in its first position and the transmission is in its drive configuration.

20. The surgical instrument of claim 19, wherein the end effector is rotatable about a longitudinal axis, and wherein the output shaft is configured to rotate the end effector when the output shaft is in its second position and the transmission is in its drive configuration, and
further comprising an articulation joint connecting the end effector to the shaft, wherein the output shaft is translatable into a third position by the rotation of the input shaft when the transmission is in the shifting configuration, and wherein the output shaft is configured to articulate the end effector when the output shaft is in its third position and the transmission is in its drive configuration.

* * * * *